US009284566B2

(12) United States Patent
Liao et al.

(10) Patent No.: US 9,284,566 B2
(45) Date of Patent: Mar. 15, 2016

(54) BIOFUEL AND CHEMICAL PRODUCTION BY RECOMBINANT MICROORGANISMS VIA FERMENTATION OF PROTEINACEOUS BIOMASS

(75) Inventors: James C. Liao, Los Angeles, CA (US); Kwang Myung Cho, Sungnam-si (KR); Yajun Yan, Bogart, GA (US); Yixin Huo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 186 days.

(21) Appl. No.: 13/883,531

(22) PCT Filed: Nov. 3, 2011

(86) PCT No.: PCT/US2011/059231

§ 371 (c)(1),
(2), (4) Date: Jul. 10, 2013

(87) PCT Pub. No.: WO2012/061653

PCT Pub. Date: May 10, 2012

(65) Prior Publication Data

US 2013/0288325 A1 Oct. 31, 2013

Related U.S. Application Data

(60) Provisional application No. 61/409,760, filed on Nov. 3, 2010, provisional application No. 61/410,174, filed on Nov. 4, 2010.

(51) Int. Cl.

| | |
|---|---|
| ***C12N 15/81*** | (2006.01) |
| ***C12N 1/20*** | (2006.01) |
| ***C12N 9/06*** | (2006.01) |
| ***C12N 9/10*** | (2006.01) |
| ***C12N 15/63*** | (2006.01) |
| ***C12N 15/75*** | (2006.01) |
| ***C12N 15/77*** | (2006.01) |
| ***C12N 15/78*** | (2006.01) |
| ***C12N 15/80*** | (2006.01) |
| ***C12P 7/04*** | (2006.01) |
| ***C12P 7/24*** | (2006.01) |
| ***C12P 7/40*** | (2006.01) |
| ***C12P 13/04*** | (2006.01) |
| ***C12P 7/16*** | (2006.01) |

(52) U.S. Cl.

CPC ................ *C12N 15/815* (2013.01); *C12N 1/20* (2013.01); *C12N 9/0016* (2013.01); *C12N 9/1096* (2013.01); *C12N 15/63* (2013.01); *C12N 15/75* (2013.01); *C12N 15/77* (2013.01); *C12N 15/78* (2013.01); *C12N 15/80* (2013.01); *C12N 15/81* (2013.01); *C12P 7/04* (2013.01); *C12P 7/16* (2013.01); *C12P 7/24* (2013.01); *C12P 7/40* (2013.01); *C12P 13/04* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 5,426,039 | A | 6/1995 | Wallace |
| 6,015,891 | A | 1/2000 | Adang |
| 7,091,014 | B1 | 8/2006 | Aristidou |

(Continued)

FOREIGN PATENT DOCUMENTS

| | | | |
|---|---|---|---|
| JP | 2009-513136 | A | 4/2009 |
| WO | 2007/050671 | A2 | 5/2007 |

(Continued)

OTHER PUBLICATIONS

Ohshima et al. (The purification, characterization, cloning and sequencing of the gene for a halostable and thermostable leucine dehydrogenase from Thermoactinomyces intermedius, Eur. J. Biochem. 222, 305-312 (1994)).*

Arnheim, N., and C.H. Levenson, "Polymerase Chain Reaction," C&EN (Chemical & Engineering News) 68(40):36-47, Oct. 1990.

Atsumi, S., et al., "Direct Photosynthetic Recycling of Carbon Dioxide to Isobutyraldehyde," Nature Biotechnology 27(12):1177-1180, Dec. 2009.

Atsumi, S., and J.C. Liao, "Metabolic Engineering for Advanced Biofuels Production From *Escherichia coli*," Current Opinion in Biotechnology 19(5):414-419, Oct. 2008.

(Continued)

*Primary Examiner* — Suzanne M Noakes
*Assistant Examiner* — Jae W Lee
(74) *Attorney, Agent, or Firm* — Christensen O'Connor Johnson Kindness PLLC

(57) ABSTRACT

Provided herein are metabolically modified microorganisms characterized by having an increased keto-acid flux when compared with the wild-type organism and comprising at least one polynucleotide encoding an enzyme that when expressed results in the production of a greater quantity of a chemical product when compared with the wild-type organism. The recombinant microorganisms are useful for producing a large number of chemical compositions from various nitrogen containing biomass compositions and other carbon sources. More specifically, provided herein are methods of producing alcohols, acetaldehyde, acetate, isobutyraldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, amino acids, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM) from a suitable nitrogen rich biomass.

41 Claims, 17 Drawing Sheets

(56) References Cited

U.S. PATENT DOCUMENTS

| | | | |
|---|---|---|---|
| 2009/0081746 | A1 | 3/2009 | Liao |
| 2010/0209986 | A1 | 8/2010 | Liao |
| 2010/0221800 | A1 | 9/2010 | Liao |

FOREIGN PATENT DOCUMENTS

| | | | |
|---|---|---|---|
| WO | 2008/098227 | A2 | 8/2008 |
| WO | 2010/071851 | A2 | 6/2010 |
| WO | 2010/076324 | A1 | 7/2010 |
| WO | 2012/001003 | A1 | 1/2012 |
| WO | 2012/096686 | A1 | 7/2012 |

OTHER PUBLICATIONS

Atsumi, S., et al., "Non-Fermentative Pathways for Synthesis of Branched-Chain Higher Alcohols as Biofuels," Nature 451(7174):86-89, Jan. 2008.

Barringer, K.J., et al., "Blunt-End and Single-Strand Ligations by *Escherichia coli* Ligase: Influence on an In Vitro Amplification Scheme," Gene 89(1):117-122, Apr. 1990.

Cheng, S., et al., "Long PCR: As Increasingly Longer DNA Targets Are Amplified Reliably, New Applications for PCR Are Becoming Possible," Nature 369(6482):684-685, Jun. 1994.

Connor, M.R., et al., "3-Methyl-1-butanol Production in *Escherichia coli*: Random Mutagenesis and Two-Phase Fermentation," Applied Microbiology and Biotechnology 86(4):1155-1164, Apr. 2010.

Dalphin, M.E., et al., "TransTerm: A Database of Translational Signals," Nucleic Acids Research 24(1):216-218, Jan. 1996.

Guatelli, J.C., et al., "Isothermal, In Vitro Amplification of Nucleic Acids by a Multienzyme Reaction Modeled After Retroviral Replication," Proceedings of the National Academy of Sciences of the United States of America (PNAS) 87(5):1874-1878, Mar. 1990.

Huo, Y.-X., et al., "Conversion of Proteins Into Biofuels by Engineering Nitrogen Flux," Nature Biotechnology 29(4):346-351, Apr. 2011.

Innis, M.A., and D.H. Gelfand, "Optimization of PCRs," in M.A. Innis et al. (eds.), "PCR Protocols: A Guide to Methods and Applications," Academic Press, Jan. 1990, Chap. 1, pp. 3-12.

Kwoh, D.Y., et al., "Transcription-Based Amplification System and Detection of Amplified Human Immunodeficiency Virus Type 1 With a Bead-Based Sandwich Hybridization Format," Proceedings of the National Academy of Science of the United States of America (PNAS) 86(4):1173-1177, Feb. 1989.

Landegren, U., et al., "A Ligase-Mediated Gene Detection Technique," Science 241(4869):1077-1080, Aug. 1988.

Lomeli, H., et al., "Quantitative Assays Based on the Use of Replicatable Hybridization Probes," Clinical Chemistry 35(9):1826-1831, Sep. 1989.

Murray, E.E., et al., "Codon Usage in Plant Genes," Nucleic Acids Research 17(2):477-498, Jan. 1989.

Sooknanan, R., and L.T. Malek, "NASBA: A Detection and Amplification System Uniquely Suited for RNA," Nature Biotechnology 13(6):563-564, Jun. 1995.

Van Brunt, J., "Amplifying Genes: PCR and Its Alternatives," Nature Biotechnology 8(4):291-294, Apr. 1990.

Wu, D.Y., and R.B. Wallace, "The Ligation Amplification Reaction (LAR)—Amplification of Specific DNA Sequences Using Sequential Rounds of Template-Dependent Ligation," Genomics 4(4):560-569, May 1989.

International Search Report mailed May 23, 2012, issued in corresponding International Application No. PCT/US2011/059231, filed Nov. 3, 2011, 6 pages.

International Preliminary Report on Patentability and Written Opinion mailed May 8, 2013, issued in corresponding International Application No. PCT/US2011/059231, filed Nov. 3, 2011, 7 pages.

Notice of the First Office Action mailed Mar. 24, 2014, issued in Corresponding Chinese Application No. 2011800639151, filed Nov. 3, 2011, with English translation, 14 pages.

Extended European Search Report, mailed Feb. 6, 2015, issued in corresponding Application No. EP11838838.8, filed Nov. 3, 2011, 6 pages.

Notice of the Second Office Action mailed Dec. 25, 2014, issued in Corresponding Chinese Application No. 201180063915.1, filed Nov. 3, 2011, 5 pages.

Notice on the Third Office Action, mailed Jul. 9, 2015, issued in Corresponding Chinese Application No. 201180063915.1, filed Nov. 3, 2011, 11 pages.

Atsumi, S., et al., "Engineering the Isobutanol Biosynthetic Pathway in *Escherichia coli* by Comparison of Three Aldehyde Reductase/Alcohol Dehydrogenase Genes," Applied Microbiology and Biotechnology 85(3):651-657, Jan. 2010.

Japanese Office Action mailed Oct. 15, 2015, issued in corresponding Japanese Application No. 2013-537839, filed Nov. 3, 2011, 13 pages.

* cited by examiner

| | | N recycled | Fixed N input (million tons) | N-rich residues (million tons) | Energy cost for chemical N fixation ($10^{12}$ KJ) | Energy used in N fixation / energy in biofuel | Percentage of potential annual US DDGS market |
|---|---|---|---|---|---|---|---|
| Plant | 11 billion gallons | No | 1.6 | 27 | 89 | 11.2% | 65% |
| | 60 billion gallons | | 9.4 | 164 | 536 | 11.2% | 390% |
| Algae | Lipid process (60 billion gallons) | | 35.5 | 589 | 2024 | 25.8% | 1402% |
| | Protein process (60 billion gallons) | Yes | ~0 | ~0 | ~0 | ~0 | ~0 |

*Fig.1C.*

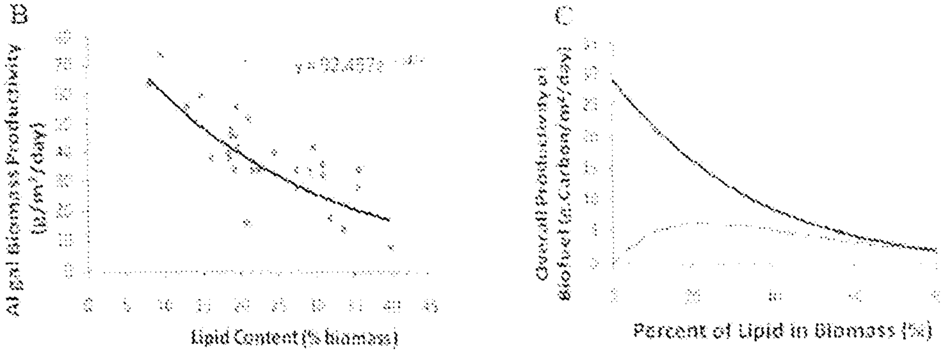
Figure 4B-C

2-Ketobutyrate
2-Ketoisovalerate
2-Ketovalerate
2-Keto-3-methyl-valerate
2-Keto-4-methyl-pentanoate
Phenylpyruvate 1-Propanol
Isobutanol
1-Butanol
2-Methyl-1-butanol
3-Methyl-1-butanol
2-Phenylethanol α-keto adipic acid
α-hydroxy adipic acid
adipic acid

BIOFUEL AND CHEMICAL PRODUCTION BY RECOMBINANT MICROORGANISMS VIA FERMENTATION OF PROTEINACEOUS BIOMASS

CROSS REFERENCE TO RELATED APPLICATIONS

This application is the National Stage of International Application No. PCT/US2011/059231, filed Nov. 3, 2011, which claims priority to U.S. Provisional Application Ser. No. 61/409,760, filed Nov. 3, 2010 and U.S. Provisional Application Ser. No. 61/410,174 filed Nov. 4, 2010, the disclosures of which are incorporated herein in their entirety by reference.

GOVERNMENT SUPPORT

This invention was made with Government support under Grant No. DE-FC02-02ER63421, awarded by the U.S. Department of Energy. The Government has certain rights in this invention.

TECHNICAL FIELD

Metabolically modified microorganisms and methods of producing such organisms are provided. The disclosure provides biofuel reactor systems for the production of biofuels from proteinaceous biomass. Also provided are methods of producing biofuels and chemicals by contacting a suitable substrate with a metabolically modified or recombiant microorganism and enzymatic preparations therefrom.

BACKGROUND

Demand for biofuels as a substitute for petroleum is expected to increase because of economic and environmental concerns. The common biofuel, ethanol, is not ideal because it has a lower energy density than gasoline and must be mixed with gasoline at a limited concentration range in order to serve as a transportation fuel. Ethanol is also hygroscopic and corrosive, which poses a problem for storage and distribution systems.

In addition, adipic acid is a compound that serves both industrial purposes in the production of various synthetics including, for example, Nylon 6-6, as well as uses in the formulation of various medicaments.

Further, gamma-aminobutyric acid is a compound that serves both industrial purposes in the production of various synthetics including, for example, Nylon 4, as well as biological roles such as in nerve cell communications.

SUMMARY

The present disclosure describes the use of nitrogen rich materials (e.g., proteinaceous materials) as a raw material for production of various chemical compounds, such as carbon-based fuels and chemicals. In various embodiments, the disclosure can involve a method of using proteins as the main raw material for any fermentation. The method can comprise heating and digesting of cellular biomass to break down the proteins partially and then using treated cellular biomass as a single carbon source in various microbial fermentations to produce various bioproducts including alcohols, organic acids and other chemicals. In another embodiment, the disclosure can include development of specific microbial strains to utilize said cellular biomass efficiently. The cellular biomass includes all kinds of bacteria, yeast, fungi, cyanobacteria, algae, and any crude materials containing proteinaceous biomass (Dried Distillers Grains with Solubles (DDGS), algae meal or cake, bacterial fermentation cake and the like).

In one embodiment, a specific microbial strain is developed to have a strong ability to degrade amino acids to make it possible to utilize proteinaceous biomass comprising proteins, polypeptides, amino acids, and mixtures thereof as a single carbon source. The metabolic pathways for digesting various amino acids are engineered both by genetic and random mutagenesis. In certain embodiments, proteins and polypeptides can be digested into small peptides, they can be transported into the recombinant microrganism and degraded into amino acids. Amino acids are converted to various 2-keto acids. Finally, these 2-keto acids are converted to a desired chemical entity, such as for example, a longer chain aldehyde or an alcohol, through various recombinant pathways introduced into the microorganism. Among them, leucine, isoleucine, and valine are directly converted to a corresponding 2-keto acid by leucine dehydrogenase or other enzymes that convert these amino acids to 2-keto acids. Serine, cysteine, tryptophan, and alanine and glycine are converted to pyruvate, which is further converted to 2-ketoisovalerate, which can be further used, for example, for isobutanol synthesis. Glutamate, glutamine, arginine, and proline are converted to 2-ketoglutarate, which is further converted to threonine, which can be used for example, for 1-propanol production, or can be converted back to pyruvate by malic enzyme. The pyruvate can be used, for example, for isobutanol production. Or, all the proteinaceous biomass converted to pyruvate can be converted to produce ethanol as well. The remaining amino acids were engineered to support growth or to act as an energy source by random mutagenesis.

In another embodiment, the proteinaceous biomass is treated and converted to key intermediates, such as, for example, pyruvate, 2-ketoglutarate, for various kinds of chemical production. The said chemicals can include, for example and not as a limitation, succinic acid, malic acid, fumaric acid and gamma-amino butyric acid (GABA). This invention is not limited to produce only the recited chemicals.

The disclosure provides in an embodiment a recombinant microorganism characterized by having an increased keto-acid flux when compared with the wild-type organism and comprising at least one polynucleotide encoding an enzyme that when expressed results in the production of a greater quantity of a chemical product when compared with the wild-type organism. More particularly, the recombinant microorganism comprises a heterologous polynucleotide which encodes a dehydrogenase, a transaminase, and/or a deaminase. In certain embodiments the dehydrogenase is a glutamate dehydrogenase (E.C. 1.4.1.2 and E.C. 1.4.1.4), a glutamic dehydrogenase (E.C. 1.4.1.3), a valine dehydrogenase (E.C. 1.4.1.8), a leucine dehydrogenase (E.C. 1.4.1.9), or a phenylalanine dehydrogenase (E.C. 1.4.1.20). In a typical embodiment the leucine dehydrogenase can be a LeuDH, which can be isolated from *Thermoactinomyces intermedius*. In certain other embodiments the recombinant microorganism can comprise a deaminase selected from aspartate ammonia lyase (4.3.1.1), L-serine ammonia lyase (E.C. 4.3.1.17), D-serine ammonia lyase (4.3.1.18), threonine ammonia lyase (E.C. 4.3.1.19), tyrosine ammonia lyase (E.C. 4.3.1.23), phenylalanine ammonia lyase (E.C. 4.3.1.24), and phenylalanine/tyrosine ammonia lyase (E.C. 4.3.1.25). More particularly, the deaminase can be the serine deaminase SdaB, which can be from, for example, *Escherichia coli, Rosebacter atrosepticum, Corynebacterium diphtheriae, Salmonella enerica, Yersinia enterocolitica*, or *Burkholderia pseudoma-*

*llei*. Still further, the recombinant microorganism can comprise a transaminase that is an L-α-transaminase (E.C. 2.6.1.X, where X is any number). In particular embodiments the L-α-transaminase can be an L-aspartate transaminase (E.C. 2.6.1.1), an L-alanine transaminase (E.C. 2.6.1.12 and E.C. 2.6.1.47), an L-asparagine transaminase (E.C. 2.6.1.14), or a glycine transaminase (E.C. 2.6.1.35). In certain embodiments the L-aspartate transaminase can be AvtA, which can be from, for example, *Escherichia coli, Neisseria meningitidis, Pantoea ananatis, Amycolatopsis mediterranei, Mannheimia succinicproducens, Salmonella enterica*, or *Yersinia pestis*.

The disclosure also provides for a recombinant microorganism that is further characterized by a reduced ammonia reuptake activity, a reduced autoinducer 2 reuptake activity, a reduced glutamate dehydrogenase activity, a reduced glutamine synthase activity, a reduced glutamate synthase activity, a reduced quorum sensing gene activity, and/or a reduced global regulator activity when compared with the wild-type organism. In certain embodiments, the reduced quorum sensing activity is from the deletion, or reduced expression or function of the genes luxS or lsrA; the reduced ammonia reuptake activity is from the deletion, or reduced expression or function of the genes gdhA and glnA, and the reduced global regulator activity is from the deletion, or reduced expression or function of the genes CRP, LRP, Fis, and/or IHF.

Recombinant microorganisms of the present invention are particular disclosed to produce a chemical product such as, for example, an alcohol, an acetaldehyde, acetate, isobutyraldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and S-adenosyl-methionine (SAM). In certain embodiments the alcohol is selected from the group consisting of ethanol, 1-proponal, n-butanol, isobutanol, 2-methyl-1-butanol and 3-methyl-butanol.

Still further, the present disclosure provides that the recombinant microorganism can be derived from a wild-type organism that is a bacterium, a *cyanobacterium*, a filamentous fungus, or a yeast. More particularly, the wild-type microorganism is from a genus, such as, for example, *Clostridium, Zymonomas, Escherichia, Salmonella, Rhodococcus, Pseudomonas, Bacillus, Lactobacillus, Enterococcus, Alcaligenes, Klesiella, Paenibacillus, Arthrobacter, Corynebacterium, Brevibacterium, Pichia, Candida, Hansenula, Synechococcus, Synechocystis, Anabaena, Ralstonia, Lactococcus, Saccharomyces, Brevibacterium, Arthrobacter*, or *Microbacterium*. More particularly, the wild-type organism can be for example, *Escherichia coli, Alcaligenes eutrophus, Bacillus licheniformis, Zymonomas mobilis, Paenibacillus macerans, Rhodococcus erythropolis, Pseudomonas putida, Bacillus subtilis, Lactobacillus plantarum, Corynebacterium glutamicum, Enterococcus faecium, Enterococcus gallinarium, Enterococcus faecalis, Saccharomyces cerevisiae, Synechocystis* sp., *Anabaena* sp., *Ralstonia eutropha, Lactococcus lactis*, and *Synechococcus elongatus*.

The disclosure also provides a recombinant microorganism that produces a desired chemical entity from a metabolite comprising a 2-keto acid and using a source of amino acids. In one embodiment, the microorganism is modified to express or over express a polypeptide having an activity selected from the group consisting of leucine or valine dehydrogenase. In yet another embodiment, the microorganism is engineered to express or over express an enzyme designated glyA, sda, tnaA, dadX, dadA which are useful for the conversion of Gly to L-Ser to Pyruvate; L-Cys to Pyruvate; L-Ala to D-Ala to Pyruvate, respectively. In yet another embodiment, the microorganism expresses or overexpresses an enzyme selected from the following: ybaS, yneH, putA, astABCDE which convert glutamine, proline, and arginine, respectively, to glutamate, which in turn is metabolized to 2-ketoglutarate by the enzyme gdhA.

In one embodiment, the recombinant microorganism produces alpha-adipic acid from the expression of one or more polypeptide engineered into the microorganism. In a glutamic acid pathway, glutamic acid is converted to 2-KG (2-keto glutarate) by a polypeptide having glutamate dehydrogenase (gdh) activity. By consecutive reactions of polypeptides having homocitrate synthase (hcs) activity and homoacornitase (hacAB) activity, 2-KG is converted to homoisocitrate, which is reductive decarboxylated to alpha-keto adipic acid by a polypeptide having homoisocitrate dehydrogenase (hicDH) activity. Polynucleotides encoding the polypeptides of the disclosure may be derived from any number of microorganisms including, for example, *Saccharomyces cerevisiae, Thermus thermophilus*, and others known in the art. The polynucleotides may be mutant or variant enzymes that have been derived from a source organism and then modified or engineered to have improved activity. In one embodiment, the polynucleotides encoding the enzymes involved in the glutamic acid pathway are cloned from various organisms including, for example, *S. cerevisiae* and *T. thermophilus*.

In a lysine pathway of the disclosure, lysine is deaminated to 2-aminoadipate-6-semialdehyde by a polypeptide having lysine aminotransferase (lat) activity. Then, a polypeptide having piperideine 6-carboxylate dehydrogenase (pcd) activity catalyzes the formation of alpha-amino adipic acid. The amine group is then deaminated by a polypeptide having 2-aminoadipate aminotransferase (aadat) activity. Polynucleotides encoding the polypeptides of the disclosure may be derived from any number of microorganisms including, for example, *Flavobacterium lutescens, Streptomyces clavuligerus, Homo sapiens*, and others known in the art. The polynucleotides may be mutant or variant enzymes that have been derived from a source organism and then modified or engineered to have improved activity. In one embodiment, the polynucleotides encoding the enzymes can be cloned from various organisms including, for example, *F. lutescens, S. clavuligerus, H. sapiens*, and the like.

For the production of adipic acid from the intermediate, alpha-keto adipic acid, two biological routes (CoA-independent pathway and CoA-dependent pathway) were engineered along with one chemical route as shown in FIG. 3. For the biological conversion, alpha-keto adipic acid is converted to alpha-hydroxy adipic acid by various polypeptides having dehydrogenase activity including polypeptides with leucine dehydrogenase (ldhA) activity, polypeptides with malate dehydrogenase (mdh) activity and polypeptides with hydroxyisocaproate dehydrogenase (hdh) activity from various microorganisms. In the CoA-independent pathway, a mimic pathway for the natural reductive TCA cycle was engineered, which converts oxaloacetate to succinate via malate and fumarate under anaerobic condition. Mutagenesis of fumarate reductase (fumA or fumB) can provide polypeptides that promote the dehydration of alpha-hydroxy adipic acid. A further step can be constructed by the mutant of crotonate dehydrogenase from *Clostridium acetobutyricum*. In CoA-dependent pathway, the pathway for isocaproate production in *Clostridium difficille* can be used to derive a polypeptide that converts alphahydroxy adipic acid to adipic acid. The first step is catalyzed by a polypeptide having CoA transferase (hadA) activity to make R-2-hydroxyisocaproyl-CoA. Then, dehydration of R-2-hydroxyisocaproyl-CoA by a dehydratase-activator complex (e.g., hadBC-hadI) makes 2-Isocaprenoyl-CoA, which is reduced to Isocaproyl CoA by a polypeptide having acyl CoA dehydrogenase (acdB-etfBA) activity. Finally, CoA moiety is removed by the CoA transferase (hadA) to produce adipic acid. Chemical reduction of alpha-keto adipic acid to adipic acid is also possible using various metal catalysts including platinum.

In one embodiment, the disclosure provides a recombinant bacterium, modified by introducing a heterologous polynucleotide that expresses a polypeptide selected from the group consisting of a polypeptide having glutamate dehydrogenase (gdh) activity, a polypeptide having homocitrate synthase (hcs) activity, a polypeptide having homoacornitase (hacAB) activity, a polypeptide having homoisocitrate dehydrogenase (hicDH) activity, a polynucleotide or plurality of polynucleotides encoding any combination of the foregoing.

In another embodiment, the disclosure provides a recombinant bacterium, modified by introducing a heterologous polynucleotide that expresses a polypeptide selected from the group consisting of a polypeptide having lysine aminotransferase (lat) activity, a polypeptide having piperideine 6-carboxylate dehydrogenase (pcd) activity, a polypeptide having 2-aminoadipate aminotransferase (aadat) activity, a polynucleotide or plurality of polynucleotides encoding any combination of the foregoing.

In yet, another embodiment, the same or different bacterium may be recombinantly modified for the expression of a polypeptide having dehydrogenase activity including polypeptides with leucine dehydrogenase (ldhA) activity, polypeptides with malate dehydrogenase (mdh) activity and polypeptides with hydroxyisocaproate dehydrogenase (hdh) activity from various microorganisms.

In another embodiment, the disclosure provides a recombinant bacterium, modified by introducing a heterologous polynucleotide that expresses a polypeptide selected from the group consisting of a polypeptide having CoA transferase (hadA) activity, a polypeptide having dehydratase-activator complex (e.g., hadBC-hadO) activity, a polypeptide having acyl CoA dehydrogenase (acdB-etfBA) activity, a polypeptide having CoA transferase (hadA) activity and any combination of the foregoing such that adipic acid is produced from alpha-keto adipic acid.

Still further, the disclosure provides a process for the production of a chemical product from a biomass comprising protein, polypeptides, or amino acids by contacting the biomass with any of the recombinant microorganism described above under conditions conducive to chemical product production, wherein the quantity of the chemical product produced is greater than that produced by the wild-type organism. The biomass used to grow the recombinant microorganism can be, for example, algae, Dried Distillers Grains with Solubles (DDGS), bacteria, animal residuals, plant, protein, polypeptides, amino acid, or mixtures thereof, and any combination thereof. In certain embodiments described herein the biomass can be green algae, red algae, green-blue algae, *cyanobacterium, Escherichia coli*, or *Baccilus subtilis*. In particular embodiments described the biomass was *Chorella vulgaris, Porphyridium purpureum, Spirulina platensis*, or *Synechococcus elongates*. Still further, the biomass can be partially degraded prior to contact with the recombinant microorganism. In certain embodiments the biomass can be treated with a protease and/or heat. Such as, for example, where the biomass was hydrolyzed by heating, such as heating at a temperature ranging from 60 to 100° C. and by treating with a protease. In certain embodiments a process is disclosed where the biomass can be contacted with a second microorganism that converts lysine, methionine, histidine, phenylalanine, tryptophan and tyrosine into a mixture of all twenty amino acid residues. In particular, the second microorganism is contacted with the biomass prior to contacting the recombinant microorganism. The second the microorganism can be *Pseudomonas* and/or *Bacillus*.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 1A-E shows a comparison of various biofuel production processes. (A) The cellulosic plant process. (B) The algal lipid process. (C) The energy cost and N-rich biomass accumulation by various biofuel production processes. See infra for detailed calculations. (D) The algal protein-to-fuel process developed in this study. (E) Theoretical yields (grams of product per grams of raw material) of biofuels from protein. Solid bars: Net yield, calculated by excluding the amino group in raw material. Cross-hatched bars: Gross yield, calculated with the amino group in raw material. See Table 3 for details.

FIG. 4A-D depict an overall design and optimization of biofuel productivity. (A) The overall process flow sheet of open pond algal cultures to biofuels (60 Billion gal/year, which is about 30% of US transportation fuel consumption).

The elemental mass flows of C (Black), N (Grey) and S (Light Grey) in each stream are listed next to the stream, without the associated mass of H and O. All values have units in million tons per year, unless specified otherwise. N-rich biomass is meant to include proteins and carbohydrites, although the conversion yield of protein-to-higher-alcohols is used for calculation. The lipid content of the algal species is assumed to be 10%. Square boxes indicate main processing steps, while ovals identify stream components. The billion gallons per year is denoted as Bgal/year. (B) Algal biomass productivity as a function of lipid content. The data (11) were converted from g/L/day to $g/m^2$/day, assuming the depth of the pond is 0.2 m. The trend line is the best fit to an exponential function shown in the figure. (C) Considering the biomass productivity in (B) and theoretical conversion yield of protein to biofuels, the effect of lipid content on the overall biofuel productivity is calculated through the combined protein-lipid process (solid line) or lipid process only (dotted line). Note that the overall productivity of the protein-lipid process decreases as lipid content increases, suggesting that the protein part is more efficient. (D) The optimal lipid content in the combined protein-lipid process as function of the protein-to-higher alcohol conversion yield. As long as the protein-to-biofuel conversion is greater than 61% of the theoretical yield, then the protein processing part of the process is more efficient than the lipid processing. The carbon conversion from lipid to fuel is assumed to be 100%.

Figure 5:
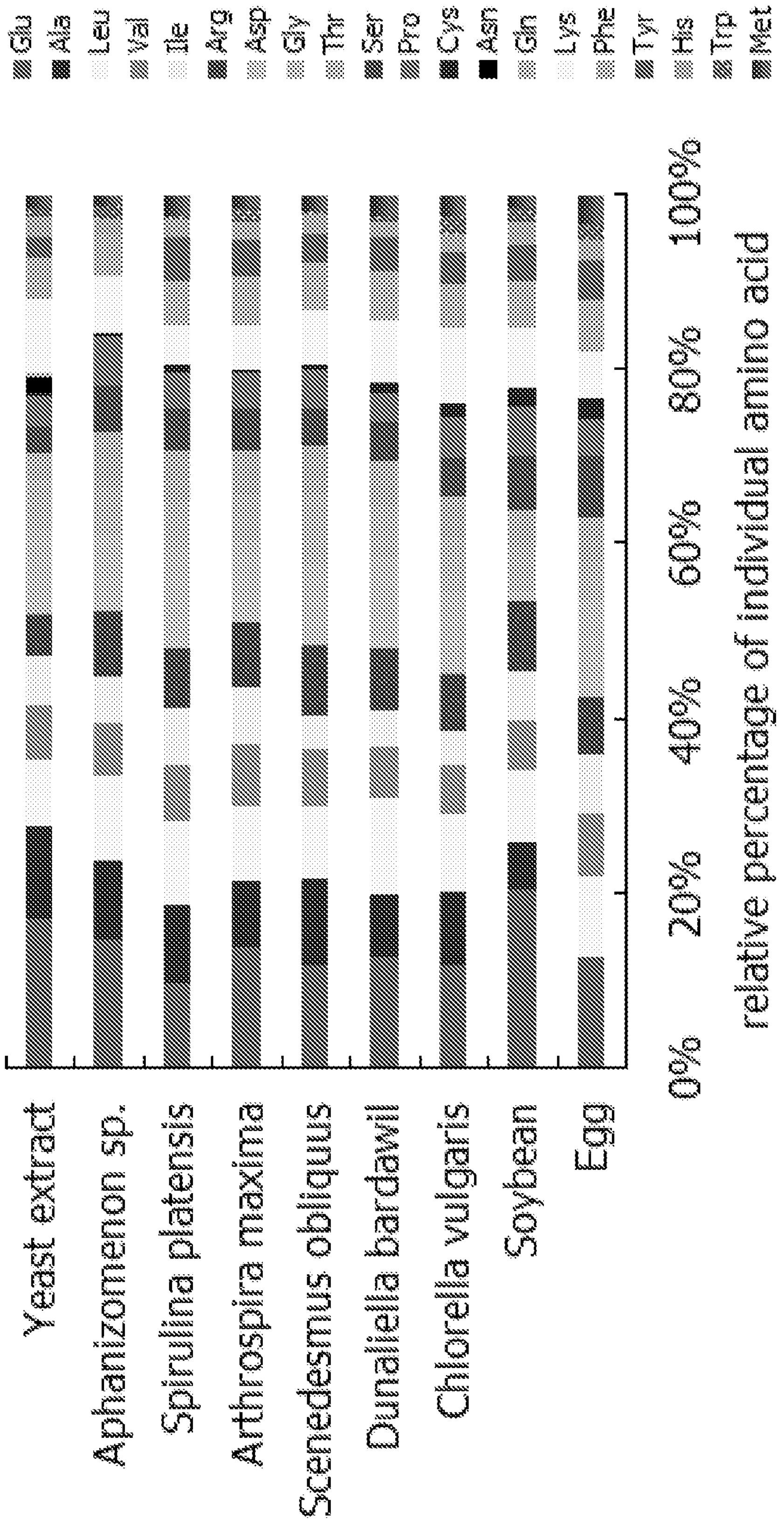

FIG. 5 shows similarity of amino acid profiles among different algae species, yeast extract and two conventional protein sources.

Figure 6A:
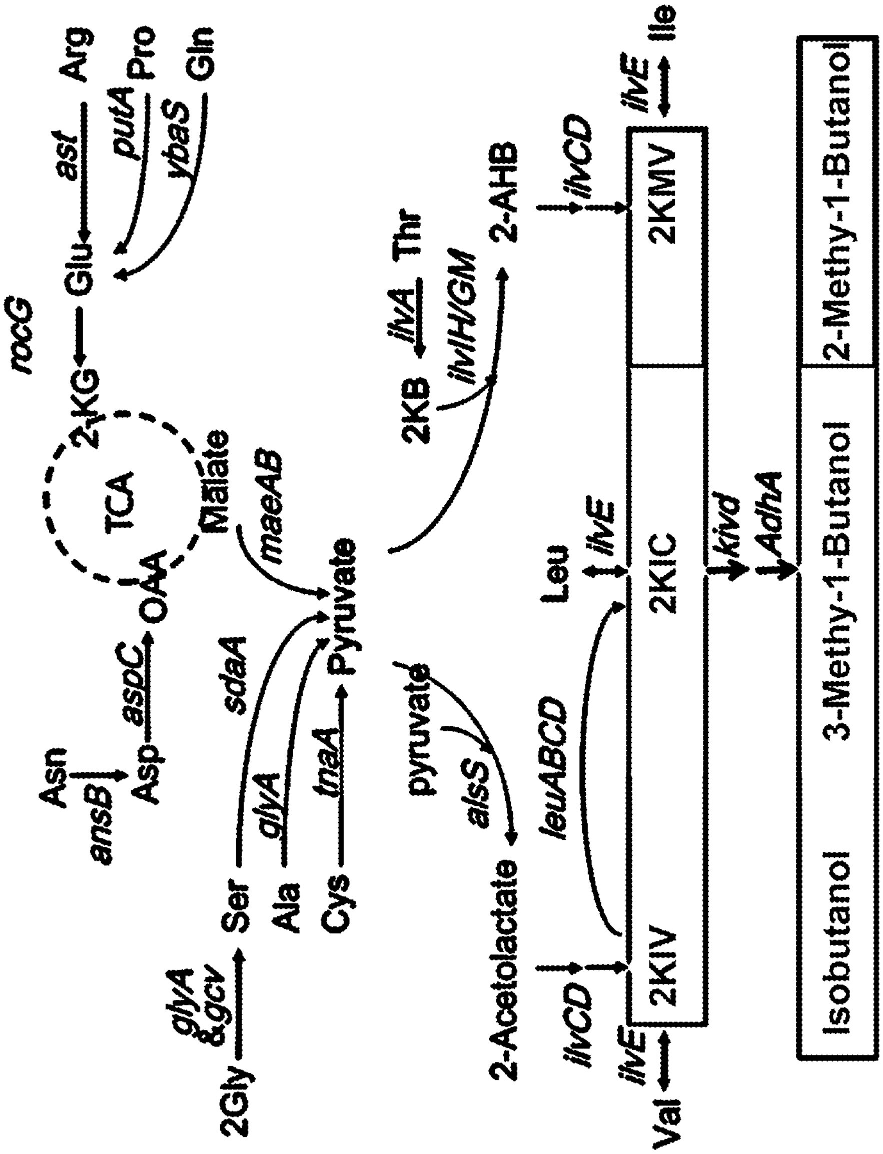
Figure 6B:
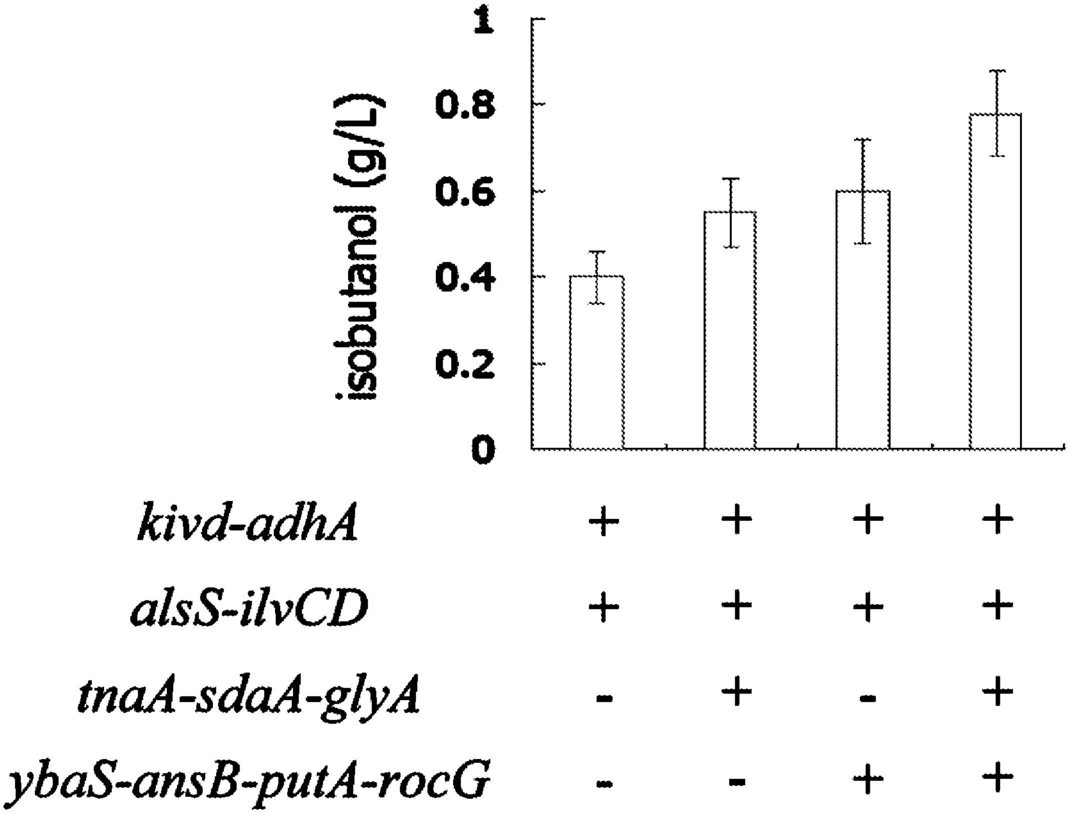

FIG. 6A-B shows that a carbon-flux driven strategy for production of higher alcohols from various amino acids. (A) The metabolic networks for the carbon-flux-driven higher alcohol production. Amino acids are degraded to various 2-keto acids, which can be converted to higher alcohols through 2-keto acid decarboxylase (KivD) and alcohol dehydrogenase (YqhD). The overexpressed genes are indicated in red. (B) Results for isobutanol production in engineered *E. coli* with overexpressed genes indicated below the axis. Error bars indicate s.d.

Figure 7:
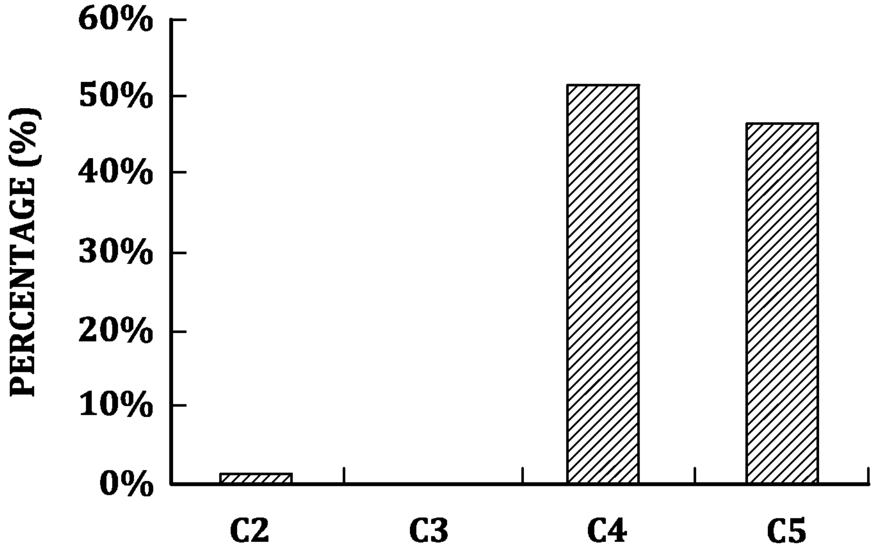

FIG. 7 shows the chain-length distribution of biofuels produced from the *E. coli* engineered using the nitrogen-centric strategy. The strain is YH83 (=YH19ΔglnAΔLgdhAΔlsrA/overexpression of alsS, ilvC, ilvD, avtA, leuDH, kivD, yqhD, ilvE, ilvA and sdaB).

Figure 8:
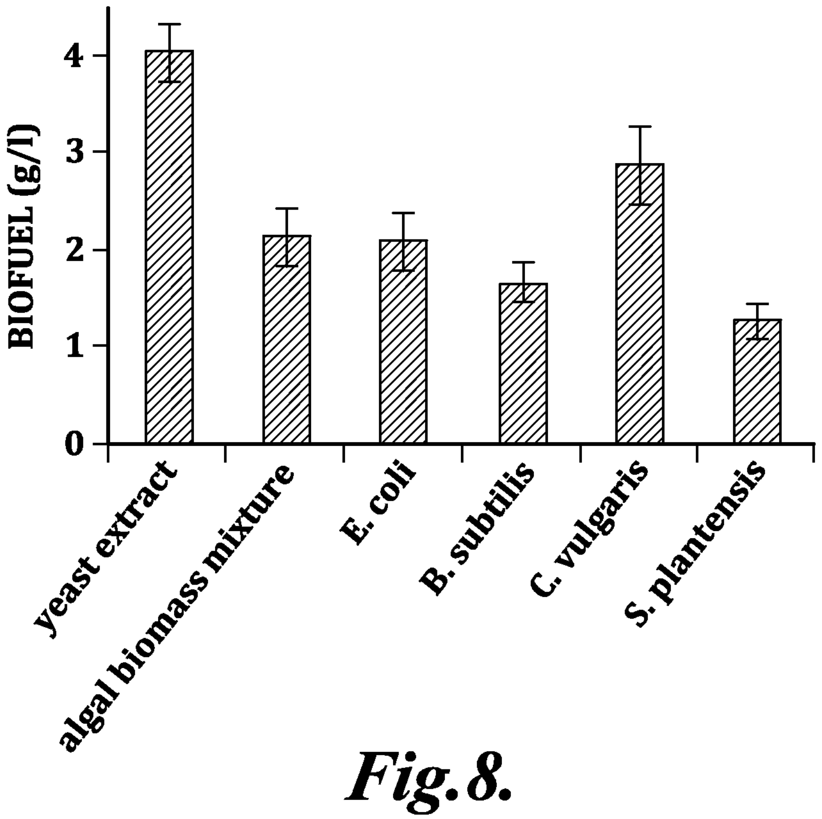

FIG. 8 shows the biofuel (EtOH, iBOH, 2MB, 3MB) produced fro the engineered *E. coli* strain YH83 grown in flasks using algal or bacterial cell hydrolysates. Small laboratory-scale reactors (1 liter or 30 liters) were used to grow bacterial and algal cells individually. The algal biomass mixture includes *C. vulgaris, P. purpureum, S. platensis* and *S. elongates*. All protein sources were adjusted to contain 21.6 g/l peptides and amino acids which is equivalent to the amount of protein in 4% yeast extract. Error bars indicate s.d. (n=3).

Figure 9:
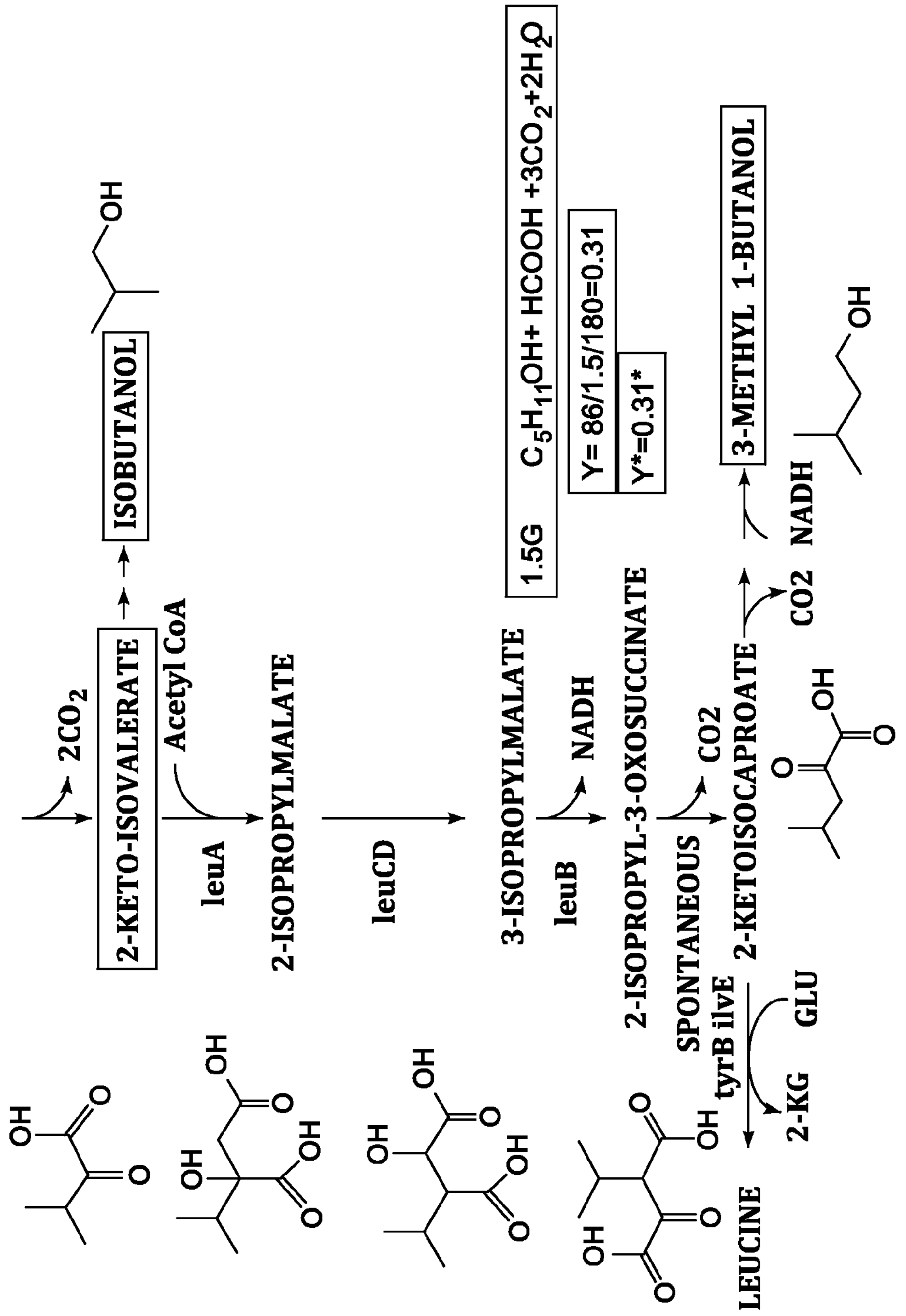

FIG. 9 shows a general schematic of conversion of keto acids to isobutanol and 3-methyl-1-butanol.

Figure 10:
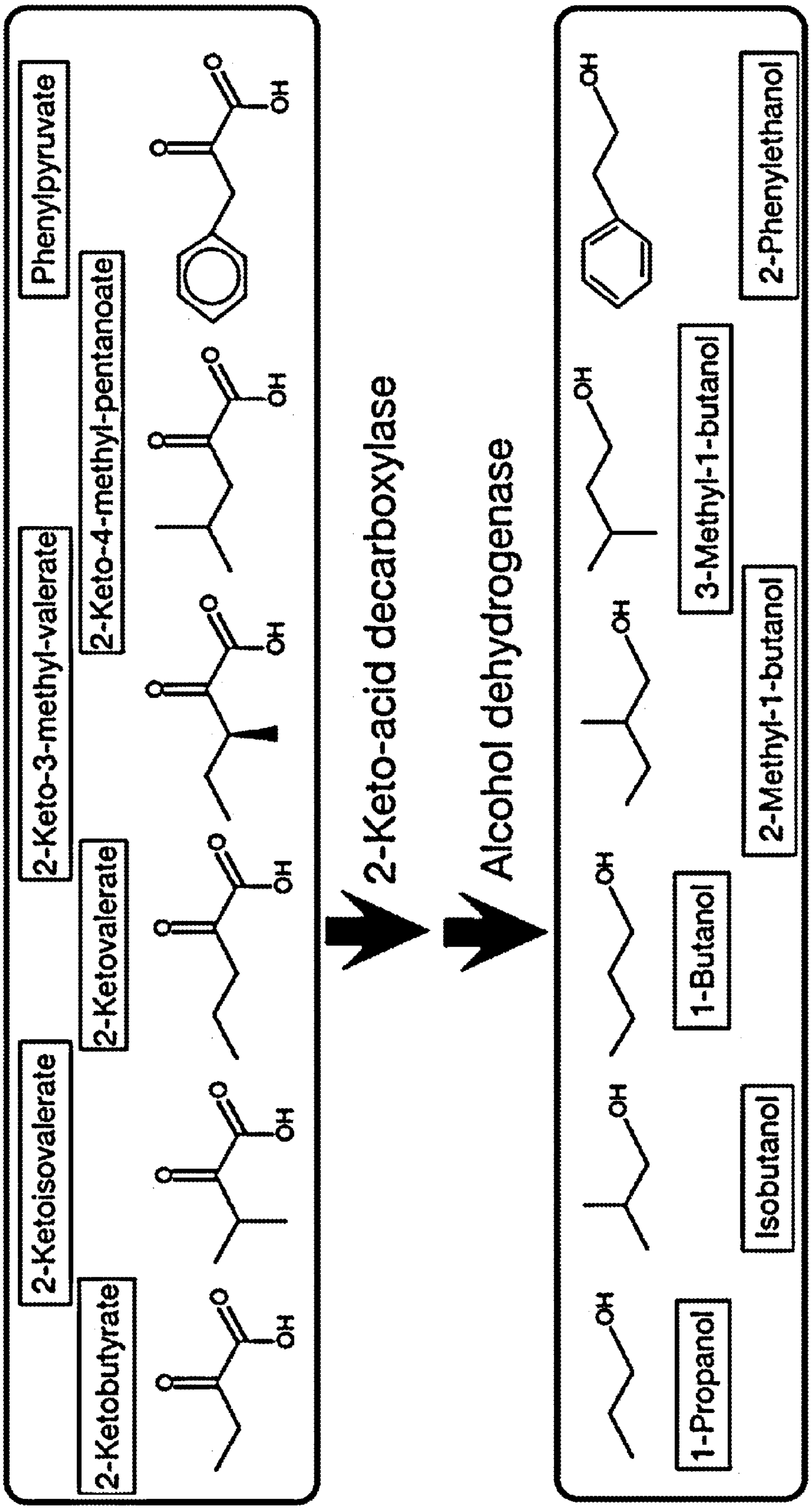

FIG. 10 shows an overall schematic of keto acid conversion to higher alcohols.

Figure 11A:
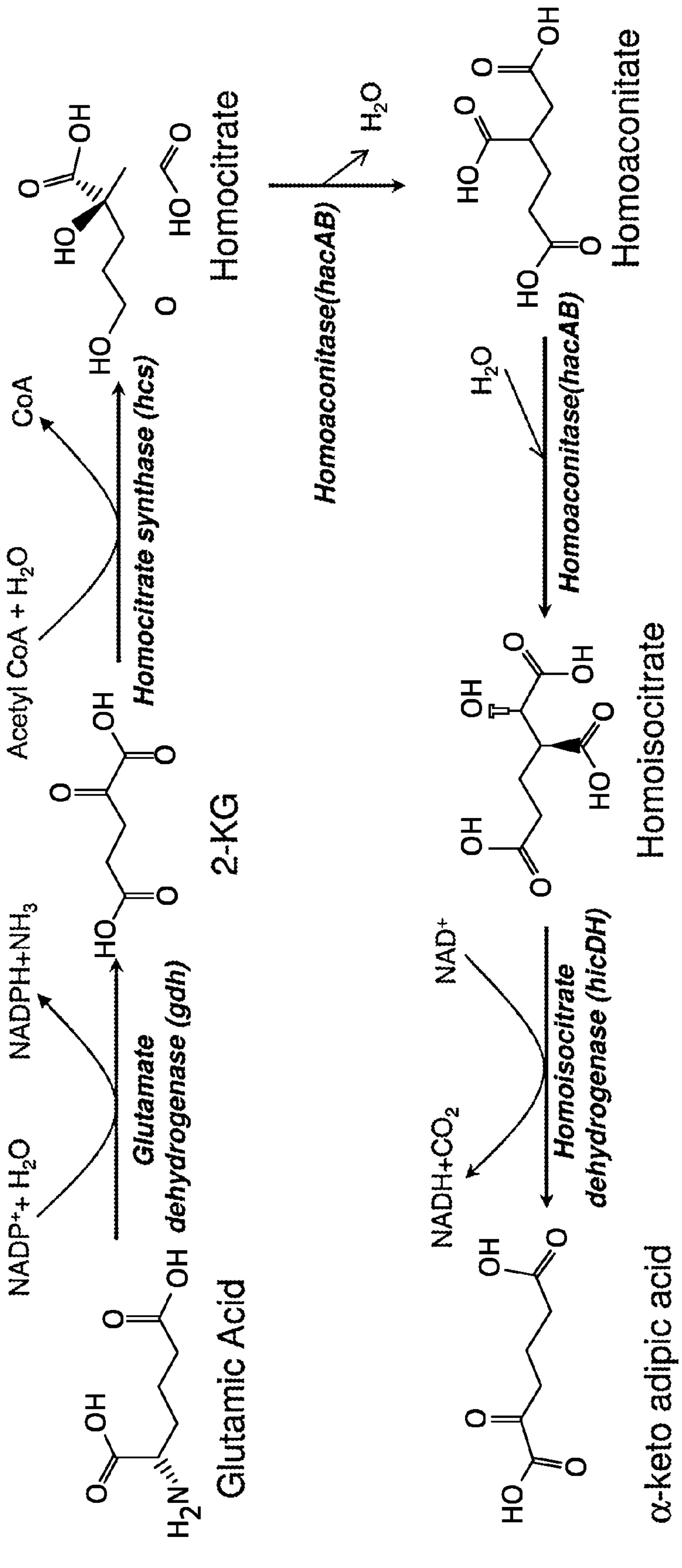
Figure 11B:
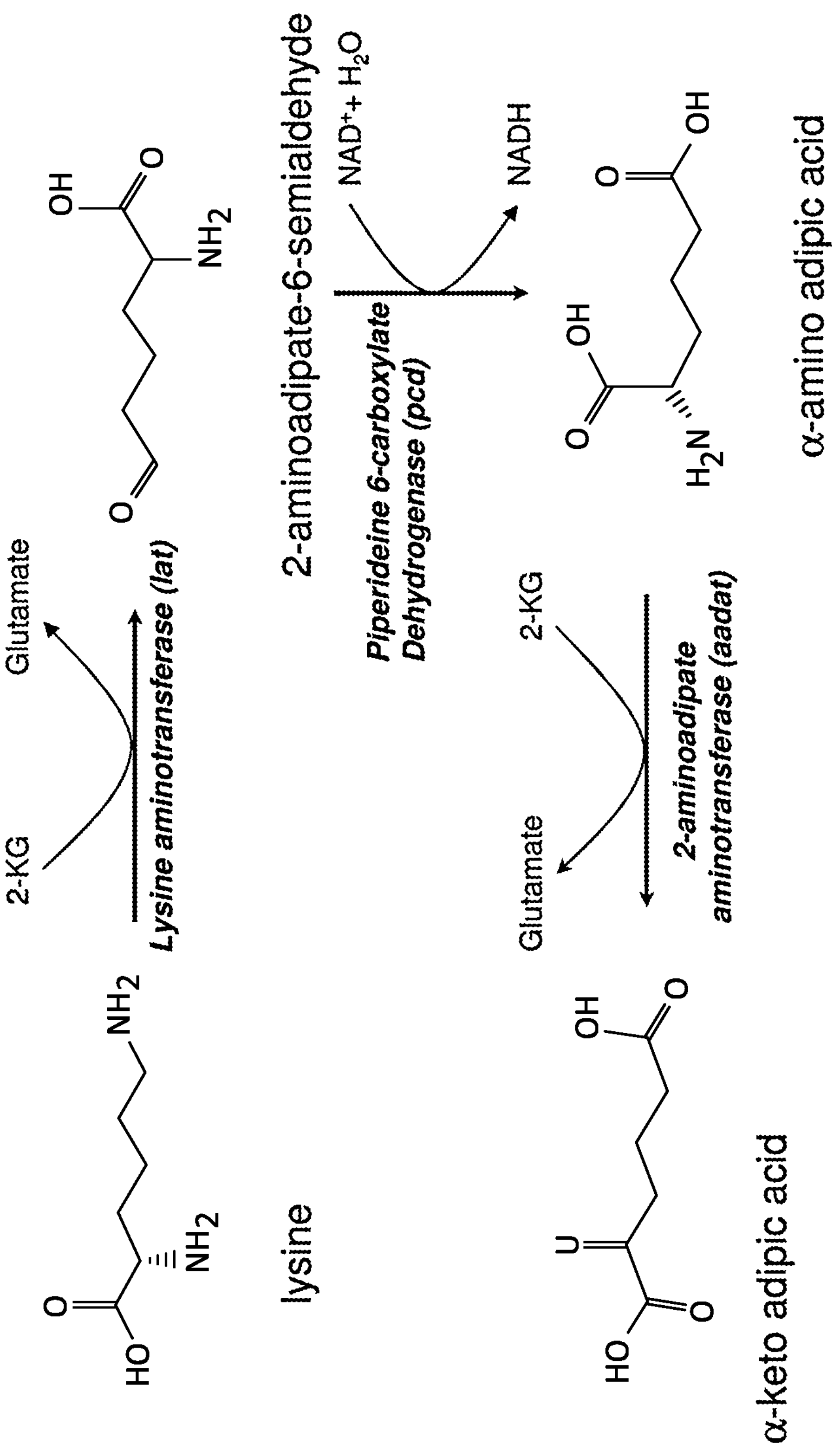
Figure 11C:
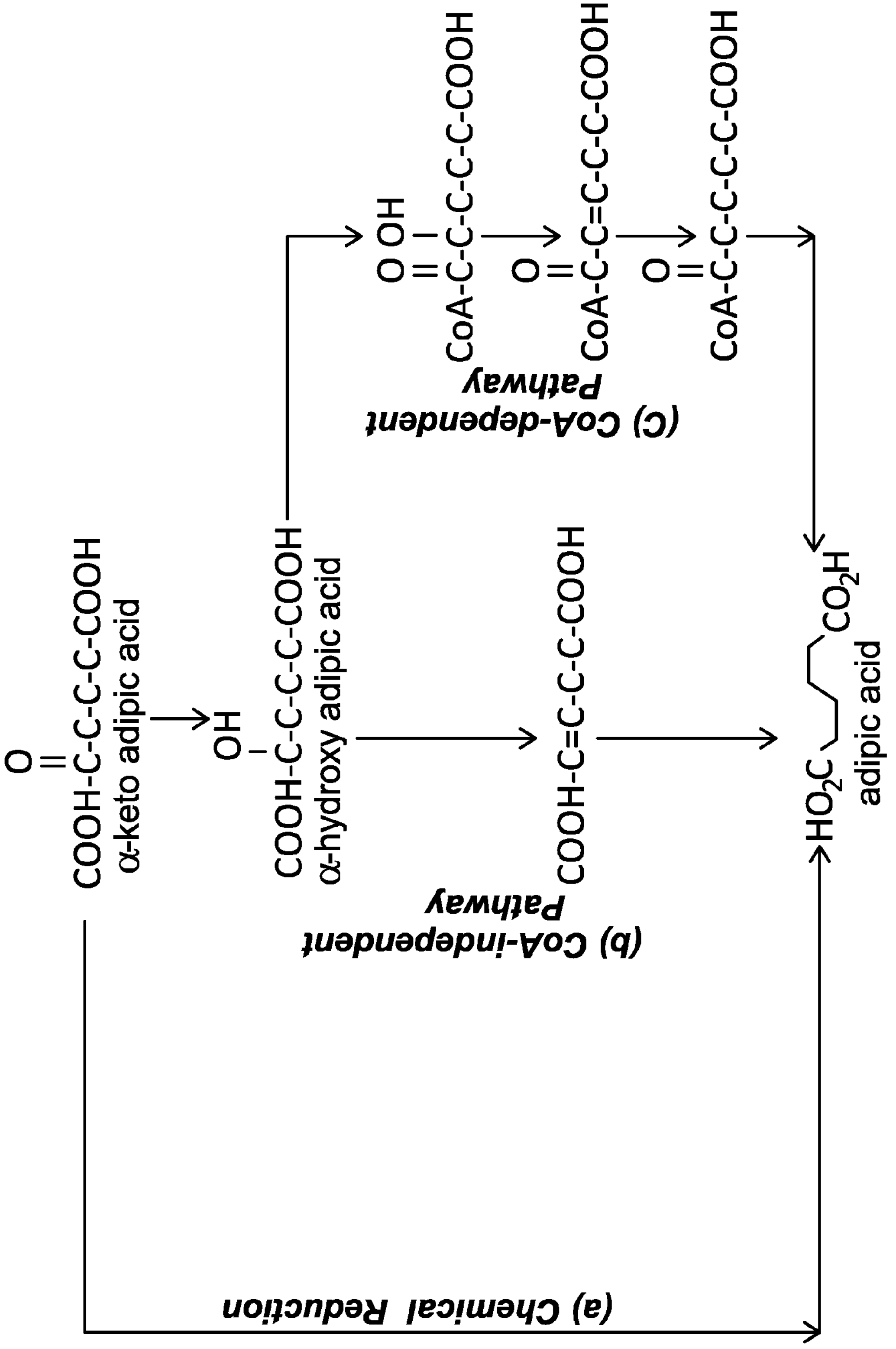

FIG. 11A-C depicts a schematic for the production of adipic acid.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The specific examples provided herein are used to demonstrate a shift and use of a substrate, including, for example, a proteinacious biomass, a protein hydrosylate, a mixture of amino acids, and single free amino acids, and the like, in the production of various 2-keto acids. As described more fully below, the 2-keto acids can then be further metabolized into additional chemical entities, in addition to biofuels.

Since plants and algae do not fix nitrogen, large scale biofuel production via plants or algae both require fixed nitrogen in the form of ammonium or nitrate, which is then incorporated into biomass mainly as proteins and a small amount of nucleic acids. Biological nitrogen fixation is a slow and energy intensive process performed by some symbiotic bacteria, such as *Rhizobia* and some free-living microorganisms such as *Anabaena*. Non-biological nitrogen fixation is achieved via a catalytic process known as the Haber-Bosch process, which is also energy intensive and environmentally unfriendly. To produce 1 mole of $NH_3$ requires 8 moles of ATP and 4 reducing equivalents via biological nitrogen fixation or 0.8 MJ via the Haber-Bosch process (57 MJ per Kg of nitrogen).

Figure 1A:
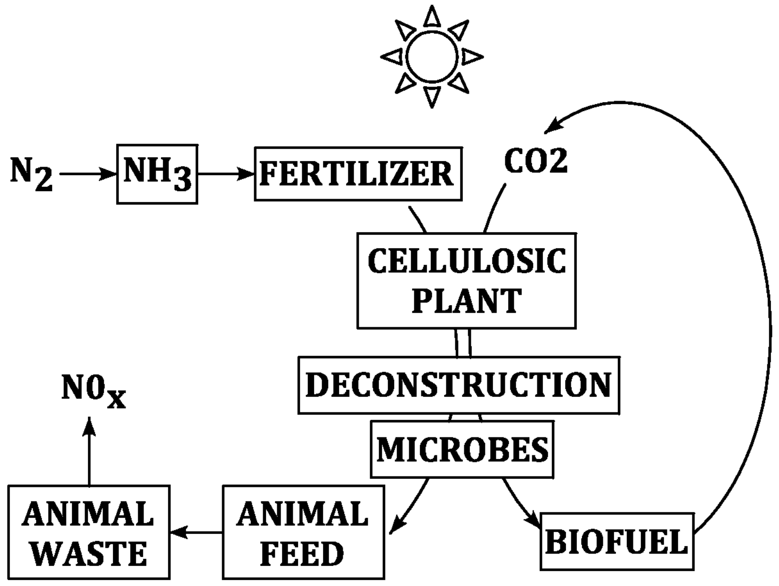
Figure 1B:
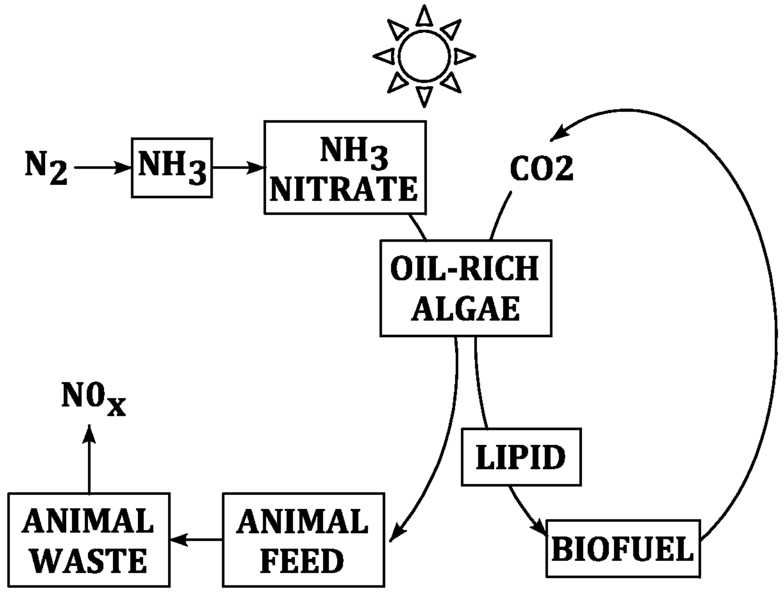

To produce biofuel, plant biomass or algal lipids are converted into carbon-based fuels, and the remaining nitrogen-rich biomass is used as animal feed (FIGS. 1A and 1B). In these cases, a net input of fixed nitrogen is required through the Haber-Bosch process (FIG. 1C). The current chemical synthesis of nitrogen fertilizer already amounts to 100 million tons per year and consumes about 1.2% of the global primary energy supply, and will increase substantially if the biofuel processes are scaled up.

The nitrogen-rich residues used as animal feed indirectly create Green House Gases (GHGs) through animal wastes. Although animal feed commands a higher price at present, the market will soon be saturated (FIG. 1C). The total potential US livestock demand of nitrogen-rich biofuel residues (i.e., Dried Distillers Grains with Solubles, DDGS) is about 42 million Tons, which corresponds to the byproduct of 15.4 billion gallons of plant-based biofuels or 4.3 billion gallons of algal biofuels, which are roughly 7.7%, or 2.1% of total US usage of liquid fuels, respectively. Thus, without recycling of nitrogen, the large-scale production of biofuel beyond the above levels will result in a net accumulation of reduced nitrogen or GHGs on earth, and the practice becomes unsustainable.

Figure 1D:
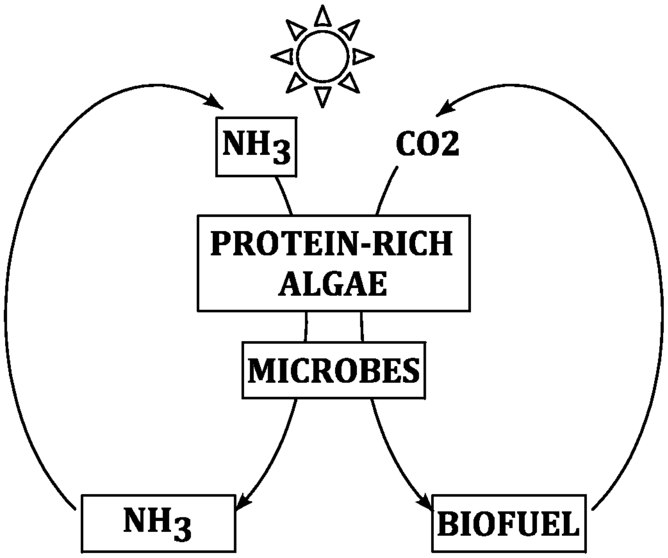

Between the two major schemes of biofuel production (FIGS. 1A and 1B), algae typically grow faster (doubling time of less than 24 hrs) than plants and do not compete with food production. However, algal biomass contains a large amount of proteins (FIG. 5), which require a large net nitrogen input. In addition, fast growing species contain higher amounts of proteins and lower amounts of liquids. Typically, nitrogen limitation is used to promote lipid accumulation at the expense of growth rate. Thus, the lipid-producing species must either be cultured in a closed bioreactor or face the possibility of being taken over by protein-rich natural species. This situation creates a paradox: either to employ costly closed culture systems or to utilize species with lower lipid content. To solve this problem, the use of native, fast-growing algal species in open ponds while recycling nitrogen is ideal, because these species are acclimated to local salinity, temperature, and pH. Since the fast growing species typically contain high protein and low lipid, the utilization of protein-rich biomass for fuel production and recycling fixed nitrogen can greatly reduce both the energy cost for ammonia synthesis and indirect GHG emissions (FIG. 1D), while enjoying the low-cost open culture systems.

Unlike celluloses, which form a recalcitrant composite with lignin, single-cell proteins can be readily hydrolyzed to short peptides and amino acids by proteases, which have already been used industrially for various applications. Peptide bond dissociation energy (308 KJ/mol) is lower than the β-glycosidic bond in cellulose (360 KJ/mol) and is easier to break. In addition, protein hydrolysis does not need to be complete, as short peptides can be utilized by microorganisms. Proteases ($K_{cat}$ on the order of 100-1000 $s^{-1}$ are more effective enzymes than cellulases ($K_{cat}$ is on the order of 0.1-10 $s^{-1}$ even for soluble substrate after pretreatment) and many microorganisms can secrete proteases naturally, providing a possibility for eventual consolidated bioprocessing in one step. As described more fully below, the present disclosure demonstrates that substrates comprising microbial protein biomass can be readily hydrolyzed by a simple process of pretreatment and enzymatic hydrolysis. As an example pretreatment can consist of 10 minutes of boiling in water. Enzymatic hydrolysis can be accomplished by minimum loading of protease at 37° C. for 4 hours. This protein biomass hydrolysis process does not require any high pressure, high temperature, chemical loading, longer pretreatment, or longer enzymatic hydrolysis times, which are common in the cellulose hydrolysis processes.

To convert peptides and amino acids as a substrate to biofuel while recycling nitrogen, the amino group can be cleaved from amino acids to form ammonium through deamination reactions catalyzed by enzymes such as deaminases, aminotransferases or dehydrogenases. Many of the products of these reactions are 2-Keto acids, which can be converted to various chemical products. Other amino acids are degraded to TCA cycle intermediates, which can be directed to pyruvate via gluconeogenic enzymes, such as, for example, malic enzymes or phosphoenolpyruvate carboxykinase, and then to longer keto acids via acetohydroxy acid synthase or isopropylmalate synthease chain elongation pathways.

Figure 1E:
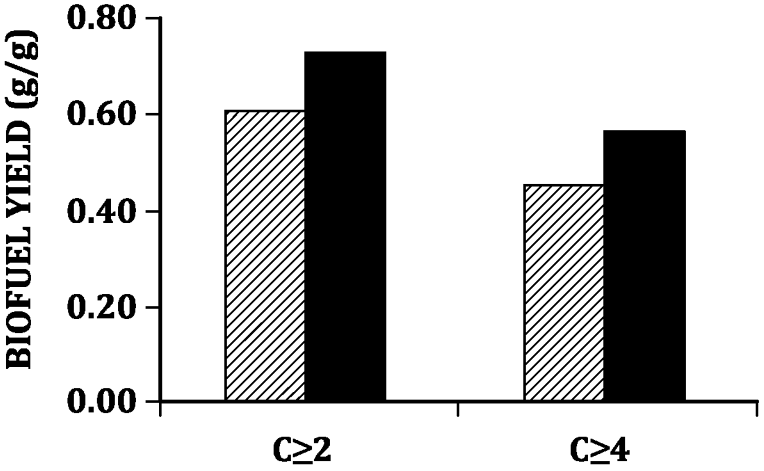

All amino acids can be degraded completely by pathways assembled from various organisms, and the maximal theoretical yields of individual amino acids to alcohols (C2 to C5) are between 35-84% (Table 1A). The yield is even higher if proteins, rather than the hydrolysis products, are used as the basis of calculation or if the amino group is excluded in the calculation of the net yield (Table 1B and C). By using a typical algal amino acid composition (FIG. 5), the maximum theoretical yield of combined alcohols from algal protein was calculated to be 60% (FIG. 1E; Table 2A and B) or 73% (net yield, excluding nitrogen in calculation), which is higher than that of ethanol from sugar (50%).

Unfortunately, peptides or amino acids are poor fermentative substrates, since microbes prefer to use amino acids for growth rather than product formation. Amino acids provide both carbon and nitrogen for microbes. As such, various regulatory systems are in place to ensure optimal consumption of nutrients for the benefit of the cell or the microbial community. The native pathways for converting amino acids to higher alcohols support only minor product formation. The inefficiency is largely due to the unfavorable thermodynamic gradient which drives the transamination reactions towards the amino acid biosynthesis direction. Therefore, the amino acid metabolism networks in bacteria need to be engineered.

TABLE 1A

Theoretical maximum yield for individual biofuel )gram alcohol per gram amino acid) from individual amino acids. Gross yield from free amino acid.

| | Ethanol | Propanol | Butanol | isoButanol | 2 MB | 3 MB |
|---|---|---|---|---|---|---|
| Ala | 0.52 | 0.67 | 0.42 | 0.42 | 0.49 | 0.33 |
| Arg | 0.26 | 0.35 | 0.21 | 0.21 | 0.25 | 0.17 |
| Asn | 0.35 | 0.45 | 0.28 | 0.28 | 0.33 | 0.22 |
| Asp | 0.35 | 0.45 | 0.28 | 0.28 | 0.33 | 0.22 |
| Cys | 0.38 | 0.50 | 0.31 | 0.31 | 0.36 | 0.24 |
| Gln | 0.31 | 0.41 | 0.25 | 0.25 | 0.30 | 0.20 |
| Glu | 0.32 | 0.41 | 0.25 | 0.25 | 0.30 | 0.20 |
| Gly | 0.61 | 0.53 | 0.49 | 0.49 | 0.47 | 0.39 |
| His | 0.30 | 0.39 | 0.24 | 0.24 | 0.28 | 0.19 |
| Ile | 0.00 | 0.00 | 0.00 | 0.00 | 0.67 | 0.00 |
| Leu | 0.00 | 0.00 | 0.00 | 0.00 | 0.00 | 0.67 |
| Lys | 0.63 | 0.00 | 0.00 | 0.00 | 0.00 | 0.00 |
| Met | 0.00 | 0.40 | 0.00 | 0.00 | 0.00 | 0.00 |
| Phe | 0.84 | 0.36 | 0.45 | 0.22 | 0.27 | 0.27 |
| Pro | 0.40 | 0.52 | 0.32 | 0.32 | 0.38 | 0.26 |
| Ser | 0.44 | 0.57 | 0.35 | 0.35 | 0.42 | 0.28 |
| Thr | 0.00 | 0.50 | 0.00 | 0.00 | 0.00 | 0.00 |
| Trp | 0.68 | 0.59 | 0.54 | 0.36 | 0.43 | 0.43 |
| Tyr | 0.76 | 0.33 | 0.41 | 0.20 | 0.24 | 0.24 |
| Val | 0.00 | 0.00 | 0.00 | 0.63 | 0.00 | 0.00 |

TABLE 1B

Theoretical maximum yield for individual biofuel )gram alcohol per gram amino acid) from individual amino acids. Gross yield form free amino acid. One molecule of peptidyl amino acid gains one molecule of water to form free amino acid during hydrolysis.

| | Ethanol | Propanol | Butanol | isoButanol | 2 MB | 3 MB |
|---|---|---|---|---|---|---|
| Ala | 0.65 | 0.85 | 0.52 | 0.52 | 0.62 | 0.41 |
| Arg | 0.29 | 0.38 | 0.24 | 0.24 | 0.28 | 0.19 |
| Asn | 0.40 | 0.53 | 0.32 | 0.32 | 0.39 | 0.26 |
| Asp | 0.40 | 0.52 | 0.32 | 0.32 | 0.38 | 0.26 |
| Cys | 0.45 | 0.58 | 0.36 | 0.36 | 0.43 | 0.28 |
| Gln | 0.36 | 0.47 | 0.29 | 0.29 | 0.34 | 0.23 |
| Glu | 0.36 | 0.47 | 0.29 | 0.29 | 0.34 | 0.23 |
| Gly | 0.81 | 0.70 | 0.65 | 0.65 | 0.62 | 0.52 |
| His | 0.34 | 0.44 | 0.27 | 0.27 | 0.32 | 0.21 |
| Ile | 0.00 | 0.00 | 0.00 | 0.00 | 0.78 | 0.00 |
| Leu | 0.00 | 0.00 | 0.00 | 0.00 | 0.00 | 0.78 |
| Lys | 0.72 | 0.00 | 0.00 | 0.00 | 0.00 | 0.00 |
| Met | 0.00 | 0.46 | 0.00 | 0.00 | 0.00 | 0.00 |
| Phe | 0.94 | 0.41 | 0.50 | 0.25 | 0.30 | 0.30 |
| Pro | 0.47 | 0.62 | 0.38 | 0.38 | 0.45 | 0.30 |
| Ser | 0.53 | 0.69 | 0.43 | 0.43 | 0.51 | 0.34 |
| Thr | 0.00 | 0.59 | 0.00 | 0.00 | 0.00 | 0.00 |
| Trp | 0.74 | 0.65 | 0.60 | 0.40 | 0.47 | 0.47 |
| Tyr | 0.85 | 0.37 | 0.45 | 0.23 | 0.27 | 0.27 |
| Val | 0.00 | 0.00 | 0.00 | 0.75 | 0.00 | 0.00 |

TABLE 1C

Theoretical maximum yield for individual biofuel )gram alcohol per gram amino acid) from individual amino acids. Net yield from peptidyl amino acid. In calculating the net yield, the molecular weight of an ammonia molecule is deducted from each peptidyl amino acid since ammonia is to be recycled.

| | Ethanol | Propanol | Butanol | isoButanol | 2 MB | 3 MB |
|---|---|---|---|---|---|---|
| Ala | 0.84 | 1.09 | 0.67 | 0.67 | 0.80 | 0.53 |
| Arg | 0.42 | 0.55 | 0.34 | 0.34 | 0.40 | 0.27 |
| Asn | 0.56 | 0.73 | 0.45 | 0.45 | 0.54 | 0.36 |
| Asp | 0.46 | 0.61 | 0.37 | 0.37 | 0.44 | 0.30 |
| Cys | 0.53 | 0.69 | 0.43 | 0.43 | 0.51 | 0.34 |
| Gln | 0.41 | 0.53 | 0.33 | 0.33 | 0.39 | 0.26 |
| Glu | 0.48 | 0.63 | 0.39 | 0.39 | 0.46 | 0.31 |
| Gly | 1.12 | 0.98 | 0.90 | 0.90 | 0.86 | 0.72 |
| His | 0.50 | 0.65 | 0.40 | 0.40 | 0.48 | 0.32 |
| Ile | 0.00 | 0.00 | 0.00 | 0.00 | 0.91 | 0.00 |

TABLE 1C-continued

Theoretical maximum yield for individual biofuel )gram alcohol per gram amino acid) from individual amino acids. Net yield from peptidyl amino acid. In calculating the net yield, the molecular weight of an ammonia molecule is deducted from each peptidyl amino acid since ammonia is to be recycled.

| | Ethanol | Propanol | Butanol | isoButanol | 2 MB | 3 MB |
|---|---|---|---|---|---|---|
| Leu | 0.00 | 0.00 | 0.00 | 0.00 | 0.00 | 0.91 |
| Lys | 0.96 | 0.00 | 0.00 | 0.00 | 0.00 | 0.00 |
| Met | 0.00 | 0.52 | 0.00 | 0.00 | 0.00 | 0.00 |
| Phe | 1.05 | 0.46 | 0.56 | 0.28 | 0.34 | 0.34 |
| Pro | 0.56 | 0.73 | 0.45 | 0.45 | 0.54 | 0.36 |
| Ser | 0.65 | 0.85 | 0.52 | 0.52 | 0.62 | 0.41 |
| Thr | 0.00 | 0.71 | 0.00 | 0.00 | 0.00 | 0.00 |
| Trp | 0.89 | 0.77 | 0.72 | 0.48 | 0.57 | 0.57 |
| Tyr | 0.94 | 0.41 | 0.50 | 0.25 | 0.30 | 0.30 |
| Val | 0.00 | 0.00 | 0.00 | 0.89 | 0.00 | 0.00 |

TABLE 2A

Theoretical optimal product distribution from a typical microorganism mass. The amino acid profile of *Chorella vulgaris* was used as the input mass flux to calculate the mass production of individual products when macimum alcohol production is achieved.

| Substrate | Mass Input | | Product | Mass Produced |
|---|---|---|---|---|
| Ala | 12.255 | | Ethanol | 0.000 |
| Arg | 9.668 | | Propanol | 0.000 |
| Asp | 11.438 | | 1-Butanol | 7.108 |
| Cys | 0.817 | | Iso-Butanol | 19.835 |
| Glu | 14.570 | ⇒ | 2-methyl-1-butanol | 3.296 |
| Gln | 0.000 | | 3-methyl-1-butanol | 18.826 |
| Gly | 9.668 | | Ammonia | 21.417 |
| His | 2.860 | | Carbon Dioxide | 81.947 |
| Ile | 4.902 | | Methanethiol | 1.143 |

TABLE 2A-continued

Theoretical optimal product distribution from a typical microorganism mass. The amino acid profile of *Chorella vulgaris* was used as the input mass flux to calculate the mass production of individual products when macimum alcohol production is achieved.

| Substrate | Mass Input | Product | Mass Produced |
|---|---|---|---|
| Leu | 9.941 | $H_2S$ | 0.083 |
| Lys | 7.626 | | |
| met | 2.043 | | |
| Phe | 6.536 | | |
| Pro | 5.311 | | |
| Ser | 5.175 | | |
| Thr | 6.945 | | |
| Trp | 0.409 | | |
| Tyr | 4.357 | | |
| Val | 8.170 | | |
| Asn | 0.000 | | |
| Oxygen | 7.770 | | |

TABLE 2B

Theoretical biofuel mass yields from different protein sources. In the right most column, the 14 aa indicates the amino acids which could be converted to biofuel engineered *E. coli*.

| | Biofuels Optimized | *Chlorella Vulgaris* (g/g) | *Dunalliela Bardawil* (g/g) | *Scenedesmus Obliquus* (g/g) | *Arthrospira Maxima* (g/g) | YE, Bacto (g/g) | YE, Bacto 14AA (g/g) |
|---|---|---|---|---|---|---|---|
| Gross Yield | C ≥ 2 | 0.60 | 0.60 | 0.60 | 0.60 | 0.51 | 0.48 |
| | C ≥ 4 | 0.46 | 0.47 | 0.47 | 0.48 | 0.40 | 0.42 |
| Net Yield | C ≥ 2 | 0.73 | 0.72 | 0.73 | 0.73 | 0.60 | 0.59 |
| | C ≥ 4 | 0.56 | 0.57 | 0.57 | 0.58 | 0.47 | 0.52 |

The disclosure provides a chemical production system that utilizes recombinant microorganism of the disclosure as one part of an overall chemical production system. For example, the disclosure provides a biofuel production system as set forth in FIG. 4, wherein algae is produced in an open pond under sunlight to produce a biomass. The lipid content of the biomass is utilized for the production of biodiesel, while the nitrogen-rich biomass is hydrolyzed as a substrate for the recombinant microorganisms of the disclosure. The hydrolyzed nitrogen-rich biomass is then fed into a reactor system comprising a recombinant microorganism of the disclosure. The recombinant microorganisms metabolize the nitrogen-rich biomass to produce various chemicals (depending upon the specific recombinant pathway, for example, an enzymatic pathway for the production of alcohols, such as higher alcohols, adipic acid, and the like). The ammonium, $CO_2$ and byproducts are then fed back to the algae growing in an open pond to support the algae growth. Residual proteins (e.g., residual N-rich biomass) can then be fed into a second bioreactor system for further recycling of various metabolites. The schematic of the nitrogen and carbon neutral biofuel process of FIG. 4 utilizes as the energy source sunlight and the carbon source is $CO_2$. The nitrogen and sulfur sources are the ammonia and sulfate recycled from the process. Natural selection under frequent or continuous harvesting conditions will generally favor fast growing and robust organisms. After harvest, the biomass produced will first be processed to obtain lipid for traditional biodiesel production. The protein portion will be hydrolyzed and fed to the first-stage converter to produce higher alcohols. The residual amino acids from the first stage will then be fed to the second stage to produce additional biomass to be recycled back to the hydrolysis unit. $CO_2$ produced in the two-stage conversion can be fed back to the algal culture to enrich $CO_2$ obtained from the atmosphere.

In one embodiment of the system, the algae are algae that are protein rich or any other protein-rich photoautotrophic microorganisms.

A benefit of this design is that it utilizes fast-growing algal species and N-rich growth conditions, which promote growth with high protein and low lipid accumulation (FIG. 4B). Theoretical derivations also show that high protein yield species have higher growth rates. Indeed, the high protein species have biomass productivity about 10 times higher than the high lipid species (FIG. 4B) primarily because protein replicates exponentially, while lipid increases linearly. Using the correlation between algal biomass productivity and lipid content and the theOretical fuel yields of both lipid and protein conversions, the overall productivity of biofuel can be computed (FIG. 4C). If only the lipid portion of algal biomass were utilized, the overall productivity increased as lipid content increased from 0 to 20%, but leveled off when lipid content increased beyond 20% (FIG. 4C, dashed line). This result is consistent when one considers that increasing lipid content of algal species does not actually increase overall fuel productivity. If both lipid and protein portions of algal biomass are used, then the overall productivity actually decreased as lipid content increased, indicating that the protein process is more efficient than the lipid process in terms of overall productivity.

The disclosure provides metabolically engineered, or recombinant, microorganisms comprising biochemical pathways for the production of various chemical compounds from a suitable substrate, such as a substrate comprising single amino acid residues, mixtures of amino acid residues, as well as N-rich biomass. A metabolically engineered microorganism of the disclosure comprises one or more recombinant polynucleotides within the genome of the organism or external to the genome within the organism. The microorganism comprises a polynucleotide sequence that encodes a dehydrogenase, a deaminase, and/or a transaminase.

The microorganism can further be characterized by having a reduced ammonia re-uptake activity, a reduced or disrupted quorum sensing system, such as a reduced or disrupted re-uptake of autoinducer-2 (AI-2), a reduced global regulator activity when compared with the wild-type organism. This reduction can be accomplished by reducing disrupting or blocking the expression of a gene associated with ammonia re-uptake, quorum sensing, for example, autoinducer-2 reuptake, and/or a global regulator activity. As such, the microorganism can comprise a reduction, disruption or knockout of a gene selected from the group consisting of glnA, gdhA, lsrA, luxS, CRP, LRP, Fis, and/or IHF, or any combination thereof found in the wild-type organism and can also include the introduction of a heterologous polynucleotide.

In one embodiment, the disclosure provides a recombinant microorganism comprising elevated expression of at least one target enzyme as compared to a parental microorganism or encodes an enzyme not found in the parental organism. The microorganism can comprise a reduction, disruption or knockout of at least one gene encoding a polypeptide involved in ammonia re-uptake, autoinducer-2 (AI-2) reuptake, a global regulator, glutamate dehydrogenase, glutamine synthase, and/or glutamate synthase, the gene being selected from the group consisting of glnA, gdhA, lsrA, luxS, CRP, Lrp, Fis, IHF, or any combination thereof.

The recombinant microorganisms of the embodiments above produce an increased keto-acid flux and thereby produce at least one metabolite involved in a biosynthetic pathway for the production of increased levels of a chemical compound when compared with the wild-type microorganism. The chemical compound can be, for example, but is not limited to, an alcohol, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, S-adenosyl-methionine (SAM), and the like. The alcohol can be a higher alcohol including, for example, isobutanol, 1-butanol, 1-propanol, 2-methyl-1-butanol, 3-methyl-1-butanol and 2-phenylethanol from a suitable substrate. In general, the recombinant microorganisms comprises at least one recombinant metabolic pathway that comprises a target enzyme and optionally can further include a reduction in activity or expression of an enzyme selected from the group consisting of glnA, gdhA, lsrA, luxS, CRP, LRP, Fis, and/or IHF, or any combination thereof. The pathways act to modify a substrate or metabolic intermediate in the production of a chemical composition as provided above. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure.

As used herein, the term "metabolically engineered" or "metabolic engineering" involves rational pathway design and assembly of biosynthetic genes, genes associated with operons, and control elements of such polynucleotides, for the production of an increased flux in a desired metabolite, such as a 2-keto acid. Additional pathways can be designed and biosynthetic genes, genes associated with operons, and control elements of such polynucleotides assembled for the increased production or de novo production of various chemical compounds including, for example, an alcohol, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, S-adenosyl-methionine (SAM) and the like, in a microorganism. "Metabolically engineered" can further include optimization of metabolic flux by regulation and optimization of transcription, translation, protein stability and protein functionality using genetic engineering and appropriate culture conditions including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one aspect, where the polynucleotide is xenogenetic to the host organism, the polynucleotide can be codon optimized.

The term "biosynthetic pathway," also referred to as "metabolic pathway," refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The leuABCD operon, for example, includes leuA, leuB, leuC and leuD genes. Among them, leuA encodes α-isopropylmalate synthase, leuB encodes β-isopropylmalate dehydrogenase, leuC and leuD encodes α-isopropylmalate isomerase. Of these enzymes, α-isopropylmalate synthase catalyzes the synthetic reaction from α-ketoisovalerate to α-isopropylmalate, α-isopropylmalate isomerase catalyzes the isomerization reaction from α-isopropylmalate to β-isopropylmalate and β-isopropylmalate dehydrogenase catalyzes the dehydrogenation reaction from β-isopropylmalate to α-ketoisocaproic acid which is the final intermediate of L-leucine biosynthesis. *Escherichia* possess four kinds of transaminases, namely, transaminase A (aspartate-glutamate aminotransferase) encoded by aspC gene, transaminase B (BCAA aminotransferase) encoded by ilvE gene which is included in ilvGMEDA operon, transaminase C (alanine-valine aminotransferase) encoded by avtA gene and transaminase D (tyrosine aminotransferase) encoded by tyrB gene. These enzymes participate in various amination reactions. Of these enzymes, transaminase B and transaminase D catalyze the above-mentioned amination reaction from α-ketoisocaproic acid to L-leucine and vice versa. Transaminase C and transaminase D catalyze the final step of L-valine biosynthetic pathway, which includes a common pathway among the L-valine biosynthesis and L-leucine biosynthesis.

Also, the expression of leuABCD operon is repressed by L-leucine. Expression of ilvBN gene encoding acetohydroxy acid synthase I suffers concerted repression by L-valine and L-leucine, expression of ilvGM gene encoding acetohydroxy acid synthase II suffers concerted repression by L-isoleucine, L-valine and L-leucine, and expression of ilvIH gene encoding acetohydroxy acid synthase III suffers repression by L-leucine.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar or $CO_2$, but also intermediate and end product metabolites used in a pathway associated with a metabolically engineered microorganism as described herein. A "biomass derived sugar" includes, but is not limited to, molecules such as glucose, sucrose, mannose, xylose, and arabinose. The term "biomass derived sugar" encompasses suitable carbon substrates ordinarily used by microorganisms, such as 6 carbon sugars, including but not limited to glucose, lactose, sorbose, fructose, idose, galactose and mannose, all in either D or L form, or a combination of 6 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

A nitrogen-rich biomass refers to a biomass that is rich in, for example, proteins, peptides, amino acids, mixtures of amino acids, nucleic acid or other molecules that can be hydrolyzed and which incorporate nitrogen. Such nitrogen-rich biomass includes large proteins as well as smaller peptides (e.g., di-, tri- or longer peptides), amino acids and mixtures of amino acids.

The term "alcohol" includes, for example, 1-propanol, isobutanol, 1-butanol, 2-methyl 1-butanol, 3-methyl 1-butanol or 2-phenylethanol.

Recombinant microorganisms provided herein can express a plurality of target enzymes involved in pathways for the production of, for example, alcohols, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, S-adenosyl-methionine (SAM), and the like, from using a suitable carbon substrate and/or nitrogen source. In specific embodiments, the recombinant microorganism comprises a knockout in a gene or homolog selected from the group consisting of glnA, gdhA, lsrA, luxS or any combination thereof. Such knockout shifts the metabolic flux of the microorganism from amino acid accumulation to the production of greater amounts of keto acids, an increased keto acid flux, and then to the production of a desired chemical compound as set forth above.

Accordingly, metabolically "engineered", "modified", or "recombinant" microorganisms are produced via the introduction of genetic material into a host or parental microorganism of choice, thereby modifying or altering the cellular physiology and biochemistry of the microorganism. Through the introduction of genetic material, the parental microorganism acquires new properties, e.g., the ability to produce a new, or greater quantities of, an intracellular metabolite. In an illustrative embodiment, the introduction of genetic material into a parental microorganism results in a new or modified ability to produce a desired chemical compound through metabolism or nitrogen rich biomass to a 2-keto acid and ultimately to, for example, an alcohol, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, S-adenosyl-methionine (SAM), and the like. The genetic material introduced into the parental microorganism contains gene(s), or parts of genes, coding for one or more of the enzymes involved in a biosynthetic pathway for the production of, for example any of the above chemical compounds and may also include additional elements for the expression and/or regulation of expression of these genes, e.g., promoter sequences.

As described above, the engineered or modified microorganism includes, in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an iotracellular metabolite, improve the flux of a metabolite, such as a keto acid, down a desired pathway, and/or reduce the production of undesirable byproducts).

For example, the disclosure demonstrates that with overexpression or the heterologous expression of heterologous kivd, yqhD, or other alcohol dehydrogenase and ilvA, leuA, leuB, leuC, leuD (or a Leu operon, e.g., leuABCD), ansB, aspC, rocG, putA, ybaS, ilvA, glyA, sdaA, tnaA, alsS, ilvCD, ilvE, the production of higher alcohols can be obtained from a N-comprising, or proteinacious biomass. The generation of 2-keto acids from a proteinacious material can also lead to the production of other chemical entities of interest, such as, for example, an alcohol, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, or S-adenosyl-methionine (SAM), from a 2-keto acid. Certain embodiments can comprise the expression or overexpression of any one or more of the above gene accompanied by a reduction or knockout of ammonia re-uptake, quorum sensing gene activity, such as autoinducer 2 (AI-2) reuptake, and/or a global regulator gene, and the like. In specific embodiments, the expression or overexpression of any one or more of the above genes can also be accompanied by a knockout or reduction in expression of genes or homologues selected from the group consisting of glnA, gdhA, lsrA, luxS, CRP, LRP, Fis, and/or IHF, or any combination thereof. The production of such an alcohol, acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium; glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, S-adenosyl-methionine (SAM), and the like involves various 2-keto acid intermediates.

The disclosure also demonstrates that the expression of one or more heterologous polynucleotides or overexpression of one or more endogenous polynucleotides encoding a polypeptide below is useful in generating a metabolic pathway for the production of any number of other desired chemical compounds. For Example, in a glutamic acid pathway, glutamic acid is converted to 2-KG (2-keto glutarate) by a polypeptide having glutamate dehydrogenase (gdh) activity. By consecutive reactions of polypeptides having homocitrate synthase (hcs) activity and homoacornitase (hacAB) activity, 2-KG is converted to homoisocitrate, which is reductive decarboxylated to alpha-keto adipic acid by a polypeptide having homoisocitrate dehydrogenase (hicDH) activity. Polynucleotides encoding the polypeptides of the disclosure may be derived from any number of microorganisms including *S. cerevisiae, T. thermophilus* and others known in the art. The polynucleotides may be mutant or variant enzymes that have been derived from a source organism and then modified or engineered to have improved expression and/or activity. In one embodiment, the polynucleotides encoding the enzymes involved in the glutamic acid pathway are cloned from various organisms including *S. cerevisiae*, and *T. thermophilus.*

In a lysine pathway of the disclosure, lysine is deaminated to 2-aminoadipate-6-semialdehyde by a polypeptide having lysine aminotransferase (lat) activity. Then, a polypeptide having piperideine 6-carboxylate dehydrogenase (pcd) activity catalyzes the formation of alpha-amino adipic acid. The amine group is then deaminated by a polypeptide having 2-aminoadipate aminotransferase (aadat) activity. Polynucleotides encoding the polypeptides of the disclosure may be derived from any number of microorganisms including *F. lutescens, S. clavuligerus, H. sapiens*, and others known in the art. The polynucleotides may be mutant or variant enzymes that have been derived from a source organism and then modified or engineered to have improved expression and/or activity. In one embodiment, the polynucleotides encoding the enzymes can be cloned from various organisms including *Flavobacterium lutescens, Streptomyces clavuligerus, Homo sapiens*, and others known in the art.

Figure 3:
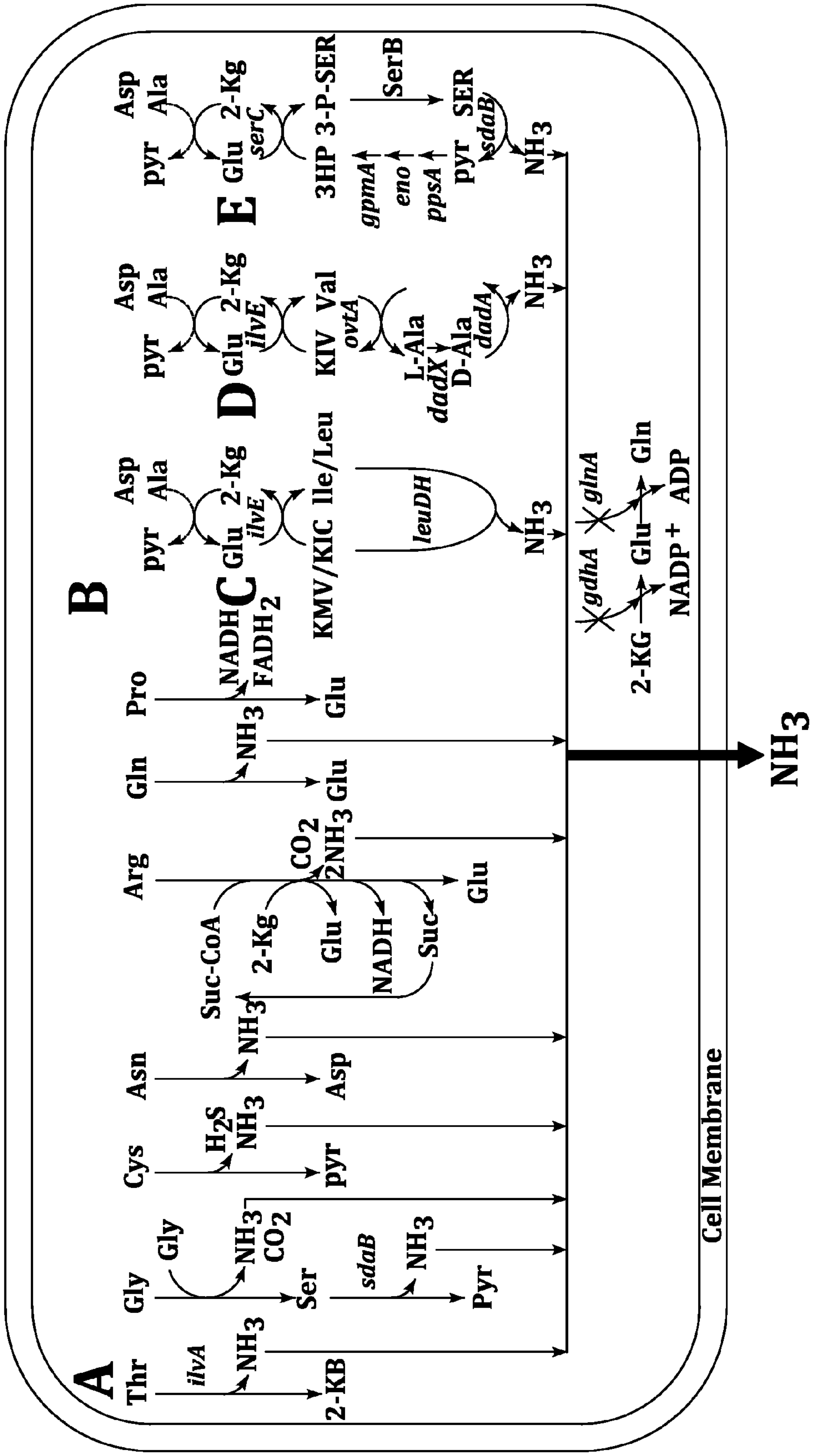
FIG. 3A-E depicts an overall design for the nitrogen-centric metabolic engineering strategy. The release of ammonia is used to drive the amino acid degradation reactions to produce 2-keto acids. The gdhA and glnA genes are deleted to block the ammonia re-uptake. The overexpressed genes are indicated in black. (A) Amino acids degraded through direct deamination and production of $NH_3$. (B) Amino acids degraded through transamination and production of glutamate. (C-E) Designed transamination and deamination cycles via IlvE and LeuDH (C), IlvE, AvtA, DadX and DadA (D), and SerC, SerB, SdaB, PpsA, Eno and GpmA (E).

For the production of, for example, adipic acid from the intermediate, alpha-keto adipic acid, two biological routes (a CoA-independent pathway and a CoA-dependent pathway) were engineered along with one chemical route as shown in FIG. 3. For the biological conversion, alpha-keto adipic acid is converted to alpha-hydroxy adipic acid by various polypeptides having dehydrogenase activity, including polypeptides with leucine dehydrogenase (ldhA) activity, polypeptides with malate dehydrogenase (mdh) activity and polypeptides with hydroxyisocaproate dehydrogenase (hdh) activity from various microorganisms. In the CoA-independent pathway, a mimic pathway for the natural reductive TCA cycle was engineered, which converts oxaloacetate to succinate via malate and fumarate under anaerobic condition. Mutagenesis of a fumarate reductase gene (for example fumA or fumB) can provide polypeptides that promote the dehydration of alpha-hydroxy adipic acid. A further step can be constructed by the mutant of crotonate dehydrogenase from *Clostridium acetobutyricum*. In CoA-dependent pathway, the pathway for isocaproate production in *Clostridium difficille* can be used to derive a polypeptide that converts alphahydroxy adipic acid to adipic acid. The first step is catalyzed by a polypeptide having CoA transferase (hadA) activity to make R-2-hydroxyisocaproyl-CoA. Then, dehydration of R-2-hydroxyisocaproyl-CoA by a dehydratase-activator complex (e.g., hadBC-hadI) makes 2-Isocaprenoyl-CoA, which is reduced to Isocaproyl CoA by a polypeptide having acyl CoA dehydrogenase (acdB-etfBA) activity. Finally, CoA moiety is removed by the CoA transferase (hadA) to produce adipic acid. Chemical reduction of alpha-keto adipic acid to adipic acid is also possible using various metal catalysts including platinum. In yet another embodiment, the microorganism comprises an endogenous glutamate production pathway. For example, useful organisms having glutamate production pathways include those bacterial or yeast species from genera such as *Brevibacterium, Arthrobacter, Microbacterium, Corynebacterium*, and the like.

Polypeptides having glutamate dehydrogenase (gdh) are known in the art or can be recombinantly produced including non-naturally occurring polypeptide that have increased or improved activity. Exemplary polypeptides having glutamate dehydrogenase activity can have 80%-99% identity to an amino acid sequence as set forth in SEQ ID NO:2 (the corresponding nucleotide sequence is set forth as SEQ ID NO:1). For example, a glutamate dehydrogenase can comprise SEQ ID NO:2 from *S. cerevisiae* or *Candida famata* var. having a sequence set forth in GenBank accession no. CAQ53143 (which is incorporated herein by reference). Other suitable glutamate dehydrogenases useful in the methods and composition of the disclosure can be easily identified by using, for example, the BLAST algorithm.

Polypeptides having homocitrate synthase are known in the art or can be recombinantly produced including non-naturally occurring polypeptides that have increased or improved activity. Exemplary polypeptides having homocitrate synthase activity can have 80%-99% identity to a sequence as set forth in SEQ ID NO:4 (the corresponding nucleotide sequence is set forth as SEQ ID NO:3). For example, a homocitrate synthase can comprise SEQ ID NO:4 from *S. cerevisiae* or *T. thermophilus* having a sequence set forth in GenBank accession no. BAA33785 (which is incorporated herein by references). Other suitable homocitrate synthases useful in the methods and composition of the disclosure can be easily identified by using, for example, the BLAST algorithm.

Polypeptides having homoaconitase activity are known in the art or can be recombinantly produced including non-naturally occurring a polypeptide having increased or improved activity. Exemplary polypeptides having homoaconitase activity can have 80%-99% identity to a sequence as set forth in SEQ ID NO:6 (the corresponding nucleotide sequence is set forth as SEQ ID NO:5). For example, a homoaconitase can comprise SEQ ID NO:6 from *S. cerevisiae* or *Ajellomyces dermatitidis* having a sequence set forth in GenBank accession no. XP_002620204 (which is incorporated herein by reference). Other suitable homocitrate synthases useful in the methods and composition of the disclosure can be easily identified by using, for example, the BLAST algorithm.

Polypeptides having homoisocitrate dehydrogenase activity are known in the art or can be recombinantly produced including non-naturally occurring polypeptides that have increased or improved activity. Exemplary polypeptides having homoisocitrate dehydrogenase activity can have 80%-99% identity to a sequence as set forth in SEQ ID NO:8 (the corresponding nucleotide sequence is set forth as SEQ ID NO:7). For example, a homoisocitrate dehydrogenase polypeptide can comprise SEQ ID NO:8 from *T. thermophilus*. Other suitable homocitrate synthases useful in the methods and composition of the disclosure can be easily identified by using, for example, the BLAST algorithm.

Polypeptides having lysine aminotransferase activity are known in the art or can be recombinantly produced including non-naturally occurring polypeptides that have increased or improved activity. Exemplary polypeptides having lysine aminotransferase activity can have 80%-99% identity to a sequence as set forth in SEQ ID NO:10 (the corresponding nucleotide sequence is set forth as SEQ ID NO:9). For example, a lysine aminotransferase polypeptide can comprise SEQ ID NO:10 from *Streptomyces clavuligerus*. Other suitable lysine aminotransferases useful in the methods and compositions of the disclosure can be easily identified by using, for example, the BLAST algorithm.

Polypeptides having piperideine 6-carboxylate dehydrogenase (pcd) activity are known in the art or can be recombinantly produced including non-naturally occurring polypeptides that have increased or improved activity. Exemplary polypeptides having piperideine 6-carboxylate dehydrogenase (pcd) activity can have 80%-99% identity to a sequence as set forth in SEQ ID NO:12 (the corresponding nucleotide sequence is set forth as SEQ ID NO:11). For example, a piperideine 6-carboxylate dehydrogenase (pcd) polypeptide can comprise SEQ ID NO:12 from *Flavobacterium lutescens*. Other suitable piperideine 6-carboxylate dehydrogenase (pcd) useful in the methods and composition of the disclosure can be easily identified by using, for example, the BLAST algorithm.

Polypeptides having 2-aminoadipate aminotransferase (aadat) activity are known in the art or can be recombinantly produced including non-naturally occurring polypeptides that have increased or improved activity. Exemplary polypeptides having 2-aminoadipate aminotransferase (aadat) activity can have 80%-99% identity to a sequence as set forth in SEQ ID NO:14 (the corresponding nucleotide sequence is set forth as SEQ ID NO:13). For example, a 2-aminoadipate aminotransferase (aadat) polypeptide can comprise SEQ ID NO:14 from *Homo sapiens*. Other suitable 2-aminoadipate aminotransferase (aadat) useful in the methods and composition of the disclosure can be easily identified by using, for example, the BLAST algorithm.

Polypeptides having leucine dehydrogenase (ldh) activity are known in the art or can be recombinantly produced including non-naturally occurring polypeptides that have increased or improved activity. Exemplary polypeptides having leucine dehydrogenase activity can have 80%-99% identity to a sequence as set forth in SEQ ID NO:16 (the corresponding nucleotide sequence is set forth as SEQ ID NO:15). For example, a leucine dehydrogenase polypeptide can comprise SEQ ID NO:16 from *Geobacillus stearothermophilus*. Other suitable leucine dehydrogenase enzymes useful in the methods and composition of the disclosure can be easily identified by using, for example, the BLAST algorithm.

Polypeptides having malate dehydrogenase (mdh) activity are known in the art or can be recombinantly produced including non-naturally occurring polypeptides that have increased or improved activity. Exemplary polypeptides having malate dehydrogenase activity can have 80%-99% identity to a sequence as set forth in SEQ ID NO:18 (the corresponding nucleotide sequence is set forth as SEQ ID NO:17). For example, a malate dehydrogenase polypeptide can comprise SEQ ID NO:18 from *E. coli*. Other suitable malate dehydrogenase enzymes useful in the methods and composition of the disclosure can be easily identified by using, for example, the BLAST algorithm.

Polypeptides having hydroxyisocaproate dehydrogenase (hdh) activity are known in the art or can be recombinantly produced including non-naturally occurring polypeptides that have increased or improved activity. Exemplary polypeptides having hydroxyisocaproate dehydrogenase activity can have 80%-99% identity to a sequence as set forth in SEQ ID NO:20 (the corresponding nucleotide sequence is set forth as SEQ ID NO:19). For example, a hydroxyisocaproate dehydrogenase polypeptide can comprise SEQ ID NO:20 from *Aspergillus fumigatus*. Other suitable hydroxyisocaproate dehydrogenase enzymes useful in the methods and composition of the disclosure can be easily identified by using, for example, the BLAST algorithm.

Two membrane-bound, FAD-containing enzymes are responsible for the catalysis of fumarate and succinate interconversion; the fumarate reductase is used in anaerobic growth, and the succinate dehydrogenase is used in aerobic growth. Fumarate reductase comprises multiple subunits (e.g., frdA, frdB, and frdC in *E. coli*). Modification of any one of the subunits can result in the desired activity herein. For example, a knockout of frdB, frdC or frdBC is useful in the methods of the disclosure. Frd homologs and variants are known. For example, homologs and variants include, for example, fumarate reductase subunit D (fumarate reductase 13 kDa hydrophobic protein) gi|67463543|sp|P0A8Q3.1|FRDD_ECOLI(67463543); fumarate reductase subunit C (fumarate reductase 15 kDa hydrophobic protein) gi|1346037|sp|P20923.2|FRDC_PROVU(1346037); fumarate reductase subunit D (fumarate reductase 13 kDa hydrophobic protein) gi|120499|sp|P20924.1|FRDD_PROVU (120499); fumarate reductase subunit C (fumarate reductase 15 kDa hydrophobic protein) gi|67463538|sp|POA8Q0.1|FRDC_ECOLI(67463538); fumarate reductase iron-sulfur subunit (*Escherichia coli*) gi|145264|gb|AAA23438.1|(145264); fumarate reductase flavoprotein subunit (*Escherichia coli*) gi|145263|gb|AAA23437.1|(145263); fumarate reductase flavoprotein subunit gi|37538290|sp|P17412.3|FRDA_WOLSU(37538290); fumarate reductase flavoprotein subunit gi|120489|sp|P00363.3|FRDA_ECOLI(120489); fumarate reductase flavoprotein subunit gi|120490|sp|P20922.1|FRDA_PROVU(120490); fumarate reductase flavoprotein subunit precursor (Flavocytochrome c) (Flavocytochrome c3) (Fcc3) gi|119370087|sp|Q07WU7.2|FRDA_SHEFN(119370087); fumarate reductase iron-sulfur subunit gi|81175308|sp|POAC47.2|FRDB_ECOLI(81175308); fumarate reductase flavoprotein subunit (Flavocytochrome c) (Flavocytochrome c3) (Fcc3) gi|119370088|sp|POC278.1|FRDA_SHEFR(119370088); Frd operon uncharacterized protein C gi|140663|sp|P20927.1|YFRC_PROVU(140663); frd operon probable iron-sulfur subunit A gi|140661|sp|P20925.1|YFRA_PROVU(140661); umarate reductase iron-sulfur subunit gi|120493|sp|P20921.2|FRDB_PROVU(120493); fumarate reductase flavoprotein subunit gi|2494617|sp|006913.2|FRDA_HELPY(2494617); fumarate reductase flavoprotein subunit precursor (Iron(III)-induced flavocytochrome C3) (Ifc3) gi|13878499|sp|Q9Z4P0.1|FRD2_SHEFN(13878499); fumarate reductase flavoprotein subunit gi|54041009|sp|P64174.1|FRDA_MYCTU(54041009); Fumarate reductase flavoprotein subunit gi|54037132|sp|P64175.1|FRDA_MYCBO(54037132); fumarate reductase flavoprotein subunit gi|12230114|sp|Q9ZMP0.1|FRDA_HELPJ(12230114); fumarate reductase flavoprotein subunit gi|1169737|sp|P44894.1|FRDA_HAEIN(1169737); fumarate reductase flavoprotein subunit (*Wolinella succinogenes*) gi|13160058|emb|CAA04214.2|(13160058); fumarate reductase flavoprotein subunit precursor (flavocytochrome c) (FL cyt) gi|25452947|sp|P83223.2|FRDA_SHEON (25452947); fumarate reductase iron-sulfur subunit (*Wolinella succinogenes*) gi|2282000|emb|CAA04215.1| (2282000); and fumarate reductase cytochrome b subunit (*Wolinella succinogenes*) gi|2281998|emb|CAA04213.1| (2281998), each sequence associated with the accession number is incorporated herein by reference in its entirety.

Polypeptides having hydroxyisocaproate CoA-transferase (hadA) activity are known in the art or can be recombinantly produced including non-naturally occurring polypeptides that have increased or improved activity. Exemplary polypeptides having hydroxyisocaproate CoA-transferase activity can have 80%-99% identity to a sequence as set forth in SEQ ID NO:22 (the corresponding nucleotide sequence is set forth as SEQ ID NO:21). For example, a hydroxyisocaproate CoA-transferase polypeptide can comprise SEQ ID NO:22 from *Clostridium difficille*. Other suitable hydroxyisocaproate CoA-transferaes enzymes useful in the methods and composition of the disclosure can be easily identified by using, for example, the BLAST algorithm.

Polypeptides having 2-hydroxyisocaproyl-CoA dehydratase activity are known in the art or can be recombinantly produced including non-naturally occurring polypeptides that have increased or improved activity. Exemplary polypeptides having 2-hydroxyisocaproyl-CoA dehydratase activity can have 80%-99% identity to a sequence as set forth in SEQ ID NO:24 (the corresponding nucleotide sequence is set forth as SEQ ID NO:23) and SEQ ID NO:26 (the corresponding nucleotide sequence is set forth as SEQ ID NO:25). For example, a 2-hydroxyisocaproyl-CoA dehydratase polypeptide can comprise SEQ ID NO:24 or SEQ ID NO:26 from *Clostridium difficille*. Other suitable 2-hydroxyisocaproyl-CoA dehydratase enzymes useful in the methods and composition of the disclosure can be easily identified by using, for example, the BLAST algorithm.

2-hydroxyisocaproyl-CoA activator polypeptides are known in the art or can be recombinantly produced including non-naturally occurring polypeptides that have increased or improved activity. Exemplary polypeptides having 2-hydroxyisocaproyl-CoA dehydratase activating activity can have 80%-99% identity to a sequence as set forth in SEQ ID NO:27 (the corresponding nucleotide sequence is set forth as SEQ ID NO:26). For example, a 2-hydroxyisocaproyl-CoA dehydratase activating polypeptide can comprise SEQ ID NO:27 from *Clostridium difficile*. Other suitable 2-hydroxyisocaproyl-CoA dehydratase activating enzymes useful in the methods and composition of the disclosure can be easily identified by using, for example, the BLAST algorithm.

Polypeptides having acyl-CoA dehydrogenase activity are known in the art or can be recombinantly produced including non-naturally occurring polypeptides that have increased or improved activity. Exemplary polypeptides having acyl-CoA dehydrogenase activity can have 80%-99% identity to a sequence as set forth in SEQ ID NO:29 (the corresponding nucleotide sequence is set forth as SEQ ID NO:28). For example, a acyl-CoA dehydrogenase polypeptide can comprise SEQ ID NO:29 from *Clostridium difficile*. Other suitable acyl-CoA dehydrogenase enzymes useful in the methods and composition of the disclosure can be easily identified by using, for example, the BLAST algorithm.

Microorganisms provided herein are modified to produce metabolites in quantities not available in the parental microorganism. A “metabolite” refers to any substance produced by metabolism or a substance necessary for or taking part in a particular metabolic process. A metabolite can be an organic compound that is a starting material (e.g., glucose, proteins/peptides, amino acids, mixtures of amino acids or pyruvate), an intermediate (e.g., 2-keto acid) in, or an end product (e.g., an alcohol, (such as, 1-propanol, isobutanol, 1-butanol, 2-methyl 1-butanol, 3-methyl 1-butanol or 2-phenylethanol), acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM), of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include proteins, peptides, nitrogen-rich biomaterials, glucose, pyruvate, 1-propanol, isobutanol, 1-butanol, 2-methyl 1-butanol, 3-methyl 1-butanol or 2-phenylethanol, and 2-keto acids. As depicted in FIG. 12, exemplary 2-keto acid intermediates include 2-ketobutyrate, 2-ketoisovalerate, 2-ketovalerate, 2-keto 3-methylvalerate, 2-keto 4-methyl-pentanoate, and phenylpyruvate. The exemplary 2-keto acids shown in FIG. 12 may be used as metabolic intermediates in the production of alcohols, (such as, 1-propanol, isobutanol, 1-butanol, 2-methyl 1-butanol, 3-methyl 1-butanol or 2-phenylethanol), acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM). For example, a recombinant microorganism metabolically engineered to provide elevated expression of 2-isopropylmalate synthase, beta-isopropylmalate dehydrogenase and isopropylmalate isomerase enzymes encoded by, for example, a Leu operon (e.g., LeuABCD) produces 2-ketovalerate from 2-ketobutyrate. The 2-ketovalerate metabolite may be used to produce 1-butanol by additional enzymes produced by the metabolically modified microorganism. Additionally, 1-propanol and 2-methyl 1-butanol can be produced from 2-ketobutyrate and 2-keto-3-methyl-valerate by a recombinant microorganism metabolically engineered to express or overexpress acetohydroxy acid synthase, alpha-ketoacid decarboxylase, and alcohol dehydrogenase enzymes encoded by, for example, ilvIHDC, kdc and adh genes. Further, the metabolite 2-ketoisovalerate can be produced by a recombinant microorganism metabolically, engineered to express or overexpress acetohydroxy acid synthase enzymes encoded by, for example, ilvIHCD genes. This metabolite can then be used in the production of isobutanol or 3-methyl 1-butanol. In addition, the metabolite 2-ketoisovalerate can be produced by a recombinant microorganism metabolically engineered to express or overexpress, in addition to amino acid/protein catabolic enzymes, acetohydroxy acid synthase enzymes encoded by, for example, ilvIHCD genes. This metabolite can then be used in the production of isobutyraldehyde, 3-methyl-1 butyraldehyde, and valine. The metabolites pyruvate and/or phenylpyruvate can be used to produce by a recombinant microorganism metabolically engineered to express or overexpress alpha-ketoacid decarboxylase, and alcohol dehydrogenase enzymes encoded by, for example, kdc and yqhD. Similarly, pyruvate can be used to produce 2-phenylethanol, acetate, acetaldehyde, isobutyraldehyde, n-butyraldehyde, 2,3-butanediol, L-lactic acid, D-lactic acid, aromatics (tryptophan, tyrosine, phenylalanine, shikimic acid), polyhydroxybutyrate (PHB), mevalonate, isoprenoids, and fatty acids.

Accordingly, provided herein are recombinant microorganisms that produce an alcohol, such as for example, isobutanol and in some aspects may include, in addition to enzymes that convert an amino acid or an intermediate to pyruvate or a 2-ketoacid, the elevated expression of target enzymes such as acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), and alcohol dehydrogenase (e.g., ADH2 or YQHD). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, as well as gene or homolog selected from the group consisting of glnA, gdhA, lsrA, luxS, CRP, LRP, Fis, and/or IHF, or any combination thereof to increase the availability of pyruvate or reduce enzymes that compete for a metabolite in a desired biosynthetic pathway or to shift metabolic flux from amino nitrogen accumulation to release. In some aspects the recombinant microorganism may include the elevated expression of acetolactate synthase (e.g., alsS), acteohydroxy acid isomeroreductase (e.g., ilvC), dihydroxy-acid dehydratase (e.g., ilvD), 2-keto acid decarboxylase (e.g., PDC6, ARO10, THI3, kivd, or pdc), and alcohol dehydrogenase (e.g., ADH2, YQHD). With reference to alcohol dehydrogenases, although ethanol dehydrogenase is an alcohol dehydrogenase, the synthesis of ethanol is undesirable as a by-product in the biosynthetic pathways. Accordingly, reference to an increase in alcohol dehydrogenase activity or expression in a microorganism specifically excludes ethanol dehydrogenase activity.

Also provided are recombinant microorganisms that produce, for example, 2-methyl 1-butanol and in some aspects may include, in addition to enzymes that convert amino acid or intermediate to pyruvate or a 2-ketoacid, the elevated expression of target enzymes such as threonine dehydratase (e.g., ilvA or tdcB), acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, and/or pdc, and alcohol dehydrogenase (e.g., ADH2, YQHD). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, as well as gene or homolog selected from the group consisting of glnA, gdhA, lsrA, luxS, CRP, LRP, Fis, and/or IHF or any combination thereof to increase the availability of pyruvate or reduce enzymes that compete for a metabolite in a desired biosynthetic pathway or to shift metabolic flux from nitrogen accumulation to release. With reference to alcohol dehydrogenases, although ethanol dehydrogenase is an alcohol dehydrogenase, the synthesis of ethanol is undesirable as a by-product in the biosynthetic pathways. Accordingly, reference to an increase in alcohol dehydrogenase activity or expression in a microorganism specifically excludes ethanol dehydrogenase activity.

Also provided are recombinant microorganisms that produce, for example, 3-methyl 1-butanol and in some aspects may include, in addition to enzymes that convert amino acid or intermediate to pyruvate or a 2-ketoacid, the elevated expression of target enzymes such as acetolactate synthase (e.g., alsS), acetohydroxy acid synthase (e.g., ilvIH), acetolactate synthase (e.g., ilvMG or ilvNB, such as for example a ilvNB with a nucleotide and amino acid sequence depicted as SEQ ID NO:63 and SEQ ID NO:64, or SEQ ID NO: 65 and SEQ ID NO:66), acetohydroxy acid isomeroreductase (e.g., ilvC), dihydroxy-acid dehydratase (e.g., ilvD), 2-isopropylmalate synthase (leuA), isopropylmalate isomerase (e.g., leuC, D or leuCD operon), beta-isopropylmalate dehydrogenase (e.g., leuB), 2-keto-acid decarboxylase (e.g., kivd, PDC6, or THI3), and alcohol dehydrogenase (e.g., ADH2, YQHD). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, as well as gene or homolog selected from the group consisting of glnA, gdhA, lsrA, luxS, CRP, LRP, Fis, and.or IHF, or any combination thereof to increase the availability of pyruvate or reduce enzymes that compete for a metabolite in a desired biosynthetic pathway or to shift metabolic flux from nitrogen accumulation to release. With reference to alcohol dehydrogenases, although ethanol dehydrogenase is an alcohol dehydrogenase, the synthesis of ethanol is undesirable as a by-product in the biosynthetic pathways. Accordingly, reference to an increase in alcohol dehydrogenase activity or expression in a microorganism specifically excludes ethanol dehydrogenase activity.

Further, provided herein are recombinant microorganisms that produce acetate, acetaldehyde, isobutyraldehyde, n-butyraldehyde, 2,3-butanediol, L-lactic acid, D-lactic acid, aromatics (such as for example, tryptophan, tyrosine, phenylalanine, shikimic acid), PHB (polyhydroxybutyrate), mevalonate, isoprenoids, fatty acids, GABA (4-aminobutyric acid), glutamic acid, succinate, malic acid, spartic acid, lysine, cadeverine, 2-ketoadipic acid, threonine, methionine, SAM (S-adenosyl-methionine), 2-methyl-1-butyraldehyde, isoleucine, homoalanine, isobutyraldehyde, 3-methyl-1-butyraldehyde, valine, 3-methyl-1-butyraldehyde, leucine, 2-methyl-1-butyraldehyde, isoleucine, and in some aspects may include, in addition to enzymes that convert amino acid or an intermediate to pyruvate or a 2-ketoacid, the elevated expression of target enzymes such as acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), and alcohol dehydrogenase (e.g., ADH2 or YQHD). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, as well as deletion or inhibition of expression of a polypeptide involved in ammonia re-uptake, autoinducer-2 (AI-2) re-uptake, and/or global regulation such as for example a gene or homolog selected from the group consisting of ginA, gdhA, lsrA, luxS, CRP, LRP, Fis, and/or IHP, or any combination thereof to increase the availability of pyruvate or reduce enzymes that compete for a metabolite in a desired biosynthetic pathway or to shift metabolic flux from amino nitrogen accumulation to release. In some aspects the recombinant microorganism may include the elevated expression of acetolactate synthase (e.g., alsS), acetohydroxy acid isomeroreductase (e.g., ilvC), dihydroxy-acid dehydratase (e.g., ilvD), 2-keto acid decarboxylase (e.g., PDC6, ARO10, THI3, kivd, or pdc), and alcohol dehydrogenase (e.g., ADH2, YQHD). With reference to alcohol dehydrogenases, although ethanol dehydrogenase is an alcohol dehydrogenase, the synthesis of ethanol is undesirable as a by-product in the biosynthetic pathways. Accordingly, reference to an increase in alcohol dehydrogenase activity or expression in a microorganism specifically excludes ethanol dehydrogenase activity.

In still another embodiment, the elevated expression of target enzymes such as threonine dehydratase (e.g., ilvA or tdcB), acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, and/or pdc, and alcohol dehydrogenase (e.g., ADH2, YQHD) can be present. The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, as well as deletion or inhibition of expression of a polypeptide involved in ammonia re-uptake, quorum sensing, such as autoinducer-2 (AI-2) re-uptake, and/or global regularion, such as for example a gene or homolog selected from the group consisting of glnA, gdhA, lsrA, luxS CRP, LRP, Fis, and/or IHP, or any combination thereof to increase the availability of pyruvate or reduce enzymes that compete for a metabolite in a desired biosynthetic pathway or to shift metabolic flux from nitrogen accumulation to release. With reference to alcohol dehydrogenases, although ethanol dehydrogenase is an alcohol dehydrogenase, the synthesis of ethanol is undesirable as a byproduct in the biosynthetic pathways. Accordingly, reference to an increase in alcohol dehydrogenase activity or expression in a microorganism specifically excludes ethanol dehydrogenase activity.

In yet another embodiment, the elevated expression of target enzymes such as acetolactate synthase (e.g., alsS), acetohydroxy acid synthase (e.g., ilvIH), acetolactate synthase (e.g., ilvMG or ilvNB), acetohydroxy acid isomeroreductase (e.g., ilvC), dihydroxy-acid dehydratase (e.g., ilvD), 2-isopropylmalate synthase (leuA), isopropylmalate isomerase (e.g., leuC, D or leuCD operon), beta-isopropylmalate dehydrogenase (e.g., leuB), 2-keto-acid decarboxylase (e.g., kivd, PDC6, or THI3), and alcohol dehydrogenase (e.g., ADH2, YQHD) can be present. The microorganism may further include the deletion or inhibition of expression of an ethanol dehydrogenase (e.g., an adhE), ldh (e.g., an ldhA), frd (e.g., an frdB, an frdC or an frdBC), fir, leuA, ilvE, poxB, ilvA, pflB, or pta gene, or any combination thereof, as well as deletion or inhibition of expression of a polypeptide involved in ammonia re-uptake, quorum sensing, such as autoinducer-2 (AI-2) re-uptake, and/or global regulation, such as for example a gene or homolog selected from the group consisting of glnA, gdhA, lsrA, luxS CRP, LRP, Fis, and/or IHP, or any combination thereof to increase the availability of pyruvate or reduce enzymes that compete for a metabolite in a desired biosynthetic pathway or to shift metabolic flux from nitrogen accumulation to release. With reference to alcohol dehydrogenases, although ethanol dehydrogenase is an alcohol dehydrogenase, the synthesis of ethanol is undesirable as a byproduct in the biosynthetic pathways. Accordingly, reference to an increase in alcohol dehydrogenase activity or expression in a microorganism specifically excludes ethanol dehydrogenase activity.

As previously noted, the target enzymes described throughout this disclosure generally produce metabolites. For example, the enzymes 2-isopropylmalate synthase (leuA), beta-isopropylmalate dehydrogenase (leuB), and isopropylmalate isomerase (leuC, leuD or leuCD operon) may produce 2-ketovalerate from a substrate that includes 2-ketobutyrate. In addition, the target enzymes described throughout this disclosure are encoded by polynucleotides. For example, threonine dehydratase can be encoded by a polynucleotide derived from an ilvA gene. Acetohydroxy acid synthase can be encoded by a polynucleotide derived from an ilvIH operon. Acetohydroxy acid isomeroreductase can be encoded by a polynucleotide derived from an ilvC gene. Dihydroxy-acid dehydratase can be encoded by a polynucleotide derived from an ilvD gene. 2-keto-acid decarboxylase can be encoded by a polynucleotide derived from a PDC6, ARO10, THI3, kivd, and/or pdc gene. Alcohol dehydrogenase can be encoded by a polynucleotide derived from an ADH2 or YQHD gene. Additional enzymes and exemplary genes are described throughout this document. Homologs of the various polypeptides and polynucleotides can be derived from any biologic source that provides a suitable polynucleotide encoding a suitable enzyme. Homologs, for example, can be identified by reference to various databases.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a function enzyme activity using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) *Nucl. Acids Res.* 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) *Nucl. Acids Res.* 24:216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites (e.g., keto thiolase, acetyl-CoA acetyl transferase, hydroxybutyryl CoA dehydrogenase, crotonase, crotonyl-CoA reductase, butyryl-CoA dehydrogenase, alcohol dehydrogenase (ADH)) are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be, introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, reference to a kivd gene includes homologs (e.g., pdc6, aro10, thI3, pdc, kdcA, pdc1, pdc5) from other organisms encoding an enzyme having substantially similar enzymatic activity, as well as genes having at least 30, 40, 50, 60, 70, 80, 85, 90, 95, 98, or 99% identity to the referenced gene and which encodes an enzyme having substantially similar enzymatic activity as the referenced gene. For example, pyruvate decarboxylase of *Kluyveromyces lactis* has 37% identity to Kivd at the amino acids level; kivd and thI3 are 32% identical at the nucleic acid level; Alcohol dehydrogenase of *Schizosaccharomyces pombe* has 52% identity to ADH2 of *Saccharomyces cerevisiae* at the amino acid sequence level; *S. cerevisiae* adh2 and *Lactococcus lactis* adh are 49% identical; KIVD (*Lactococcus lactis* (SEQ ID NO:31 and 32)) and PDC6 (*Saccharomyces cerevisiae* (SEQ ID NO:33 and 34)) share 36% identity (Positives=322/562 (57%), Gaps=24/562 (4%)); KIVD (*Lactococcus lactis* and THI3 (*Saccharomyces cerevisiae*) share 32% identity (Positives=307/571 (53%), Gaps=35/571 (6%)); kivd (*Lactococcus lactis*) and ARO10 (*Saccharomyces cerevisiae* (SEQ ID NO:35 and SEQ ID NO:36)) share 30% identity (Positives=296/598 (49%), Gaps=65/598 (10%)); ARO10 (*Saccharomyces cerevisiae*) and PDC6 (*Saccharomyces cerevisiae*) share 34% identity (Positives=320/616 (51%), Gaps=61/616 (9%)); ARO10 (*Saccharomyces cerevisiae*) and THI3 (*Saccharomyces cerevisiae* (SEQ ID NO:37 and SEQ ID NO:38)) share 30% identity (Positives=304/599 (50%), Gaps=48/599 (8%)); ARO10 (*Saccharomyces cerevisiae*) and pyruvate decarboxylase (*Clostridium acetobutylicum* ATCC 824) share 30% identity (Positives=291/613 (47%), Gaps=73/613 (11%)); PDC6 ((*Saccharomyces cerevisiae*) and THI3 (*Saccharomyces cerevisiae*) share 50% identity (Positives=402/561 (71%), Gaps=17/561 (3%)); PDC6 (*Saccharomyces cerevisiae*) and pyruvate decarboxylase (*Clostridium acetobutylicum* ATCC 824 (SEQ ID NO:39 and SEQ ID NO:40)) share 38% identity (Positives=328/570 (57%), Gaps=30/570 (5%)); and THI3 (*Saccharomyces cerevisiae*) and pyruvate decarboxylase (*Clostridium acetobutylicum* ATCC 824) share 35% identity (Positives=284/521 (54%), Gaps=25/521 (4%)). Sequence for each of the genes and polypeptides/enzymes listed herein can be readily identified using databases available on the World-Wide-Web (see, e.g., the *E. coli* Protein Database maintained by the Department of Chemical and Biomolecular Engineering, Korea Advanced Institute of Science and Technology. In addition, the amino acid sequence and nucleic acid sequence can be readily compared for identity using commonly used algorithms well known in the art.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., (1994), *Meth. Mol. Biol.* 25:365-389, hereby incorporated herein by reference).

The following six groups each contain amino acids that are conservative substitutions for one another:

1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, (1990) *J. Mol. Biol.* 215:403-441; Gish, (1993) *Nature Genet.* 3:266-272; Madden, (1996) *Meth. Enzymol.* 266:131-141; Altschul, (1997) *Nucl. Acids Res.* 25:3389-3402; Zhang, (1997) *Genome Res.* 7:649-656), especially blastp or tblastn (Altschul, (1997) *Nucl. Acids Res.* 25:3389-3402). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Table 3 and the disclosure provide non-limiting examples of genes and homologs for each gene having polynucleotide and polypeptide sequences available to the skilled person in the art.

TABLE 3

Depicts recombinant pathways for the production of various higher alcohols ("+" = expression, increase expression or activity/"–" = reduced expression or activity or knockout*).

| Enzyme | Exemplary Gene(s) | isobutanol | 1-butanol (via L-threonine) | 1-butanol (via pyruvate) | 1-propanol (via pyruvate) | 3-M-1-butanol (via pyruvate) | 2-M-1-butanol (via L-threonine) |
|---|---|---|---|---|---|---|---|
| Ethanol Dehydrogenase | adhE | – | – | – | – | – | – |
| Lactate Dehydrogenase | ldhA | – | – | – | – | – | – |
| Fumarate reductase | frdBC | – | | | | – | – |
| | fnr | – | | | | – | – |
| acetate kinase | ackA | – | – | – | – | – | – |
| Phosphate acetyltransferase | pta | – | – | – | – | – | – |
| Formate acetyltransferase | pflB | – | | | | – | – |
| α-isopropylmalate synthase | leuA | – | + | + | | + | |
| β-isopropylmalate dehydrogenase, | leuB | | + | + | + | + | |
| α-isopropylmalate isomerase | leuC | | + | + | + | + | |
| α-isopropylmalate isomerase | leuD | | + | + | + | | |
| BCAA aminotransferase | ilvE | – | | | | – | |
| tyrosine aminotransferase | tyrB, tyrAT | | | | | – | |
| pyruvate dehydrogenase | poxB | – | – | – | – | | |
| acetolactate synthase | ilvB | | – | – | – | | |
| acetolactate synthase | ilvI, alsS | | – | – | – | | |
| threonine dehydratase | ilvA, tdcB | – | + | + | + | | + |
| homoserine transsuccinylase | metA | | – | – | – | | – |
| L-threonine 3-dehydrogenase | tdh | | – | – | – | | – |
| acetohydroxy acid synthase | ilvHI, ilvNB, ilvGM, alsS | + | | | | + | + |
| acetohydroxy acid isomeroredutase | ilvC, ilv5 | + | | | | + | + |
| dihydroxy-acid dehyratase | ilvD, ilv3 | + | | | | + | + |
| 2-ketoacid decarboxylase | pdc6, aro10, thI3, kivd, pdc, kdcA, pdc1, pdc5 | + | + | + | + | + | + |
| alcohol dehydrogenase | adh1, adh2, adh3, adh4, adh5, adh6, sfa1 | + | + | + | + | + | + |
| citramalate synthase | cimA | | | + | + | | |

*knockout or a reduction in expression are optional in the synthesis of the product, however, such knockouts increase various substrate intermediates and improve yield.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Ethanol Dehydrogenase (also referred to as Aldehyde-alcohol dehydrogenase) is encoded in *E. coli* by adhE. adhE comprises three activities: alcohol dehydrogenase (ADH); acetaldehyde/acetyl-CoA dehydrogenase (ACDH); pyruvate-formate-lyase deactivase (PFL deactivase); PFL deactivase activity catalyzes the quenching of the pyruvate-formate-lyase catalyst in an iron, NAD, and CoA dependent reaction. Homologs are known in the art (see, e.g., aldehyde-alcohol dehydrogenase (*Polytomella* sp. *pringsheim* 198.80) gi|40644910|emb|CAD42653.2|(40644910); aldehyde-alcohol dehydrogenase (*Clostridium botulinum* A str. ATCC 3502) gi|148378348|ref|YP_001252889.1|(148378348); aldehyde-alcohol dehydrogenase (*Yersinia pestis* CO92) gi|16122410|ref|NP_405723.1|(16122410); aldehyde-alcohol dehydrogenase (*Yersinia pseudotuberculosis* IP 32953) gi|51596429|ref|YP_070620.1|(51596429); aldehyde-alcohol dehydrogenase (*Yersinia pestis* CO92) gi|115347889|emb|CAL20810.1|(115347889); aldehyde-alcohol dehydrogenase (*Yersinia pseudotuberculosis* IP 32953) gi|51589711|emb|CAH21341.1|(5158011); Aldehyde-alcohol dehydrogenase (*Escherichia coli* CFT073) gi|26107972|gb|AAN80172.1|AE016760_31(26107972); aldehyde-alcohol dehydrogenase (*Yersinia pestis* biovar Microtus str. 91001) gi|45441777|ref|NP_993316.1|(45441777); aldehyde-alcohol dehydrogenase (*Yersinia pestis* biovar Microtus str. 91001) gi|45436639|gb|AAS62193.1|(45436639); aldehyde-alcohol dehydrogenase (*Clostridium perfringens* ATCC 13124) gi|110798574|ref|YP_697219.1|(110798574); aldehyde-alcohol dehydrogenase (*Shewanella oneidensis* MR-1)gi|24373696|ref|NP_717739.1|(24373696); aldehyde-alcohol dehydrogenase (*Clostridium

*botulinum* A str. ATCC 19397) gi|153932445|ref|YP_001382747.1|(153932445); aldehyde-alcohol dehydrogenase (*Yersinia pestis* biovar Antigua str. E1979001) gi|165991833|gb|EDR44134.1|(165991833); aldehyde-alcohol dehydrogenase (*Clostridium botulinum* A str. Hall) gi|153937530|ref|YP_001386298.1|(153937530); aldehyde-alcohol dehydrogenase (*Clostridium perfringens* ATCC 13124) gi|110673221|gb|ABG82208.1|(110673221); aldehyde-alcohol dehydrogenase (*Clostridium botulinum* A str. Hall) gi|152933444|gb|ABS38943.1|(152933444); aldehyde-alcohol dehydrogenase (*Yersinia pestis* biovar Orientalis str. F1991016) gi|165920640|gb|EDR37888.1|(165920640); aldehyde-alcohol dehydrogenase (*Yersinia pestis* biovar Orientalis str. IP275) gi|165913933|gb|EDR32551.1|(165913933); aldehyde-alcohol dehydrogenase (*Yersinia pestis* Angola) gi|162419116|ref|YP_001606617.1|(162419116); aldehyde-alcohol dehydrogenase (*Clostridium botulinum* F str. Langeland) gi|153940830|ref|YP_001389712.1|(153940830); aldehyde-alcohol dehydrogenase (*Escherichia coli* HS) gi|157160746|ref|YP_001458064.1|(157160746); aldehyde-alcohol dehydrogenase (*Escherichia coli* E24377A) gi|157155679|ref|YP_001462491.1|(157155679); aldehyde-alcohol dehydrogenase (*Yersinia enterocolitica* subsp. *enterocolitica* 8081) gi|123442494|ref|YP_001006472.1|(123442494); aldehyde-alcohol dehydrogenase (*Synechococcus* sp. JA-3-3Ab) gi|86605191|ref|YP_473954.1|(86605191); aldehyde-alcohol dehydrogenase (*Listeria monocytogenes* str. 4b F2365) gi|46907864|ref|YP_014253.1|(46907864); aldehyde-alcohol dehydrogenase (*Enterococcus faecalis* V583) gi|29375484|ref|NP_814638.1|(29375484); aldehyde-alcohol dehydrogenase (*Streptococcus agalactiae* 2603V/R) gi|22536238|ref|NP_687089.1|(22536238); aldehyde-alcohol dehydrogenase (*Clostridium botulinum* A str. ATCC 19397) gi|152928489|gb|ABS33989.1|(152928489); aldehyde-alcohol dehydrogenase (*Escherichia coli* E24377A) gi|157077709|gb|ABV17417.1|(157077709); aldehyde-alcohol dehydrogenase (*Escherichia coli* HS) gi|157066426|gb|AB V05681.1|(157066426); aldehyde-alcohol dehydrogenase (*Clostridium botulinum* F str. Langeland) gi|152936726|gb|ABS42224.1|(152936726); aldehyde-alcohol dehydrogenase (*Yersinia pestis* CA88-4125) gi|149292312|gb|EDM42386.1|(149292312); aldehyde-alcohol dehydrogenase (*Yersinia enterocolitica* subsp. *enterocolitica* 8081) gi|122089455|emb|CAL12303.1|(122089455); aldehyde-alcohol dehydrogenase (*Chlamydomonas reinhardtii*) gi|92084840|emb|CAF04128.1|(92084840); aldehyde-alcohol dehydrogenase (*Synechococcus* sp. JA-3-3Ab) gi|86553733|gb|ABC98691.1|(86553733); aldehyde-alcohol dehydrogenase (*Shewanella oneidensis* MR-1) gi|24348056|gb|AAN55183.1|AE015655_9(24348056); aldehyde-alcohol dehydrogenase (*Enterococcus faecalis* V583) gi|29342944|gb|AAO80708.1|(29342944); aldehyde-alcohol dehydrogenase (*Listeria monocytogenes* str. 4b F2365) gi|46881133|gb|AAT04430.1|(46881133); aldehyde-alcohol dehydrogenase (*Listeria monocytogenes* str. 1/2a F6854) gi|47097587|ref|ZP_00235115.1|(47097587); aldehyde-alcohol dehydrogenase (*Listeria monocytogenes* str. 4b H7858) gi|47094265|ref|ZP_00231973.1|(47094265); aldehyde-alcohol dehydrogenase (*Listeria monocytogenes* str. 4b H7858) gi|47017355|gb|EAL08180.1|(47017355); aldehyde-alcohol dehydrogenase (*Listeria monocytogenes* str. 1/2a F6854) gi|47014034|gb|EAL05039.1|(47014034); aldehyde-alcohol dehydrogenase (*Streptococcus agalactiae* 2603V/R) gi|22533058|gb|AAM98961.1|AE014194_6(22533058)$_p$; aldehyde-alcohol dehydrogenase (*Yersinia pestis* biovar Antigua str. E1979001) gi|166009278|ref|ZP_02230176.1|(166009278); aldehyde-alcohol dehydrogenase (*Yersinia pestis* biovar Orientalis str. IP275) gi|165938272|ref|ZP_02226831.1|(165938272); aldehyde-alcohol dehydrogenase (*Yersinia pestis* biovar Orientalis str. F1991016) gi|165927374|ref|ZP_02223206.1|(165927374); aldehyde-alcohol dehydrogenase (*Yersinia pestis* Angola) gi|162351931|gb|ABX85879.1|(162351931); aldehyde-alcohol dehydrogenase (*Yersinia pseudotuberculosis* IP 31758) gi|153949366|ref|YP_001400938.1|(153949366); aldehyde-alcohol dehydrogenase (*Yersinia pseudotuberculosis* IP 31758) gi|152960861|gb|ABS48322.1|(152960861); aldehyde-alcohol dehydrogenase (*Yersinia pestis* CA88-4125) gi|149365899|ref|ZP_01887934.1|(149365899); Acetaldehyde dehydrogenase (acetylating) (*Escherichia coli* CFT073) gi|26247570|ref|NP_753610.1|(26247570); aldehyde-alcohol dehydrogenase (includes: alcohol dehydrogenase; acetaldehyde dehydrogenase (acetylating) (EC 1.2.1.10) (acdh); pyruvate-formate-lyase deactivase (pfl deactivase)) (*Clostridium botulinum* A str. ATCC 3502) gi|148287832|emb|CAL81898.1|(148287832); aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152980|sp|P0A9Q7.2|ADHE_ECOLI(71152980); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCR11043) gi|50121254|ref|YP_050421.1|(50121254); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCR11043) gi|49611780|emb|CAG75229.1|(49611780); Aldehyde-alcohol dehydrogenase (Includes: Alcohol dehydrogenase (ADH); Acetaldehyde dehydrogenase (acetylating) (ACDH)) gi|19858620|sp|P33744.3|ADHE_CLOAB(19858620); Aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152683|sp|P0A9Q8.2|ADHE_ECO57(71152683); aldehyde-alcohol dehydrogenase (includes: alcohol dehydrogenase; acetaldehyde dehydrogenase (acetylating); pyruvate-formate-lyase deactivase (*Clostridium difficile* 630) gi|126697906|ref|YP_001086803.1|(126697906); aldehyde-alcohol dehydrogenase (includes: alcohol dehydrogenase; acetaldehyde dehydrogenase (acetylating); pyruvate-formate-lyase deactivase (*Clostridium difficile* 630) gi|115249343|emb|CAJ67156.1|(115249343); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|37526388|ref|NP_929732.1|(37526388); aldehyde-alcohol dehydrogenase 2 (includes: alcohol dehydrogenase; acetaldehyde dehydrogenase) (*Streptococcus pyogenes* str. Manfredo) gi|134271169|emb|CAM29381.1|(134271169); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|36785819|emb|CAE14870.1|(36785819); aldehyde-alcohol dehydrogenase (includes: alcohol dehydrogenase and pyruvate-formate-lyase deactivase (*Clostridium difficile* 630) gi|126700586|ref|YP_

001089483.1|(126700586); aldehyde-alcohol dehydrogenase (includes: alcohol dehydrogenase and pyruvate-formate-lyase deactivase (*Clostridium difficile* 630) gi|115252023 |emb|CAJ69859.1|(115252023); aldehyde-alcohol dehydrogenase 2 (*Streptococcus pyogenes* str. Manfredo) gi|139472923|ref|YP_001127638.1|(139472923); aldehyde-alcohol dehydrogenase E (*Clostridium perfringens* str. 13) gi|18311513|ref|NP_563447.1|(18311513); aldehyde-alcohol dehydrogenase E (*Clostridium perfringens* str. 13) gi|18146197|dbj|BAB82237.1|(18146197); Aldehyde-alcohol dehydrogenase, ADHE1 (*Clostridium acetobutylicum* ATCC 824) gi|15004739|ref|NP_149199.1|(15004739); Aldehyde-alcohol dehydrogenase, ADHE1 (*Clostridium acetobutylicum* ATCC 824) gi|14994351|gb|AAK76781.1|AE001438_34(14994351); Aldehyde-alcohol dehydrogenase 2 (Includes: Alcohol dehydrogenase (ADH); acetaldehyde/acetyl-CoA dehydrogenase (ACDH)) gi|2492737|sp|Q24803.1|ADH2_ENTHI (2492737); alcohol dehydrogenase (*Salmonella enterica* subsp. *enterica* serovar Typhi str. CT18) gi|16760134|ref|NP_455751.1|(16760134); and alcohol dehydrogenase (*Salmonella enterica* subsp. *enterica* serovar Typhi) gi|16502428|emb|CAD08384.1|(16502428)), each sequence associated with the accession number is incorporated herein by reference in its entirety.

Lactate Dehydrogenase (also referred to as D-lactate dehydrogenase and fermentive dehydrognase) is encoded in *E. coli* by ldhA and catalyzes the NADH-dependent conversion of pyruvate to D-lactate. ldhA homologs and variants are known. In fact there are currently 1664 bacterial lactate dehydrogenases available through NCBI. For example, such homologs and variants include, for example, D-lactate dehydrogenase (D-LDH) (Fermentative lactate dehydrogenase) gi|1730102|sp|P52643.1|LDHD_ECOLI(1730102); D-lactate dehydrogenase gi|1049265|gb|AAB51772.1|(1049265); D-lactate dehydrogenase (*Escherichia coli* APEC O1) gi|117623655|ref|YP_852568.1|(117623655); D-lactate dehydrogenase (*Escherichia coli* CFT073) gi|26247689|ref|NP_753729.1|(26247689); D-lactate dehydrogenase (*Escherichia coli* O157:H7 EDL933) gi|15801748|ref|NP_287766.1|(15801748); D-lactate dehydrogenase (*Escherichia coli* APEC O1) gi|115512779|gb|ABJ00854.1|(115512779); D-lactate dehydrogenase (*Escherichia coli* CFT073) gi|26108091|gb|AAN80291.1|AE016760_150(26108091); fermentative D-lactate dehydrogenase, NAD-dependent (*Escherichia coli* K12) gi|16129341|ref|NP_415898.1|(16129341); fermentative D-lactate dehydrogenase, NAD-dependent (*Escherichia coli* UTI89) gi|91210646|ref|YP_540632.1|(91210646); fermentative D-lactate dehydrogenase, NAD-dependent (*Escherichia coli* K12) gi|1787645|gb|AAC74462.1|(1787645); fermentative D-lactate dehydrogenase, NAD-dependent (*Escherichia coli* W3110) gi|89108227|ref|AP_002007.1|(89108227); fermentative D-lactate dehydrogenase, NAD-dependent (*Escherichia coli* W3110) gi|1742259|dbj|BAA14990.1|(1742259); fermentative D-lactate dehydrogenase, NAD-dependent (*Escherichia coli* UTI89) gi|91072220|gb|ABE07101.1|(91072220); fermentative D-lactate dehydrogenase, NAD-dependent (*Escherichia coli* O157:H7 EDL933) gi|12515320|gb|AAG56380.1|AE005366_6(12515320); fermentative D-lactate dehydrogenase (*Escherichia coli* O157:H7 str. Sakai) gi|13361468|dbj|BAB35425.1|(13361468); COG1052: Lactate dehydrogenase and related dehydrogenases (*Escherichia coli* 101-1) gi|83588593|ref|ZP_00927217.1|(83588593); COG1052: Lactate dehydrogenase and related dehydrogenases (*Escherichia coli* 53638) gi|75515985|ref|ZP_00738103.1|(75515985); COG1052: Lactate dehydrogenase and related dehydrogenases (*Escherichia coli* E22) gi|75260157|ref|ZP_00731425.1|(75260157); COG1052: Lactate dehydrogenase and related dehydrogenases (*Escherichia coli* F11) gi|75242656|ref|ZP_00726400.1|(75242656); COG1052: Lactate dehydrogenase and related dehydrogenases (*Escherichia coli* E110019) gi|75237491|ref|ZP_00721524.1|(75237491); COG1052: Lactate dehydrogenase and related dehydrogenases (*Escherichia coli* B7A) gi|75231601|ref|ZP_00717959.1|(75231601); and COG1052: Lactate dehydrogenase and related dehydrogenases (*Escherichia coli* B171) gi|75211308|ref|ZP_00711407.1|(75211308), each sequence associated with the accession number is incorporated herein by reference in its entirety.

Two membrane-bound, FAD-containing enzymes are responsible for the catalysis of fumarate and succinate interconversion; the fumarate reductase is used in anaerobic growth, and the succinate dehydrogenase is used in aerobic growth. Fumarate reductase comprises multiple subunits (e.g., frdA, B, and C in *E. coli*). Modification of any one of the subunits can result in the desired activity herein. For example, a knockout of frdB, frdC or frdBC is useful in the methods of the disclosure. Frd homologs and variants are known. For example, homologs and variants includes, for example, Fumarate reductase subunit D (Fumarate reductase 13 kDa hydrophobic protein) gi|67463543|sp|P0A8Q3.1|FRDD_ECOLI(67463543); Fumarate reductase subunit C (Fumarate reductase 15 kDa hydrophobic protein) gi|1346037|sp|P20923.2|FRDC_PROVU(1346037); Fumarate reductase subunit D (Fumarate reductase 13 kDa hydrophobic protein) gi|120499|sp|P20924.1|FRDD_PROVU (120499); Fumarate reductase subunit C (Fumarate reductase 15 kDa hydrophobic protein) gi|67463538|sp|P0A8Q0.1|FRDC_ECOLI(67463538); fumarate reductase iron-sulfur subunit (*Escherichia coli*) gi|145264|gb|AAA23438.1|(145264); fumarate reductase flavoprotein subunit (*Escherichia coli*) gi|145263|gb|AAA23437.1|(145263); Fumarate reductase flavoprotein subunit gi|37538290|sp|P17412.3|FRDA_WOLSU(37538290); Fumarate reductase flavoprotein subunit gi|120489|sp|P00363.3|FRDA_ECOLI(120489); Fumarate reductase flavoprotein subunit gi|120490|sp|P20922.1|FRDA_PROVU(120490); Fumarate reductase flavoprotein subunit precursor (Flavocytochrome c) (Flavocytochrome c3) (Fcc3) gi|119370087|sp|Q07WU7.2|FRDA_SHEFN(119370087); Fumarate reductase iron-sulfur subunit gi|81175308|sp|P0AC47.2|FRDB_ECOLI(81175308); Fumarate reductase flavoprotein subunit (Flavocytochrome c) (Flavocytochrome c3) (Fcc3) gi|119370088|sp|P0C278.1|FRDA_SHEFR(119370088); Frd operon uncharacterized protein C gi|140663|sp|P20927.1|YFRC_PROVU(140663); Frd operon probable iron-sulfur subunit A gi|140661|sp|P20925.1|YFRA_PROVU(140661); Fumarate reductase iron-sulfur subunit gi|120493|sp|P20921.2|FRDB_PROVU(120493); Fumarate reductase flavoprotein subunit gi|2494617|sp|O06913.2|FRDA_HELPY(2494617); Fumarate reductase flavoprotein subunit precursor (Iron(III)-induced flavocytochrome C3) (Ifc3) gi|13878499|sp|Q9Z4P0.1|FRD2_SHEFN(13878499);

Fumarate reductase flavoprotein subunit gi|54041009|sp|P64174.1|FRDA_MYCTU(54041009); Fumarate reductase flavoprotein subunit gi|54037132|sp|P64175.1|FRDA_MYCBO(54037132); Fumarate reductase flavoprotein subunit gi|12230114|sp|Q9ZMP0.1|FRDA_HELPJ(12230114); Fumarate reductase flavoprotein subunit gi|1169737|sp|P44894.1|FRDA_HAEIN(1169737); fumarate reductase flavoprotein subunit (*Wolinella succinogenes*) gi|13160058|emb|CAA04214.2|(13160058); Fumarate reductase flavoprotein subunit precursor (Flavocytochrome c) (FL cyt) gi|25452947|sp|P83223.2|FRDA_SHEON (25452947); fumarate reductase iron-sulfur subunit (*Wolinella succinogenes*) gi|2282000|emb|CAA04215.1| (2282000); and fumarate reductase cytochrome b subunit (*Wolinella succinogenes*) gi|2281998|emb|CAA04213.1| (2281998), each sequence associated with the accession number is incorporated herein by reference in its entirety.

Acetate kinase is encoded in *E. coli* by ackA. AckA is involved in conversion of acetyl-coA to acetate. Specifically, ackA catalyzes the conversion of acetyl-phosphate to acetate. AckA homologs and variants are known. The NCBI database list approximately 1450 polypeptides as bacterial acetate kinases. For example, such homologs and variants include acetate kinase (*Streptomyces coelicolor* A3(2)) gi|21223784|ref|NP_629563.1|(21223784); acetate kinase (*Streptomyces coelicolor* A3(2)) gi|6808417|emb|CAB70654.1|(6808417); acetate kinase (*Streptococcus pyogenes* M1 GAS) gi|15674332|ref|NP_268506.1|(15674332); acetate kinase (*Campylobacter jejuni* subsp. *jejuni* NCTC 11168) gi|15792038|ref|NP_281861.1| (15792038); acetate kinase (*Streptococcus pyogenes* M1 GAS) gi|13621416|gb|AAK33227.1|(13621416); acetate kinase (*Rhodopirellula baltica* SH 1) gi|32476009|ref|NP_869003.1|(32476009); acetate kinase (*Rhodopirellula baltica* SH 1) gi|32472045|ref|NP_865039.1|(32472045); acetate kinase (*Campylobacter jejuni* subsp. *jejuni* NCTC 11168) gi|112360034|emb|CAL34826.1|(112360034); acetate kinase (*Rhodopirellula baltica* SH 1) gi|32446553|emb|CAD76388.1|(32446553); acetate kinase (*Rhodopirellula baltica* SH 1) gi|32397417|emb|CAD72723.1|(32397417); AckA (*Clostridium kluyveri* DSM 555) gi|153954016|ref|YP_001394781.1|(153954016); acetate kinase (*Bifidobacterium longum* NCC2705) gi|23465540|ref|NP_696143.1| (23465540); AckA (*Clostridium kluyveri* DSM 555) gi|146346897|gb|EDK33433.1|(146346897); Acetate kinase (*Corynebacterium diphtheriae*) gi|38200875|emb|CAE50580.1|(38200875); acetate kinase (*Bifidobacterium longum* NCC2705) gi|23326203|gb|AAN24779.1|(23326203); Acetate kinase (Acetokinase) gi|67462089|sp|P0A6A3.1|ACKA_ECOLI (67462089); and AckA (*Bacillus licheniformis* DSM 13) gi|52349315|gb|AAU41949.1|(52349315), the sequences associated with such accession numbers are incorporated herein by reference.

Phosphate acetyltransferase is encoded in *E. coli* by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (*Rickettsia felis* URRWXCal2) gi|67004021|gb|AAY60947.1| (67004021); phosphate acetyltransferase (*Buchnera aphidicola* str. Cc (Cinara cedri)) gi|116256910|gb|ABJ90592.1| (116256910); pta (*Buchnera aphidicola* str. Cc (Cinara cedri)) gi|116515056|ref|YP_802685.1|(116515056); pta (*Wigglesworthia glossinidia* endosymbiont of *Glossina brevipalpis*) gi|25166135|dbj|BAC24326.1|(25166135); Pta (*Pasteurella multocida* subsp. *multocida* str. Pm70) gi|12720993|gb|AAK02789.1|(12720993); Pta (*Rhodospirillum rubrum*) gi|25989720|gb|AAN75024.1|(25989720); pta (*Listeria welshimeri* serovar 6b str. SLCC5334) gi|116742418|emb|CAK21542.1|(116742418); Pta (*Mycobacterium avium* subsp. *paratuberculosis* K-10) gi|41398816|gb|AAS06435.1|(41398816); phosphate acetyltransferase (pta) (*Borrelia burgdorferi* B31) gi|15594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|1574131|gb|AAC22857.1|(1574131); phosphate acetyltransferase Pta (*Rickettsia bellii* RML369-C) gi|91206026|ref|YP_538381.1|(91206026); phosphate acetyltransferase Pta (*Rickettsia bellii* RML369-C) gi|91206025|ref|YP_538380.1|(91206025); phosphate acetyltransferase pta (*Mycobacterium tuberculosis* F11) gi|148720131|gb|ABR04756.1|(148720131); phosphate acetyltransferase pta (*Mycobacterium tuberculosis* str. Haarlem) gi|134148886|gb|EBA40931.1|(134148886); phosphate acetyltransferase pta (*Mycobacterium tuberculosis* C) gi|124599819|gb|EAY58829.1|(124599819); phosphate acetyltransferase Pta (*Rickettsia bellii* RML369-C) gi|91069570|gb|ABE05292.1|(91069570); phosphate acetyltransferase pta (*Rickettsia bellii* RML369-C) gi|91069569|gb|ABE05291.1|(91069569); phosphate acetyltransferase (pta). (*Treponema pallidum* subsp. *pallidum* str. Nichols) gi|15639088|ref|NP_218534.1| (15639088); and phosphate acetyltransferase (pta) (*Treponema pallidum* subsp. *pallidum* str. Nichols) gi|3322356|gb|AAC65090.1|(3322356), each sequence associated with the accession number is incorporated herein by reference in its entirety.

Pyruvate-formate lyase (formate acetyltransferase) is an enzyme that catalyzes the conversion of pyruvate to acetyl-coA and formate. It is induced by pfl-activating enzyme under anaerobic conditions by generation of an organic free radical and decreases significantly during phosphate limitation. Formate acetyltransferase is encoded in *E. coli* by pflB. PFLB homologs and variants are known. For examples, such homologs and variants include, for example, formate acetyltransferase 1 (pyruvate formate-lyase 1) gi|129879|sp|P09373.2|PFLB_ECOLI(129879); formate acetyltransferase 1 (*Yersinia pestis* CO92) gi|16121663|ref|NP_404976.1|(16121663); formate acetyltransferase 1 (*Yersinia pseudotuberculosis* IP 32953) gi|51595748|ref|YP_069939.1|(51595748); formate acetyltransferase 1 (*Yersinia pestis* biovar Microtus str. 91001) gi|45441037|ref|NP_992576.1|(45441037); formate acetyltransferase 1 (*Yersinia pestis* CO92) gi|115347142|emb|CAL20035.1|(115347142); formate acetyltransferase 1 (*Yersinia pestis* biovar Microtus str. 91001) gi|45435896|gb|AAS61453.1|(45435896); formate acetyltransferase 1 (*Yersinia pseudotuberculosis* IP 32953) gi|51589030|emb|CAH20648.1|(51589030); formate acetyltransferase 1 (*Salmonella enterica* subsp. *enterica* serovar Typhi str. CT18) gi|16759843|ref|NP_455460.1| (16759843); formate acetyltransferase 1 (*Salmonella enterica* subsp. *enterica* serovar Paratyphi A str. ATCC 9150) gi|56413977|ref|YP_151052.1|(56413977); formate acetyltransferase 1 (*Salmonella enterica* subsp. *enterica* serovar Typhi) gi|16502136|emb|CAD05373.1|(16502136); formate acetyltransferase 1 (*Salmonella enterica* subsp. *enterica* serovar Paratyphi A str. ATCC 9150) gi|56128234|gb|AAV77740.1|(56128234); formate acetyltransferase 1 (*Shigella dysenteriae* Sd197) gi|82777577|ref|YP_403926.1|(82777577); formate acetyltransferase 1 (*Shigella flexneri* 2a str. 2457T) gi|30062438|ref|NP_836609.1|(30062438); formate acetyltransferase 1 (*Shigella flexneri* 2a str. 2457T) gi|30040684|gb|AAP16415.1|(30040684); formate acetyltransferase 1 (*Shigella flexneri* 5 str. 8401) gi|110614459|gb|ABF03126.1|(110614459); formate acetyltransferase 1 (*Shigella dysenteriae* Sd197) gi|81241725|gb|ABB62435.1|(81241725); formate acetyltransferase 1 (*Escherichia coli* O157:H7 EDL933) gi|12514066|gb|AAG55388.1|AE005279_8(12514066); formate acetyltransferase 1 (*Yersinia pestis* KIM) gi|22126668|ref|NP_670091.1|(22126668); formate acetyltransferase 1 (*Streptococcus agalactiae* A909) gi|76787667|ref|YP_330335.1|(76787667); formate acetyltransferase 1 (*Yersinia pestis* KIM) gi|21959683|gb|AAM86342.1|AE013882_3(21959683); formate acetyltransferase 1 (*Streptococcus agalactiae* A909) gi|76562724|gb|ABA45308.1|(76562724); formate acetyltransferase 1 (*Yersinia enterocolitica* subsp. *enterocolitica* 8081) gi|123441844|ref|YP_001005827.1|(123441844); formate acetyltransferase 1 (*Shigella flexneri* 5 str. 8401) gi|110804911|ref|YP_688431.1|(110804911); formate acetyltransferase 1 (*Escherichia coli* UTI89) gi|91210004|ref|YP_539990.1|(91210004); formate acetyltransferase 1 (*Shigella boydii* Sb227) gi|82544641|ref|YP_408588.1|(82544641); formate acetyltransferase 1 (*Shigella sonnei* Ss046) gi|74311459|ref|YP_309878.1|(74311459); formate acetyltransferase 1 (*Klebsiella pneumoniae* subsp. *pneumoniae* MGH 78578) gi|152969488|ref|YP_001334597.1|(152969488); formate acetyltransferase 1 (*Salmonella enterica* subsp. *enterica* serovar Typhi Ty2) gi|29142384|ref|NP_805726.1|(29142384) formate acetyltransferase 1 (*Shigella flexneri* 2a str. 301) gi|24112311|ref|NP_706821.1|(24112311); formate acetyltransferase 1 (*Escherichia coli* O157:H7 EDL933) gi|15800764|ref|NP_286778.1|(15800764); formate acetyltransferase 1 (*Klebsiella pneumoniae* subsp. *pneumoniae* MGH 78578) gi|150954337|gb|ABR76367.1|(150954337); formate acetyltransferase 1 (*Yersinia pestis* CA88-4125) gi|149366640|ref|ZP_01888674.1|(149366640); formate acetyltransferase 1 (*Yersinia pestis* CA88-4125) gi|149291014|gb|EDM41089.1|(149291014); formate acetyltransferase 1 (*Yersinia enterocolitica* subsp. *enterocolitica* 8081) gi|122088805|emb|CAL11611.1|(122088805); formate acetyltransferase 1 (*Shigella sonnei* Ss046) gi|73854936|gb|AAZ87643.1|(73854936); formate acetyltransferase 1 (*Escherichia coli* UTI89) gi|91071578|gb|ABE06459.1|(91071578); formate acetyltransferase 1 (*Salmonella enterica* subsp. *enterica* serovar Typhi Ty2) gi|29138014|gb|AAO69575.1|(29138014); formate acetyltransferase 1 (*Shigella boydii* Sb227) gi|81246052|gb|ABB66760.1|(81246052); formate acetyltransferase 1 (*Shigella flexneri* 2a str. 301) gi|24051169|gb|AAN42528.1|(24051169); formate acetyltransferase 1 (*Escherichia coli* O157:H7 str. Sakai) gi|13360445|dbj|BAB34409.1|(13360445); formate acetyltransferase 1 (*Escherichia coli* O157:H7 str. Sakai) gi|15830240|ref|NP_309013.1|(15830240); formate acetyltransferase I (pyruvate formate-lyase 1) (*Photorhabdus luminescens* subsp. *laumondii* TTO1) gi|36784986|emb|CAE13906.1|(36784986); formate acetyltransferase I (pyruvate formate-lyase 1) (*Photorhabdus luminescens* subsp. *laumondii* TTO1) gi|37525558|ref|NP_928902.1|(37525558); formate acetyltransferase (*Staphylococcus aureus* subsp. *aureus* Mu50) gi|14245993|dbj|BAB56388.1|(14245993); formate acetyltransferase (*Staphylococcus aureus* subsp. *aureus* Mu50) gi|15923216|ref|NP_370750.1|(15923216); formate acetyltransferase (Pyruvate formate-lyase) gi|81706366|sp|Q7A7X6.1|PFLB_STAAN(81706366); formate acetyltransferase (pyruvate formate-lyase) gi|81782287|sp|Q99WZ7.1|PFLB_STAAM(81782287); formate acetyltransferase (pyruvate formate-lyase) gi|81704726|sp|Q7A1W9.1|PFLB_STAAW(81704726); formate acetyltransferase (*Staphylococcus aureus* subsp. *aureus* Mu3) gi|156720691|dbj|BAF77108.1|(156720691); formate acetyltransferase (*Erwinia carotovora* subsp. *atroseptica* SCR11043) gi|50121521|ref|YP_050688.1|(50121521); formate acetyltransferase (*Erwinia carotovora* subsp. *atroseptica* SCR11043) gi|49612047|emb|CAG75496.1|(49612047); formate acetyltransferase (*Staphylococcus aureus* subsp. *aureus* str. Newman) gi|150373174|dbj|BAF66434.1|(150373174); formate acetyltransferase (*Shewanella oneidensis* MR-1) gi|24374439|ref|NP_718482.1|(24374439); formate acetyltransferase (*Shewanella oneidensis* MR-1) gi|24349015|gb|AAN55926.1|AE015730_3(24349015); formate acetyltransferase (*Actinobacillus pleuropneumoniae* serovar 3 str. JL03) gi|165976461|ref|YP_001652054.1|(165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. *aureus* MW2) gi|21203365|dbj|BAB94066.1|(21203365); formate acetyltransferase (*Staphylococcus aureus* subsp. *aureus* N315) gi|13700141|dbj|BAB41440.1|(13700141); formate acetyltransferase (*Staphylococcus aureus* subsp. *aureus* str. Newman) gi|151220374|ref|YP_001331197.1|(151220374); formate acetyltransferase (*Staphylococcus aureus* subsp. *aureus* Mu3) gi|156978556|ref|YP_001440815.1|(156978556); formate acetyltransferase (*Synechococcus* sp. JA-2-3B'a(2-13)) gi|86607744|reffP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1|(116517188); formate acetyltransferase (*Synechococcus* sp. JA-2-3B'a(2-13)) gi|86556286|gb|ABD01243.1|(86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. *aureus* MRSA252) gi|49482458|ref|YP_039682.1|(49482458); and formate acetyltransferase (*Staphylococcus aureus* subsp. *aureus* MRSA252) gi|49240587|emb|CAG39244.1|(49240587), each sequence associated with the accession number is incorporated herein by reference in its entirety.

Alpha isopropylmalate synthase (EC 2.3.3.13, sometimes referred to a 2-isopropylmalate synthase, alpha-IPM synthetase) catalyzes the condensation of the acetyl group of acetyl-CoA with 3-methyl-2-oxobutanoate (2-oxoisovalerate) to form 3-carboxy-3-hydroxy-4-methylpentanoate (2-isopropylmalate). Alpha isopropylmalate synthase is encoded in *E. coli* by leuA. LeuA homologs and variants are known. For example, such homologs and variants include, for example, 2-isopropylmalate synthase (*Corynebacterium glutamicum*) gi|452382|emb|CAA50295.1|(452382); 2-isopropylmalate synthase (*Escherichia coli* K12) gi|16128068|ref|NP_414616.1|(16128068); 2-isopropylmalate synthase (*Escherichia coli* K12) gi|1786261|gb|AAC73185.1|(1786261); 2-isopropylmalate synthase (*Arabidopsis thaliana*) gi|15237194|ref|NP_197692.1|(15237194); 2-isopropylmalate synthase (*Arabidopsis thaliana*) gi|42562149|ref|NP_173285.2|(42562149); 2-isopropylmalate synthase (*Arabidopsis thaliana*) gi|15221125|ref|NP_177544.1|(15221125); 2-isopropylmalate synthase (*Streptomyces coelicolor* A3(2)) gi|32141173|ref|NP_733575.1|(32141173); 2-isopropylmalate synthase (*Rhodopirellula baltica* SH 1) gi|32477692|ref|NP_870686.1|(32477692); 2-isopropylmalate synthase (*Rhodopirellula baltica* SH 1) gi|32448246|emb|CAD77763.1|(32448246); 2-isopropylmalate synthase (*Akkermansia muciniphila* ATCC BAA-835) gi|166241432|gb|EDR53404.1|(166241432); 2-isopropylmalate synthase (*Herpetosiphon aurantiacus* ATCC 23779) gi|159900959|ref|YP_001547206.1|(159900959); 2-isopropylmalate synthase (*Dinoroseobacter shibae* DFL 12) gi|159043149|ref|YP_001531943.1|(159043149); 2-isopropylmalate synthase (*Salinispora arenicola* CNS-205) gi|159035933|ref|YP_001535186.1|(159035933); 2-isopropylmalate synthase (*Clavibacter michiganensis* subsp. *michiganensis* NCPPB 382) gi|148272757|ref|YP_001222318.1|(148272757); 2-isopropylmalate synthase (*Escherichia coli* B) gi|124530643|ref|ZP_01701227.1|(124530643); 2-isopropylmalate synthase (*Escherichia coli* C str. ATCC 8739) gi|124499067|gb|EAY46563.1|(124499067); 2-isopropylmalate synthase (*Bordetella pertussis* Tohama I) gi|33591386|ref|NP_879030.1|(33591386); 2-isopropylmalate synthase (*Polynucleobacter necessarius* STIR1) gi|164564063|ref|ZP_02209880.1|(164564063); 2-isopropylmalate synthase (*Polynucleobacter necessarius* STIR1) gi|164506789|gb|EDQ94990.1|(164506789); and 2-isopropylmalate synthase (*Bacillus weihenstephanensis* KBAB4) gi|163939313|ref|YP_001644197.1|(163939313), any sequence associated with the accession number is incorporated herein by reference in its entirety.

BCAA aminotransferases catalyze the formation of branched chain amino acids (BCAA). A number of such aminotranferases are known and are exemplified by ilvE in *E. coli*. Exemplary homologs and variants include sequences designated by the following accession numbers: ilvE (*Microcystis aeruginosa* PCC 7806) gi|159026756|emb|CAO86637.1|(159026756); IlvE (*Escherichia coli*) gi|87117962|gb|ABD20288.1|(87117962); IlvE (*Escherichia coli*) gi|87117960|gb|ABD20287.1|(87117960); IlvE (*Escherichia coli*) gi|87117958|gb|ABD20286.1|(87117958); IlvE (*Shigella flexneri*) gi|87117956|gb|ABD20285.1|(87117956); IlvE (*Shigella flexneri*) gi|87117954|gb|ABD20284.1|(87117954); IlvE (*Shigella flexneri*) gi|87117952|gb|ABD20283.1|(87117952); IlvE (*Shigella flexneri*) gi|87117950|gb|ABD20282.1|(87117950); IlvE (*Shigella flexneri*) gi|87117948|gb|ABD20281.1|(87117948); IlvE (*Shigella flexneri*) gi|87117946|gb|ABD20280.1|(87117946); IlvE (*Shigella flexneri*) gi|87117944|gb|ABD20279.1|(87117944); IlvE (*Shigella flexneri*) gi|87117942|gb|ABD20278.1|(87117942); IlvE (*Shigella flexneri*) gi|87117940|gb|ABD20277.1|(87117940); IlvE (*Shigella flexneri*) gi|87117938|gb|ABD20276.1|(87117938); IlvE (*Shigella dysenteriae*) gi|87117936|gb|ABD20275.1|(87117936); IlvE (*Shigella dysenteriae*) gi|87117934|gb|ABD20274.1|(87117934); IlvE (*Shigella dysenteriae*) gi|87117932|gb|ABD20273.1|(87117932); IlvE (*Shigella dysenteriae*) gi|87117930|gb|ABD20272.1|(87117930); and IlvE (*Shigella dysenteriae*) gi|87117928|gb|ABD20271.1|(87117928), each sequence associated with the accession number is incorporated herein by reference.

Tyrosine aminotransferases catalyzes transamination for both dicarboxylic and aromatic amino-acid substrates. A tyrosine aminotransferase of *E. coli* is encoded by the gene tyrB. TyrB homologs and variants are known. For example, such homologs and variants include tyrB (*Bordetella petrii*) gi|163857093|ref|YP_001631391.1|(163857093); tyrB (*Bordetella petrii*) gi|163260821|emb|CAP43123.1|(163260821); aminotransferase gi|551844|gb|AAA24704.1|(551844); aminotransferase (*Bradyrhizobium* sp. BTAi1) gi|146404387|gb|ABQ32893.1|(146404387); tyrosine aminotransferase TyrB (*Salmonella enterica*) gi|4775574|emb|CAB40973.2|(4775574); tyrosine aminotransferase (*Salmonella typhimurium* LT2) gi|16422806|gb|AAL23072.1|(16422806); and tyrosine aminotransferase gi|148085|gb|AAA24703.1|(148085), each sequence of which is incorporated herein by reference.

Pyruvate oxidase catalyzes the conversion of pyruvate to acetate and $CO_2$. In *E. coli*, pyruvate oxidase is encoded by poxB. PoxB and homologs and variants thereof include, for example, pyruvate oxidase; PoxB (*Escherichia coli*) gi|685128|gb|AAB31180.1||bbm|348451|bbs|154716 (685128); PoxB (*Pseudomonas fluorescens*) gi|32815820|gb|AAP88293.1|(32815820); poxB (*Escherichia coli*) gi|25269169|emb|CAD57486.1|(25269169); pyruvate dehydrogenase (*Salmonella enterica* subsp. *enterica* serovar Typhi) gi|16502101|emb|CD05337.1|(16502101); pyruvate oxidase (*Lactobacillus plantarum*) gi|41691702|gb|AAS10156.1|(41691702); pyruvate dehydrogenase (*Bradyrhizobium japonicum*) gi|20257167|gb|AAM12352.1|(20257167); pyruvate dehydrogenase (*Yersinia pestis* KIM) gi|22126698|ref|NP_670121.1|(22126698); pyruvate dehydrogenase (cytochrome) (*Yersinia pestis* biovar Antigua str. B42003004) gi|166211240|ref|ZP_02237275.1|(166211240); pyruvate dehydrogenase (cytochrome) (*Yersinia pestis* biovar Antigua str. B42003004) gi|166207011|gb|EDR51491.1|(166207011); pyruvate dehydrogenase (*Pseudomonas syringae* pv. tomato str. DC3000) gi|28869703|ref|NP_792322.1|(28869703); pyruvate dehydrogenase (*Salmonella typhimurium* LT2) gi|16764297|ref|NP_459912.1|(16764297); pyruvate dehydrogenase (*Salmonella enterica* subsp. *enterica* serovar Typhi str. CT18) gi|16759808|ref|NP_455425.1|(16759808); pyruvate dehydrogenase (cytochrome) (*Coxiella burnetii* Dugway 5J108-111) gi|154706110|ref|YP_001424132.1|(154706110); pyruvate dehydrogenase (*Clavibacter michiganensis* subsp. *michiganensis* NCPPB 382) gi|148273312|ref|YP_001222873.1|(148273312); pyruvate oxidase (*Lactobacillus acidophilus* NCFM) gi|58338213|ref|YP_194798.1|(58338213); and pyruvate dehydrogenase (*Yersinia pestis* CO92) gi|16121638|ref|NP_404951.1|(16121638), the sequences of each accession number are incorporated herein by reference.

L-threonine 3-dehydrogenase (EC 1.1.1.103) catalyzes the conversion of L-threonine to L-2-amino-3-oxobutanoate. The gene tdh encodes an L-threonine 3-dehydrogenase. There are approximately 700 L-threonine 3-dehydrogenases from bacterial organism recognized in NCBI. Various homologs and variants of tdh include, for example, L-threonine 3-dehydrogenase gi|135560|sp|P07913.1|TDH_ECOLI (135560); L-threonine 3-dehydrogenase gi|166227854|sp|A4TSC6.1|TDH_YERPP(166227854); L-threonine 3-dehydrogenase gi|166227853|sp|A1JHX8.1|TDH_YERE8(166227853); L-threonine 3-dehydrogenase gi|166227852|sp|A6UBM6.1|TDH_SINMW(166227852); L-threonine 3-dehydrogenase gi|166227851|sp|A1RE07.1|TDH_SHESW(166227851); L-threonine 3-dehydrogenase gi|166227850|sp|A0L2Q3.1|TDH_SHESA(166227850); L-threonine 3-dehydrogenase gi|166227849|sp|A4YCC5.1|TDH_SHEPC(166227849); L-threonine 3-dehydrogenase gi|166227848|sp|A3QJC8.1 |TDH_SHELP(166227848); L-threonine 3-dehydrogenase gi|166227847|sp|A6WUG6.1|TDH_SHEB8(166227847); L-threonine 3-dehydrogenase gi|166227846|sp|A3CYN0.1|TDH_SHEB5 (166227846); L-threonine 3-dehydrogenase gi|166227845|sp|A1S1Q3.1|TDH_SHEAM(166227845); L-threonine 3-dehydrogenase gi|166227844|sp|A4FND4.1|TDH_SACEN(166227844); L-threonine 3-dehydrogenase gi|166227843|sp|A1SVW5.1|TDH_PSYIN(166227843); L-threonine 3-dehydrogenase gi|166227842|sp|A51GK7.1|TDH_LEGPC(166227842); L-threonine 3-dehydrogenase gi|166227841|sp|A6TFL2.1|TDH_KLEP7(166227841); L-threonine 3-dehydrogenase gi|166227840|sp|A4IZ92.1|TDH_FRATW(166227840); L-threonine 3-dehydrogenase gi|166227839|sp|A0Q5K3.1|TDH_FRATN(166227839); L-threonine 3-dehydrogenase gi|166227838|sp|A7NDM9.1|TDH_FRATF(166227838); L-threonine 3-dehydrogenase gi|166227837|sp|A7MID0.1|TDH_ENTS8(166227837); and L-threonine 3-dehydrogenase gi|166227836|sp|A1AHF3.1|TDH_ECOK1(166227836), the sequences associated with each accession number are incorporated herein by reference.

Acetohydroxy acid synthases (e.g., ilvH) and acetolactate synthases (e.g., alsS, ilvB, ilvI) catalyze the synthesis of the branched-chain amino acids (valine, leucine, and isoleucine). IlvH encodes an acetohydroxy acid synthase in *E. coli* (see, e.g., acetohydroxy acid synthase AHAS III (IlvH) (*Escherichia coli*) gi|40846|emb|CAA38855.1|(40846), incorporated herein by reference, also see SEQ ID NO:45 and SEQ ID NO:46). Homologs and variants as well as operons comprising ilvH are known and include, for example, ilvH (*Microcystis aeruginosa* PCC 7806) gi|159026908|emb|CAO89159.1|(159026908); IlvH (*Bacillus amyloliquefaciens FZB*42) gi|154686966|ref|YP_001422127.1|(154686966); IlvH (*Bacillus amyloliquefaciens* FZB42) gi|154352817|gb|ABS74896.1|(154352817); IlvH (*Xenorhabdus nematophila*) gi|131054140|gb|AB032787.1|(131054140); IlvH (*Salmonella typhimurium*) gi|7631124|gb|AAF65177.1|AF117227_2(7631124), ilvN (*Listeria innocua*) gi|16414606|emb|CAC97322.1|(16414606); ilvN (*Listeria monocytogenes*) gi|16411438|emb|CAD00063.1|(16411438); acetohydroxy acid synthase (*Caulobacter crescentus*) gi|408939|gb|AAA23048.1|(408939); acetohydroxy acid synthase I, small subunit (*Salmonella enterica* subsp. *enterica* serovar Typhi) gi|16504830|emb|CAD03199.1|(16504830); acetohydroxy acid synthase, small subunit (*Tropheryma whipplei* TW08/27) gi|28572714|ref|NP_789494.1|(28572714); acetohydroxy acid synthase, small subunit (*Tropheryma whipplei* TW08/27) gi|28410846|emb|CAD67232.1|(28410846); acetohydroxy acid synthase I, small subunit (*Salmonella enterica* subsp. *enterica* serovar Paratyphi A str. ATCC 9150) gi|56129933|gb|AAV79439.1|(56129933); acetohydroxy acid synthase small subunit; acetohydroxy acid synthase, small subunit gi|551779|gb|AAA62430.1|(551779); acetohydroxy acid synthase I, small subunit (*Salmonella enterica* subsp. *enterica* serovar Typhi Ty2) gi|29139650|gb|AAO71216.1|(29139650); acetohydroxy acid synthase small subunit (*Streptomyces cinnamonensis*) gi|5733116|gb|AAD49432.1|AF175526_1(5733116); acetohydroxy acid synthase large subunit; and acetohydroxy acid synthase, large subunit gi|400334|gb|AAA62429.1|(400334), the sequences associated with the accession numbers are incorporated herein by reference. Acetolactate synthase genes include alsS and ilvI. Homologs of ilvI and alsS are known and include, for example, acetolactate synthase small subunit (*Bifidobacterium longum* NCC2705) gi|23325489|gb|AAN24137.1|(23325489); acetolactate synthase small subunit (*Geobacillus stearothermophilus*) gi|19918933|gb|AAL99357.1|(19918933); acetolactate synthase (*Azoarcus* sp. BH72) gi|119671178|emb|CAL95091.1|(119671178); acetolactate synthase small subunit (*Corynebacterium diphtheriae*) gi|38199954|emb|CAE49622.1|(38199954); acetolactate synthase (*Azoarcus* sp. BH72) gi|119669739|emb|CAL93652.1|(119669739); acetolactate synthase small subunit (*Corynebacterium jeikeium* K411) gi|68263981|emb|CAI37469.1|(68263981); acetolactate synthase small subunit (*Bacillus subtilis*) gi|1770067|emb|CAA99562.1|(1770067); acetolactate synthase isozyme 1 small subunit (AHAS-I) (acetohydroxy-acid synthase I small subunit) (ALS-I) gi|83309006|sp|P0ADF8.1|ILVN_ECOLI(83309006); acetolactate synthase large subunit (*Geobacillus stearothermophilus*) gi|19918932|gb|AAL99356.1|(19918932); and acetolactate synthase, small subunit (*Thermoanaerobacter tengcongensis* MB4) gi|20806556|ref|NP_621727.1|(20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. IlvC encodes an acetohydroxy acid isomeroreductase in *E. coli* (see, for example, SEQ ID NO:47 and SEQ ID NO:48). Homologs and variants of ilvC are known and include, for example, acetohydroxyacid reductoisomerase (*Schizosaccharomyces pombe* 972h-) gi|162312317|ref|NP_001018845.2|(162312317); acetohydroxyacid reductoisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxyacid reductoisomerase (*Saccharomyces cerevisiae*) gi|609403|gb|AAB67753.1|(609403); ACL198Wp (*Ashbya gossypii* ATCC 10895) gi|45185490|ref|NP_983206.1|(45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1||bbm|369068|bbs|165406 (957238); acetohydroxy-acid isomeroreductase; Ilv5g (*Saccharomyces cerevisiae*) gi|957236|gb|AAB33578.1||bbm|369064|bbs|165405 (957236); and ketol-acid reductoisomerase (*Schizosaccharomyces pombe*) gi|2696654|dbj|BAA24000.1|(2696654), each sequence associated with the accession number is incorporated herein by reference.

Dihydroxy-acid dehydratases catalyzes the fourth step in the biosynthesis of isoleucine and valine, the dehydratation of 2,3-dihydroxy-isovaleic acid into alpha-ketoisovaleric acid. IlvD, in for example *E. coli* (see SEQ ID NO: 49 and SEQ ID NO:50) and ilv3 encode a dihydroxy-acid dehydratase. Homologs and variants of dihydroxy-acid dehydratases are known and include, for example, IlvD (*Mycobacterium leprae*) gi|2104594|emb|CAB08798.1|(2104594); dihydroxy-acid dehydratase (*Tropheryma whipplei* TW08/27) gi|28410848|emb|CAD67234.1|(28410848); dihydroxy-acid dehydratase (*Mycobacterium leprae*) gi|13093837|emb|CAC32140.1|(13093837); dihydroxy-acid, dehydratase (*Rhodopirellula baltica* SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1|(49242408), each sequence associated with the accession numbers are incorporated herein by reference.

2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thI3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1|branched-chain alpha-keto acid decarboxylase (*Lactococcus lactis*); gi|15004729|ref|NP_149189.1| pyruvate decarboxylase (*Clostridium acetobutylicum* ATCC 824); gi|82749898|ref|YP_415639.1|probable pyruvate decarboxylase (*Staphylococcus aureus* RF122); gi|77961217|ref|ZP_00825060.1|COG3961: pyruvate decarboxylase and related thiamine pyrophosphate-requiring enzymes (*Yersinia mollaretii* ATCC 43969); gi|71065418|ref|YP_264145.1|putative pyruvate decarboxylase (*Psychrobacter arcticus* 273-4); gi|16761331|ref|NP_456948.1|putative decarboxylase (*Salmonella enterica* subsp. *enterica* serovar Typhi str. CT18); gi|93005792|ref|YP_580229.1|pyruvate decarboxylase (*Psychrobacter cryohalolentis* K5); gi|23129016|ref|ZP_00110850.1|COG3961: pyruvate decarboxylase and related thiamine pyrophosphate-requiring enzymes (*Nostoc punctiforme* PCC 73102); gi|16417060|gb|AAL18557.1|AF354297_1 pyruvate decarboxylase (*Sarcina ventriculi*); gi|15607993|ref|NP_215368.1|probable pyruvate or indole-3-pyruvate decarboxylase pdc (*Mycobacterium tuberculosis* H37Rv); gi|41406881|ref|NP_959717.1|pdc (*Mycobacterium avium* subsp. *paratuberculosis* K-10); gi|91779968|ref|YP_555176.1|putative pyruvate decarboxylase (*Burkholderia xenovorans* LB400); gi|15828161|ref|NP_302424.1|pyruvate (or indolepyruvate) decarboxylase (*Mycobacterium leprae* TN); gi|118616174|ref|YP_904506.1|pyruvate or indole-3-pyruvate decarboxylase Pdc (*Mycobacterium ulcerans* Agy99); gi|67989660|ref|NP_001018185.1|hypothetical protein SPAC3H8.01 (*Schizosaccharomyces pombe* 972h-); gi|21666011|gb|AAM73540.1|AF282847_1 pyruvate decarboxylase PdcB (*Rhizopus oryzae*); gi|69291130|ref|ZP_00619161.1|pyruvate decarboxylase: pyruvate decarboxylase (*Kineococcus radiotolerans* SRS30216); gi|66363022|ref|XP_628477.1|pyruvate decarboxylase (*Cryptosporidium parvum* Iowa II); gi|70981398|ref|XP_731481.1|pyruvate decarboxylase (*Aspergillus fumigatus* Af293); gi|121704274|ref|XP_001270401.1|pyruvate decarboxylase, putative (*Aspergillus clavatus* NRRL 1); gi|119467089|ref|XP|001257351.1|pyruvate decarboxylase, putative (*Neosartorya fischeri* NRRL 181); gi|26554143|ref|NP_758077.1|pyruvate decarboxylase (*Mycoplasma penetrans* HF-2); gi|21666009|gb|AAM73539.1|AF282846_1 pyruvate decarboxylase PdcA (*Rhizopus oryzae*).

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh 6 and sfa1 (see, e.g., SFA (*Saccharomyces cerevisiae*) gi|288591|emb|CAA48161.1|(288591); the sequence associated with the accession number is incorporated herein by reference, see also SEQ ID NO: 40 and SEQ ID NO:41).

Citramalate synthase catalyzes the condensation of pyruvate and acetate. CimA encodes a citramalate synthase in, for example, *Methanocaldococcus jannaschii* (SEQ ID NO:61 and SEQ ID NO:62) or *Leptospira interrogans* (SEQ ID NO:73 and SEQ ID NO: 74). Homologs and variants are known and include, for example, citramalate synthase (*Leptospira biflexa* serovar Patoc) gi|116664687|gb|ABK13757.1|(116664687); citramalate synthase (*Leptospira biflexa* serovar Monteralerio) gi|116664685|gb|ABK13756.1|(116664685); citramalate synthase (*Leptospira interrogans* serovar Hebdomadis) gi|116664683|gb|ABK13755.1|(116664683); citramalate synthase (*Leptospira interrogans* serovar Pomona) gi|116664681|gb|ABK13754.1|(116664681); citramalate synthase (*Leptospira interrogans* serovar Australis) gi|116664679|gb|ABK13753.1|(116664679); citramalate synthase (*Leptospira interrogans* serovar Autumnalis) gi|116664677|gb|ABK13752.1|(116664677); citramalate synthase (*Leptospira interrogans* serovar Pyrogenes) gi|116664675|gb|ABK13751.1|(116664675); citramalate synthase (*Leptospira interrogans* serovar Canicola) gi|116664673|gb|ABK13750.1|(116664673); citramalate synthase (*Leptospira interrogans* serovar Lai) gi|116664671|gb|ABK13749.1|(116664671); CimA (*Leptospira meyeri* serovar Semaranga) gi|119720987|gb|ABL98031.1|(119720987); (R)-citramalate synthase gi|2492795|sp|Q58787.1|CIMA_METJA(2492795); (R)-citramalate synthase gi|22095547|sp|P58966.1|CIMA_METMA(22095547); (R)-citramalate synthase gi|22001554|sp|Q8TJJ1.1|CIMA_METAC(22001554); (R)-citramalate synthase gi|22001553|sp|026819.1|CIMA_METTH(22001553); (R)-citramalate synthase gi|22001555|sp|Q8TYB1.1|CIMA_METKA(22001555); (R)-citramalate synthase (*Methanococcus maripaludis* S2) gi|45358581|ref|NP_988138.1|(45358581); (R)-citramalate synthase (*Methanococcus maripaludis* S2) gi|44921339|emb|CAF30574.1|(44921339); and similar to (R)-citramalate synthase (*Candidatus Kuenenia* stuttgartiensis) gi|91203541|emb|CAJ71194.1|(91203541), each sequence associated with the foregoing accession numbers is incorporated herein by reference.

A deaminase of the present invention include, for example, aspartate ammonia lyase (4.3.1.1), L-serine ammonia lyase (E.C. 4.3.1.17), D-serine ammonia lyase (4.3.1.18), threonine ammonia lyase (E.C. 4.3.1.19), tyrosine ammonia lyase (E.C. 4.3.1.23), phenylalanine ammonia lyase (E.C. 4.3.1.24), and phenylalanine/tyrosine ammonia lyase (E.C. 4.3.1.25). Homologs and variants are known and include, for example, homologs and variants isolated from, for example *Proteus, Sinorhizobium, Streptomyces, Bordetella, Gluconacetobacter, Acinetobacter, Pseudomonas, Ralstonia, Rhizo-*

*bium, Ruegeria, Burkholderia, Roseobacter, Nocardia, Thioalkalivibrio, Kineococcus, Tsukamurella, Escherichia*, and the like. In a particular embodiment the deaminase gene is sdaB. The nucleotide sequence of the sdaB gene of *E. coli* and its corresponding amino acid sequence are set forth as SEQ ID NO: 117 and SEQ ID NO:118.

A dehydrogenase of the present invention includes, for example, a glutamate dehydrogenase (E.C. 1.4.1.2 and E.C. 1.4.1.4), a glutamic dehydrogenase (E.C. 1.4.1.3), a valine dehydrogenase (E.C. 1.4.1.8), a leucine dehydrogenase (E.C. 1.4.1.9), and/or a phenylalanine dehydrogenase (E.C. 1.4.1.20). In a certain embodiment the leucine dehydrogenase is LeuDH which can be from *Thermoactinomyces intermedius* (SEQ ID NO:119 and SEQ ID NO: 120. Additional homologs and variants are well known in the art.

A transaminase of the present invention includes, for example, an L-α-transaminase (E.C. 2.6.1.X, where X is any number). In certain embodiments, the L-α-transaminase is a L-aspartate transaminase (E.C.2.6.1.1), L-alanine transaminase (E.C. 2.6.1.12 and E.C. 2.6.1.47), L-asparagine transaminase (E.C. 2.6.1.14), or a glycine transaminase (E.C. 2.6.1.35). In a certain embodiment the L-aspartate transaminase is AvtA. The AvtA gene can be from *Escherichia coli, Neisseria meningitidis, Pantoea ananatis, Amycolatopsis mediterranei, Mannheimia succinicproducens, Salmonella enterica*, or *Yersinia pestis*. The nucleotide sequence and amino acid sequence of AvtA from *E. coli* is provided as SEQ ID NO: 121 and SEQ ID NO: 122.

In one embodiment a microorganism of the disclosure can be characterized as an *E. coli* comprising rrnBT14DlacZWJ16 hsdR514DaraBADAH33 DrhaBADLD78 (with F' transduced from XL-1 blue to supply lacIq), ΔadhE, ΔldhA, ΔfrdBC, Δfnr, Δpta and ΔpflB and containing plasmids pSA55 and pSA69, wherein plasmid pSA55 is a ColE1 origin derived plasmid with kivd (*Lactococcus lactis*, SEQ ID NO: 31 and SEQ ID NO:32) and adh2 (*Saccharomyces cerevisiae* SEQ ID NO:41 and 42)) genes under the control of the pLlacO1 and an ampicillin resistance gene and plasmid pSA69 is a p15A origin derived plasmid with alsS (*Bacillus subtilis*; SEQ ID NO: 85 and SEQ ID NO:86), ilvC (*E. coli*; SEQ ID NO:47 and SEQ ID NO:48) and ilvD (*E. coli*; SEQ ID NO:49 and SEQ ID NO:50) genes under the control of the pLlacO1 and a kanamycin resistance gene.

In another embodiment a microorganism of the disclosure can be characterized as an *E. coli* comprising rrnBT14DlacZWJ16 hsdR514DaraBADAH33 DrhaBADLD78 (with F' transduced from XL-1 blue to supply lacIq), ΔmetA, Δtdh, ΔilvB, ΔilyI and ΔadhE with plasmids pCS49, pSA62 and pSA55I, wherein plasmid pSA55I comprises a ColE1 origin derived plasmid with kivd (*Lactococcus lactis*) and adh2 (*Saccharomyces cerevisiae*) genes under the control of the pLlacO1 and an ampicillin resistance gene with lacI after the ampicillin resistance gene, plasmid pSA62 is a p15A origin derived plasmid with ilvA (*E. coli*; SEQ ID NO:51 and SEQ ID NO:52) and leuABCD (*E. coli*) genes (individual nucleotide and amino acid sequences for leuA, leuB, leuC and leuD are provided as SEQ ID NO:53 through SEQ ID NO:60, and SEQ ID NO:75 through 80) under the control of the pLlacO1 and a kanamycin resistance gene, and plasmid pCS49 is a pSC101* origin derived plasmid with thrA(fbr)BC (*E. coli*) genes under the control of the pLlacO1 and a spectinomycin resistance gene.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, (1990), *Meth. Enzymol.* 183:63-98 hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

It is understood that a range of microorganisms can be modified to include a recombinant metabolic pathway suitable for the production of, e.g., various chemical entities. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ((NaCl)); and extreme (hyper) thermophilus (prokaryotes that live at very high temperatures). Besides the unifying archaeal features that distinguish them from Bacteria (i.e., no murein in cell wall, ester-linked membrane lipids, and the like), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria," or "eubacteria," refers to a domain of prokaryotic organisms. Bacteria include at least 11 distinct groups as follows: (1) Gram-positive (gram+) bacteria, of which there are two major subdivisions: (1) high G+C group (Actinomycetes, *Mycobacteria, Micrococcus*, and others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles.*

"Gram-negative bacteria" include cocci, nonenteric rods, and enteric rods. The genera of Gram-negative bacteria include, for example, *Neisseria, Spirillum, Pasteurella, Bru-*

*cella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or over-express endogenous polynucleotides, or to express non-endogenous sequences, such as those included in a vector, or which have a reduction in expression of an endogenous gene. The polynucleotide generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

A "parental microorganism" refers to a cell used to generate a recombinant microorganism. The term "parental microorganism" describes a cell that occurs in nature, i.e., a "wild-type" cell that has not been genetically modified. The term "parental microorganism" also describes a cell that has been genetically modified but which does not express or over-express a target enzyme, e.g., an enzyme involved in the biosynthetic pathway for the production of a desired metabolite. For example, a wild-type microorganism can be genetically modified to express or over express a first target enzyme such as thiolase. This microorganism can act as a parental microorganism in the generation of a microorganism modified to express or overexpress a second target enzyme, e.g., hydroxybutyryl CoA dehydrogenase. In turn, the microorganism modified to express or overexpress e.g., thiolase and hydroxybutyryl CoA dehydrogenase can be modified to express or over express a third target enzyme, e.g., crotonase. Accordingly, a parental microorganism functions as a reference cell for successive genetic modification events. Each modification event can be accomplished by introducing a nucleic acid molecule in to the reference cell. The introduction facilitates the expression or over-expression of a target enzyme. It is understood that the term "facilitates" encompasses the activation of endogenous polynucleotides encoding a target enzyme through genetic modification of, e.g., a promoter sequence in a parental microorganism. It is further understood that the term "facilitates" encompasses the introduction of exogenous polynucleotides encoding a target enzyme in to a parental microorganism.

In another embodiment a method of producing a recombinant microorganism that converts a suitable carbon substrate to, e.g., 1-propanol, isobutanol, 1-butanol, 2-methyl 1-butanol, 3-methyl 1-butanol or 2-phenylethanol is provided. The method includes transforming a microorganism with one or more recombinant polynucleotides encoding polypeptides that include, for example, acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), 2-isopropylmalate synthase (e.g., leuA), beta-isopropylmalate dehydrogenase (e.g., leuB), isopropylmalate isomerase (e.g., leuCD operon), threonine dehydratase (e.g., ilvA), alpha-isopropylmalate synthase (e.g., cimA), beta-isopropylmalate dehydrogenase (e.g., leuB), isopropylmalate isomerase (e.g., leuCD operon), threonine dehydratase (e.g., ilvA), acetolactate synthase (e.g., ilvMG or ilvNB), acetohydroxy acid isomeroreductase (e.g., ilvC), dihydroxy-acid dehydratase (e.g., ilvD), beta-isopropylmalate dehydrogenase (e.g., leuB), chorismate mutase P/prephenate dehydratase (e.g., pheA, such as for example the nucleotide and amino acid sequence depicted as SEQ ID NO:81 and SEQ ID NO:82), chorismate mutase T/prephenate dehydrogenase (e.g., tyrA, such as for example the nucleotide and amino acid sequence depicted as SEQ ID NO:83 and SEQ ID NO:84)), 2-keto-acid decarboxylase (e.g., kivd, PDC6, or THIS), and alcohol dehydrogenase activity. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants. In particular embodiments, the method also includes knocking out the expression of a gene selected from the group consisting of glnA, gdhA, lsrA, luxS or any combination thereof.

In still another embodiment, a method of producing a recombinant microorganism that converts a suitable carbon substrate to, e.g., adipic acid, gamma-aminobuytric acid is provided. The method includes transforming a microorganism with one or more recombinant polynucleotides. The method can also include in certain embodiments knocking out the expression of a gene selected from the group consisting of glnA, gdhA, lsrA, luxS or any combination thereof.

A "protein" or "polypeptide," which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

It is understood that the polynucleotides described above include "genes" and that the nucleic acid molecules described above include "vectors" or "plasmids." For example, a polynucleotide encoding a keto thiolase can be encoded by an atoB gene or homolog thereof, or a fadA gene or homolog thereof. Accordingly, the term "gene," also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

"Transformation" refers to the process by which a vector is introduced into a host cell. Transformation (or transduction, or transfection) can be achieved by any one of a number of means including electroporation, microinjection, biolistics (or particle bombardment-mediated delivery), or agrobacterium mediated transformation.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the heterologous expression of one or more of the biosynthetic genes involved in alcohol, (such as, 1-propanol, isobutanol, 1-butanol, 2-methyl 1-butanol, 3-methyl 1-butanol or 2-phenylethanol), acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM), and the like biosynthesis and recombinant DNA expression vectors useful in the method. Thus, included within the scope of the disclosure are recombinant expression vectors that include such nucleic acids. The term "expression vector" refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433) can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

A nucleic acid of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment, a method for producing, e.g., alcohols, (such as, 1-propanol, isobutanol, 1-butanol, 2-methyl 1-butanol, 3-methyl 1-butanol or 2-phenylethanol), acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM), and the like is provided. The method includes culturing a recombinant microorganism as provided herein in the presence of a suitable substrate (e.g., a nitrogen-rich biomass) and under conditions suitable for the conversion of the substrate to an alcohol, (such as, 1-propanol, isobutanol, 1-butanol, 2-methyl 1-butanol, 3-methyl 1-butanol or 2-phenylethanol), acetaldehyde, acetate, isobutyaldehyde, isobutyric acid, n-butyraldehyde, n-butyric acid, 2-methyl-1-butyraldehyde, 2-methyl-1-butyric acid, 3-methyl-1-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and/or S-adenosyl-methionine (SAM) and the like. The method may include the recombinant microorganism in a bioreactor system as part of a larger production system that includes biodiesel production from algae lipids. The products produced by a microorganism provided herein can be detected by any method known to the skilled artisan. Culture conditions suitable for the growth and maintenance of a recombinant microorganism provided herein are described in the Examples below. The skilled artisan will recognize that such conditions can be modified to accommodate the requirements of each microorganism.

As previously discussed, general texts which describe molecular biological techniques useful herein, including the use of vectors, promoters and many other relevant topics, include Berger and Kimmel, *Guide to Molecular Cloning Techniques, Methods in Enzymology Volume* 152, (Academic Press, Inc., San Diego, Calif.) ("Berger"); Sambrook et al., *Molecular Cloning—A Laboratory Manual,* 2d ed., Vol. 1-3, Cold Spring Harbor Laboratory, Cold Spring Harbor, N.Y., 1989 ("Sambrook"), and *Current Protocols in Molecular Biology*, F. M. Ausubel et al., eds., *Current Protocols*, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) *PCR Protocols: A Guide to Methods and Applications* (Academic Press Inc. San Diego, Calif.) ("Innis"); Arnheim & Levinson (Oct. 1, 1990) C&EN 36-47; *The Journal of NIH Research* (1991) 3:81-94; Kwoh et al. (1989) *Proc. Natl. Acad. Sci. USA* 86:1173; Guatelli et al. (1990) *Proc. Nat'l. Acad. Sci. USA* 87:1874; Lomell et al. (1989) *J. Clin. Chem*

35:1826; Landegren et al. (1988) *Science* 241:1077-1080; Van Brunt (1990) *Biotechnology* 8:291-294; Wu and Wallace (1989) *Gene* 4:560; Barringer et al. (1990) *Gene* 89:117; and Sooknanan and Malek (1995) *Biotechnology* 13:563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369:684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Appropriate culture conditions are conditions of culture medium pH, ionic strength, nutritive content, and the like; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

Methods, vectors and polynucleotides useful for synthesis of alcohols from 2-keto acids are disclosed, for example, in U.S. Patent Application Publication Nos. 20100221800 and 20100209986, 20090081746, the disclosures of which are incorporated herein by reference. The present disclosure provides methods of generating various useful intermediates from a proteinacious biomass, these intermediates can subsequently be metabolized to various alcohols and chemical compositions.

The recombinant microorganisms of the disclosure can be modified to convert a nitrogen containing biomass, such as proteinacious biomass, to various intermediates and those intermediates can, in turn, be converted to additional chemicals and/or biofuels as set forth below:

serine, glycine, alanine, cysteine===>pyruvate;

glutamate, glutamine, proline, arginine====>2-KG (2-ketoglutarate);

aspartate, asparagine===>OAA (oxaloacetate);

threonine===>2-KB (2-ketobutyrate);

valine===>2-KIV (2-ketoisovalerate);

leucine====>2-KIC (2-ketoisocaproate); and isoleucine===>2-KMV (2-keto-3-methylvalerate).

The products produced from a biomass via the above intermediates can be further metabolized by recombinant microorganisms or wild-type microorganism as follows:

pyruvate to: ethanol, acetate, acetaldehyde, isobutanol, isobutyraldehyde, n-butanol, n-butyraldehyde, 2,3-butanediol, L-lactic acid, D-lactic acid, aromatics (tryptophan, tyrosine, phenylalanine, shikimic acid), PHB (polyhydroxybutyrate), mevalonate, isoprenoids, fatty acids and all chemicals listed in below (from other intermediates);

2-KG (2-ketoglutarate) to: GABA(4-aminobutyric acid), glutamic acid, succinate, malic acid;

OAA (oxaloacetate) to: aspartic acid, lysine, cadeverine, 2-ketoadipic acid, threonine, methionine, SAM (S-adenosylmethionine);

2-KB (2-ketobutyrate) to: 2-methyl-1-butanol, 2-meth yl-1-butyraldehyde, isoleucine, homoalanine;

2-KIV (2-ketoisovalerate) to: isobutanol, isobutyraldehyde, 3-methyl-1-butanol, 3-methyl-1-butyraldehyde, valine;

2-KIC (2-ketoisocaproate) to: 3-methyl-1-butanol, 3-methyl-1-butyraldehyde, leucine; and 2-KMV (2-keto-3-methylvalerate) to: 2-methyl-1-butanol, 2-methyl-1-butyraldehyde, isoleucine.

The disclosure is illustrated in the following examples, which are provided by way of illustration and are not intended to be limiting.

EXAMPLES

*Escherichia coli* was chosen as the host organism for engineering, because of the versatility demonstrated by this organism. To test the efficiency of *E. coli* for utilizing algal amino acids, the cells were grown in yeast extract or mixtures of 20 amino acids, which were used to simulate algae extract. As expected, *E. coli* grew well in these rich media. However, the utilization of amino acids was incomplete, presumably due to the imbalance of amino acids and the lack of pathways for degradation of branched chain amino acids (BCAA). Wild-type *E. coli* could utilize only 4 of the amino acids (Ala, Asp, Pro and Gln) individually as the sole carbon source to form colonies. When introducing the isobutanol synthesis pathway (overexpression of alsS, ilvC, ilvD, KivD and AdhA genes) into *E. coli*, the cell could only produce 0.17 g/L of isobutanol from the medium containing 4% yeast extract supplemented with M9 salts (Table 4, below), representing 2.3% of the theoretical yield.

TABLE 4

Higher alcohol (C ≥ 4) production in *E. coli* from a yeast extract medium containing 21.6 g/L amino acids, of which 14 amino acids could be converted to higher alcohol by *E. coli*. The theoretical maximum titer is 7.24 gram per liter. The products were identified by GC-MS and quantified by GC-FID.

| Strain | Gene Overexpressed | Consumed AA (g/L) | Biomass (g/L) | Alcohol C ≥ 4 (g/L) | % of Theor-yield |
|---|---|---|---|---|---|
| JCL16 | none | 19.8 ± 0.4 | 3.6 ± 0.3 | 0 | 0 |
| YH19 | none | 18.3 ± 0.5 | 3.8 ± 0.4 | 0 | 0 |
| JCL16 | alsS, ilvC, ilvD, kivd, adhA | 17.7 ± 0.9 | 1.1 ± 0.2 | 0.17 ± 0.02 | 2.3 |
| YH19 | alsS, ilvC, ilvD, kivd, adhA | 16.6 ± 0.8 | 1.2 ± 0.2 | 0.4 ± 0.03 | 5.6 |
| YH19ΔluxS | alsS, ilvC, ilvD, kivd, adhA | 16.7 ± 0.7 | 2.0 ± 0.3 | 0.9 ± 0.1 | 12.4 |
| YH19ΔlsrA | alsS, ilvC, ilvD, kivd, adhA | 16.8 ± 0.5 | 1.9 ± 0.2 | 1.0 ± 0.06 | 13.1 |
| YH19ΔglnAΔgdhA | alsS, ilvC, ilvD, kivd, adhA | 10.0 ± 0.5 | 0.6 ± 0.1 | 0.4 ± 0.05 | 5.8 |

TABLE 4-continued

Higher alcohol (C ≥ 4) production in *E. coli* from a yeast extract medium containing 21.6 g/L amino acids, of which 14 amino acids could be converted to higher alcohol by *E. coli*. The theoretical maximum titer is 7.24 gram per liter. The products were identified by GC-MS and quantified by GC-FID.

| Strain | Gene Overexpressed | Consumed AA (g/L) | Biomass (g/L) | Alcohol C ≥ 4 (g/L) | % of Theor-yield |
|---|---|---|---|---|---|
| YH19ΔglnAΔgdhAΔluxS | alsS, ilvC, ilvD, kivd, adhA | 9.5 ± 0.5 | 0.7 ± 0.1 | 1.3 ± 0.2 | 18.4 |
| YH19ΔglnAΔgdhAΔlsrA | alsS, ilvC, ilvD, kivd, adhA | 9.7 ± 0.4 | 0.7 ± 0.1 | 1.5 ± 0.1 | 20.6 |
| YH19ΔglnAΔgdhAΔlsrAΔilvE | alsS, ilvC, ilvD, kivd, adhA | 8.9 ± 0.5 | 0.6 ± 0.1 | 1.2 ± 0.1 | 16.7 |
| YH19ΔglnAΔgdhAΔlsrA | alsS, ilvC, ilvD, leuDH, kivd, yqhD | 17.0 ± 0.3 | 0.7 ± 0.1 | 3.8 ± 0.2 | 52.8 |
| YH19ΔglnAΔgdhAΔlsrAΔilvE | alsS, ilvC, ilvD, leuDH, kivd, yqhD | 11.1 ± 0.4 | 0.6 ± 0.1 | 3.6 ± 0.3 | 49.1 |
| YH19ΔglnAΔgdhAΔlsrA | alsS, ilvC, ilvD, avtA, leuDH, kivd, yqhD | 17.2 ± 0.2 | 0.7 ± 0.1 | 3.9 ± 0.3 | 53.8 |
| YH19ΔglnAΔgdhAΔlsrA | alsS, ilvC, ilvD, avtA, leuDH, kivd, yqhD, ilvE, ilvA, sdaB | 18.0 ± 0.3 | 0.7 ± 0.1 | 4.0 ± 0.3 | 55.7 |

To improve amino acid utilization, a series of chemical mutagenesis were performed followed by growth on either single or multiple amino acids. After multiple rounds of mutagenesis, enrichment, and selection, a strain (YH19) was obtained, which is able to utilize up to 13 amino acids individually as the sole carbon source. This strain could produce a higher amount of isobutanol in the presence of isobutanol pathway genes compared to the wild-type host with the same pathway genes. To further improve the amino acid utilization, a carbon-flux-driven approach was used by overexpressing the individual amino acid degradation genes in *E. coli*. However, this approach achieved only minor success (FIGS. 6A and 6B), presumably due to various regulatory mechanisms that control carbon and nitrogen flux.

Figure 2A:
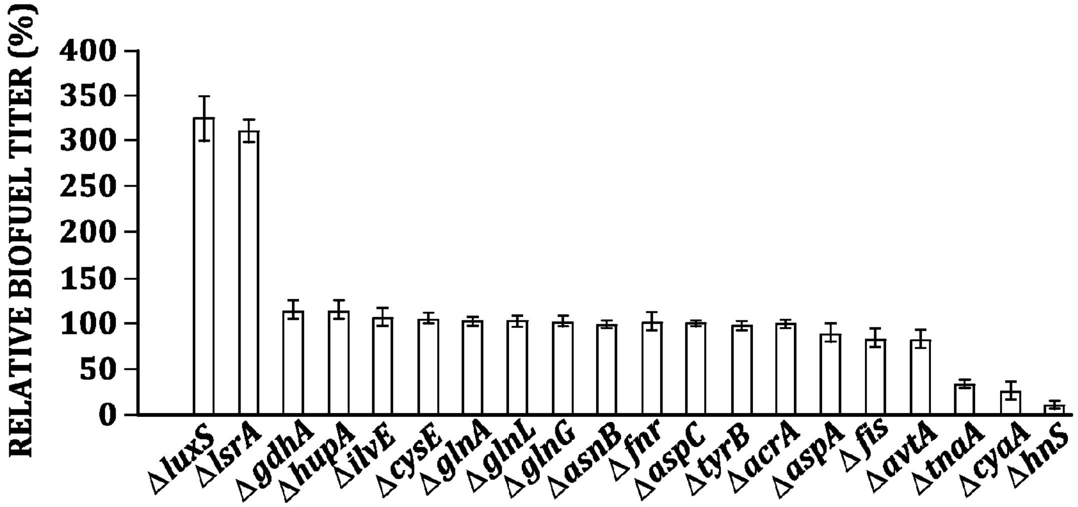
FIG. 2A-C shows the effect of inactivating quorum sensing on the biofuel production. Error bars indicate s.d. (A) Relative biofuel production titer from twenty stains containing different gene knockouts. The biofuel production titer from the wild type strain is used as the normalization basis. (B and C) The biofuel production (B) and OD (C) from YH19 (an improved amino acid utilizing strain) and its quorum sensing gene knockout derivatives, with and without overexpressing the isobutanol production pathway genes (*Bacillus subtilis* alsS, *Escherichia coli* ilvCD, *Lactococcus lactis* kivd and adhA).
Figure 2B:
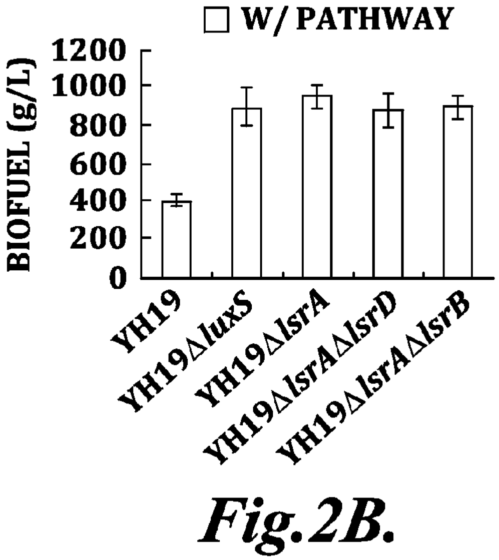
Figure 2C:
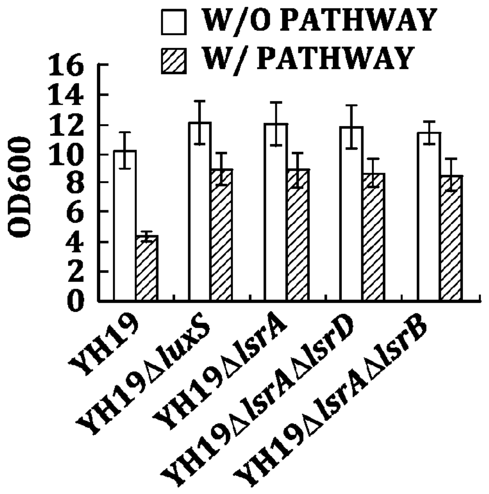

To deactivate the native regulation and competing pathways in *E. coli* to allow better production of higher alcohols from amino acids further genetic manipulation was performed. Twenty target genes were chosen to knockout based on their potential impact on carbon and nitrogen metabolism and screened for improved production (FIG. 2A). Among these knockout strains, the quorum sensing negative mutants, ΔlsrA and ΔluxS, showed an increased production in the presence of the isobutanol pathway (FIG. 2A). LuxS is autoinducer-2 (AI-2) synthase and LsrA is one of the subunits of the AI-2 transporter (LsrABCD). The transporter is involved in the re-uptake of extracellular during transition into the stationary phase. Deletion of genes encoding LuxS or AI-2 transporter subunits from YH19 increased the biofuel production (FIGS. 2B and 2C). Since AI-2 uptake is inhibited by glucose, these deletions had no effect in glucose medium, as expected. The deletion also did not show a significant phenotype in cells without the isobutanol pathway. These results suggest that AI-2 re-uptake at the late growth phase may be involved in carbon and nitrogen regulation. The role of AI-2 system in amino acid utilization and fuel production remains to be characterized.

Since the carbon-flux-driven strategy only achieved limited success, a nitrogen-centric strategy in addition to inactivating quorum sensing was examined. This strategy used the secretion of ammonia instead of carbon compounds to drive the thermodynamic gradient toward the desired direction. To block ammonia re-uptake, the two ammonium assimilation genes, gdhA and glnA, were deleted to drive the nitrogen flux towards deamination. This approach improved the degradation of several amino acids (Thr, Gly, Ser, Cys, Asn, Arg and Gln) that directly generate ammonia during degradation (FIG. 3A). Indeed, deletion of gdhA and glnA increased the production of alcohols in the presence of the isobutanol pathway (Table 4). However, other amino acids (Asp, Ala, Leu, Ile, Val) are degraded via transamination, and the amino groups are transferred to 2-ketoglurate to form glutamate (FIG. 3B). In addition, the carbon skeleton of some amino acids are converted to glutamate directly (Gln and Pro) after deamination or reduction (FIG. 3A). The amino group on glutamate is further redistributed to BCAA. Indeed, glutamate and the BCAA accumulated in the medium as a result of transamination during the course of the bacteria cultivation. It appears that these groups of amino acids serve as the nitrogen reservoir in the cell to keep the reduced nitrogen inside the cell.

To drain the intracellular nitrogen reservoir, several transamination/deamination cycles were designed. First, IlvE and LeuDH form a cycle (FIG. 3C) to drain the glutamate pool (along with Asp, and Ala) to excrete ammonia via Leu and Ile. Second, IlvE, AvtA, DadX and DadA form another cycle to drain the glutamate pool to ammonia via Val, L-Ala, and D-Ala (FIG. 3D). Finally, SerC, SerB, SdaB, PpsA, Eno, and GpmA form the third cycle to drain ammonia via Ser (FIG. 3E)). The genes ilvA (FIG. 3A), ilvE (FIG. 3C) and sdaB (FIG. 3E) do not need to be overexpressed when Thr, Glu and Ser are depleted, which occurs near the transition into the stationary phase. Therefore, these genes were expressed from the rrnB promoter, which is a $\sigma^{70}$-dependent promoter and is not fully functional in the stationary phase due to the competition of $\sigma^{s}$, which dominates the core polymerase binding in the stationary phase. This strategy successfully increased the yield of biofuels (isobutanol, 2MB, 3MB) to 4.0 g/L, 55.7% of the theoretical yield (Table 4; FIG. 10).

The remaining amino acids (rAAs) include Lys, Met, His, and the three aromatic amino acids. The metabolic conditions for degrading the rAAs are much different compared to the 14 fuel-convertible amino acids (fcAAs). Thus, it would be beneficial to use another strategy for converting the rAAs. This second strategy involves redistributing the rAAs into proteins containing all 20 amino acids, which are then fed back to the protein biomass stream to be recycled. To do so, the rAAs are used as carbon and nitrogen sources for growing organisms such as *Pseudomonas*. This bacterial growth process converts rAAs to all 20 AAs and generates ammonia and methanethiol, which can be recycled as N and S sources to support algal growth after processing. The theoretical yield for using the six rAAs to grow *Pseudomonas* is 41.4%, which contains 77.9% fcAA (Table 8). Thus, the first organism (e.g., *E. coli*) converts 14 amino acids into fuels, and the second organism (e.g., *Pseudomonas*, or *Bacillus*) converts the rAAs back to the 14 fcAAs. The use of the two-stage conversion has advantages, since the two processes require different amounts of aeration. In addition, some of the rAAs may be used as chemical feedstocks or for other applications. Separating the process into two will increase flexibility.

Since the minimal lipid content of algae is about 10%, this scenario was used to map the complete mass flow (FIG. 4A) of the process. The minimal size of the open ponds needed to produce 60 billion gallons of biofuels based on the algal biomass productivity of such protein-rich species (FIG. 4A) is about 21,420 square kilometers, equivalent to 1.6% of the U.S. agriculture land. Because of the ability to use high protein native algal species, these organisms are acclimated to local salinity, temperature, and pH, and do not require closed photobioreactors. In this scenario, 56.3 million tons of nitrogen, and 2.1 million tons of sulfur are recycled for algal growth. The carbon produced during bioconversion and fuel combustion is eventually recaptured by the algal species.

Calculation for Plant Process Scenario:

1) Fertilizer-N Needed to Produce 60 Billion Gallons of Ethanol by Plant Process=9.4 Million Tons.

Sixty billion (gallons of ethanol) multiplied by 3.785 (liters per gallon), multiplied by 0.789 (kg per liter (ethanol density))=179.18 billion kilograms of ethanol produced by the plant scenario.

179.18 billion (kilograms of ethanol) divided by 0.5 (grams of ethanol per gram of glucose (or 50% yield)), and then divided by 60% (glucose yield of corn)=597.27 billion kilograms of corn needed.

To calculate fertilizer input, 597.273 billion (kilograms of corn) is multiplied by 9.8% (protein content of corn), and then by 16% (percentage of nitrogen in protein by weight). This final multiplication gives $9.4\times10^9$ kilograms of nitrogen, which is equivalent to 9.4 million tons.

2) Energy Cost to Produce 9.4 Million Tons Fertilizer-N=$536\times10^{12}$ Kilojoules.

$9.4\times10^9$ (kilograms of nitrogen) multiplied by 57 (megajoules needed to produce one kilogram of fertilizer-N)=$536\times10^{12}$ kilojoules.

3) Ratio of Fertilizer-N Energy Input of Ethanol Production to the Ethanol Energy Content=11.2%.

Ethanol energy content equals 60 billion (gallons of ethanol) multiplied by 79.9 (megajoules per gallon (lower heating value of ethanol)), which gives $4{,}794\times10^{12}$ (kilojoules). $536\times10^{12}$ (kilojoules required for fertilizer synthesis) divided by this number=11.2%.

Today's fertilizer-N energy input of ethanol production is calculated in another method. Energy cost of fertilizer-N is calculated as 57 MJ/Kg, and N application rate is 150 kg/ha. It gives an energy cost of fertilizer-N as 8,550 MJ/ha. The ethanol energy yield per land area is calculated as 73,424 MJ/ha. Therefore, the ratio of fertilizer-N energy input of ethanol production to the ethanol energy content is 11.64%. This number is slightly higher compared with our above calculation, confirming that our assumptions are reasonable.

4) The N-Rich Biomass Accumulated when 60 Billion Gallons of Ethanol are Produced by Plant Process=164 Million Tons of DDGS.

60 billion (gallons of ethanol) multiplied by 2.73 (kilograms of DDGS produced per gallon of ethanol)=164 million tons of DDGS.

5) Ratio of 164 Million Tons of N-Rich Biomass to the Potential Annual US DDGS Market=390%.

164 million (tons of DDGS) divided by 42 million (tons of DDGS (potential annual US DDGS market))=390%.

6) Annual Ethanol Productivity to Satisfy the Potential Annual US DDGS Market=15.4 Billion Gallons.

60 billion (gallons of ethanol annually) divided by 390%=15.4 billion gallons of ethanol to satisfy the US DDGS market.

7) Percentage of 15.4 Billion Gallons of Ethanol to the US Annual Fuel Consumption=7.7%.

15.4 billion (gallons of ethanol) divided by 200 billion (gallons (annual US fuel consumption))=7.7%.

Calculation of algal process scenario without nitrogen recycling (lipid content is 30%).

8) Fertilizer-N Needed to Produce 60 Billion Gallons of Biodiesel by Algal Process=35.5 Million Tons.

60 billion (gallons of biodiesel) multiplied by 3.785 (liters per gallon), multiplied by 0.88 (kilograms per liter (biodiesel's density))=199.848 billion kilograms of biodiesel.

199.848 billion (kilograms of biodiesel) divided by 90% (conversion ratio of lipid to biodiesel) gives 222.1 (kilograms lipid). Under nitrogen-stressed conditions, both lipid and protein each make up 30% of algal biomass by weight, thus giving 222.1 kilograms of protein.

222.1 billion (kilograms of protein) multiplied by 16% (percentage of nitrogen in protein by weight) gives 35.5 billion kilograms of nitrogen, which is equivalent to 35.5 million tons.

9) Energy Cost of Producing 35.5 Million Tons of Fertilizer-N=$2{,}024\times10^{12}$ Kilojoules.

35.5 billion (kilograms of nitrogen) multiplied by 57 (megajoules needed to produce one kilogram of fertilizer-N)= $2{,}024\times10^{12}$ kilojoules.

10) Ratio of Fertilizer-N Energy Input for Biodiesel Production to the Biodiesel Energy Content=25.8%.

Biodiesel energy content equals 60 billion (gallons of biodiesel) multiplied by 130.7 (megajoules per gallon (lower heating value of biodiesel)), which gives $7{,}842\times10^{12}$ (kilojoules). $2{,}024\times10^{12}$ (kilojoules required for fertilizer synthesis) divided by this number=25.8%.

11) The N-Rich Biomass Accumulated when 60 Billion Gallons of Biodiesel are Produced by Algal Process=589 Million Tons of DDGS.

60 billion (gallons of biodiesel) multiplied by 3.785 (liters per gallon), and then divided by 90% (conversion ratio of lipid to biodiesel) gives 252.3 liters of lipid. 252.3 (liters of lipid) divided by 30% (percentage of lipid content of biomass), and then multiplied by 70% (percentage of nitrogen-rich content of biomass) gives 589 billion kilograms or 589 million tons of DDGS.

12) Ratio of 589 Million Tons of N-Rich Biomass to the Potential Annual US DDGS Market=1,402%.

589 million (tons of DDGS) divided by 42 million (tons of DDGS (potential annual US DDGS market))=1,402%.

13) Annual Biodiesel Productivity to Satisfy the Potential Annual US DDGS Market=4.3 Billion Gallons.

60 billion (gallons of biodiesel annually) divided by 1,402%=4.3 billion gallons of biodiesel to satisfy the US DDGS market.

14) Percentage of 4.3 Billion Gallons of Biodiesel to the US Annual Fuel Consumption=2.1%.

4.3 billion [gallons of biodiesel] divided by 200 billion (gallons (annual US fuel consumption))=2.1%.

15) Minimal Size of Open Pond Needed to Produce 60 Billion Gallons of Biofuel=21,420 Kilometers Squared.

205 million [tons (carbon necessary to produce 60 billions gallons of biofuel)] divided by 52.443% (percentage of carbon content of biomass) gives 391 million tons of biomass per year. 391 million (tons of biomass per year) divided by 50 (grams per square meter per day (biomass productivity of algae in an open pond) (2)) gives area, which multiplied by the conversions for days to years, grams to million tons, and meters squared to kilometers squared gives 21,420 kilometers squared.

16) Percentage of California Equal to 21,420 Kilometers Squared=1.6%.

21,420 (kilometers squared) divided by 1.3 (million kilometers squared) (area of total US cropping land)=1.6%.

Restriction enzymes and Antarctic phosphatase were from New England Biolabs. KOD DNA polymerase was from EMD Chemicals. Rapid DNA ligation kit was from Roche. Yeast extract was from BD. Amino acids, 2-ketobutyrate, 2-ketoisovalerate, 2-ketovalerate, 2-keto-3-methyl-valerate and 2-keto-4-methyl-pentanoate were from Sigma. Oligonucleotides were from IDT. Amino acid standard (0.25 nmol/μL) and ophthaldialdehyde (OPA) were from Agilent Technologies.

The JCL16 strain is a BW25113 (rrn$B_{T14}$ ΔlacZ$_{WJ16}$ hsdR514 ΔaraBAD$_{AH33}$ ΔrhaBAD$_{LD78}$) derivative with F' transduced from XL-1 blue to supply lacI$^q$. Twenty Keio collection strains were used as shown in FIG. 2A. Genome-wide random mutagenesis by N-methyl-N'-nitro-N-Nitrosoguanidine (NTG) was used to achieve strains which could produce higher alcohol from nBCAA. After each round of the NTG treatment, mutations were screened for growth on an agar plate containing one individual nBCAA as sole carbon source. In addition, L-valine analogue DL-norvaline which is toxic to the cell partly due to its incorporation into polypeptide was added (2 g/L). Some mutant strains could survive such a challenge through over-producing L-valine to outcompete the analogue for polypeptide biosynthesis. Since L-valine's precursor, 2-keto-isovalerate (KIV), is also the precursor for isobutanol production, certain norvaline resistant strains might have had the ability to produce higher concentration of isobutanol, compared with the wild type strain, in the presence of the isobutanol pathway genes. After multiple rounds of NTG mutagenesis and screening, strain YH19 was obtained. Strain YH19 derivatives with certain gene deletions (such as ΔluxS, ΔlsrA, ΔlsrD, ΔlsrB, ΔglnA, ΔgdhA, ΔilvE) were created through P1 transduction. The strains containing both ΔglnA and ΔgdhA can use amino acids, but not ammonium salts as sole nitrogen source for growth. Phages were prepared from the Keio collection. Plasmid pCP20 was transformed into single colonies containing the correct deletions to remove the Kanamycin resistance marker.

A list of the plasmids used is given in Table 5. Construction of plasmids is described below, and the primers used are listed in Table 6.

TABLE 5

List of plasmids

| Plasmids | Overexpressed Genes | Origin | Resistance | Inducer | Reference |
|---|---|---|---|---|---|
| pSA55I | PLlacO1:kivd-adh2; lacI | colE1 | Ampicillin | IPTG | 1 |
| pSA65 | PLlacO1:kivd-adhA | colE1 | Ampicillin | IPTG | 2 |
| pSA69 | PLlacO1:alsS-ilvC-ilvD | p15A | Kanamycin | IPTG | 3 |
| pSA40 | Empty vector containing PLlacO1 | ColE1 | Kanamycin | IPTG | 1 |
| pSA74 | Empty vector containing PLlacO1 | PSC101 | Chloramphenicol | IPTG | This study |
| pYK | Empty vector containing PLlacO1 | ColA | Kanamycin | IPTG | This study |
| pYX41 | PLlacO1:kivd-yqhD-adhA | colE1 | Ampicillin | IPTG | This study |
| pYX45 | PLlacO1:kivd-yqhD-adhA-dadX | colE1 | Ampicillin | IPTG | This study |
| pYX47 | PLlacO1:kivd-yqhD-adhA-dadX-dadA | colE1 | Ampicillin | IPTG | This study |
| pYX51 | PLlacO1:leuDH; lacI | ColA | Kanamycin | IPTG | This study |
| pYX52 | PLlacO1:leuDH-avtA; lacI | ColA | Kanamycin | IPTG | This study |
| pYX54 | PLlacO1:alsS-ilvC-ilvD; PLlacO1:leuDH-avtA | p15A | Spectinomycin | IPTG | This study |
| pYX60 | PLlacO1:ilvE | PSC101 | Chloramphenicol | IPTG | This study |
| pYX61 | PLlacO1:ilvE-ilvA | PSC101 | Chloramphenicol | IPTG | This study |
| pYX62 | PLlacO1:ilvE-ilvA-tdcB | PSC101 | Chloramphenicol | IPTG | This study |
| pYX64 | PLlacO1:ilvE-ilvA-tdcB-tdcG-sdaB | PSC101 | Chloramphenicol | IPTG | This study |
| pYX67 | PrrnB:ilvE-ilvA-tdcB-tdcG-sdaB | PSC101 | Chloramphenicol | | This study |
| pYX68 | PrrnB:ilvE-ilvA-sdaB | PSC101 | Chloramphenicol | | This study |
| pYX75 | PLlacO1:ilvA-tdcB-tdcG-sdaB | PSC101 | Chloramphenicol | IPTG | This study |
| pYX79 | PLlacO1:ilvA-sdaB | PSC101 | Chloramphenicol | IPTG | This study |
| pYX90 | PLlacO1:alsS-ilvC-ilvD-avtA | p15A | Spectinomycin | IPTG | This study |
| pYX97 | PLlacO1:leuDH-kivd-yqhD; lacI | colE1 | Ampicillin | IPTG | This study |
| pKS103 | PLlacO1:alsS-ilvC-ilvD | p15A | Spectinomycin | IPTG | This study |

| Strain | Relevant information |
|---|---|
| JCL16 | BW25113/F' [traD36, proAB$^+$, lacI$^q$ ZΔM15] |
| YH19 | A JCL16 derivative with enhanced ability of amino acid utilization |
| YH30 | YH19 but with ΔglnA, ΔgdhA |
| YH39 | YH19 but with ΔluxS |
| YH40 | YH19 but with ΔlsrA |
| YH48 | YH19 but with ΔilvE |
| YH83 | Best production strain, YH40 with plasmids pYX68, pYX90 and pYX97 |

[1]US2009/0081746

[2]Atsumi et al., 2010, *Appl. Microbiol. Biotechnol.* 85: 651-657

[3]Atsumi et al., 2009, *Nature* 451: 86-89

TABLE 6

| List of Primers |
|---|
| Name Sequence |
| YX274acgcgtcgacaagaaggagatataccatgacattctcccttttttggtgacaaatttaccc SEQ ID NO: 95 |
| YX275ccgggctgcagttagtgactttcagcccaggctctttctatctc SEQ ID NO: 96 |
| YX278gacatgcatgcaagaaggagatataccatgaacaactttaatctgcacaccccaacccgc SEQ ID NO: 97 |
| YX279ctcctgcatgcttagcgggcggcttcgtatatacggcggctgac SEQ ID NO: 98 |
| YX283gcatggtcgacttagctgtgtgcgccatgtaaatggcccggacg SEQ ID NO: 99 |
| YX284gcatggtaccatgaccacgaagaaagctgattacatttggttc SEQ ID NO: 100 |
| YX285gccaatgcatttattgattaacttgatctaaccagcccc SEQ ID NO: 101 |
| YX288cgggctgcagaagaaggagatataccatgcatattacatacgatctgccggttgctattg SEQ ID NO: 102 |
| YX289ccggaggatccgaagcggccgcacctctagattaagcgtcaacgaaaccggtgatttgag SEQ ID NO: 103 |
| YX290ctagtctagaaagaaggagatataccatgattagtgcattcgatattttcaaaattggg SEQ ID NO: 104 |
| YX291gctgacggccgtcagccgcagaccactttaatggccagtcc SEQ ID NO: 105 |
| YX292gctgacggccgaagaaggagatataccatgattagcgtattcgatattttcaaaatcggc SEQ ID NO: 106 |
| YX293ccggaggatccttaatcgcaggcaacgatcttcattgccagg SEQ ID NO: 107 |
| YX294ccacctcgagcaagtgctgccagagggaacccggctggtgg SEQ ID NO: 108 |
| YX295gcatggtacctttctcctctttaatcccggcggcgtgtttgccgttgttccgtgtcag SEQ ID NO: 109 |
| YX326gtcgatgcataagaaggagatataccatggctgactcgcaacccctgtccggtgctccgg SEQ ID NO: 110 |
| YX327ccgggctgcagctaacccgccaaaaagaacctgaacgccgggttattgg SEQ ID NO: 111 |
| YX340ctagtctagaaagaaggagatataccatgacccgtccgatacaggccagcctcgatctgc SEQ ID NO: 112 |
| YX341ctcgcctaggccagtcgaccacggatccttacaccgtcacaaccgggacgcgtagcgcc SEQ ID NO: 113 |
| YX342gcatgggatccaagaaggagatataccatgcgagttgtcatactgggaagtggtgtgg SEQ ID NO: 114 |
| YX344gcatgtcgacggcatcaaataaaacgaaaggctcagtcg SEQ ID NO: 115 |
| YX345gagcactagtcatgaccaaaatcccttaacgtgagttttcgttccactg SEQ ID NO: 116 |
| YX346gagcactagtaattgtgagcggataacaattgacattgtg SEQ ID NO: 117 |
| YX347gcatggagctctctagggcggcggatttgtcctactcaggag SEQ ID NO: 118 |
| YX355gaaaggtaccatggctgactcgcaacccctgtccggtgctccgg SEQ ID NO: 119 |

TABLE 6-continued

| List of Primers |
|---|
| Name Sequence |
| YX356cttcttctgcaggctaacccgccaaaaagaacctgaacgccggg<br>SEQ DI NO: 120 |
| YX382ccgggctgcagaagaaggagatataccatgattagcgtattcgatattttcaaaatcggc<br>SEQ ID NO: 121 |
| YX397acgcacgcgtaagaaggagatataccatgacattctcccttttggtgacaaatttaccc<br>SEQ ID NO: 122 |
| YX398ccgggacgcgtttagtgactttcagcccaggctctttctatctc<br>SEQ ID NO: 123 |
| YXH01cgcatggtaccatgaaaatcttcgattacatggaaaaatatg<br>SEQ ID NO: 124 |
| YXH02gcatggtcgacttatttgttgttaaaattgatcaggttgcg<br>SEQ ID NO: 125 |
| YXH03gcatggtcgacaggagatataccatgtatacagtaggagattacc<br>SEQ ID NO: 126 |
| YXH04ccggaggatccttagcgggcggcttcgtatatacggcggctgac<br>SEQ ID NO: 127 |

To clone pYX41, primers YX278 (SEQ ID NO:97) and YX279 (SEQ ID NO:98) were used to amplify yqhD from *E. coli* K-12 genomic DNA. The PCR product was digested with SphI and cloned into pSA65 digested with the same enzyme. The colony with correct orientation was selected and verified by sequencing.

To clone pYX45, primers YX340 (SEQ ID NO:112) and YX341 (SEQ ID NO:113) were used to amplify dadX from *E. coli* K-12 genomic DNA. The PCR product was digested with XbaI and AvrII and cloned into pYX41 digested with the same enzymes. The correct colony was selected and verified by sequencing. Restriction sites for BamHI and SalI were introduced into pYX45 by primer YX341 (SEQ ID NO:113).

Primers YX342 (SEQ ID NO:114) and YX283 (SEQ ID NO:99) were used to amplify dadA from *E. coli* K-12 genomic DNA. The PCR product was digested with BamHI and SalI and cloned into pYX45 digested with the same enzymes. The correct colony was selected and verified by sequencing, creating pYX46. As a result of the cloning, the T1 terminator was deleted in pYX46. Primers YX344 (SEQ ID NO:115) and YX345 (SEQ ID NO:116) were used to amplify T1 terminator and ColE1 from pYX45. This PCR product was digested with SpeI and SalI and cloned into pYX46 digested with the same enzymes. The correct colony was selected and verified by sequencing, creating pYX47.

To clone pYX51, primers YXH01 (SEQ ID NO:124) and YXH02 (SEQ ID NO:125) were used to amplify leuDH from *Thermoactinomyces intermedius* genomic DNA. The PCR product was digested with Acc65I and SalI and cloned into an empty plasmid pYK (a derivative of pSA40) digested with the same enzymes. The correct colony was selected and verified by sequencing.

To clone pYX52, primers YX274 (SEQ ID NO:95) and YX275 (SEQ ID NO:96) were used to amplify avtA from *E. coli* K-12 genomic DNA. The PCR product was digested with SalI and PstI and cloned into pYX51 digested with the same enzymes. The correct colony was selected and verified by sequencing.

To clone pYX54, primers YX346 (SEQ ID NO:117) and YX347 (SEQ ID NO:118) were used to amplify pLlac01: leuDH-avtA from pYX52. The PCR product was digested with SacI and SpeI and cloned into pKS103 digested with the same enzymes. The correct colony was selected and verified by sequencing.

To clone pYX60, primers YX284 (SEQ ID NO:100) and YX285 (SEQ ID NO:101) were used to amplify ilvE from *E. coli* K-12 genomic DNA. The PCR product was digested with Acc651 and NsiI and cloned into pSA74' digested with the same enzymes. The correct colony was selected and verified by sequencing.

To clone pYX61, primers YX326 (SEQ ID NO:110) and YX327 (SEQ ID NO:111) were used to amplify ilvA from *E. coli* K-12 genomic DNA. The PCR product was digested with NsiI and PstI and cloned into pYX60 digested with the same enzymes. The correct colony was selected and verified by sequencing.

To clone pYX62, primers YX288 (SEQ ID NO:102) and YX289 (SEQ ID NO:103) were used to amplify tdcB from *E. coli* K-12 genomic DNA. The PCR product was digested with PstI and BamHI and cloned into pYX61 digested with the same enzymes. The correct colony was selected and verified by sequencing. Restriction sites for XbaI and EagI were introduced into pYX61 by primer YX289 (SEQ ID NO:103).

To clone pYX64, primers YX290 (SEQ ID NO:104) and YX291 (SEQ ID NO:105) were used to amplify tdcG from *E. coli* K-12 genomic DNA, and primers YX292 (SEQ ID NO:106) and YX293 (SEQ ID NO:107) were used to amplify sdaB from *E. coli* K-12 genomic DNA. PCR fragment containing tdcG was digested with XbaI and EagI, and PCR fragment containing sdaB was digested with EagI and BamHI. The two digested fragments were cloned into pYX62 digested with XbaI and BamHI. The correct colony was selected and verified by sequencing.

To clone pYX67, primers YX294 (SEQ ID NO:108) and YX295 (SEQ ID NO:109) were used to amplify the rrnB promoter from *E. coli* K-12 genomic DNA. The PCR product was digested with XhoI and Acc65I and cloned into pYX64 digested with the same enzymes. The correct colony was selected and verified by sequencing.

To clone pYX68, primers YX382 (SEQ ID NO:121) and YX293 (SEQ ID NO:107) were used to amplify sdaB from *E. coli* K-12 genomic DNA. The PCR product was digested with PstI and BamHI and cloned into pYX67 digested with the same enzymes (Digestion of pYX67 with PstI and BamHI caused the removal of tdcB, tdcG and sdaB from pYX67). The correct colony was selected and verified by sequencing.

To clone pYX75, primers YX355 (SEQ ID NO:119) and YX356 (SEQ ID NO:120) were used to amplify ilvA from *E. coli* K-12 genomic DNA. The PCR product was digested with Acc65I and PstI and cloned into pYX64 digested with the same enzymes (Digestion of pYX64 with Acc65I and PstI caused the removal of ilvE and ilvA from pYX64). The correct colony was selected and verified by sequencing.

To clone pYX79, primers YX382 (SEQ ID NO:121) and YX293 (SEQ ID NO:107) were used to amplify sdaB from *E. coli* K-12 genomic DNA. The PCR product was digested with PstI and BamHI and cloned into pYX75 digested with the same enzymes (Digestion of pYX75 with PstI and BamHI caused the removal of tdcB, tdcG and sdaB from pYX75). The correct colony was selected and verified by sequencing.

To clone pYX90, primers YX397 (SEQ ID NO:122) and YX398 (SEQ ID NO:123) were used to amplify avtA from *E. coli* K-12 genomic DNA. The PCR product was digested with MluI and cloned into pKS103 digested with the same enzyme. The colony with correct orientation was selected and verified by sequencing.

To clone pYX97, three fragments were generated. Plasmid pYX51 was digested with Acc65I and SalI to obtain a fragment containing leuDH. Primers YXH03 (SEQ ID NO:126) and YXH04 (SEQ ID NO:127) were used to amplify kivD and yqhD from pYX41 and the PCR fragment was digested with SalI and BamHI. Plasmid pSA40 was digested with Acc65I and BamHI. The above three fragments were ligated together to create a plasmid. The plasmid was then digested with AatII and SpeI, and the fragment containing leuDH, kivD, yqhD and ColE1 was cloned into pSA55I digested with the same enzymes, creating pYX97. The correct colony was selected and verified by sequencing.

To clone pKS103, the Kan resistant cassette of pSA69 was removed by the digestion of AatII and SacI enzymes. The remaining part of pSA69 was ligated with a Spectinomycin cassette digested with the same enzymes. The correct colony was selected and verified by sequencing.

Unless stated otherwise, 1× modified M9 salt (31.5 g/L $NaHPO_4$, 15 g/L $KH_2PO_4$, 2.5 g/L NaCl, 120 mg/L $MgSO_4$, 11 mg/L $CaCl_2$ and 10 mg/L Vitamin B1 per liter water) containing 40 g/L BD Bacto™ Yeast extract (containing 21.64 g/L amino acids, 4.48 g/L ash, 3.05 g/L various salts, 1.24 g/L $H_2O$ as well as 6.53 g/L carbohydrate which is non-degradable by *E. coli*) was used for cell growth. Ampicillin (100 μg/ml) kanamycin (50 μg/ml), Chloramphenicol (30 μg/ml) and Spectinomycin (50 μg/ml) were added as appropriate. Pre-culture in test tubes containing 3 ml of medium was performed at 37° C. overnight on a rotary shaker (250 r.p.m.). Overnight culture was diluted 1:100 into 20 ml of fresh medium in a 250-ml screw-cap conical flask. Cells were grown two hours at 37° C. before adding 0.1 mM isopropyl-β-d-thiogalactoside (IPTG). Cultivation was performed at 37° C. on a rotary shaker (250 r.p.m.). In certain cases, two-phase fermentation was preformed as described in (Connor et al., 2010, *Appl. Microbiol. Biotechnol.* 86:1155-1164) to reduce the products' toxicity effect to the *Escherichia coli* cell. To obtain the biomass used in FIG. 8, the *E. coli* and *B. subtilis* were grown in LB medium. The *Chlorella vulgaris* (ATCC 13482), *Porphyridium purpureum* (ATCC 50161), *Spirulina platensis* (UTEX LB2340) and *Synechococcus elongates* PCC7942 were grown in ATCC medium 5, ATCC medium 1495, UTEX *spirulina* medium and BG-11 medium, respectively. After harvest, some biomass was treated by a mini beadbeater for 1 min or hot 0.5 N NaOH for 30 min to release the proteins for a concentration measurement through Bradford assay. The rest of the protein biomass was hydrolyzed by heating in 60 or 80-100° C. water for 10-20 min followed by an overnight protease hydrolysis at 50° C. The amount of protease was 1-3% of the biomass's dry weight (0.3-0.9 mg/ml). The concentrations of free amine groups before and after the protease treatment was measured by Ninhydrin Assay Kit (Sigma). All protease treated protein biomass were then filtered for medium preparation. Gas chromatography-mass spectrometry (GC-MS), gas chromatography-flame ionization detector (GC-FID) and high-performance liquid chromatography (HPLC) were used to analyze the substrates and products.

Alcohol compounds produced by our strains were identified by GC-MS as described previously (Atsumi et al., 2008, *Nature* 451:86-89 and Connor et al., 2010, *Appl. Microbiol. Biotechnol.* 86:1155-1164) and quantified by GC-FID. The separation of alcohol compounds was carried out by A DB-FFAP capillary column (30 m, 0.32-mm internal diameter, 0.25-μm film thickness; Agilent Technologies). GC oven temperature was initially held at 40° C. for 2 min and raised with a gradient of 5° C. $min^{-1}$ until 45° C. and held for 4 min. And then it was raised with a gradient 15° C. $min^{-1}$ until 230° C. and held for 4 min. Helium was used as the carrier gas with 14 p.s.i. inlet pressure. The injector and detector were maintained at 225° C. A 0.5-μl sample was injected. 1-propanol was used as the internal standard.

Amino acids (except L-Proline) were quantified using ZORBAX Eclipse AAA column (Agilent Technologies) with OPA (ophthaldialdehyde) derivatization method. L-Proline was derivatized with FMOC (9-fluorenylmethyl chloroformate). Derivatized amino acids were analyzed using PDA detector (338 nm, 262 nm (L-Pro)) of HPLC.

In order to calculate the theoretical yields of biofuel production, the material balance of individual metabolites involved in the production can be represented as follows: $S_v$=B, where S is the stoichiometric matrix, with each column corresponding to a reaction in the network and each row containing the stoichiometric coefficient of each metabolite in the particular reaction. Vector v contains the molar fluxes for each reaction and their product, B, contains the rate of accumulation/depletion of each metabolite. S was constructed to represent the metabolic network consisting of the pathways for central carbon metabolism, amino acid biosynthesis, amino acid degradation, biofuel production and product export and B to be a column vector of zeros except for the rows corresponding to the amino acids which are equal to the negative of their import flux in order to represent the system with a constant amino acid influx, but at steady state. Since S contains more reactions than metabolites (more columns than rows), it is under determined and can therefore be subject to optimization in order to find a solution. To optimize the system for biofuel production the objective function was defined to be: min(fv), where f is a row vector containing the coefficient of each flux in the objective function. Since the maximum mass yield of biofuel is desired, f is assigned to be all zeros except for the coefficients corresponding to the export reaction of the biofuels being optimized, in which case it is assigned as the negative of the molecular weight of the corresponding biofuel. After this linear optimization problem was defined, it was used as input for the MATLAB function "linprog" which outputs the optimal molar flux distribution for the system. Additionally, reactions that are known to be irreversible where given a lower bound of zero whereas all other reactions have a lower bound of −200. The amino acids degradation pathways and the higher alcohol biosynthesis pathways are summarized in FIG. 9A and Table 7.

TABLE 7

| Amino acid degradation pathways. |
|---|
| L-Alanine + Ubiquinone → Ubiquinol + ammonia + pyruvate |
| L-Valine + pyruvate → L-alanine + 2-ketoisovalerate |
| L-Leucine + $NAD^+$ → ammonia + NADH + 2-Ketoisocarproate (through overexpressed LeuDH) |
| L-Isoleucine + $NAD^+$ → ammonia + NADH + 2-keto-3-methyl-valerate (through overexpressed LeuDH) |
| L-Serine → $H^+$ + ammonia + pyruvate |
| L-Proline + FAD + $2H_2O$ + $NAD^+$ → $FADH_2$ + NADH + $H^+$ + L-Glutamate |
| L-Glutamate + oxaloacetate → L-Aspartate + 2-Ketoglutarate |
| L-Aspartate → $H^+$ + ammonia + fumarate |
| L-cysteine + $H_2O$ → ammonia + $H_2S$ + $H^+$ + pyruvate |
| L-Arginine + succinyl-CoA + $4H_2O$ + 2-oxoglutarate + NAD → CoA + $3H^+$ + $CO_2$ + 2 ammonia + 2 L-Glutamate + NADH + succinate |
| L-Glutamine + $H_2O$ → ammonia + $H^+$ + L-Glutamate |
| L-Asparagine + $H_2O$ → ammonia + $H^+$ + L-Aspartate |
| L-Threonine → ammonia + $H^+$ + 2-Ketobutyrate |
| GLycine + 5,10 methylene-THF + $H_2O$ → L-serine + tetrahydrofolate + $2H^+$ |
| Glycine + tetrahydrofolate + $H^+$ + $NAD^+$ → ammonia + $CO_2$ + NADH + 5,10 methylene-THF |
| L-Phenylalanine + $H^+$ + $O_2$ + NADH → L-Tryrosine[Tyrosine?] + $NAD^+$ + $H_2O$ |
| L-Tyrosine + 2 $O_2$ + $H_2O$ + succinyl-CoA + 2-oxoglutarate → fumarate + L-Glutamate + $CO_2$ + $2H^+$ + 2 acetyl-CoA + succinate |
| L-Tryptophan + 3 $O_2$ + 3 $H_2O$ + NADH + CoA → formate + alanine + $NAD^+$ + $CO_2$ + succinate + ammonia + $3H^+$ + acetyl-CoA |
| L-Histidine + 4 $H_2O$ → L-Glutamate + formate + 2 ammonia + 2 $H^+$ |
| L-Methionine + $H_2O$ → 2-Ketobutyrate + methanethiol + ammonia + $H^+$ |
| L-Lysine + $O_2$ + oxoglutarate + $NADP^+$ + $NAD^+$ + ATP + 2CoA + FAD + H2O[$H_2O$?] → $2CO_2$ + ammonia + L-Glutamate + NADPH + NADH + $2H^+$ + $FADH_2$ + ADP + Pi + 2 acetyl-CoA |

To calculate the theoretical yield of conversion of the 6 rAA back into the 20AA by *Pseudomonas*, the strategy mentioned above was used, but applied to the *Pseudomonas* metabolic network. This network consists of the pathways for central carbon metabolism, amino acid biosynthesis, amino acid degradation and a biomass output reaction. For simplification purposes, no additional energy requirements were imposed to biomass formation in addition to those of amino acid synthesis. The biomass reaction consisted of an amino acid consumption reaction with stoichiometric coefficients as the molar ratios of the amino acids in the *Pseudomonas* biomass. In this case the f matrix is all zeros except for the coefficient corresponding to the biomass reaction which is given a value of −1.

Figure 4A:
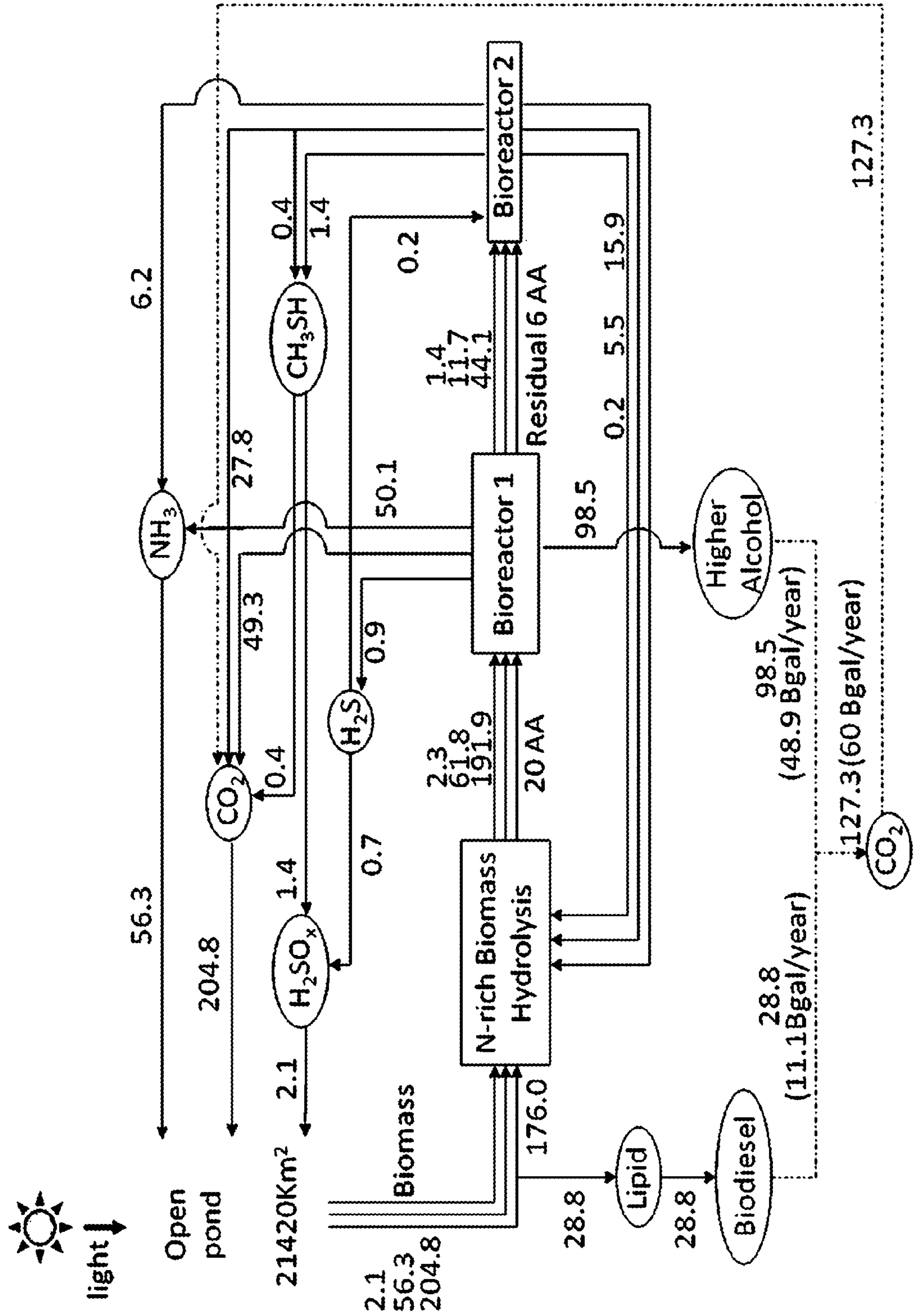

To calculate theoretical fluxes through the overall process design, as shown in FIG. 4A, each unit is considered independently. There are four main subunits which require detailed calculation, these are shown below:

Lipid/N-Rich Biomass Separation

The algal biomass to be processed was assumed to consist of lipid ($C_{19}H_{34}O_2$) and protein (average composition per peptidyl amino acid $C_{4.51}N_{1.24}O_{1.49}S_{0.02}H_{7.10}$) with amino acid composition from *Scenedesmus obliquus* (Table 5).

TABLE 8

Theoretical optima conversion of six remaining amino acids to protein biomass by *pseudomonas*. The mass of amino acid after *E. coli* fermentation was used as the input flux to calculate the mass yield of twenty amino acids in the *pseudomonas* protein biomass.

| Substrates | Mass Input | | Products Products | Mass Yield Mass Yield |
|---|---|---|---|---|
| $O_2$ | 44.0492 | | $NH_4$ | 14.714 |
| $H_2S$ | 0.31571 | | $CO_2$ | 202.662 |
| His | 19.076 | | Methanethiol | 4.080 |
| Lys | 50.872 | | Ala | 4.920 |
| Met | 13.627 | ⇨ | Arg | 5.539 |

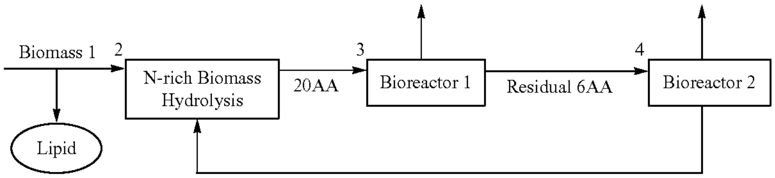

TABLE 8-continued

Theoretical optima conversion of six remaining amino acids to protein biomass by *pseudomonas*. The mass of amino acid after *E. coli* fermentation was used as the input flux to calculate the mass yield of twenty amino acids in the *pseudomonas* protein biomass.

| Substrates | Mass Input | Products Products | Mass Yield Mass Yield |
|---|---|---|---|
| Phe | 43.604 | Asn | 3.424 |
| Trp | 2.725 | Asp | 3.449 |
| Tyr | 29.070 | Cys | 1.193 |
| Total AA | 158.974 | Glu | 4.162 |
| | | Gln | 4.134 |
| | | Gly | 1.724 |
| | | His | 4.846 |
| | | Ile | 6.353 |
| | | Leu | 4.839 |
| | | Lys | 2.415 |
| | | Met | 0.036 |
| | | Phe | 3.290 |
| | | Pro | 0.456 |
| | | Ser | 2.438 |
| | | Thr | 3.248 |
| | | Trp | 1.248 |
| | | Tyr | 2.686 |
| | | Val | 5.329 |
| | | Total AA | 65.729 |
| | | AA | 41.4% |

Although algal biomass from *Scenedesmus* also contains 10-17% carbohydrates, these carbohydrates can be degraded to sugars after pretreatment and become common *E. coli* fermentation substrates. For simplicity, all N-rich biomass was assumed to be protein during the calculation. To this effect, the molar composition of the biomass was calculated as follows:

$$Moles_{protein} = \frac{(1 - Fraction_{lipid}) * Moles_{biomass}}{Fraction_{lipid} * \frac{MW_{protein}}{MW_{lipid}} + (1 - Fraction_{lipid})}$$

$$Moles_{lipid} = Moles_{biomass} - Moles_{protein}$$

Using these numbers and the data, the molar flux of amino acid from the pond which was put into the hydrolysis unit can be calculated. Additionally the lipid flux was used to calculate the amount of biodiesel produced. The efficiency of converting lipid to biodiesel was taken as 100%.

N-Rich Biomass Hydrolysis

This unit hydrolyzes the proteins (peptidyl amino acids) into free amino acids or small peptides. In the calculation it represents the sum of protein in the open pond algal biomass together with the recycled protein from Bioreactor 2.

*E. coli* Fermentation (14AA to Higher Alcohol)

This unit utilizes the output of the hydrolysis unit and performs a maximum theoretical yield of higher alcohols calculation as described in "Theoretical production yields." Each output-flux was separated into its corresponding stream in the diagram.

Biomass Generation by *Pseudomonas*

This unit utilizes the amino acid output of Bioreactor 1 (6 rAA) and performs a maximum theoretical yield of protein biomass calculation as described in "Theoretical production yields." The carbon flux in this process was less than 10% of the carbon flux in process 2. The efficiency of this process does not have a significant impact on the overall efficiency. For simplification, no energy requirements, in addition to those of synthesizing the amino acids, were imposed on the cell for the production of biomass.

Having mathematically defined each unit, the fluxes through each stream when 1 mole of biomass (10% lipid) was processed were calculated. Since the process contains recycle streams, iterative calculations were used. The iterative process was started assuming the recycle stream from Bioreactor 2 was empty and proceeding with calculations 1, 2, 3 and 4 in order. After the fluxes for each unit were calculated, the fluxes through the recycle stream were considered and the values for units 2, 3 and 4 were recalculated. This process was repeated until the fluxes through each stream converged (approximately 6 iterations). All values were converted to elemental mass fluxes by using the molecular formula of each compound and the molecular weight of each element. In order to upscale the process for annual fuel production by volume, the following formula was used:

$$Fuel_{total}^{vol.} = C_{biomass}^{total\ mass}\left[\left(\frac{C_{alcohol}}{C_{biomass}}\right)\left(\frac{MW_{alcohol}}{CW_{alcohol}}\right) * \rho_{alcohol} + \left(\frac{C_{biodiesel}}{C_{biomass}}\right)\left(\frac{MW_{biodiesel}}{CW_{biodiesel}}\right) * \rho_{biodiesel}\right]$$

where C was used to denote the carbon flux through the particular stream in the process before scaling, MW indicated molecular weight of the subscripted stream, CW indicated the weight of carbon atoms in a mole of the subscripted stream and ρ indicated density. Using this formula, the total carbon mass requirement was determined and all streams scaled by the same factor in order to have the total biomass carbon equal to the determined necessary carbon flux. The resulting flow sheet represents the production of the desired amount of fuel (60 billion gallons in FIG. 4A).

In order to calculate the optimal lipid content for algae growth in our system, we define the following variables as:

α=Grams of Carbon per gram of lipid biomass=0.7752

β=Grams of Carbon per gram of protein biomass=0.5244

ρ=Maximum mass of carbon in alcohols produced per mass of carbon in protein fed to *E. coli*=0.46

$Y_0$=Y-intercept of biomass productivity correlation=92.46 (See FIG. 4B)

k=Exponential coefficient of biomass productivity correlation=0.0425 (See FIG. 4B)

ϵ=Percent of maximum yield at which process operates

Y=Biomass Productivity

X=Percent lipid in algae biomass

Using these variables we can express the productivity of carbon in biofuel (FIG. 4) as:

$$C_{fuel}=YX\alpha/100+Y(1-X/100)\beta\rho\epsilon$$

$$C_{fuel}=Y[(\alpha-\beta\rho\epsilon)X/100+/\beta\rho\epsilon].$$

Assuming total biomass production is an exponential function of lipid percentage:

$$C_{fuel}=(Y_0e^{-kX})[(\alpha-\beta\rho\epsilon)X/100+\beta\rho\epsilon]$$

$$C_{fuel}=(\alpha-\beta\rho\epsilon)Y_0Xe^{-kX}/100+Y_0\beta\rho\epsilon e^{-kX}$$

Which means the value of X that would maximize $C_{fuel}$ would occur at:

$$C_{fuel}=-(\alpha-\beta\rho\epsilon)Y_0kXe^{-kX}/100+(\alpha-\beta\rho\epsilon)Y_0e^{-kX}/100-Y_0k\beta\rho\epsilon e^{-kX}=0$$

Therefore, $$X_{optimal} = \frac{(\alpha - \beta\rho\varepsilon) - 100\ k\beta\rho\varepsilon}{k(\alpha - \beta\rho\varepsilon)}$$

After substituting the variables with their corresponding values and analyzing $X_{optimal}$ as a function of $\epsilon$, it was determined that lipid content should be kept to a minimum when alcohol yields were higher than 61% of the theoretical yield.

To calculate the productivity of carbon in biofuel without the incorporation of the above disclosed method, the following expression was derived:

$$C_{fuel} = YX\alpha/100,$$

where plots incorporating biomass productivity data use $Y=Y_0e^{-kx}$ and plots assuming constant biomass productivity use $Y=Y_0$. Lipid content was set as 10% in FIG. 4A.

Figure 4D:
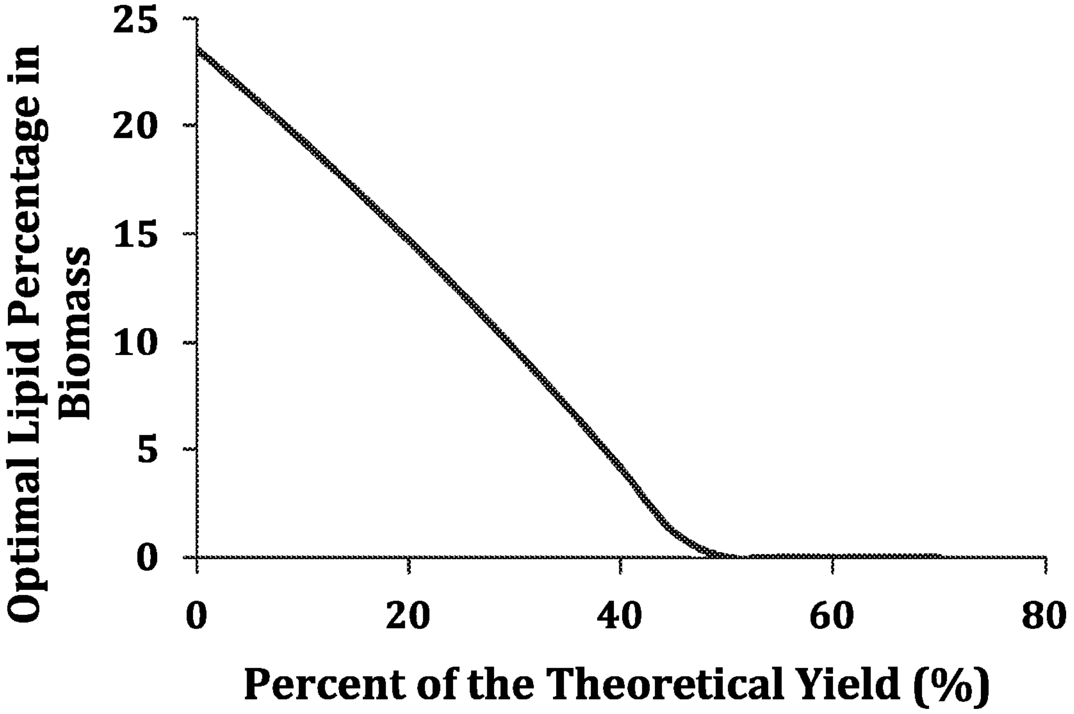

In practice, protein-to-fuel conversion will not reach 100% of the theoretical yield. To account for this deficiency, the optimal lipid content as a function of percent theoretical yield that protein-to-fuel conversion actually achieves was calculated, while keeping the lipid-to-fuel conversion at the theoretical yield (FIG. 4D). Results show that as long as protein-to-higher alcohol yield is greater than 38% of the theoretical value, lipid content can be lower than 10% (which is the minimum lipid content in algae) to achieve optimal fuel productivity. Note that the methods and systems of the disclosure achieved protein-to-higher alcohol yield greater than 50% of the theoretical maximum (Table 4). This result suggests that lipid production is unnecessary even at the current sub-theoretical protein-to-fuel conversion yields.

This protein-to-fuel conversion technology can also utilize N-rich single cell biomass produced from other processes, such as direct $CO_2$ conversion to fuels, cellulosic alcohol fermentation, or any other industrial whole-cell bioreactions. In addition to higher alcohol production, the protein conversion scheme can be utilized for the production of ethanol, or other fuels and chemicals, thus providing a pathway for eventual replacement of petroleum.

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant microorganism comprising a deletion, reduced expression, or reduced function of a gene involved in synthesis or uptake of a quorum sensing-related autoinducer molecule and/or of a gene involved in ammonia reuptake, and further comprising at least one heterologous polynucleotide encoding a dehydrogenase, a transaminase, or a deaminase that deaminates an amino acid substrate to produce an increased keto-acid flux when compared with the wild-type organism;

wherein the dehydrogenase is selected from the group consisting of glutamate dehydrogenase (E.C. 1.4.1.2 and E.C. 1.4.1.4), glutamic dehydrogenase (E.C. 1.4.1.3), valine dehydrogenase (E.C. 1.4.1.8), leucine dehydrogenase (E.C. 1.4.1.9), and phenylalanine dehydrogenase (E.C. 1.4.1.20);

wherein the deaminase is selected from the group consisting of aspartate ammonia lyase (4.3.1.1), L-serine ammonia lyase (E.C. 4.3.1.17), D-serine ammonia lyase (4.3.1.18), threonine ammonia lyase (E.C. 4.3.1.19), tyrosine ammonia lyase (E.C. 4.3.1.23), phenylalanine ammonia lyase (E.C. 4.3.1.24), and phenylalanine/tyrosine ammonia lyase (E.C. 4.3.1.25);

wherein the transaminase is an L-α-transaminase (E.C. 2.6.I.X, where X is any number);

wherein the deletion, reduced expression, or reduced function of a gene involved in synthesis or uptake of a quorum sensing related autoinducer molecule is from the deletion, or reduced expression or function of the genes luxS or lsrA; and wherein the deletion, reduced expression, or reduced function of a gene involved in ammonia reuptake is from the deletion, or reduced expression or function of the genes gdhA or glnA.

2. The recombinant microorganism according to claim 1, wherein the microorganism further metabolizes the keto-acid into a chemical product.

3. The recombinant microorganism according to claim 1, wherein the leucine dehydrogenase is LeuDH.

4. The recombinant microorganism according to claim 3, wherein the leucine dehydrogenase LeuDH is from *Thermoactinomyces intermedins.*

5. The recombinant microorganism according to claim 1, wherein the deaminase is the serine deaminase SdaB.

6. The recombinant microorganism according to claim 5, wherein the serine deaminase SdaB is from *Escherichia coli, Rosebacter atrosepticum, Corynebacterium diphtheriae, Salmonella enerica, Yersinia enterocolitica*, or *Burkholderia pseudomallei.*

7. The recombinant microorganism according to claim 1, wherein the L-α-transaminase is selected from the group consisting of L-aspartate transaminase (E.C. 2.6.1.1), L-alanine transaminase (E.C. 2.6.1.12 and E.C. 2.6.1.47), L-asparagine transaminase (E.C. 2.6.1.14), and glycine transaminase (E.C. 2.6.1.35).

8. The recombinant microorganism according to claim 7, wherein the L-aspartate transaminase is AvtA.

9. The recombinant microorganism according to claim 8, AvtA is from *Escherichia coli, Neisseria meningitidis, Pantoea ananatis, Amycolatopsis mediterranei, Mannheimia succinicproducens, Salmonella enterica*, or *Yersinia pestis.*

10. The recombinant microorganism according claim 1, wherein the microorganism is further characterized by, a reduced autoinducer 2 reuptake activity, a reduced glutamate dehydrogenase activity, a reduced glutamine synthase activity, a reduced glutamate synthase activity, and/or a reduced global regulator activity when compared with the wild-type organism.

11. The recombinant microorganism according to claim 10, wherein the reduced global regulator activity is from the deletion, or reduced expression or function of the genes CRP, LRP, Fis, and/or IHF.

12. The recombinant microorganism according to claim 2, wherein the chemical product is selected from the group consisting of an alcohol, an acetaldehyde, acetate, isobutyraldehyde, isobutyric acid, n-butyraldehyde, n-butyric acid, 2-methyl-1-butyraldehyde, 2-methyl-1-butyric acid, 3-methyl-l-butyraldehyde, 3-methyl-1-butyric acid, ammonia, ammonium, glutamic acid, threonine, methionine, isoleucine, valine, leucine, tryptophan, tyrosine, phenylalanine, 2,3-butanediol, 1,4-butanediol, 2-methyl-1,4-butanediol, 2-methyl-1,4-butanediamine, isobutene, itaconate, acetoin, acetone, isobutene, 1,5-diaminopentane, L-lactic acid, D-lactic acid, shikimic acid, mevalonate, polyhydroxybutyrate (PHB), isoprenoids, fatty acids, homoalanine, 4-aminobutyric acid (GABA), succinic acid, malic acid, citric acid, adipic acid, p-hydroxy-cinnamic acid, tetrahydrofuran, 3-methyl-tetrahydrofuran, gamma-butyrolactone, pyrrolidinone, n-methylpyrrolidone, aspartic acid, lysine, cadeverine, 2-ketoadipic acid, and S-adenosyl-methionine (SAM).

13. The recombinant microorganism according to claim 12, wherein the alcohol is selected from the group consisting of ethanol, 1-proponal, n-butanol, isobutanol, 2-methyl-l-butanol and 3-methyl-butanol.

14. The recombinant microorganism according to claim 2, wherein the chemical product is produced from pyruvate.

15. The recombinant microorganism of claim 14, wherein the chemical product is selected from the group consisting of acetate, acetaldehyde, isobutyraldehyde, n-butyraldehyde, 2,3-butanediol, L-lactic acid, D-lactic acid, an aromatic, polyhydroxybutyrate (PHB), mevalonate, an isoprenoid, ethanol, isobutanol, n-butanol, and a fatty acid.

16. The recombinant microorganism of claim 15, wherein the aromatic is selected from the group consisting of tryptophan, tyrosine, phenylalanine, and shikimic acid.

17. The recombinant microorganism according to claim 2, wherein the chemical product is produced from 2-ketoglutarate.

18. The recombinant microorganism according to claim 17, wherein the chemical product is selected from the group consisting of GABA (4-aminobutyric acid), glutamic acid, succinate and malic acid.

19. The recombinant microorganism according to claim 2, wherein the chemical product is produced from oxaloacetate.

20. The recombinant microorganism according to claim 19, wherein the chemical product is selected from the group consisting of aspartic acid, lysine, cadeverine, 2-ketoadipic acid, threonine, methionine and S-adenosyl-methionine (SAM).

21. The recombinant microorganism according to claim 2, wherein the chemical product is produced from 2-ketobutyrate.

22. The recombinant microorganism of claim 21, wherein the chemical product is 2-methyl-l-butyraldehyde, isoleucine, homoalanine, and 2-methyl-l-butanol.

23. The recombinant microorganism according to claim 2, wherein the chemical product is produced from 2-ketoisovalerate.

24. The recombinant microorganism of claim 23, wherein the chemical product is selected from the group consisting of isobutyraldehyde, 3-methyl-l-butyraldehyde, isobutanol, 3-methyl-l-butanol, and valine.

25. The recombinant microorganism according to claim 2, wherein the chemical product is produced from 2-ketoisocaproate.

26. The recombinant microorganism of claim 25, wherein the chemical product is selected from the group consisting of 3-methyl-l-butyraldehyde, leucine, and 1-butanol.

27. The recombinant microorganism according to claim 2, wherein the chemical product is produced from 2-keto-3-methylvalerate.

28. The recombinant microorganism of claim 27, wherein the chemical product is selected from the group consisting of 2-methyl-l-butyraldehyde, isoleucine, and 2-methyl-1-butanol.

29. The recombinant microorganism according to claim 1, wherein the wild-type organism is selected from the group consisting of bacterium, *cyanobacterium*, filamentous fungus, and yeast.

30. The recombinant microorganism according to claim 29, wherein the wild-type organism is selected from a group of genera consisting of *Clostridium, Zymonomas, Escherichia, Salmonella, Rhodococcus, Pseudomonas, Bacillus, Lactobacillus, Enterococcus, Alcaligenes, Klesiella, Paenibacillus, Arthrobacter, Corynebacterium, Brevibacterium, Pichia, Candida, Hansenula, Synechococcus, Synechocystis, Anabaena, Ralstonia, Lactococcus, Saccharomyces, Brevibacterium*, and *Microbacterium.*

31. The recombinant microorganism according to claim 30, wherein the wild-type organism is selected from the group consisting of *Escherichia coli, Alcaligenes eutrophus, Bacillus licheniformis, Zymonomas mobilis, Paenibacillus macerans, Rhodococcus erythropolis, Pseudomonas putida, Bacillus subtilis, Lactobacillus plantarum, Corynebacterium glutamicum, Enterococcus faecium, Enterococcus gallinarium, Enterococcus faecalis, Saccharomyces cerevisiae, Synechocystis* sp., *Anabaena* sp., *Ralstonia eutropha, Lactococcus lactis*, and *Synechococcus elongatus.*

32. A process for the production of a chemical product from a biomass comprising protein, polypeptides, or amino acids by contacting the biomass with the recombinant microorganism according to claim 1 under conditions conducive to chemical product production, wherein the quantity of the chemical product produced is greater than that produced by the wild-type organism.

33. The process according to claim 32, wherein the biomass is selected from the group consisting of algae, Dried Distillers Grains with Solubles (DDGS), bacteria, animal residuals, plant, protein, polypeptides, amino acid, or mixtures thereof, and any combination thereof.

34. The process according to claim 33, wherein the biomass was green algae, red algae, green-blue algae, *cyanobacterium, Escherichia coli*, or *Baccilus subtilis.*

35. The process according to claim 34, wherein the biomass was *Chorella vulgaris, Porphyridium purpureum, Spirulina platensis*, or *Synechococcus elongates.*

36. The process according to claim 32, wherein the biomass is partially degraded prior to contact with the recombinant microorganism.

37. The process according to claim 36, wherein the biomass was treated with a protease and/or heat.

38. The process according to claim 37, wherein the biomass was hydrolyzed by heating at a temperature ranging from 60 to 100° C. and by treating with a protease.

39. The process according to claim 32, further comprising contacting the biomass with the recombinant microorganism and contacting the biomass with a second microorganism that converts lysine, methionine, histidine, phenylalanine, tryptophan and tyrosine into a mixture of all twenty amino acid residues.

40. The process according to claim 39, wherein the second microorganism is contacted with the biomass prior to contacting the recombinant microorganism.

41. The process according to claim 39, wherein the second microorganism is *Pseudomonas* and/or *Bacillus.*

* * * * *

SEQUENCE LISTING

```
<160> NUMBER OF SEQ ID NOS: 133

<210> SEQ ID NO 1
<211> LENGTH: 1362
<212> TYPE: DNA
<213> ORGANISM: Saccharomyces cerevisiae

<400> SEQUENCE: 1

atgtcagagc cagaatttca acaagcttac gaagaagttg tctcctcttt ggaagactct     60

actcttttcg aacaacaccc agaatacaga aaggttttgc caattgtttc tgttccagaa    120

agaatcatac aattcagagt cacctgggaa aatgacaagg gtgaacaaga agttgctcaa    180

ggttacagag tgcaatataa ctccgccaag ggtccataca agggtggtct acgtttccat    240

ccttccgtga acttgtctat cttgaaattc ttgggtttcg aacaaatctt caagaactcc    300

ttgaccggcc tagacatggg tggtggtaaa ggtggtctat gtgtggactt gaagggaaga    360

tctaataacg aaatcagaag aatctgttat gctttcatga gagaattgag cagacacatt    420

ggtcaagaca ctgacgtgcc agctggtgat atcggtgttg gtggtcgtga aattggttac    480

ctgttcggtg cttacagatc atacaagaac tcctgggaag gtgtcttaac cggtaagggt    540

ttgaactggg gtggttcttt gatcagacca gaagccactg gttacggttt agtttactat    600

acccaagcta tgatcgacta tgccacaaac ggtaaggaat ctttcgaagg taagcgcgtc    660

accatctctg gtagtggtaa cgttgctcaa tacgctgcct tgaaggttat tgagctaggt    720

ggtactgtcg tttccctatc tgactccaag ggttgtatca tctctgaaac tggtatcacc    780

tccgaacaag tcgctgatat ttccagtgct aaggtcaact tcaagtcctt ggaacaaatc    840

gtcaacgaat actctacttt ctccgaaaac aaagtgcaat acattgctgg tgctcgtcca    900

tggacccacg tccaaaaggt cgacattgct ttgccatgtg ccacccaaaa tgaagtcagc    960

ggtgaagaag ccaaggcctt ggttgctcaa ggtgtcaagt ttattgccga aggttccaac   1020

atgggttcca ctccagaagc tattgccgtc tttgaaactg ctcgttccac gccactggac   1080

caagcgactg tttggtacgg tccaccaaag gctgctaact tgggtggtgt tgctgtttct   1140

ggtttagaaa tggcacaaaa ctctcaaaga atcacatgga ctagcgaaag agttgaccaa   1200
```

```
gagttgaaga gaattatgat caactgtttc aatgaatgta tcgactatgc caagaagtac   1260

actaaggacg gtaaggtctt gccatctttg gtcaaaggtg ctaatattgc aagtttcatc   1320

aaggtctctg atgctatgtt tgaccaaggt gatgtatttt aa                       1362


<210> SEQ ID NO 2
<211> LENGTH: 453
<212> TYPE: PRT
<213> ORGANISM: Saccharomyces cerevisiae

<400> SEQUENCE: 2

Met Ser Glu Pro Glu Phe Gln Gln Ala Tyr Glu Glu Val Val Ser Ser
1               5                   10                  15

Leu Glu Asp Ser Thr Leu Phe Glu Gln His Pro Glu Tyr Arg Lys Val
            20                  25                  30

Leu Pro Ile Val Ser Val Pro Glu Arg Ile Ile Gln Phe Arg Val Thr
        35                  40                  45

Trp Glu Asn Asp Lys Gly Glu Gln Glu Val Ala Gln Gly Tyr Arg Val
    50                  55                  60

Gln Tyr Asn Ser Ala Lys Gly Pro Tyr Lys Gly Gly Leu Arg Phe His
65                  70                  75                  80

Pro Ser Val Asn Leu Ser Ile Leu Lys Phe Leu Gly Phe Glu Gln Ile
                85                  90                  95

Phe Lys Asn Ser Leu Thr Gly Leu Asp Met Gly Gly Gly Lys Gly Gly
            100                 105                 110

Leu Cys Val Asp Leu Lys Gly Arg Ser Asn Asn Glu Ile Arg Arg Ile
        115                 120                 125

Cys Tyr Ala Phe Met Arg Glu Leu Ser Arg His Ile Gly Gln Asp Thr
    130                 135                 140

Asp Val Pro Ala Gly Asp Ile Gly Val Gly Gly Arg Glu Ile Gly Tyr
145                 150                 155                 160

Leu Phe Gly Ala Tyr Arg Ser Tyr Lys Asn Ser Trp Glu Gly Val Leu
                165                 170                 175

Thr Gly Lys Gly Leu Asn Trp Gly Gly Ser Leu Ile Arg Pro Glu Ala
            180                 185                 190

Thr Gly Tyr Gly Leu Val Tyr Tyr Thr Gln Ala Met Ile Asp Tyr Ala
        195                 200                 205

Thr Asn Gly Lys Glu Ser Phe Glu Gly Lys Arg Val Thr Ile Ser Gly
    210                 215                 220

Ser Gly Asn Val Ala Gln Tyr Ala Ala Leu Lys Val Ile Glu Leu Gly
225                 230                 235                 240

Gly Thr Val Val Ser Leu Ser Asp Ser Lys Gly Cys Ile Ile Ser Glu
                245                 250                 255

Thr Gly Ile Thr Ser Glu Gln Val Ala Asp Ile Ser Ser Ala Lys Val
            260                 265                 270

Asn Phe Lys Ser Leu Glu Gln Ile Val Asn Glu Tyr Ser Thr Phe Ser
        275                 280                 285

Glu Asn Lys Val Gln Tyr Ile Ala Gly Ala Arg Pro Trp Thr His Val
    290                 295                 300

Gln Lys Val Asp Ile Ala Leu Pro Cys Ala Thr Gln Asn Glu Val Ser
305                 310                 315                 320

Gly Glu Glu Ala Lys Ala Leu Val Ala Gln Gly Val Lys Phe Ile Ala
                325                 330                 335

Glu Gly Ser Asn Met Gly Ser Thr Pro Glu Ala Ile Ala Val Phe Glu
```

-continued 340 345 350

Thr Ala Arg Ser Thr Pro Leu Asp Gln Ala Thr Val Trp Tyr Gly Pro
355 360 365

Pro Lys Ala Ala Asn Leu Gly Gly Val Ala Val Ser Gly Leu Glu Met
370 375 380

Ala Gln Asn Ser Gln Arg Ile Thr Trp Thr Ser Glu Arg Val Asp Gln
385 390 395 400

Glu Leu Lys Arg Ile Met Ile Asn Cys Phe Asn Glu Cys Ile Asp Tyr
405 410 415

Ala Lys Lys Tyr Thr Lys Asp Gly Lys Val Leu Pro Ser Leu Val Lys
420 425 430

Gly Ala Asn Ile Ala Ser Phe Ile Lys Val Ser Asp Ala Met Phe Asp
435 440 445

Gln Gly Asp Val Phe
450

<210> SEQ ID NO 3
<211> LENGTH: 1287
<212> TYPE: DNA
<213> ORGANISM: Saccharomyces cerevisiae

<400> SEQUENCE: 3
atgactgctg ctaaaccaaa tccatatgct gccaaaccgg gcgactatct ttctaatgta 60
aataatttcc agttaatcga ttcgacgctg agagaaggtg aacaatttgc caacgcattc 120
ttcgatactg aaaaaaagat cgaaattgct agagccttgg acgatttcgg tgtggactac 180
atcgagttaa cctcaccagt agcatctgaa caatcaagaa aggactgtga agctatatgt 240
aaactaggtt taaaggccaa gatccttaca cacattcgtt gtcatatgga tgacgccaaa 300
gtcgccgtag agactggtgt cgacggtgtc gatgtcgtta tcggcacctc caaatttta 360 agacaatatt cccacggtaa ggatatgaac tacatcgcca agagtgctgt tgaagtcatt 420
gaatttgtca aatccaaagg tattgaaatc agattttcct ctgaagattc cttcagaagt 480
gatctcgttg atcttttgaa catttataaa accgttgaca agatcggtgt aaatagagtc 540
ggtattgccg acacagttgg atgtgccaac ccaagacaag tatatgaact gatcagaact 600
ttgaagagtg ttgtttcatg tgacatcgaa tgccatttcc acaacgatac tggttgtgcc 660
attgcaaacg cctacactgc tttggaaggt ggtgccagat tgattgacgt cagtgtactg 720
ggtattggtg aaagaaacgg tatcactcct ctaggtgggc tcatggcaag aatgattgtt 780
gccgcaccag actatgtcaa gtccaaatac aagttgcaca agatcagaga cattgaaaac 840
ctggtcgctg atgctgtgga agttaacatt ccattcaaca accctatcac agggttctgt 900
gcattcacac ataaagcagg tatccatgcc aaggccattt tggctaaccc atctacctac 960
gaaatcttgg accctcacga tttcggtatg aagaggtata tccacttcgc caacagacta 1020
actggctgga acgccatcaa agccagagtc gaccagttga acttgaactt gacggatgac 1080
caaatcaagg aagttactgc taagattaag aagctgggtg atgtcagatc gctgaatatc 1140
gatgatgttg actctatcat caagaacttc cacgcagagg tcagcactcc tcaagtacta 1200
tctgcaaaaa agaacaagaa gaatgacagc gatgtaccgg aactggccac catccccgcc 1260
gccaagcgga ctaagccatc cgcctaa 1287

<210> SEQ ID NO 4
<211> LENGTH: 428
<212> TYPE: PRT

<213> ORGANISM: Saccharomyces cerevisiae

<400> SEQUENCE: 4

```
Met Thr Ala Ala Lys Pro Asn Pro Tyr Ala Ala Lys Pro Gly Asp Tyr
1               5                   10                  15

Leu Ser Asn Val Asn Asn Phe Gln Leu Ile Asp Ser Thr Leu Arg Glu
            20                  25                  30

Gly Glu Gln Phe Ala Asn Ala Phe Phe Asp Thr Glu Lys Lys Ile Glu
        35                  40                  45

Ile Ala Arg Ala Leu Asp Asp Phe Gly Val Asp Tyr Ile Glu Leu Thr
    50                  55                  60

Ser Pro Val Ala Ser Glu Gln Ser Arg Lys Asp Cys Glu Ala Ile Cys
65                  70                  75                  80

Lys Leu Gly Leu Lys Ala Lys Ile Leu Thr His Ile Arg Cys His Met
                85                  90                  95

Asp Asp Ala Lys Val Ala Val Glu Thr Gly Val Asp Gly Val Asp Val
            100                 105                 110

Val Ile Gly Thr Ser Lys Phe Leu Arg Gln Tyr Ser His Gly Lys Asp
        115                 120                 125

Met Asn Tyr Ile Ala Lys Ser Ala Val Glu Val Ile Glu Phe Val Lys
    130                 135                 140

Ser Lys Gly Ile Glu Ile Arg Phe Ser Ser Glu Asp Ser Phe Arg Ser
145                 150                 155                 160

Asp Leu Val Asp Leu Leu Asn Ile Tyr Lys Thr Val Asp Lys Ile Gly
                165                 170                 175

Val Asn Arg Val Gly Ile Ala Asp Thr Val Gly Cys Ala Asn Pro Arg
            180                 185                 190

Gln Val Tyr Glu Leu Ile Arg Thr Leu Lys Ser Val Val Ser Cys Asp
        195                 200                 205

Ile Glu Cys His Phe His Asn Asp Thr Gly Cys Ala Ile Ala Asn Ala
    210                 215                 220

Tyr Thr Ala Leu Glu Gly Gly Ala Arg Leu Ile Asp Val Ser Val Leu
225                 230                 235                 240

Gly Ile Gly Glu Arg Asn Gly Ile Thr Pro Leu Gly Gly Leu Met Ala
                245                 250                 255

Arg Met Ile Val Ala Ala Pro Asp Tyr Val Lys Ser Lys Tyr Lys Leu
            260                 265                 270

His Lys Ile Arg Asp Ile Glu Asn Leu Val Ala Asp Ala Val Glu Val
        275                 280                 285

Asn Ile Pro Phe Asn Asn Pro Ile Thr Gly Phe Cys Ala Phe Thr His
    290                 295                 300

Lys Ala Gly Ile His Ala Lys Ala Ile Leu Ala Asn Pro Ser Thr Tyr
305                 310                 315                 320

Glu Ile Leu Asp Pro His Asp Phe Gly Met Lys Arg Tyr Ile His Phe
                325                 330                 335

Ala Asn Arg Leu Thr Gly Trp Asn Ala Ile Lys Ala Arg Val Asp Gln
            340                 345                 350

Leu Asn Leu Asn Leu Thr Asp Asp Gln Ile Lys Glu Val Thr Ala Lys
        355                 360                 365

Ile Lys Lys Leu Gly Asp Val Arg Ser Leu Asn Ile Asp Asp Val Asp
    370                 375                 380

Ser Ile Ile Lys Asn Phe His Ala Glu Val Ser Thr Pro Gln Val Leu
385                 390                 395                 400
```

```
Ser Ala Lys Lys Asn Lys Lys Asn Asp Ser Asp Val Pro Glu Leu Ala
                405                 410                 415

Thr Ile Pro Ala Ala Lys Arg Thr Lys Pro Ser Ala
            420                 425


<210> SEQ ID NO 5
<211> LENGTH: 2082
<212> TYPE: DNA
<213> ORGANISM: Saccharomyces cerevisiae

<400> SEQUENCE: 5

atgctacgat caaccacatt tactcgttcg ttccacagtt ctagggcctg gttgaaaggt     60

cagaacctaa ctgaaaaaat tgttcagtcg tatgcggtca accttcccga gggtaaagtt    120

gtgcattctg gtgactatgt atcgatcaag ccggcacact gtatgtccca cgataattcg    180

tggcctgtag ctttgaaatt catggggctt ggcgctacca agatcaagaa tccttcacag    240

attgtgacca ctctggacca cgatattcag aacaaatcag agaaaaattt gaccaagtac    300

aagaacatcg aaaatttgc taagaaacac catatagacc actaccctgc cggtagaggt    360

attggtcatc aaattatgat tgaggagggc tatgctttcc ccttgaacat gactgtcgca    420

tctgactcgc attcaaacac ctacggtggt ctggggtcgc tgggcactcc aatagtgaga    480

acagacgctg cagccatatg ggccacggga cagacgtggt ggcagatccc accagtggct    540

caggttgagt tgaaaggtca attgcctcag ggtgtttccg gaaaagatat cattgtcgca    600

ttatgtgggc ttttcaacaa tgatcaagtt ctaaatcacg ccattgaatt cacgggtgac    660

tctttgaatg cattgcctat cgatcacaga ctcactattg ctaacatgac caccgagtgg    720

ggggctcttt ctggtttgtt ccccgtggac aaaactttga tcgactggta taaaaaccgt    780

ttgcaaaagc tgggcaccaa taatcatcca aggattaatc caaagactat ccgcgcacta    840

gaagaaaagg cgaagattcc gaaagcagac aaggatgcac attatgccaa gaaactgatc    900

atcgatctag ccacgctaac tcactacgtc tcaggtccaa atagtgttaa ggtctccaac    960

accgtgcaag atctatctca acaagacatc aagataaata aagcttatct agtgtcatgt   1020

acaaactccc gtctatctga tttgcaatct gcagcggatg tggtttgtcc tactggagac   1080

ttaaacaaag tcaacaaggt ggctccaggt gtggagttct atgtcgctgc tgcctcttca   1140

gaaattgagg ctgatgcccg taaatcaggc gcttgggaaa agctgctaaa ggctggctgt   1200

atcccactgc cttctggttg tggtccatgc atcggtctag gtgcgggatt actggaacca   1260

ggtgaagttg gtatcagtgc cacaaacaga aacttcaaag gtagaatggg ttccaaggat   1320

gcattggctt acttagcttc ccctgctgta gtcgccgctt ctgccgtgct gggtaagatt   1380

agttctcctg ctgaggtatt gtccacaagc gaaattccat tcagcggcgt taagactgag   1440

ataattgaga atcccgtggt tgaagaggaa gttaacgctc aaacagaggc tccaaaacaa   1500

tccgttgaga tattagaagg tttcccaaga gagttttctg gtgaattagt tttatgtgat   1560

gccgataaca tcaataccga tggtatatat cctggtaagt acacttatca ggatgatgtg   1620

cctaaagaaa agatggcgca agtttgtatg gaaaattatg atgccgagtt cagaaccaag   1680

gttcatccag gtgatatagt ggtcagtggg ttcaatttcg gtaccggttc ctccagggaa   1740

caagcggcca ccgccttatt ggctaaaggt atcaacttag ttgtttcagg atcttttggt   1800

aatatttttt caagaaactc cattaacaat gctcttctga ccttggaaat cccagcatta   1860

atcaaaaaat tacgtgagaa atatcaaggt gctccaaaag aacttacaag aagaactggt   1920

tggtttttga aatgggatgt agctgatgct aaagtggtcg ttaccgaagg ttctttggac   1980
```

ggccctgtga tcttggagca aaaagtgggt gagctaggta agaacctaca agaaattatt 2040
gtaaaaggag gcttggaagg ttgggtcaaa tcccaactat aa 2082

<210> SEQ ID NO 6
<211> LENGTH: 693
<212> TYPE: PRT
<213> ORGANISM: Saccharomyces cerevisiae

<400> SEQUENCE: 6

Met Leu Arg Ser Thr Thr Phe Thr Arg Ser Phe His Ser Ser Arg Ala
1 5 10 15

Trp Leu Lys Gly Gln Asn Leu Thr Glu Lys Ile Val Gln Ser Tyr Ala
20 25 30

Val Asn Leu Pro Glu Gly Lys Val Val His Ser Gly Asp Tyr Val Ser
35 40 45

Ile Lys Pro Ala His Cys Met Ser His Asp Asn Ser Trp Pro Val Ala
50 55 60

Leu Lys Phe Met Gly Leu Gly Ala Thr Lys Ile Lys Asn Pro Ser Gln
65 70 75 80

Ile Val Thr Thr Leu Asp His Asp Ile Gln Asn Lys Ser Glu Lys Asn
85 90 95

Leu Thr Lys Tyr Lys Asn Ile Glu Asn Phe Ala Lys Lys His His Ile
100 105 110

Asp His Tyr Pro Ala Gly Arg Gly Ile Gly His Gln Ile Met Ile Glu
115 120 125

Glu Gly Tyr Ala Phe Pro Leu Asn Met Thr Val Ala Ser Asp Ser His
130 135 140

Ser Asn Thr Tyr Gly Gly Leu Gly Ser Leu Gly Thr Pro Ile Val Arg
145 150 155 160

Thr Asp Ala Ala Ala Ile Trp Ala Thr Gly Gln Thr Trp Trp Gln Ile
165 170 175

Pro Pro Val Ala Gln Val Glu Leu Lys Gly Gln Leu Pro Gln Gly Val
180 185 190

Ser Gly Lys Asp Ile Ile Val Ala Leu Cys Gly Leu Phe Asn Asn Asp
195 200 205

Gln Val Leu Asn His Ala Ile Glu Phe Thr Gly Asp Ser Leu Asn Ala
210 215 220

Leu Pro Ile Asp His Arg Leu Thr Ile Ala Asn Met Thr Thr Glu Trp
225 230 235 240

Gly Ala Leu Ser Gly Leu Phe Pro Val Asp Lys Thr Leu Ile Asp Trp
245 250 255

Tyr Lys Asn Arg Leu Gln Lys Leu Gly Thr Asn Asn His Pro Arg Ile
260 265 270

Asn Pro Lys Thr Ile Arg Ala Leu Glu Glu Lys Ala Lys Ile Pro Lys
275 280 285

Ala Asp Lys Asp Ala His Tyr Ala Lys Lys Leu Ile Ile Asp Leu Ala
290 295 300

Thr Leu Thr His Tyr Val Ser Gly Pro Asn Ser Val Lys Val Ser Asn
305 310 315 320

Thr Val Gln Asp Leu Ser Gln Gln Asp Ile Lys Ile Asn Lys Ala Tyr
325 330 335

Leu Val Ser Cys Thr Asn Ser Arg Leu Ser Asp Leu Gln Ser Ala Ala
340 345 350

-continued

```
Asp Val Val Cys Pro Thr Gly Asp Leu Asn Lys Val Asn Lys Val Ala
        355                 360                 365

Pro Gly Val Glu Phe Tyr Val Ala Ala Ala Ser Ser Glu Ile Glu Ala
    370                 375                 380

Asp Ala Arg Lys Ser Gly Ala Trp Glu Lys Leu Leu Lys Ala Gly Cys
385                 390                 395                 400

Ile Pro Leu Pro Ser Gly Cys Gly Pro Cys Ile Gly Leu Gly Ala Gly
                405                 410                 415

Leu Leu Glu Pro Gly Glu Val Gly Ile Ser Ala Thr Asn Arg Asn Phe
            420                 425                 430

Lys Gly Arg Met Gly Ser Lys Asp Ala Leu Ala Tyr Leu Ala Ser Pro
        435                 440                 445

Ala Val Val Ala Ala Ser Ala Val Leu Gly Lys Ile Ser Ser Pro Ala
    450                 455                 460

Glu Val Leu Ser Thr Ser Glu Ile Pro Phe Ser Gly Val Lys Thr Glu
465                 470                 475                 480

Ile Ile Glu Asn Pro Val Val Glu Glu Glu Val Asn Ala Gln Thr Glu
                485                 490                 495

Ala Pro Lys Gln Ser Val Glu Ile Leu Glu Gly Phe Pro Arg Glu Phe
            500                 505                 510

Ser Gly Glu Leu Val Leu Cys Asp Ala Asp Asn Ile Asn Thr Asp Gly
        515                 520                 525

Ile Tyr Pro Gly Lys Tyr Thr Tyr Gln Asp Asp Val Pro Lys Glu Lys
    530                 535                 540

Met Ala Gln Val Cys Met Glu Asn Tyr Asp Ala Glu Phe Arg Thr Lys
545                 550                 555                 560

Val His Pro Gly Asp Ile Val Val Ser Gly Phe Asn Phe Gly Thr Gly
                565                 570                 575

Ser Ser Arg Glu Gln Ala Ala Thr Ala Leu Leu Ala Lys Gly Ile Asn
            580                 585                 590

Leu Val Val Ser Gly Ser Phe Gly Asn Ile Phe Ser Arg Asn Ser Ile
        595                 600                 605

Asn Asn Ala Leu Leu Thr Leu Glu Ile Pro Ala Leu Ile Lys Lys Leu
    610                 615                 620

Arg Glu Lys Tyr Gln Gly Ala Pro Lys Glu Leu Thr Arg Arg Thr Gly
625                 630                 635                 640

Trp Phe Leu Lys Trp Asp Val Ala Asp Ala Lys Val Val Val Thr Glu
                645                 650                 655

Gly Ser Leu Asp Gly Pro Val Ile Leu Glu Gln Lys Val Gly Glu Leu
            660                 665                 670

Gly Lys Asn Leu Gln Glu Ile Ile Val Lys Gly Gly Leu Glu Gly Trp
        675                 680                 685

Val Lys Ser Gln Leu
    690
```

<210> SEQ ID NO 7
<211> LENGTH: 1005
<212> TYPE: DNA
<213> ORGANISM: Thermus thermophilus

<400> SEQUENCE: 7

```
atggcgtacc ggatctgctt gattgagggc gacggcatcg ggcacgaggt catccccgcg     60

gcgcggaggg tgctggaggc caccggcctc cccctggagt tcgtggaggc ggaggcgggc    120

tgggagacct ttgagagaag agggacctcc gtccccgagg agacggtgga gaagatcctg    180
```

-continued tcctgccacg ccaccctctt cggggccgcc accagcccca cccgtaaagt gccgggcttc 240
ttcggggcga tccgctacct caggcgcagg ctggacctct acgccaacgt ccgccccgcc 300
aagagccgcc ccgtcccggg aagccgcccc ggcgtggacc tggtcatcgt ccgggagaac 360
accgaagggc tttacgtgga gcaggaaagg cgctacctgg acgtggccat cgccgacgcc 420
gtcatctcca agaaggccag cgagcgcatc ggccgggccg ccttaaggat cgccgagggc 480
cggccccgca aaacccttca catcgcccac aaggccaacg tcctcccct cacccagggg 540 ctcttcctgg acacggtcaa ggaggtggcc aaggacttcc ccctggtgaa cgtgcaggac 600
atcatcgtgg acaactgcgc catgcagctc gtcatgcgtc ccgagcgctt tgacgtcatc 660
gtcaccacca acctcctggg ggacatcctc tccgacctcg ccgcggggct cgtgggggc 720 ctgggcctcg ccccctcggg caacatcggg gacaccaccg cggtctttga gcccgtccac 780
ggctccgccc ccgacatcgc cggcaagggc atcgccaacc ccacggcggc catcctctcc 840
gcggccatga tgctggacta cctgggggag aaggaggcgg ccaagcgggt ggagaaggcg 900
gtggacctgg tgctggagcg ggggcccagg acccctgacc tgggcgggga cgccaccacg 960
gaagccttca ccgaggccgt ggtggaggcg ctcaagagcc tgtag 1005

<210> SEQ ID NO 8
<211> LENGTH: 333
<212> TYPE: PRT
<213> ORGANISM: Thermus thermophilus

<400> SEQUENCE: 8

Ala Tyr Arg Ile Cys Leu Ile Glu Gly Asp Gly Ile Gly His Glu Val
1 5 10 15

Ile Pro Ala Ala Arg Arg Val Leu Glu Ala Thr Gly Leu Pro Leu Glu
20 25 30

Phe Val Glu Ala Glu Ala Gly Trp Glu Thr Phe Glu Arg Arg Gly Thr
35 40 45

Ser Val Pro Glu Glu Thr Val Glu Lys Ile Leu Ser Cys His Ala Thr
50 55 60

Leu Phe Gly Ala Ala Thr Ser Pro Thr Arg Lys Val Pro Gly Phe Phe
65 70 75 80

Gly Ala Ile Arg Tyr Leu Arg Arg Arg Leu Asp Leu Tyr Ala Asn Val
85 90 95

Arg Pro Ala Lys Ser Arg Pro Val Pro Gly Ser Arg Pro Gly Val Asp
100 105 110

Leu Val Ile Val Arg Glu Asn Thr Glu Gly Leu Tyr Val Glu Gln Glu
115 120 125

Arg Arg Tyr Leu Asp Val Ala Ile Ala Asp Ala Val Ile Ser Lys Lys
130 135 140

Ala Ser Glu Arg Ile Gly Arg Ala Ala Leu Arg Ile Ala Glu Gly Arg
145 150 155 160

Pro Arg Lys Thr Leu His Ile Ala His Lys Ala Asn Val Leu Pro Leu
165 170 175

Thr Gln Gly Leu Phe Leu Asp Thr Val Lys Glu Val Ala Lys Asp Phe
180 185 190

Pro Leu Val Asn Val Gln Asp Ile Ile Val Asp Asn Cys Ala Met Gln
195 200 205

Leu Val Met Arg Pro Glu Arg Phe Asp Val Ile Val Thr Thr Asn Leu
210 215 220

```
Leu Gly Asp Ile Leu Ser Asp Leu Ala Ala Gly Leu Val Gly Gly Leu
225                 230                 235                 240

Gly Leu Ala Pro Ser Gly Asn Ile Gly Asp Thr Thr Ala Val Phe Glu
                245                 250                 255

Pro Val His Gly Ser Ala Pro Asp Ile Ala Gly Lys Gly Ile Ala Asn
            260                 265                 270

Pro Thr Ala Ala Ile Leu Ser Ala Ala Met Met Leu Asp Tyr Leu Gly
        275                 280                 285

Glu Lys Glu Ala Ala Lys Arg Val Glu Lys Ala Val Asp Leu Val Leu
    290                 295                 300

Glu Arg Gly Pro Arg Thr Pro Asp Leu Gly Gly Asp Ala Thr Thr Glu
305                 310                 315                 320

Ala Phe Thr Glu Ala Val Val Glu Ala Leu Lys Ser Leu
                325                 330
```

<210> SEQ ID NO 9
<211> LENGTH: 1374
<212> TYPE: DNA
<213> ORGANISM: Streptomyces clavuligerus

<400> SEQUENCE: 9

```
atgggcgaag cagcacgcca ccccgacggc gatttctcgg acgtgggaaa cctccacgct      60

caggacgtgc accaggcact tgagcagcat atgctcgtcg acgggtacga cctcgttctc     120

gacctcgacg ccagctccgg cgtctggctc gtcgacgccg tcacccagaa gcggtatctc     180

gacctctttt ccttctttgc ctcggcgccg ctcggaatca acccgcccag cattgtcgag     240

gacccggcat tcatgcggga gctggccgtg gccgcggtca acaagccgtc gaaccccgat     300

ctttattcgg tgccgtacgc ccgtttcgtc aagaccttcg cccgggtcct cggcgacccc     360

cggctgccgc ggctgttctt cgtggacggc ggggcgctgg ccgtggagaa cgcgctcaag     420

gcggccctcg actggaaggc ccagaagctg ggcctcgccg agccggacac cgaccggctc     480

caggtgctgc atctggagcg ctcgttccac ggccgcagcg gctacaccat gtcgctgacg     540

aacaccgagc cgtccaagac cgcccgcttc cccaagttcg gctggccacg gatctcgtcc     600

cccgccctcc agcacccgcc ggccgagcac accggcgcca accaggaggc cgagcgacgg     660

gcgctggagg ccgcccggga ggcgttcgca gcggcggacg gcatgatcgc ctgcttcatc     720

gcggagccca tccagggcga gggcggcgac aaccacctca gcgcggagtt cctccaggcc     780

atgcagcggc tctgccacga gaacgacgcc ctgttcgtcc tggacgaggt gcagagcggc     840

tgcggcatca ccggtaccgc ctgggcctac cagcagctcg gcctccagcc cgacctggtg     900

gccttcggca agaagaccca ggtctgcggg gtgatgggcg gcggccggat cgacgaggtc     960

cccgagaacg tcttcgccgt ctcctcccgg atcagctcca cctggggcgg caacctcgcc    1020

gacatggtcc gcgccacccg gctgctggag acgatcgagc gcacccaggt cttcgacacc    1080

gtcgtccagc gcggcaagta cttccgggac ggcctggagg acctggccgc ccgccacccc    1140

tccgtcgtga ccaacgcccg cggccggggc ctgatgtgcg cggtcgacct gccggacacc    1200

cggacccgca atgaggtgct gcggcttatg tacacggagc accaggtcat cgccctgccc    1260

tgcggcgggc gcagcctccg gttccgcccc gcgctgacga tcgccgagca cgagatcgac    1320

caggcccttc aggcgctggc gagcagtgtc acggcggtcg ccgagagcgt ctga          1374
```

<210> SEQ ID NO 10
<211> LENGTH: 457
<212> TYPE: PRT

<213> ORGANISM: Streptomyces clavuligerus

<400> SEQUENCE: 10

Met Gly Glu Ala Ala Arg His Pro Asp Gly Asp Phe Ser Asp Val Gly
1 5 10 15

Asn Leu His Ala Gln Asp Val His Gln Ala Leu Glu Gln His Met Leu
20 25 30

Val Asp Gly Tyr Asp Leu Val Leu Asp Leu Asp Ala Ser Ser Gly Val
35 40 45

Trp Leu Val Asp Ala Val Thr Gln Lys Arg Tyr Leu Asp Leu Phe Ser
50 55 60

Phe Phe Ala Ser Ala Pro Leu Gly Ile Asn Pro Pro Ser Ile Val Glu
65 70 75 80

Asp Pro Ala Phe Met Arg Glu Leu Ala Val Ala Ala Val Asn Lys Pro
85 90 95

Ser Asn Pro Asp Leu Tyr Ser Val Pro Tyr Ala Arg Phe Val Lys Thr
100 105 110

Phe Ala Arg Val Leu Gly Asp Pro Arg Leu Pro Arg Leu Phe Phe Val
115 120 125

Asp Gly Gly Ala Leu Ala Val Glu Asn Ala Leu Lys Ala Ala Leu Asp
130 135 140

Trp Lys Ala Gln Lys Leu Gly Leu Ala Glu Pro Asp Thr Asp Arg Leu
145 150 155 160

Gln Val Leu His Leu Glu Arg Ser Phe His Gly Arg Ser Gly Tyr Thr
165 170 175

Met Ser Leu Thr Asn Thr Glu Pro Ser Lys Thr Ala Arg Phe Pro Lys
180 185 190

Phe Gly Trp Pro Arg Ile Ser Ser Pro Ala Leu Gln His Pro Pro Ala
195 200 205

Glu His Thr Gly Ala Asn Gln Glu Ala Glu Arg Arg Ala Leu Glu Ala
210 215 220

Ala Arg Glu Ala Phe Ala Ala Ala Asp Gly Met Ile Ala Cys Phe Ile
225 230 235 240

Ala Glu Pro Ile Gln Gly Glu Gly Gly Asp Asn His Leu Ser Ala Glu
245 250 255

Phe Leu Gln Ala Met Gln Arg Leu Cys His Glu Asn Asp Ala Leu Phe
260 265 270

Val Leu Asp Glu Val Gln Ser Gly Cys Gly Ile Thr Gly Thr Ala Trp
275 280 285

Ala Tyr Gln Gln Leu Gly Leu Gln Pro Asp Leu Val Ala Phe Gly Lys
290 295 300

Lys Thr Gln Val Cys Gly Val Met Gly Gly Gly Arg Ile Asp Glu Val
305 310 315 320

Pro Glu Asn Val Phe Ala Val Ser Ser Arg Ile Ser Ser Thr Trp Gly
325 330 335

Gly Asn Leu Ala Asp Met Val Arg Ala Thr Arg Leu Leu Glu Thr Ile
340 345 350

Glu Arg Thr Gln Val Phe Asp Thr Val Val Gln Arg Gly Lys Tyr Phe
355 360 365

Arg Asp Gly Leu Glu Asp Leu Ala Ala Arg His Pro Ser Val Val Thr
370 375 380

Asn Ala Arg Gly Arg Gly Leu Met Cys Ala Val Asp Leu Pro Asp Thr
385 390 395 400

-continued

```
Arg Thr Arg Asn Glu Val Leu Arg Leu Met Tyr Thr Glu His Gln Val
                405                 410                 415

Ile Ala Leu Pro Cys Gly Gly Arg Ser Leu Arg Phe Arg Pro Ala Leu
            420                 425                 430

Thr Ile Ala Glu His Glu Ile Asp Gln Ala Leu Gln Ala Leu Ala Ser
        435                 440                 445

Ser Val Thr Ala Val Ala Glu Ser Val
    450                 455


<210> SEQ ID NO 11
<211> LENGTH: 1533
<212> TYPE: DNA
<213> ORGANISM: Flavobacterium lutescens

<400> SEQUENCE: 11

atgtcgtttg aactgctcaa ggccttaggg ctggacgcca ccaattccgg cacctacctg     60

ggtgatggag aatggtccag cgctaccggt gccgggacca tcagcccgcg caacccgacc    120

accggcgagg tcattgccca ggtccaggcc accaccgagg cggactacga aaccatcctg    180

gcccgcgccc agcaggcctt caaggtctgg cgcaccaccc cggcaccgcg ccgcggcgag    240

gccatccgcc tgtgtggcga ggccctgcgc cgccacaagg acgcgctggg ttcgctggtc    300

gcgctggaaa tgggcaagtc caagccggaa ggcgacggcg aagtccagga aatgatcgac    360

atcgccgact ttgccgtcgg ccagagccgc atgctgtatg gctacaccat gcacagcgag    420

cgccccggcc accgcatgta cgagcagtac cagccgctgg gcatcgtcgg catcatctcg    480

gccttcaact tcccggtcgc ggtctgggcc tggaacagct tcctggccgc gatctgtggt    540

gatgtctgca tctggaagcc gtccaacaag accccgctga ccgcgatcgc gtccatgcgc    600

atctgcaacg aagcactgcg cgaaggcggc ttcccggaca tcttcttcct gatcaacgac    660

gccggcaccg cgttgtcgga gaagctggtc gaggacaagc gcgtgccgct gatctccttc    720

accggctcga cccaggtcgg gcgcatcgtc aaccagaagg tcgccgcccg cctgggccgc    780

tgcctgctcg agctgggcgg caacaacgcg atcatcctgg acgaaaccgc cgacctgaag    840

ctggccgtgc cgggcatcgt cttcggcgcc gtcggcaccg ccggccagcg ctgcaccacc    900

acccgccgcc tgatcgtgca cgaatcgatc tacgacaacg tgctggccac cttgatcaag    960

gcctacaagc aggtcgaagg caagatcggc gatccgctgg atgccgccaa cctgatgggc   1020

ccgctcaaca gccccgaagc ggtgcagcag ttcctggcct cgatcgagaa agccaaggcc   1080

gctggcggca ccgttcaaac cggtggtacc gcgatcgacc gcccgggcaa cttcgtgctg   1140

ccggccatcg tcaccggcct gaagaacagc gatgaggtgg tccagcacga gaccttcgcc   1200

ccgatcctgt acgtaatgaa gtactccacc ctggacgaag ccatcgagat gcagaacggc   1260

gtgccgcagg gcctgtcctc gtcgatcttc accacgaacc tgaaggcagc cgagaagttc   1320

ctgtcggcgg ccggcagcga ctgcggcatt gccaacgtca acatcggcac ttccggtgcc   1380

gagatcggcg gcgccttcgg tggcgagaag gaaaccggcg gtggccgtga gtccggctcg   1440

gatgcgtgga aggtctacat gcgccgccag accaacacca tcaactactc cgactcgctg   1500

ccgctggccc agggcatcaa gttcgacctg taa                                1533


<210> SEQ ID NO 12
<211> LENGTH: 510
<212> TYPE: PRT
<213> ORGANISM: Flavobacterium lutescens

<400> SEQUENCE: 12
```

-continued

```
Met Ser Phe Glu Leu Leu Lys Ala Leu Gly Leu Asp Ala Thr Asn Ser
1               5                   10                  15

Gly Thr Tyr Leu Gly Asp Gly Glu Trp Ser Ser Ala Thr Gly Ala Gly
            20                  25                  30

Thr Ile Ser Pro Arg Asn Pro Thr Thr Gly Glu Val Ile Ala Gln Val
        35                  40                  45

Gln Ala Thr Thr Glu Ala Asp Tyr Glu Thr Ile Leu Ala Arg Ala Gln
    50                  55                  60

Gln Ala Phe Lys Val Trp Arg Thr Thr Pro Ala Pro Arg Arg Gly Glu
65                  70                  75                  80

Ala Ile Arg Leu Cys Gly Glu Ala Leu Arg Arg His Lys Asp Ala Leu
                85                  90                  95

Gly Ser Leu Val Ala Leu Glu Met Gly Lys Ser Lys Pro Glu Gly Asp
            100                 105                 110

Gly Glu Val Gln Glu Met Ile Asp Ile Ala Asp Phe Ala Val Gly Gln
        115                 120                 125

Ser Arg Met Leu Tyr Gly Tyr Thr Met His Ser Glu Arg Pro Gly His
    130                 135                 140

Arg Met Tyr Glu Gln Tyr Gln Pro Leu Gly Ile Val Gly Ile Ile Ser
145                 150                 155                 160

Ala Phe Asn Phe Pro Val Ala Val Trp Ala Trp Asn Ser Phe Leu Ala
                165                 170                 175

Ala Ile Cys Gly Asp Val Cys Ile Trp Lys Pro Ser Asn Lys Thr Pro
            180                 185                 190

Leu Thr Ala Ile Ala Ser Met Arg Ile Cys Asn Glu Ala Leu Arg Glu
        195                 200                 205

Gly Gly Phe Pro Asp Ile Phe Phe Leu Ile Asn Asp Ala Gly Thr Ala
    210                 215                 220

Leu Ser Glu Lys Leu Val Glu Asp Lys Arg Val Pro Leu Ile Ser Phe
225                 230                 235                 240

Thr Gly Ser Thr Gln Val Gly Arg Ile Val Asn Gln Lys Val Ala Ala
                245                 250                 255

Arg Leu Gly Arg Cys Leu Leu Glu Leu Gly Gly Asn Asn Ala Ile Ile
            260                 265                 270

Leu Asp Glu Thr Ala Asp Leu Lys Leu Ala Val Pro Gly Ile Val Phe
        275                 280                 285

Gly Ala Val Gly Thr Ala Gly Gln Arg Cys Thr Thr Thr Arg Arg Leu
    290                 295                 300

Ile Val His Glu Ser Ile Tyr Asp Asn Val Leu Ala Thr Leu Ile Lys
305                 310                 315                 320

Ala Tyr Lys Gln Val Glu Gly Lys Ile Gly Asp Pro Leu Asp Ala Ala
                325                 330                 335

Asn Leu Met Gly Pro Leu Asn Ser Pro Glu Ala Val Gln Gln Phe Leu
            340                 345                 350

Ala Ser Ile Glu Lys Ala Lys Ala Ala Gly Gly Thr Val Gln Thr Gly
        355                 360                 365

Gly Thr Ala Ile Asp Arg Pro Gly Asn Phe Val Leu Pro Ala Ile Val
    370                 375                 380

Thr Gly Leu Lys Asn Ser Asp Glu Val Val Gln His Glu Thr Phe Ala
385                 390                 395                 400

Pro Ile Leu Tyr Val Met Lys Tyr Ser Thr Leu Asp Glu Ala Ile Glu
                405                 410                 415
```

```
Met Gln Asn Gly Val Pro Gln Gly Leu Ser Ser Ser Ile Phe Thr Thr
            420                 425                 430

Asn Leu Lys Ala Ala Glu Lys Phe Leu Ser Ala Ala Gly Ser Asp Cys
        435                 440                 445

Gly Ile Ala Asn Val Asn Ile Gly Thr Ser Gly Ala Glu Ile Gly Gly
    450                 455                 460

Ala Phe Gly Gly Glu Lys Glu Thr Gly Gly Gly Arg Glu Ser Gly Ser
465                 470                 475                 480

Asp Ala Trp Lys Val Tyr Met Arg Arg Gln Thr Asn Thr Ile Asn Tyr
                485                 490                 495

Ser Asp Ser Leu Pro Leu Ala Gln Gly Ile Lys Phe Asp Leu
            500                 505                 510


<210> SEQ ID NO 13
<211> LENGTH: 1278
<212> TYPE: DNA
<213> ORGANISM: Homo sapiens

<400> SEQUENCE: 13

atgaattacg cacggttcat cacggcagcg agcgcagcca gaaacccttc tcccatccgg      60

accatgactg acatattgag cagaggacca aaatcgatga tctccttggc tggtggctta     120

ccaaatccaa acatgtttcc ttttaagact gccgtaatca ctgtagaaaa tggaaagacc     180

atccaatttg gagaagagat gatgaagaga gcacttcagt attctccgag tgctggaatt     240

ccagagcttt tgtcctggct aaaacagtta caaataaaat tgcataatcc tcctaccatc     300

cattacccac ccagtcaagg acaaatggat ctatgtgtca catctggcag ccaacaaggt     360

ctttgtaagg tgtttgaaat gatcattaat cctggagata atgtcctcct agatgaacct     420

gcttattcag gaactcttca aagtctgcac ccactgggct gcaacattat taatgttgcc     480

agtgatgaaa gtgggattgt tccagattcc ctaagagaca tactttccag atggaaacca     540

gaagatgcaa agaatcccca gaaaaacacc cccaaatttc tttatactgt tccaaatggc     600

aacaacccta ctggaaactc attaaccagt gaacgcaaaa aggaaatcta tgagcttgca     660

agaaaatatg atttcctcat aatagaagat gatccttact attttctcca gtttaacaag     720

ttcagggtac caacatttct ttccatggat gttgatggac gtgtcatcag agctgactct     780

ttttcaaaaa tcatttcctc tgggttgaga ataggatttt taactggtcc aaaaccctta     840

atagagagag ttattttaca catacaagtt tcaacattgc accccagcac ttttaaccag     900

ctcatgatat cacagcttct acacgaatgg ggagaagaag gtttcatggc tcatgtagac     960

agggttattg atttctatag taaccagaag gatgcaatac tggcagctgc agacaagtgg    1020

ttaactggtt tggcagaatg gcatgttcct gctgctggaa tgtttttatg gattaaagtt    1080

aaaggcatta atgatgtaaa agaactgatt gaagaaaagg ccgttaagat gggggtatta    1140

atgctccctg gaaatgcttt ctacgtcgat agctcagctc ctagccctta cttgagagca    1200

tccttctctt cagcttctcc agaacagatg gatgtggcct tccaggtatt agcacaactt    1260

ataaaagaat ctttatga                                                  1278


<210> SEQ ID NO 14
<211> LENGTH: 425
<212> TYPE: PRT
<213> ORGANISM: Homo sapiens

<400> SEQUENCE: 14

Met Asn Tyr Ala Arg Phe Ile Thr Ala Ala Ser Ala Ala Arg Asn Pro
```

-continued

```
1               5                   10                  15

Ser Pro Ile Arg Thr Met Thr Asp Ile Leu Ser Arg Gly Pro Lys Ser
            20                  25                  30

Met Ile Ser Leu Ala Gly Gly Leu Pro Asn Pro Asn Met Phe Pro Phe
        35                  40                  45

Lys Thr Ala Val Ile Thr Val Glu Asn Gly Lys Thr Ile Gln Phe Gly
    50                  55                  60

Glu Glu Met Met Lys Arg Ala Leu Gln Tyr Ser Pro Ser Ala Gly Ile
65                  70                  75                  80

Pro Glu Leu Leu Ser Trp Leu Lys Gln Leu Gln Ile Lys Leu His Asn
                85                  90                  95

Pro Pro Thr Ile His Tyr Pro Pro Ser Gln Gly Gln Met Asp Leu Cys
            100                 105                 110

Val Thr Ser Gly Ser Gln Gln Gly Leu Cys Lys Val Phe Glu Met Ile
        115                 120                 125

Ile Asn Pro Gly Asp Asn Val Leu Leu Asp Glu Pro Ala Tyr Ser Gly
    130                 135                 140

Thr Leu Gln Ser Leu His Pro Leu Gly Cys Asn Ile Ile Asn Val Ala
145                 150                 155                 160

Ser Asp Glu Ser Gly Ile Val Pro Asp Ser Leu Arg Asp Ile Leu Ser
                165                 170                 175

Arg Trp Lys Pro Glu Asp Ala Lys Asn Pro Gln Lys Asn Thr Pro Lys
            180                 185                 190

Phe Leu Tyr Thr Val Pro Asn Gly Asn Asn Pro Thr Gly Asn Ser Leu
        195                 200                 205

Thr Ser Glu Arg Lys Lys Glu Ile Tyr Glu Leu Ala Arg Lys Tyr Asp
    210                 215                 220

Phe Leu Ile Ile Glu Asp Asp Pro Tyr Tyr Phe Leu Gln Phe Asn Lys
225                 230                 235                 240

Phe Arg Val Pro Thr Phe Leu Ser Met Asp Val Asp Gly Arg Val Ile
                245                 250                 255

Arg Ala Asp Ser Phe Ser Lys Ile Ile Ser Ser Gly Leu Arg Ile Gly
            260                 265                 270

Phe Leu Thr Gly Pro Lys Pro Leu Ile Glu Arg Val Ile Leu His Ile
        275                 280                 285

Gln Val Ser Thr Leu His Pro Ser Thr Phe Asn Gln Leu Met Ile Ser
    290                 295                 300

Gln Leu Leu His Glu Trp Gly Glu Glu Gly Phe Met Ala His Val Asp
305                 310                 315                 320

Arg Val Ile Asp Phe Tyr Ser Asn Gln Lys Asp Ala Ile Leu Ala Ala
                325                 330                 335

Ala Asp Lys Trp Leu Thr Gly Leu Ala Glu Trp His Val Pro Ala Ala
            340                 345                 350

Gly Met Phe Leu Trp Ile Lys Val Lys Gly Ile Asn Asp Val Lys Glu
        355                 360                 365

Leu Ile Glu Glu Lys Ala Val Lys Met Gly Val Leu Met Leu Pro Gly
    370                 375                 380

Asn Ala Phe Tyr Val Asp Ser Ser Ala Pro Ser Pro Tyr Leu Arg Ala
385                 390                 395                 400

Ser Phe Ser Ser Ala Ser Pro Glu Gln Met Asp Val Ala Phe Gln Val
                405                 410                 415

Leu Ala Gln Leu Ile Lys Glu Ser Leu
            420                 425
```

<210> SEQ ID NO 15
<211> LENGTH: 1104
<212> TYPE: DNA
<213> ORGANISM: Geobacillus stearothermophilus

<400> SEQUENCE: 15

```
atggaattgt tcaaatatat ggaaacttac gattatgagc aagtgctgtt ttgccaagat     60

aaagaatcgg gtttgaaagc gatcattgcc attcatgaca caacgctcgg cccggcgctc    120

ggcgggacgc gcatgtggat gtacaattcg gaagaagaag cgcttgaaga cgccttgcgc    180

ctcgcccgcg gcatgacgta caaaaacgcg gccgccggcc tcaacttggg cgggggcaaa    240

acggtcatca tcggcgaccc gcgcaaagat aaaaacgaag cgatgttccg ggcgttcggc    300

cgcttcattc aagggctgaa cggccgctac atcacggcgg aagacgtcgg cacgaccgtc    360

gccgatatgg acatcatcta ccaggaaacg gactatgtca ccggcatttc gccggaattc    420

ggctcatccg gcaacccgtc gccggccacg gcttacggcg tatatcgcgg gatgaaagcg    480

gcagcgaagg aagcatttgg aagtgattcg cttgaaggaa aagttgtcgc cgtccaagga    540

gtcggcaatg tcgcctacca tttatgccgc catttgcacg aagaaggagc gaaactcatc    600

gttaccgaca tcaacaagga agcggtggcg cgcgcggtcg aggaattcgg agcgaaagcg    660

gtcgacccga acgacattta cggcgtggag tgcgacattt ttgctccatg cgcgctcggc    720

ggcatcatca acgatcaaac gattccgcaa ctgaaagcga aagtgatcgc cggatcggcg    780

aacaaccagc tgaaagagcc gcgccatggc gacatcatcc atgaaatggg catcgtctat    840

gccccggatt atgtgatcaa cgccggcggc gtcatcaatg tcgcggacga actgtacggc    900

tacaatcggg aacgggcgat gaaaaaaatc gagcaaattt atgacaacat cgaaaaagtg    960

tttgccatcg ccaagcgcga caacattcca acgtatgtgg ccgccgaccg gatggcggaa   1020

gaacggattg aaacgatgcg caaagcgcgc agtcaatttt tgcaaaatgg tcaccatatt   1080

ttaagccgcc gtcgcgcccg ctaa                                          1104
```

<210> SEQ ID NO 16
<211> LENGTH: 367
<212> TYPE: PRT
<213> ORGANISM: Geobacillus stearothermophilus

<400> SEQUENCE: 16

```
Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Leu Gly Gly Thr Arg Met Trp Met Tyr
        35                  40                  45

Asn Ser Glu Glu Glu Ala Leu Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
        115                 120                 125
```

```
Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Ala
        195                 200                 205

Val Ala Arg Ala Val Glu Glu Phe Gly Ala Lys Ala Val Asp Pro Asn
    210                 215                 220

Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asn Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
                325                 330                 335

Arg Met Ala Glu Glu Arg Ile Glu Thr Met Arg Lys Ala Arg Ser Gln
            340                 345                 350

Phe Leu Gln Asn Gly His His Ile Leu Ser Arg Arg Arg Ala Arg
        355                 360                 365


<210> SEQ ID NO 17
<211> LENGTH: 644
<212> TYPE: DNA
<213> ORGANISM: Escherichia coli

<400> SEQUENCE: 17

tgctgtgaaa atcaaaggtt tttctggtga agatgcgact ccggcgctgg aaggcgcaga     60

tgtcgttctt atctctgcag gtgtagcgcg taaaccgggt atggatcgtt ccgacctgtt    120

taacgttaac gccggcatcg tgaaaaacct ggtacagcaa gtttcgaaaa cctgcccgaa    180

agcgtgcatt ggtattatca ctaacccggt taacaccaca gttgcgattg ctgctgaagt    240

gctgaaaaaa gccggtgttt atgacaaaaa caaactgttc ggcgttacca cgctggatat    300

cattcgttcc aacacctttg ttgcggaact gaaaggcaaa cagccaggcg aagttgaagt    360

gccggttatt ggcggtcact ctggtgttac cattctgccg ctgctgtcac aggttcctgg    420

cgttagtttt accgagcagg aagtggctga tctgaccaaa cgtatccaga acgcaggtac    480

tgaagtggtt gaagcgaaag ccggtggcgg gtctgcaacc ctgtctatgg gccaggcagc    540

tgcacgtttt ggtctgtctc tggttcgtgc actgcagggc gaacaaggcg ttgtcgaatg    600

tgcctacgtt gaaggcgacg gtcagtacgc ccgtttcttc tctc                      644


<210> SEQ ID NO 18
<211> LENGTH: 214
<212> TYPE: PRT
```

<213> ORGANISM: Escherichia coli

<400> SEQUENCE: 18

```
Ala Val Lys Ile Lys Gly Phe Ser Gly Glu Asp Ala Thr Pro Ala Leu
1               5                   10                  15

Glu Gly Ala Asp Val Val Leu Ile Ser Ala Gly Val Ala Arg Lys Pro
            20                  25                  30

Gly Met Asp Arg Ser Asp Leu Phe Asn Val Asn Ala Gly Ile Val Lys
        35                  40                  45

Asn Leu Val Gln Gln Val Ser Lys Thr Cys Pro Lys Ala Cys Ile Gly
    50                  55                  60

Ile Ile Thr Asn Pro Val Asn Thr Thr Val Ala Ile Ala Ala Glu Val
65                  70                  75                  80

Leu Lys Lys Ala Gly Val Tyr Asp Lys Asn Lys Leu Phe Gly Val Thr
                85                  90                  95

Thr Leu Asp Ile Ile Arg Ser Asn Thr Phe Val Ala Glu Leu Lys Gly
            100                 105                 110

Lys Gln Pro Gly Glu Val Glu Val Pro Val Ile Gly Gly His Ser Gly
        115                 120                 125

Val Thr Ile Leu Pro Leu Leu Ser Gln Val Pro Gly Val Ser Phe Thr
    130                 135                 140

Glu Gln Glu Val Ala Asp Leu Thr Lys Arg Ile Gln Asn Ala Gly Thr
145                 150                 155                 160

Glu Val Val Glu Ala Lys Ala Gly Gly Gly Ser Ala Thr Leu Ser Met
                165                 170                 175

Gly Gln Ala Ala Ala Arg Phe Gly Leu Ser Leu Val Arg Ala Leu Gln
            180                 185                 190

Gly Glu Gln Gly Val Val Glu Cys Ala Tyr Val Glu Gly Asp Gly Gln
        195                 200                 205

Tyr Ala Arg Phe Phe Ser
    210
```

<210> SEQ ID NO 19
<211> LENGTH: 1008
<212> TYPE: DNA
<213> ORGANISM: Aspergillus fumigatus

<400> SEQUENCE: 19

```
atgccttcgg ctctactcat tggtgccatc acccacgcgc gcaaggagtg gaaagatctc     60

tcgtccattc tgactctaaa ggaatttccc gaaggcacca gagacgagtt catccggaat    120

tgcaaagacg gccagtacga tgatgtggta gtgatttacc gatccaatgc gtctaccaag    180

ttcaccggtc cattcgacgc agagttgctc tctgtccttc ccaagtcatt aaagtatatc    240

tgccacaatg gggctggcta tgacaacatt gacatcccgg cctgttcaga gaagggaatt    300

gccgtctcca gtaccccagt cgccgtgaac cacgcaactg ctgacgtagg catcttcctg    360

atgattggcg ctttgcgcca ggcttatatc cccttatctg ctctccgcgc cggtcaatgg    420

cagggaaaga ctacgctcgg gcatgaccct cagggcaagg tgcttggtat tctcgggatg    480

ggaggaatcg gaagggaaat ggccaatcgt gcacgagctt tcggcatgaa gatacaatac    540

cacaacagat cgagactctc gccagagctt gagggagatg cgcagtatgt ctcgtttgat    600

gagttgctgg cgaacgcgga tgtcctcagc ttgaatctcg ctctcaatgc caaaactcgc    660

catatcattg gcgagaagga gttccagaag atgaaagacg gtgtggtcat tgtgaacacg    720

gctcgtggcg ctttaattga cgaaaaagct ctggtggccg ctttggattc cgggaaggtc    780
```

```
atgtcggctg gtttggatgt gtatgagaac gagccggaga tcgaacctgg acttgtaaat    840

aacccccgcg tgatgctact accgcacatt ggaaccgcga cctatgagac ccagaaagaa    900

atggagctgt tggtcttgaa caacttgcgc tcggcggtgg agaagggcga gatgatcaca    960

ttggtgccgg agcagaagga tatcttcaag ggcagaacgg gaaagtaa               1008


<210> SEQ ID NO 20
<211> LENGTH: 335
<212> TYPE: PRT
<213> ORGANISM: Aspergillus fumigatus

<400> SEQUENCE: 20

Met Pro Ser Ala Leu Leu Ile Gly Ala Ile Thr His Ala Arg Lys Glu
1               5                   10                  15

Trp Lys Asp Leu Ser Ser Ile Leu Thr Leu Lys Glu Phe Pro Glu Gly
            20                  25                  30

Thr Arg Asp Glu Phe Ile Arg Asn Cys Lys Asp Gly Gln Tyr Asp Asp
        35                  40                  45

Val Val Val Ile Tyr Arg Ser Asn Ala Ser Thr Lys Phe Thr Gly Pro
    50                  55                  60

Phe Asp Ala Glu Leu Leu Ser Val Leu Pro Lys Ser Leu Lys Tyr Ile
65                  70                  75                  80

Cys His Asn Gly Ala Gly Tyr Asp Asn Ile Asp Ile Pro Ala Cys Ser
                85                  90                  95

Glu Lys Gly Ile Ala Val Ser Ser Thr Pro Val Ala Val Asn His Ala
            100                 105                 110

Thr Ala Asp Val Gly Ile Phe Leu Met Ile Gly Ala Leu Arg Gln Ala
        115                 120                 125

Tyr Ile Pro Leu Ser Ala Leu Arg Ala Gly Gln Trp Gln Gly Lys Thr
    130                 135                 140

Thr Leu Gly His Asp Pro Gln Gly Lys Val Leu Gly Ile Leu Gly Met
145                 150                 155                 160

Gly Gly Ile Gly Arg Glu Met Ala Asn Arg Ala Arg Ala Phe Gly Met
                165                 170                 175

Lys Ile Gln Tyr His Asn Arg Ser Arg Leu Ser Pro Glu Leu Glu Gly
            180                 185                 190

Asp Ala Gln Tyr Val Ser Phe Asp Glu Leu Leu Ala Asn Ala Asp Val
        195                 200                 205

Leu Ser Leu Asn Leu Ala Leu Asn Ala Lys Thr Arg His Ile Ile Gly
    210                 215                 220

Glu Lys Glu Phe Gln Lys Met Lys Asp Gly Val Val Ile Val Asn Thr
225                 230                 235                 240

Ala Arg Gly Ala Leu Ile Asp Glu Lys Ala Leu Val Ala Ala Leu Asp
                245                 250                 255

Ser Gly Lys Val Met Ser Ala Gly Leu Asp Val Tyr Glu Asn Glu Pro
            260                 265                 270

Glu Ile Glu Pro Gly Leu Val Asn Asn Pro Arg Val Met Leu Leu Pro
        275                 280                 285

His Ile Gly Thr Ala Thr Tyr Glu Thr Gln Lys Glu Met Glu Leu Leu
    290                 295                 300

Val Leu Asn Asn Leu Arg Ser Ala Val Glu Lys Gly Glu Met Ile Thr
305                 310                 315                 320

Leu Val Pro Glu Gln Lys Asp Ile Phe Lys Gly Gln Asn Gly Lys
                325                 330                 335
```

<210> SEQ ID NO 21
<211> LENGTH: 1194
<212> TYPE: DNA
<213> ORGANISM: Clostridium difficile

<400> SEQUENCE: 21

```
cttttagaag gagttaaagt agtagaactt tcaagtttca tcgcagcacc atgttgtgca     60

aaaatgttag gtgactgggg tgcagaggtt attaagattg aacctataga aggtgatgga    120

ataagagtta tgggtggaac atttaaatct ccagcatcag atgatgaaaa ccctatgttt    180

gaattagaaa atggaaataa aaagggtgta agtattaatg taaaatcaaa agaaggagta    240

gaaatattac ataaattatt atcagaagca gacatatttg taactaatgt tagagttcaa    300

gcattagaaa aaatgggtat agcttatgac caaataaaag ataagtatcc aggattaata    360

ttctctcaaa tattaggata tggtgaaaaa ggacctttaa aagataaacc aggatttgac    420

tatactgcat acttcgcaag aggaggagtt agccaatctg ttatggaaaa aggaacatct    480

ccagcaaata cagcagcagg atttggtgac cactatgcag gtctagcact agcagcagga    540

agtttagcag cattacataa aaaagctcaa actggtaaag gtgagagagt aacagtaagt    600

cttttccata cagctatata tggaatggga acaatgataa caacagcaca atacggaaat    660

gaaatgcctt tatcaagaga aaatccaaac agcccattaa tgactacata taaatgtaaa    720

gatggaagat ggattcaatt agctttaata caatacaaca agtggttagg caaattctgt    780

aaggttataa atagagaata tatattagaa gacgatagat ataataacat agattcaatg    840

gttaatcatg ttgaagattt agttaagata gttggagaag ctatgttaga aaaaacatta    900

gacgagtggt cagctttatt agaagaagca gacttaccat ttgaaaaaat tcaaagctgt    960

gaagatttat tagatgacga acaagcttgg gcaaatgact tcttatttaa gaaaacatac   1020

gatagcggaa atacaggtgt cttagttaat actccagtta tgtttagaaa tgaaggaatt   1080

aaagaatata caccagcacc aaaagtaggt caacatactg tagaagtatt aaaatcttta   1140

ggctacgatg aagagaaaat aaataacttt aaagatagta aagttgtaag atat         1194
```

<210> SEQ ID NO 22
<211> LENGTH: 398
<212> TYPE: PRT
<213> ORGANISM: Clostridium difficile

<400> SEQUENCE: 22

```
Leu Leu Glu Gly Val Lys Val Val Glu Leu Ser Ser Phe Ile Ala Ala
1               5                   10                  15

Pro Cys Cys Ala Lys Met Leu Gly Asp Trp Gly Ala Glu Val Ile Lys
            20                  25                  30

Ile Glu Pro Ile Glu Gly Asp Gly Ile Arg Val Met Gly Gly Thr Phe
        35                  40                  45

Lys Ser Pro Ala Ser Asp Asp Glu Asn Pro Met Phe Glu Leu Glu Asn
    50                  55                  60

Gly Asn Lys Lys Gly Val Ser Ile Asn Val Lys Ser Lys Glu Gly Val
65                  70                  75                  80

Glu Ile Leu His Lys Leu Leu Ser Glu Ala Asp Ile Phe Val Thr Asn
                85                  90                  95

Val Arg Val Gln Ala Leu Glu Lys Met Gly Ile Ala Tyr Asp Gln Ile
            100                 105                 110

Lys Asp Lys Tyr Pro Gly Leu Ile Phe Ser Gln Ile Leu Gly Tyr Gly
```

```
        115                 120                 125

Glu Lys Gly Pro Leu Lys Asp Lys Pro Gly Phe Asp Tyr Thr Ala Tyr
    130                 135                 140

Phe Ala Arg Gly Gly Val Ser Gln Ser Val Met Glu Lys Gly Thr Ser
145                 150                 155                 160

Pro Ala Asn Thr Ala Ala Gly Phe Gly Asp His Tyr Ala Gly Leu Ala
                165                 170                 175

Leu Ala Ala Gly Ser Leu Ala Ala Leu His Lys Lys Ala Gln Thr Gly
            180                 185                 190

Lys Gly Glu Arg Val Thr Val Ser Leu Phe His Thr Ala Ile Tyr Gly
        195                 200                 205

Met Gly Thr Met Ile Thr Thr Ala Gln Tyr Gly Asn Glu Met Pro Leu
    210                 215                 220

Ser Arg Glu Asn Pro Asn Ser Pro Leu Met Thr Thr Tyr Lys Cys Lys
225                 230                 235                 240

Asp Gly Arg Trp Ile Gln Leu Ala Leu Ile Gln Tyr Asn Lys Trp Leu
                245                 250                 255

Gly Lys Phe Cys Lys Val Ile Asn Arg Glu Tyr Ile Leu Glu Asp Asp
            260                 265                 270

Arg Tyr Asn Asn Ile Asp Ser Met Val Asn His Val Glu Asp Leu Val
        275                 280                 285

Lys Ile Val Gly Glu Ala Met Leu Glu Lys Thr Leu Asp Glu Trp Ser
    290                 295                 300

Ala Leu Leu Glu Glu Ala Asp Leu Pro Phe Glu Lys Ile Gln Ser Cys
305                 310                 315                 320

Glu Asp Leu Leu Asp Asp Glu Gln Ala Trp Ala Asn Asp Phe Leu Phe
                325                 330                 335

Lys Lys Thr Tyr Asp Ser Gly Asn Thr Gly Val Leu Val Asn Thr Pro
            340                 345                 350

Val Met Phe Arg Asn Glu Gly Ile Lys Glu Tyr Thr Pro Ala Pro Lys
        355                 360                 365

Val Gly Gln His Thr Val Glu Val Leu Lys Ser Leu Gly Tyr Asp Glu
    370                 375                 380

Glu Lys Ile Asn Asn Phe Lys Asp Ser Lys Val Val Arg Tyr
385                 390                 395
```

<210> SEQ ID NO 23
<211> LENGTH: 993
<212> TYPE: DNA
<213> ORGANISM: Clostridium difficile

<400> SEQUENCE: 23

```
aaaatactag tatttggagc acgcgattat gaagaaccag taataaaaaa atggtctgaa      60

gaacataagg atgttcaagt ggatatttat cctgaaaaca tgactgaaga aaatgtagtt     120

aaagctaaag ggtatgatgg tatatctata caacaaacta actatataga taatccttat     180

atttatgaaa ctttaaaaga tgctggggtt aaagttatag cttcaagaac tgcaggggtt     240

gacatgatac attttgattt agttaatgaa aatggactta tcgttacaaa cgttccttct     300

tattcaccta atgcaatagc tgaattagct gttactcaag ctatgaacct tttaagaaag     360

actcctctag taaagaaaaa agtctgtgaa ggtgattacc gttggatagc tgaacttctt     420

ggaacagaag ttagatctat tacagttggt gttataggta caggaaaaat aggtgctact     480

tctgcaaaat tattcaaagg cctaggagct aatgtaattg catttgacca atatccaaat     540
```

-continued agtgatttaa atgatatatt aacttacaaa gattctttag aagaccttct aaaagaagct 600
gaccttataa cattacatac tcctttactt gaaggaacaa aacatatgat aaataaagat 660
actctagcta taatgaagga tggagcttac atagtaaata ctggccgtgg tggtttaatt 720
aatacagggg atttaataga agcactagag tcaggaaaaa ttagagctgc tgcccttgat 780
acatttgaaa ctgaaggatt gttcttaaac aaaaaaatga atcctggaga attaactgac 840
ccagaaataa ataaacttct ttctatggaa caagttatat tcactcatca ccttggtttc 900
ttcactagta cagcgattga aaatatagtt tattctagtt taagcagtgc tgtagaagtt 960
ataaaaacag gaactgctac taatagagta aat 993

<210> SEQ ID NO 24
<211> LENGTH: 331
<212> TYPE: PRT
<213> ORGANISM: Clostridium difficile

<400> SEQUENCE: 24

Lys Ile Leu Val Phe Gly Ala Arg Asp Tyr Glu Glu Pro Val Ile Lys
1 5 10 15

Lys Trp Ser Glu Glu His Lys Asp Val Gln Val Asp Ile Tyr Pro Glu
20 25 30

Asn Met Thr Glu Glu Asn Val Val Lys Ala Lys Gly Tyr Asp Gly Ile
35 40 45

Ser Ile Gln Gln Thr Asn Tyr Ile Asp Asn Pro Tyr Ile Tyr Glu Thr
50 55 60

Leu Lys Asp Ala Gly Val Lys Val Ile Ala Ser Arg Thr Ala Gly Val
65 70 75 80

Asp Met Ile His Phe Asp Leu Val Asn Glu Asn Gly Leu Ile Val Thr
85 90 95

Asn Val Pro Ser Tyr Ser Pro Asn Ala Ile Ala Glu Leu Ala Val Thr
100 105 110

Gln Ala Met Asn Leu Leu Arg Lys Thr Pro Leu Val Lys Lys Lys Val
115 120 125

Cys Glu Gly Asp Tyr Arg Trp Ile Ala Glu Leu Leu Gly Thr Glu Val
130 135 140

Arg Ser Ile Thr Val Gly Val Ile Gly Thr Gly Lys Ile Gly Ala Thr
145 150 155 160

Ser Ala Lys Leu Phe Lys Gly Leu Gly Ala Asn Val Ile Ala Phe Asp
165 170 175

Gln Tyr Pro Asn Ser Asp Leu Asn Asp Ile Leu Thr Tyr Lys Asp Ser
180 185 190

Leu Glu Asp Leu Leu Lys Glu Ala Asp Leu Ile Thr Leu His Thr Pro
195 200 205

Leu Leu Glu Gly Thr Lys His Met Ile Asn Lys Asp Thr Leu Ala Ile
210 215 220

Met Lys Asp Gly Ala Tyr Ile Val Asn Thr Gly Arg Gly Gly Leu Ile
225 230 235 240

Asn Thr Gly Asp Leu Ile Glu Ala Leu Glu Ser Gly Lys Ile Arg Ala
245 250 255

Ala Ala Leu Asp Thr Phe Glu Thr Glu Gly Leu Phe Leu Asn Lys Lys
260 265 270

Met Asn Pro Gly Glu Leu Thr Asp Pro Glu Ile Asn Lys Leu Leu Ser
275 280 285

Met Glu Gln Val Ile Phe Thr His His Leu Gly Phe Phe Thr Ser Thr

-continued

```
    290                 295                 300

Ala Ile Glu Asn Ile Val Tyr Ser Ser Leu Ser Ser Ala Val Glu Val
305                 310                 315                 320

Ile Lys Thr Gly Thr Ala Thr Asn Arg Val Asn
                325                 330


<210> SEQ ID NO 25
<211> LENGTH: 1227
<212> TYPE: DNA
<213> ORGANISM: Clostridium difficile

<400> SEQUENCE: 25

atgtctgaaa aaaaagaagc tagagtagta attaatgatt tattagctga acaatatgca      60

aatgcattta aagctaaaga agaaggaaga cctgtaggtt ggtcaacatc agtatttcct     120

caagagttag cagaagtatt tgacttaaac gtattatatc cagaaaacca agcagctgga     180

gtagcagcta aaaaaggttc tttagaatta tgtgaaatag ctgaatctaa aggatattct     240

attgacctat gtgcatatgc aagaacaaat tttggtcttt tagaaaatgg tggatgtgaa     300

gctttggata tgccagctcc agatttccta ctttgctgta acaatatatg taaccaagtt     360

ataaaatggt atgaaaatat ttcaagagaa ttagatatac ctttaataat gattgataca     420

actttcaata atgaagacga agttactcaa tcaagaatag attatattaa agctcaattt     480

gaagaagcta taaaacaact agaaattata tcaggaaaga aatttgaccc taagaagttt     540

gaagaagtaa tgaaaatatc agctgaaaac ggaagactat ggaagtattc tatgagttta     600

ccagcagatt cttctccttc tccaatgaat ggatttgact tatttactta catggctgta     660

atagtttgtg ctagaggtaa aaaagaaact acagaagcat ttaagttact tatagaagaa     720

ttagaggaca acatgaaaac tggtaaatct tctttcagag gggaagaaaa atacagaata     780

atgatggaag gtataccttg ttggccatat ataggataca agatgaaaac attagctaaa     840

tttggagtta acatgacagg tagtgtttac ccacatgctt gggcattaca atatgaagtt     900

aatgatttag atggaatggc agtagcatat agtactatgt ttaacaatgt aaacctagac     960

cgtatgacaa aatatagagt tgattcttta gtagagggta aatgtgatgg agcattctat    1020

catatgaaca gaagctgtaa acttatgagt ttaatacaat atgaaatgca aagaagagca    1080

gctgaagaaa ctggattacc atatgctgga tttgatggtg accaagcaga ccctagagct    1140

ttcactaatg ctcaatttga aacaagaatt caaggtttag ttgaagtaat ggaagaaaga    1200

aaaaaactta atagaggtga gatataa                                         1227


<210> SEQ ID NO 26
<211> LENGTH: 408
<212> TYPE: PRT
<213> ORGANISM: Clostridium difficile

<400> SEQUENCE: 26

Met Ser Glu Lys Lys Glu Ala Arg Val Val Ile Asn Asp Leu Leu Ala
1               5                   10                  15

Glu Gln Tyr Ala Asn Ala Phe Lys Ala Lys Glu Glu Gly Arg Pro Val
            20                  25                  30

Gly Trp Ser Thr Ser Val Phe Pro Gln Glu Leu Ala Glu Val Phe Asp
        35                  40                  45

Leu Asn Val Leu Tyr Pro Glu Asn Gln Ala Ala Gly Val Ala Ala Lys
    50                  55                  60

Lys Gly Ser Leu Glu Leu Cys Glu Ile Ala Glu Ser Lys Gly Tyr Ser
```

-continued

```
65                  70                  75                  80

Ile Asp Leu Cys Ala Tyr Ala Arg Thr Asn Phe Gly Leu Leu Glu Asn
                85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
    130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Glu Ile Ile Ser Gly Lys Lys Phe Asp
                165                 170                 175

Pro Lys Lys Phe Glu Glu Val Met Lys Ile Ser Ala Glu Asn Gly Arg
            180                 185                 190

Leu Trp Lys Tyr Ser Met Ser Leu Pro Ala Asp Ser Ser Pro Ser Pro
        195                 200                 205

Met Asn Gly Phe Asp Leu Phe Thr Tyr Met Ala Val Ile Val Cys Ala
    210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
                245                 250                 255

Lys Tyr Arg Ile Met Met Glu Gly Ile Pro Cys Trp Pro Tyr Ile Gly
            260                 265                 270

Tyr Lys Met Lys Thr Leu Ala Lys Phe Gly Val Asn Met Thr Gly Ser
        275                 280                 285

Val Tyr Pro His Ala Trp Ala Leu Gln Tyr Glu Val Asn Asp Leu Asp
    290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
                325                 330                 335

Gly Ala Phe Tyr His Met Asn Arg Ser Cys Lys Leu Met Ser Leu Ile
            340                 345                 350

Gln Tyr Glu Met Gln Arg Arg Ala Ala Glu Glu Thr Gly Leu Pro Tyr
        355                 360                 365

Ala Gly Phe Asp Gly Asp Gln Ala Asp Pro Arg Ala Phe Thr Asn Ala
    370                 375                 380

Gln Phe Glu Thr Arg Ile Gln Gly Leu Val Glu Val Met Glu Glu Arg
385                 390                 395                 400

Lys Lys Leu Asn Arg Gly Glu Ile
                405


<210> SEQ ID NO 27
<211> LENGTH: 798
<212> TYPE: DNA
<213> ORGANISM: Clostridium difficile

<400> SEQUENCE: 27

atgtacacaa tgggattaga tataggttca actgcatcaa agggagtaat cttaaagaat      60

ggggaagata ttgtagcttc tgaaacaata tcctctggta ctgggactac tggaccatca     120

agagttttag aaaaattata tggcaagaca ggtcttgcaa gagaagatat taaaaaagtt     180
```

-continued

```
gtagttacag gatatggaag aatgaactat tcagatgctg ataagcaaat aagtgaatta    240

agctgtcatg ctagaggggt aaatttcata attccagaga caagaaccat tattgacata    300

ggtggtcaag atgcaaaggt attaaaatta gataataatg gaagactatt aaactttctt    360

atgaatgaca aatgtgctgc aggtacagga agatttttag atgtaatggc aaaaataata    420

gaggttgatg tatctgaact cggaagtata tctatgaatt ctcaaaatga agtatcaata    480

agcagtacat gtacagtatt tgcagagtct gaggttatat cacatttatc tgaaaatgca    540

aaaattgaag atatagtggc aggtattcat acttcagtag caaagagagt ttctagccta    600

gtaaaaagaa taggagtaca aagaaatgta gttatggttg gtggggttgc tagaaatagt    660

ggtattgtaa gagctatggc aagagaaatc aacacagaaa ttattgtacc tgatatacct    720

caattaactg gtgctttagg agcagcgtta tatgcttttg atgaagcaaa agaatcacaa    780

aaagaagtga aaaatata                                                  798
```

<210> SEQ ID NO 28
<211> LENGTH: 266
<212> TYPE: PRT
<213> ORGANISM: Clostridium difficile

<400> SEQUENCE: 28

```
Met Tyr Thr Met Gly Leu Asp Ile Gly Ser Thr Ala Ser Lys Gly Val
1               5                   10                  15

Ile Leu Lys Asn Gly Glu Asp Ile Val Ala Ser Glu Thr Ile Ser Ser
            20                  25                  30

Gly Thr Gly Thr Thr Gly Pro Ser Arg Val Leu Glu Lys Leu Tyr Gly
        35                  40                  45

Lys Thr Gly Leu Ala Arg Glu Asp Ile Lys Lys Val Val Val Thr Gly
    50                  55                  60

Tyr Gly Arg Met Asn Tyr Ser Asp Ala Asp Lys Gln Ile Ser Glu Leu
65                  70                  75                  80

Ser Cys His Ala Arg Gly Val Asn Phe Ile Ile Pro Glu Thr Arg Thr
                85                  90                  95

Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
        115                 120                 125

Thr Gly Arg Phe Leu Asp Val Met Ala Lys Ile Ile Glu Val Asp Val
    130                 135                 140

Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
                165                 170                 175

Ser Glu Asn Ala Lys Ile Glu Asp Ile Val Ala Gly Ile His Thr Ser
            180                 185                 190

Val Ala Lys Arg Val Ser Ser Leu Val Lys Arg Ile Gly Val Gln Arg
        195                 200                 205

Asn Val Val Met Val Gly Gly Val Ala Arg Asn Ser Gly Ile Val Arg
    210                 215                 220

Ala Met Ala Arg Glu Ile Asn Thr Glu Ile Ile Val Pro Asp Ile Pro
225                 230                 235                 240

Gln Leu Thr Gly Ala Leu Gly Ala Ala Leu Tyr Ala Phe Asp Glu Ala
                245                 250                 255

Lys Glu Ser Gln Lys Glu Val Lys Asn Ile
```

260 265

<210> SEQ ID NO 29
<211> LENGTH: 1134
<212> TYPE: DNA
<213> ORGANISM: Clostridium difficle

<400> SEQUENCE: 29
atgttatata acaaagaaca agaactttta agaaaagcag taagagattt tgttagtaaa 60
gaattagata ctttaccagc agaaatggat aaaacaggtg taatgcctaa ggaattaatc 120
aaaaaattag ctgatgcaaa atttataagc agtaatatcc cagaagaata tggtggtggg 180
ggagcaggat atgtttctta cgctatagta atggaagaaa tagctagaag atgtgcttca 240
acagctactt ttgttacagc tggttcttct cttgcttcat taccaatact ttacaatggt 300
actgaagagc aaaaacaaaa atacttaaaa ggtatagcaa caggtgaatt aataggagca 360
tttggtttaa ctgagccagg agctggttct gatgcaggtg gacaacaaac aacagcagaa 420
ttagttggag atcactatat attaaatggt agaaaaactt tcataactaa tggaccattc 480
tgtgatgtag ctatagtaat agcagttaca gatagaagta aaggacttag aggaacatca 540
gcgtttatag tagaaagtaa atgggatggt ttctcaacag gagctcatga agataagatg 600
ggtataagag gaactgaaac ttctgactta atatttgaaa acgttaaagt tccaaaagaa 660
aacttacttg gaaaagaagg tcaaggattt aagatagcaa tgggtactct agaagttggt 720
agaataggtg ttgctgcctt agctctagga atagctcaag gtgctttaga tgaagctgtt 780
aaatatacaa aacaaagagt tcaatttggt aagcctatag ctaaattcca aaatactcaa 840
tttactatag ctgacatgga aacaaaagtt tgtgcagcta gaggattagt ttatgatgca 900
gcacaaaaga gagatgcagg aatgagagtt gctcaagaat ctgctatggc taaatactat 960
gcatcagaaa ttgcaaatga agttgcttat aaagcattac aacttcacgg tggatatgga 1020
tttataaaag attatgaaat cgaaagaatg tacagagatg ctagaatcgt atcaatatac 1080
gaaggaacat cagaagttca aaaaatggta atttcatcaa acgtattaaa ataa 1134

<210> SEQ ID NO 30
<211> LENGTH: 377
<212> TYPE: PRT
<213> ORGANISM: Clostridium difficile

<400> SEQUENCE: 30

Met Leu Tyr Asn Lys Glu Gln Glu Leu Leu Arg Lys Ala Val Arg Asp
1 5 10 15

Phe Val Ser Lys Glu Leu Asp Thr Leu Pro Ala Glu Met Asp Lys Thr
20 25 30

Gly Val Met Pro Lys Glu Leu Ile Lys Lys Leu Ala Asp Ala Lys Phe
35 40 45

Ile Ser Ser Asn Ile Pro Glu Glu Tyr Gly Gly Gly Gly Ala Gly Tyr
50 55 60

Val Ser Tyr Ala Ile Val Met Glu Glu Ile Ala Arg Arg Cys Ala Ser
65 70 75 80

Thr Ala Thr Phe Val Thr Ala Gly Ser Ser Leu Ala Ser Leu Pro Ile
85 90 95

Leu Tyr Asn Gly Thr Glu Glu Gln Lys Gln Lys Tyr Leu Lys Gly Ile
100 105 110

Ala Thr Gly Glu Leu Ile Gly Ala Phe Gly Leu Thr Glu Pro Gly Ala
115 120 125

```
Gly Ser Asp Ala Gly Gly Gln Gln Thr Thr Ala Glu Leu Val Gly Asp
    130                 135                 140

His Tyr Ile Leu Asn Gly Arg Lys Thr Phe Ile Thr Asn Gly Pro Phe
145                 150                 155                 160

Cys Asp Val Ala Ile Val Ile Ala Val Thr Asp Arg Ser Lys Gly Leu
                165                 170                 175

Arg Gly Thr Ser Ala Phe Ile Val Glu Ser Lys Trp Asp Gly Phe Ser
            180                 185                 190

Thr Gly Ala His Glu Asp Lys Met Gly Ile Arg Gly Thr Glu Thr Ser
        195                 200                 205

Asp Leu Ile Phe Glu Asn Val Lys Val Pro Lys Glu Asn Leu Leu Gly
    210                 215                 220

Lys Glu Gly Gln Gly Phe Lys Ile Ala Met Gly Thr Leu Glu Val Gly
225                 230                 235                 240

Arg Ile Gly Val Ala Ala Leu Ala Leu Gly Ile Ala Gln Gly Ala Leu
                245                 250                 255

Asp Glu Ala Val Lys Tyr Thr Lys Gln Arg Val Gln Phe Gly Lys Pro
            260                 265                 270

Ile Ala Lys Phe Gln Asn Thr Gln Phe Thr Ile Ala Asp Met Glu Thr
        275                 280                 285

Lys Val Cys Ala Ala Arg Gly Leu Val Tyr Asp Ala Ala Gln Lys Arg
    290                 295                 300

Asp Ala Gly Met Arg Val Ala Gln Glu Ser Ala Met Ala Lys Tyr Tyr
305                 310                 315                 320

Ala Ser Glu Ile Ala Asn Glu Val Ala Tyr Lys Ala Leu Gln Leu His
                325                 330                 335

Gly Gly Tyr Gly Phe Ile Lys Asp Tyr Glu Ile Glu Arg Met Tyr Arg
            340                 345                 350

Asp Ala Arg Ile Val Ser Ile Tyr Glu Gly Thr Ser Glu Val Gln Lys
        355                 360                 365

Met Val Ile Ser Ser Asn Val Leu Lys
    370                 375


<210> SEQ ID NO 31
<211> LENGTH: 1647
<212> TYPE: DNA
<213> ORGANISM: Lactococcus lactis
<220> FEATURE:
<221> NAME/KEY: CDS
<222> LOCATION: (1)..(1647)

<400> SEQUENCE: 31

atg tat aca gta gga gat tac cta tta gac cga tta cac gag tta gga       48
Met Tyr Thr Val Gly Asp Tyr Leu Leu Asp Arg Leu His Glu Leu Gly
1               5                   10                  15

att gaa gaa att ttt gga gtc cct gga gac tat aac tta caa ttt tta       96
Ile Glu Glu Ile Phe Gly Val Pro Gly Asp Tyr Asn Leu Gln Phe Leu
            20                  25                  30

gat caa att att tcc cgc aag gat atg aaa tgg gtc gga aat gct aat      144
Asp Gln Ile Ile Ser Arg Lys Asp Met Lys Trp Val Gly Asn Ala Asn
        35                  40                  45

gaa tta aat gct tca tat atg gct gat ggc tat gct cgt act aaa aaa      192
Glu Leu Asn Ala Ser Tyr Met Ala Asp Gly Tyr Ala Arg Thr Lys Lys
    50                  55                  60

gct gcc gca ttt ctt aca acc ttt gga gta ggt gaa ttg agt gca gtt      240
Ala Ala Ala Phe Leu Thr Thr Phe Gly Val Gly Glu Leu Ser Ala Val
65                  70                  75                  80
```

```
aat gga tta gca gga agt tac gcc gaa aat tta cca gta gta gaa ata      288
Asn Gly Leu Ala Gly Ser Tyr Ala Glu Asn Leu Pro Val Val Glu Ile
                85                  90                  95

gtg gga tca cct aca tca aaa gtt caa aat gaa gga aaa ttt gtt cat      336
Val Gly Ser Pro Thr Ser Lys Val Gln Asn Glu Gly Lys Phe Val His
            100                 105                 110

cat acg ctg gct gac ggt gat ttt aaa cac ttt atg aaa atg cac gaa      384
His Thr Leu Ala Asp Gly Asp Phe Lys His Phe Met Lys Met His Glu
        115                 120                 125

cct gtt aca gca gct cga act tta ctg aca gca gaa aat gca acc gtt      432
Pro Val Thr Ala Ala Arg Thr Leu Leu Thr Ala Glu Asn Ala Thr Val
    130                 135                 140

gaa att gac cga gta ctt tct gca cta tta aaa gaa aga aaa cct gtc      480
Glu Ile Asp Arg Val Leu Ser Ala Leu Leu Lys Glu Arg Lys Pro Val
145                 150                 155                 160

tat atc aac tta cca gtt gat gtt gct gct gca aaa gca gag aaa ccc      528
Tyr Ile Asn Leu Pro Val Asp Val Ala Ala Ala Lys Ala Glu Lys Pro
                165                 170                 175

tca ctc cct ttg aaa aaa gaa aac tca act tca aat aca agt gac caa      576
Ser Leu Pro Leu Lys Lys Glu Asn Ser Thr Ser Asn Thr Ser Asp Gln
            180                 185                 190

gag atc ttg aac aaa att caa gaa agc ttg aaa aat gcc aaa aaa cca      624
Glu Ile Leu Asn Lys Ile Gln Glu Ser Leu Lys Asn Ala Lys Lys Pro
        195                 200                 205

atc gtg att aca gga cat gaa ata att agt ttt ggc tta gaa aaa aca      672
Ile Val Ile Thr Gly His Glu Ile Ile Ser Phe Gly Leu Glu Lys Thr
    210                 215                 220

gtc tct caa ttt att tca aag aca aaa cta cct att acg aca tta aac      720
Val Ser Gln Phe Ile Ser Lys Thr Lys Leu Pro Ile Thr Thr Leu Asn
225                 230                 235                 240

ttt gga aaa agt tca gtt gat gaa gct ctc cct tca ttt tta gga atc      768
Phe Gly Lys Ser Ser Val Asp Glu Ala Leu Pro Ser Phe Leu Gly Ile
                245                 250                 255

tat aat ggt aaa ctc tca gag cct aat ctt aaa gaa ttc gtg gaa tca      816
Tyr Asn Gly Lys Leu Ser Glu Pro Asn Leu Lys Glu Phe Val Glu Ser
            260                 265                 270

gcc gac ttc atc ctg atg ctt gga gtt aaa ctc aca gac tct tca aca      864
Ala Asp Phe Ile Leu Met Leu Gly Val Lys Leu Thr Asp Ser Ser Thr
        275                 280                 285

gga gcc ttc act cat cat tta aat gaa aat aaa atg att tca ctg aat      912
Gly Ala Phe Thr His His Leu Asn Glu Asn Lys Met Ile Ser Leu Asn
    290                 295                 300

ata gat gaa gga aaa ata ttt aac gaa agc atc caa aat ttt gat ttt      960
Ile Asp Glu Gly Lys Ile Phe Asn Glu Ser Ile Gln Asn Phe Asp Phe
305                 310                 315                 320

gaa tcc ctc atc tcc tct ctc tta gac cta agc gaa ata gaa tac aaa     1008
Glu Ser Leu Ile Ser Ser Leu Leu Asp Leu Ser Glu Ile Glu Tyr Lys
                325                 330                 335

gga aaa tat atc gat aaa aag caa gaa gac ttt gtt cca tca aat gcg     1056
Gly Lys Tyr Ile Asp Lys Lys Gln Glu Asp Phe Val Pro Ser Asn Ala
            340                 345                 350

ctt tta tca caa gac cgc cta tgg caa gca gtt gaa aac cta act caa     1104
Leu Leu Ser Gln Asp Arg Leu Trp Gln Ala Val Glu Asn Leu Thr Gln
        355                 360                 365

agc aat gaa aca atc gtt gct gaa caa ggg aca tca ttc ttt ggc gct     1152
Ser Asn Glu Thr Ile Val Ala Glu Gln Gly Thr Ser Phe Phe Gly Ala
    370                 375                 380

tca tca att ttc tta aaa cca aag agt cat ttt att ggt caa ccc tta     1200
Ser Ser Ile Phe Leu Lys Pro Lys Ser His Phe Ile Gly Gln Pro Leu
```

```
385                 390                 395                 400

tgg gga tca att gga tat aca ttc cca gca gca tta gga agc caa att      1248
Trp Gly Ser Ile Gly Tyr Thr Phe Pro Ala Ala Leu Gly Ser Gln Ile
                405                 410                 415

gca gat aaa gaa agc aga cac ctt tta ttt att ggt gat ggt tca ctt      1296
Ala Asp Lys Glu Ser Arg His Leu Leu Phe Ile Gly Asp Gly Ser Leu
            420                 425                 430

caa ctt acg gtg caa gaa tta gga tta gca atc aga gaa aaa att aat      1344
Gln Leu Thr Val Gln Glu Leu Gly Leu Ala Ile Arg Glu Lys Ile Asn
        435                 440                 445

cca att tgc ttt att atc aat aat gat ggt tat aca gtc gaa aga gaa      1392
Pro Ile Cys Phe Ile Ile Asn Asn Asp Gly Tyr Thr Val Glu Arg Glu
    450                 455                 460

att cat gga cca aat caa agc tac aat gat att cca atg tgg aat tac      1440
Ile His Gly Pro Asn Gln Ser Tyr Asn Asp Ile Pro Met Trp Asn Tyr
465                 470                 475                 480

tca aaa tta cca gaa tca ttt gga gca aca gaa gaa cga gta gtc tcg      1488
Ser Lys Leu Pro Glu Ser Phe Gly Ala Thr Glu Glu Arg Val Val Ser
                485                 490                 495

aaa atc gtt aga act gaa aat gaa ttt gtg tct gtc atg aaa gaa gct      1536
Lys Ile Val Arg Thr Glu Asn Glu Phe Val Ser Val Met Lys Glu Ala
            500                 505                 510

caa gca gat cca aat aga atg tac tgg att gag tta att ttg gca aaa      1584
Gln Ala Asp Pro Asn Arg Met Tyr Trp Ile Glu Leu Ile Leu Ala Lys
        515                 520                 525

gaa gat gca cca aaa gta ctg aaa aaa atg ggc aaa cta ttt gct gaa      1632
Glu Asp Ala Pro Lys Val Leu Lys Lys Met Gly Lys Leu Phe Ala Glu
    530                 535                 540

caa aat aaa tca taa                                                  1647
Gln Asn Lys Ser
545


<210> SEQ ID NO 32
<211> LENGTH: 548
<212> TYPE: PRT
<213> ORGANISM: Lactococcus lactis

<400> SEQUENCE: 32

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160
```

```
Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
545
```

<210> SEQ ID NO 33
<211> LENGTH: 1691

```
<212> TYPE: DNA
<213> ORGANISM: Saccharomyces cerevisiae
<220> FEATURE:
<221> NAME/KEY: CDS
<222> LOCATION: (1)..(1689)

<400> SEQUENCE: 33

atg tct gaa att act ctt gga aaa tac tta ttt gaa aga ttg aag caa       48
Met Ser Glu Ile Thr Leu Gly Lys Tyr Leu Phe Glu Arg Leu Lys Gln
1               5                   10                  15

gtt aat gtt aac acc att ttt ggg cta cca ggc gac ttc aac ttg tcc       96
Val Asn Val Asn Thr Ile Phe Gly Leu Pro Gly Asp Phe Asn Leu Ser
            20                  25                  30

cta ttg gac aag att tac gag gta gat gga ttg aga tgg gct ggt aat      144
Leu Leu Asp Lys Ile Tyr Glu Val Asp Gly Leu Arg Trp Ala Gly Asn
        35                  40                  45

gca aat gag ctg aac gcc gcc tat gcc gcc gat ggt tac gca cgc atc      192
Ala Asn Glu Leu Asn Ala Ala Tyr Ala Ala Asp Gly Tyr Ala Arg Ile
    50                  55                  60

aag ggt tta tct gtg ctg gta act act ttt ggc gta ggt gaa tta tcc      240
Lys Gly Leu Ser Val Leu Val Thr Thr Phe Gly Val Gly Glu Leu Ser
65                  70                  75                  80

gcc ttg aat ggt att gca gga tcg tat gca gaa cac gtc ggt gta ctg      288
Ala Leu Asn Gly Ile Ala Gly Ser Tyr Ala Glu His Val Gly Val Leu
            85                  90                  95

cat gtt gtt ggt gtc ccc tct atc tcc gct cag gct aag caa ttg ttg      336
His Val Val Gly Val Pro Ser Ile Ser Ala Gln Ala Lys Gln Leu Leu
            100                 105                 110

ttg cat cat acc ttg ggt aac ggt gat ttt acc gtt ttt cac aga atg      384
Leu His His Thr Leu Gly Asn Gly Asp Phe Thr Val Phe His Arg Met
        115                 120                 125

tcc gcc aat atc tca gaa act aca tca atg att aca gac att gct aca      432
Ser Ala Asn Ile Ser Glu Thr Thr Ser Met Ile Thr Asp Ile Ala Thr
    130                 135                 140

gcc cct tca gaa atc gat agg ttg atc agg aca aca ttt ata aca caa      480
Ala Pro Ser Glu Ile Asp Arg Leu Ile Arg Thr Thr Phe Ile Thr Gln
145                 150                 155                 160

agg cct agc tac ttg ggg ttg cca gcg aat ttg gta gat cta aag gtt      528
Arg Pro Ser Tyr Leu Gly Leu Pro Ala Asn Leu Val Asp Leu Lys Val
                165                 170                 175

cct ggt tct ctt ttg gaa aaa ccg att gat cta tca tta aaa cct aac      576
Pro Gly Ser Leu Leu Glu Lys Pro Ile Asp Leu Ser Leu Lys Pro Asn
            180                 185                 190

gat ccc gaa gct gaa aag gaa gtt att gat acc gta cta gaa ttg atc      624
Asp Pro Glu Ala Glu Lys Glu Val Ile Asp Thr Val Leu Glu Leu Ile
        195                 200                 205

cag aat tcg aaa aac cct gtt ata cta tcg gat gcc tgt gct tct agg      672
Gln Asn Ser Lys Asn Pro Val Ile Leu Ser Asp Ala Cys Ala Ser Arg
    210                 215                 220

cac aac gtt aaa aaa gaa acc cag aag tta att gat ttg acg caa ttc      720
His Asn Val Lys Lys Glu Thr Gln Lys Leu Ile Asp Leu Thr Gln Phe
225                 230                 235                 240

cca gct ttt gtg aca cct cta ggt aaa ggg tca ata gat gaa cag cat      768
Pro Ala Phe Val Thr Pro Leu Gly Lys Gly Ser Ile Asp Glu Gln His
                245                 250                 255

ccc aga tat ggc ggt gtt tat gtg gga acg ctg tcc aaa caa gac gtg      816
Pro Arg Tyr Gly Gly Val Tyr Val Gly Thr Leu Ser Lys Gln Asp Val
            260                 265                 270

aaa cag gcc gtt gag tcg gct gat ttg atc ctt tcg gtc ggt gct ttg      864
Lys Gln Ala Val Glu Ser Ala Asp Leu Ile Leu Ser Val Gly Ala Leu
        275                 280                 285
```

```
ctc tct gat ttt aac aca ggt tcg ttt tcc tac tcc tac aag act aaa      912
Leu Ser Asp Phe Asn Thr Gly Ser Phe Ser Tyr Ser Tyr Lys Thr Lys
    290                 295                 300

aat gta gtg gag ttt cat tcc gat tac gta aag gtg aag aac gct acg      960
Asn Val Val Glu Phe His Ser Asp Tyr Val Lys Val Lys Asn Ala Thr
305                 310                 315                 320

ttc ctc ggt gta caa atg aaa ttt gca cta caa aac tta ctg aag gtt     1008
Phe Leu Gly Val Gln Met Lys Phe Ala Leu Gln Asn Leu Leu Lys Val
                325                 330                 335

att ccc gat gtt gtt aag ggc tac aag agc gtt ccc gta cca acc aaa     1056
Ile Pro Asp Val Val Lys Gly Tyr Lys Ser Val Pro Val Pro Thr Lys
            340                 345                 350

act ccc gca aac aaa ggt gta cct gct agc acg ccc ttg aaa caa gag     1104
Thr Pro Ala Asn Lys Gly Val Pro Ala Ser Thr Pro Leu Lys Gln Glu
        355                 360                 365

tgg ttg tgg aac gaa ttg tcc aaa ttc ttg caa gaa ggt gat gtt atc     1152
Trp Leu Trp Asn Glu Leu Ser Lys Phe Leu Gln Glu Gly Asp Val Ile
    370                 375                 380

att tcc gag acc ggc acg tct gcc ttc ggt atc aat caa act atc ttt     1200
Ile Ser Glu Thr Gly Thr Ser Ala Phe Gly Ile Asn Gln Thr Ile Phe
385                 390                 395                 400

cct aag gac gcc tac ggt atc tcg cag gtg ttg tgg ggg tcc atc ggt     1248
Pro Lys Asp Ala Tyr Gly Ile Ser Gln Val Leu Trp Gly Ser Ile Gly
                405                 410                 415

ttt aca aca gga gca act tta ggt gct gcc ttt gcc gct gag gag att     1296
Phe Thr Thr Gly Ala Thr Leu Gly Ala Ala Phe Ala Ala Glu Glu Ile
            420                 425                 430

gac ccc aac aag aga gtc atc tta ttc ata ggt gac ggg tct ttg cag     1344
Asp Pro Asn Lys Arg Val Ile Leu Phe Ile Gly Asp Gly Ser Leu Gln
        435                 440                 445

tta acc gtc caa gaa atc tcc acc atg atc aga tgg ggg tta aag ccg     1392
Leu Thr Val Gln Glu Ile Ser Thr Met Ile Arg Trp Gly Leu Lys Pro
    450                 455                 460

tat ctt ttt gtc ctt aac aac gac ggc tac act atc gaa aag ctg att     1440
Tyr Leu Phe Val Leu Asn Asn Asp Gly Tyr Thr Ile Glu Lys Leu Ile
465                 470                 475                 480

cat ggg cct cac gca gag tac aac gaa atc cag acc tgg gat cac ctc     1488
His Gly Pro His Ala Glu Tyr Asn Glu Ile Gln Thr Trp Asp His Leu
                485                 490                 495

gcc ctg ttg ccc gca ttt ggt gcg aaa aag tac gaa aat cac aag atc     1536
Ala Leu Leu Pro Ala Phe Gly Ala Lys Lys Tyr Glu Asn His Lys Ile
            500                 505                 510

gcc act acg ggt gag tgg gat gcc tta acc act gat tca gag ttc cag     1584
Ala Thr Thr Gly Glu Trp Asp Ala Leu Thr Thr Asp Ser Glu Phe Gln
        515                 520                 525

aaa aac tcg gtg atc aga cta att gaa ctg aaa ctg ccc gtc ttt gat     1632
Lys Asn Ser Val Ile Arg Leu Ile Glu Leu Lys Leu Pro Val Phe Asp
    530                 535                 540

gct ccg gaa agt ttg atc aaa caa gcg caa ttg act gcc gct aca aat     1680
Ala Pro Glu Ser Leu Ile Lys Gln Ala Gln Leu Thr Ala Ala Thr Asn
545                 550                 555                 560

gcc aaa caa ta                                                      1691
Ala Lys Gln
```

<210> SEQ ID NO 34
<211> LENGTH: 563
<212> TYPE: PRT
<213> ORGANISM: Saccharomyces cerevisiae

<400> SEQUENCE: 34

-continued

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415
```

-continued

```
Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln


<210> SEQ ID NO 35
<211> LENGTH: 1908
<212> TYPE: DNA
<213> ORGANISM: Saccharomyces cerevisiae
<220> FEATURE:
<221> NAME/KEY: CDS
<222> LOCATION: (1)..(1908)

<400> SEQUENCE: 35

atg gca cct gtt aca att gaa aag ttc gta aat caa gaa gaa cga cac       48
Met Ala Pro Val Thr Ile Glu Lys Phe Val Asn Gln Glu Glu Arg His
1               5                   10                  15

ctt gtt tcc aac cga tca gca aca att ccg ttt ggt gaa tac ata ttt       96
Leu Val Ser Asn Arg Ser Ala Thr Ile Pro Phe Gly Glu Tyr Ile Phe
            20                  25                  30

aaa aga ttg ttg tcc atc gat acg aaa tca gtt ttc ggt gtt cct ggt      144
Lys Arg Leu Leu Ser Ile Asp Thr Lys Ser Val Phe Gly Val Pro Gly
        35                  40                  45

gac ttc aac tta tct cta tta gaa tat ctc tat tca cct agt gtt gaa      192
Asp Phe Asn Leu Ser Leu Leu Glu Tyr Leu Tyr Ser Pro Ser Val Glu
    50                  55                  60

tca gct ggc cta aga tgg gtc ggc acg tgt aat gaa ctg aac gcc gct      240
Ser Ala Gly Leu Arg Trp Val Gly Thr Cys Asn Glu Leu Asn Ala Ala
65                  70                  75                  80

tat gcg gcc gac gga tat tcc cgt tac tct aat aag att ggc tgt tta      288
Tyr Ala Ala Asp Gly Tyr Ser Arg Tyr Ser Asn Lys Ile Gly Cys Leu
                85                  90                  95

ata acc acg tat ggc gtt ggt gaa tta agc gcc ttg aac ggt ata gcc      336
Ile Thr Thr Tyr Gly Val Gly Glu Leu Ser Ala Leu Asn Gly Ile Ala
            100                 105                 110

ggt tcg ttc gct gaa aat gtc aaa gtt ttg cac att gtt ggt gtg gcc      384
Gly Ser Phe Ala Glu Asn Val Lys Val Leu His Ile Val Gly Val Ala
        115                 120                 125

aag tcc ata gat tcg cgt tca agt aac ttt agt gat cgg aac cta cat      432
Lys Ser Ile Asp Ser Arg Ser Ser Asn Phe Ser Asp Arg Asn Leu His
    130                 135                 140

cat ttg gtc cca cag cta cat gat tca aat ttt aaa ggg cca aat cat      480
His Leu Val Pro Gln Leu His Asp Ser Asn Phe Lys Gly Pro Asn His
145                 150                 155                 160
```

```
aaa gta tat cat gat atg gta aaa gat aga gtc gct tgc tcg gta gcc      528
Lys Val Tyr His Asp Met Val Lys Asp Arg Val Ala Cys Ser Val Ala
                165                 170                 175

tac ttg gag gat att gaa act gca tgt gac caa gtc gat aat gtt atc      576
Tyr Leu Glu Asp Ile Glu Thr Ala Cys Asp Gln Val Asp Asn Val Ile
            180                 185                 190

cgc gat att tac aag tat tct aaa cct ggt tat att ttt gtt cct gca      624
Arg Asp Ile Tyr Lys Tyr Ser Lys Pro Gly Tyr Ile Phe Val Pro Ala
        195                 200                 205

gat ttt gcg gat atg tct gtt aca tgt gat aat ttg gtt aat gtt cca      672
Asp Phe Ala Asp Met Ser Val Thr Cys Asp Asn Leu Val Asn Val Pro
    210                 215                 220

cgt ata tct caa caa gat tgt ata gta tac cct tct gaa aac caa ttg      720
Arg Ile Ser Gln Gln Asp Cys Ile Val Tyr Pro Ser Glu Asn Gln Leu
225                 230                 235                 240

tct gac ata atc aac aag att act agt tgg ata tat tcc agt aaa aca      768
Ser Asp Ile Ile Asn Lys Ile Thr Ser Trp Ile Tyr Ser Ser Lys Thr
                245                 250                 255

cct gcg atc ctt gga gac gta ctg act gat agg tat ggt gtg agt aac      816
Pro Ala Ile Leu Gly Asp Val Leu Thr Asp Arg Tyr Gly Val Ser Asn
            260                 265                 270

ttt ttg aac aag ctt atc tgc aaa act ggg att tgg aat ttt tcc act      864
Phe Leu Asn Lys Leu Ile Cys Lys Thr Gly Ile Trp Asn Phe Ser Thr
        275                 280                 285

gtt atg gga aaa tct gta att gat gag tca aac cca act tat atg ggt      912
Val Met Gly Lys Ser Val Ile Asp Glu Ser Asn Pro Thr Tyr Met Gly
    290                 295                 300

caa tat aat ggt aaa gaa ggt tta aaa caa gtc tat gaa cat ttt gaa      960
Gln Tyr Asn Gly Lys Glu Gly Leu Lys Gln Val Tyr Glu His Phe Glu
305                 310                 315                 320

ctg tgc gac ttg gtc ttg cat ttt gga gtc gac atc aat gaa att aat     1008
Leu Cys Asp Leu Val Leu His Phe Gly Val Asp Ile Asn Glu Ile Asn
                325                 330                 335

aat ggg cat tat act ttt act tat aaa cca aat gct aaa atc att caa     1056
Asn Gly His Tyr Thr Phe Thr Tyr Lys Pro Asn Ala Lys Ile Ile Gln
            340                 345                 350

ttt cat ccg aat tat att cgc ctt gtg gac act agg cag ggc aat gag     1104
Phe His Pro Asn Tyr Ile Arg Leu Val Asp Thr Arg Gln Gly Asn Glu
        355                 360                 365

caa atg ttc aaa gga atc aat ttt gcc cct att tta aaa gaa cta tac     1152
Gln Met Phe Lys Gly Ile Asn Phe Ala Pro Ile Leu Lys Glu Leu Tyr
    370                 375                 380

aag cgc att gac gtt tct aaa ctt tct ttg caa tat gat tca aat gta     1200
Lys Arg Ile Asp Val Ser Lys Leu Ser Leu Gln Tyr Asp Ser Asn Val
385                 390                 395                 400

act caa tat acg aac gaa aca atg cgg tta gaa gat cct acc aat gga     1248
Thr Gln Tyr Thr Asn Glu Thr Met Arg Leu Glu Asp Pro Thr Asn Gly
                405                 410                 415

caa tca agc att att aca caa gtt cac tta caa aag acg atg cct aaa     1296
Gln Ser Ser Ile Ile Thr Gln Val His Leu Gln Lys Thr Met Pro Lys
            420                 425                 430

ttt ttg aac cct ggt gat gtt gtc gtt tgt gaa aca ggc tct ttt caa     1344
Phe Leu Asn Pro Gly Asp Val Val Val Cys Glu Thr Gly Ser Phe Gln
        435                 440                 445

ttc tct gtt cgt gat ttc gcg ttt cct tcg caa tta aaa tat ata tcg     1392
Phe Ser Val Arg Asp Phe Ala Phe Pro Ser Gln Leu Lys Tyr Ile Ser
    450                 455                 460

caa gga ttt ttc ctt tcc att ggc atg gcc ctt cct gcc gcc cta ggt     1440
Gln Gly Phe Phe Leu Ser Ile Gly Met Ala Leu Pro Ala Ala Leu Gly
```

-continued

```
465                 470                 475                 480

gtt gga att gcc atg caa gac cac tca aac gct cac atc aat ggt ggc      1488
Val Gly Ile Ala Met Gln Asp His Ser Asn Ala His Ile Asn Gly Gly
                485                 490                 495

aac gta aaa gag gac tat aag cca aga tta att ttg ttt gaa ggt gac      1536
Asn Val Lys Glu Asp Tyr Lys Pro Arg Leu Ile Leu Phe Glu Gly Asp
            500                 505                 510

ggt gca gca cag atg aca atc caa gaa ctg agc acc att ctg aag tgc      1584
Gly Ala Ala Gln Met Thr Ile Gln Glu Leu Ser Thr Ile Leu Lys Cys
        515                 520                 525

aat att cca cta gaa gtt atc att tgg aac aat aac ggc tac act att      1632
Asn Ile Pro Leu Glu Val Ile Ile Trp Asn Asn Asn Gly Tyr Thr Ile
    530                 535                 540

gaa aga gcc atc atg ggc cct acc agg tcg tat aac gac gtt atg tct      1680
Glu Arg Ala Ile Met Gly Pro Thr Arg Ser Tyr Asn Asp Val Met Ser
545                 550                 555                 560

tgg aaa tgg acc aaa cta ttt gaa gca ttc gga gac ttc gac gga aag      1728
Trp Lys Trp Thr Lys Leu Phe Glu Ala Phe Gly Asp Phe Asp Gly Lys
                565                 570                 575

tat act aat agc act ctc att caa tgt ccc tct aaa tta gca ctg aaa      1776
Tyr Thr Asn Ser Thr Leu Ile Gln Cys Pro Ser Lys Leu Ala Leu Lys
            580                 585                 590

ttg gag gag ctt aag aat tca aac aaa aga agc ggg ata gaa ctt tta      1824
Leu Glu Glu Leu Lys Asn Ser Asn Lys Arg Ser Gly Ile Glu Leu Leu
        595                 600                 605

gaa gtc aaa tta ggc gaa ttg gat ttc ccc gaa cag cta aag tgc atg      1872
Glu Val Lys Leu Gly Glu Leu Asp Phe Pro Glu Gln Leu Lys Cys Met
    610                 615                 620

gtt gaa gca gcg gca ctt aaa aga aat aaa aaa tag                      1908
Val Glu Ala Ala Ala Leu Lys Arg Asn Lys Lys
625                 630                 635


<210> SEQ ID NO 36
<211> LENGTH: 635
<212> TYPE: PRT
<213> ORGANISM: Saccharomyces cerevisiae

<400> SEQUENCE: 36

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140

His Leu Val Pro Gln Leu His Asp Ser Asn Phe Lys Gly Pro Asn His
145                 150                 155                 160
```

-continued

```
Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
    210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
    290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
    370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                405                 410                 415

Gln Ser Ser Ile Ile Thr Gln Val His Leu Gln Lys Thr Met Pro Lys
            420                 425                 430

Phe Leu Asn Pro Gly Asp Val Val Val Cys Glu Thr Gly Ser Phe Gln
        435                 440                 445

Phe Ser Val Arg Asp Phe Ala Phe Pro Ser Gln Leu Lys Tyr Ile Ser
    450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
        515                 520                 525

Asn Ile Pro Leu Glu Val Ile Ile Trp Asn Asn Asn Gly Tyr Thr Ile
    530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575
```

-continued

```
Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Glu Leu Asp Phe Pro Glu Gln Leu Lys Cys Met
    610                 615                 620

Val Glu Ala Ala Ala Leu Lys Arg Asn Lys Lys
625                 630                 635


<210> SEQ ID NO 37
<211> LENGTH: 1830
<212> TYPE: DNA
<213> ORGANISM: Saccharomyces cerevisiae
<220> FEATURE:
<221> NAME/KEY: CDS
<222> LOCATION: (1)..(1830)

<400> SEQUENCE: 37

atg aat tct agc tat aca cag aga tat gca ctg ccg aag tgt ata gca       48
Met Asn Ser Ser Tyr Thr Gln Arg Tyr Ala Leu Pro Lys Cys Ile Ala
1               5                   10                  15

ata tca gat tat ctt ttc cat cgg ctc aac cag ctg aac ata cat acc       96
Ile Ser Asp Tyr Leu Phe His Arg Leu Asn Gln Leu Asn Ile His Thr
            20                  25                  30

ata ttt gga ctc tcc gga gaa ttt agc atg ccg ttg ctg gat aaa cta      144
Ile Phe Gly Leu Ser Gly Glu Phe Ser Met Pro Leu Leu Asp Lys Leu
        35                  40                  45

tac aac att ccg aac tta cga tgg gcc ggt aat tct aat gag tta aat      192
Tyr Asn Ile Pro Asn Leu Arg Trp Ala Gly Asn Ser Asn Glu Leu Asn
    50                  55                  60

gct gcc tac gca gca gat gga tac tca cga cta aaa ggc ttg gga tgt      240
Ala Ala Tyr Ala Ala Asp Gly Tyr Ser Arg Leu Lys Gly Leu Gly Cys
65                  70                  75                  80

ctc ata aca acc ttt ggt gta ggc gaa tta tcg gca atc aat ggc gtg      288
Leu Ile Thr Thr Phe Gly Val Gly Glu Leu Ser Ala Ile Asn Gly Val
                85                  90                  95

gcc gga tct tac gct gaa cat gta gga ata ctt cac ata gtg ggt atg      336
Ala Gly Ser Tyr Ala Glu His Val Gly Ile Leu His Ile Val Gly Met
            100                 105                 110

ccg cca aca agt gca caa acg aaa caa cta cta ctg cat cat act ctg      384
Pro Pro Thr Ser Ala Gln Thr Lys Gln Leu Leu Leu His His Thr Leu
        115                 120                 125

ggc aat ggt gat ttc acg gta ttt cat aga ata gcc agt gat gta gca      432
Gly Asn Gly Asp Phe Thr Val Phe His Arg Ile Ala Ser Asp Val Ala
    130                 135                 140

tgc tat aca aca ttg att att gac tct gaa tta tgt gcc gac gaa gtc      480
Cys Tyr Thr Thr Leu Ile Ile Asp Ser Glu Leu Cys Ala Asp Glu Val
145                 150                 155                 160

gat aag tgc atc aaa aag gct tgg ata gaa cag agg cca gta tac atg      528
Asp Lys Cys Ile Lys Lys Ala Trp Ile Glu Gln Arg Pro Val Tyr Met
                165                 170                 175

ggc atg cct gtc aac cag gta aat ctc ccg att gaa tca gca agg ctt      576
Gly Met Pro Val Asn Gln Val Asn Leu Pro Ile Glu Ser Ala Arg Leu
            180                 185                 190

aat aca cct ctg gat tta caa ttg cat aaa aac gac cca gac gta gag      624
Asn Thr Pro Leu Asp Leu Gln Leu His Lys Asn Asp Pro Asp Val Glu
        195                 200                 205

aaa gaa gtt att tct cga ata ttg agt ttt ata tac aaa agc cag aat      672
Lys Glu Val Ile Ser Arg Ile Leu Ser Phe Ile Tyr Lys Ser Gln Asn
    210                 215                 220
```

```
ccg gca atc atc gta gat gca tgt act agt cga cag aat tta atc gag      720
Pro Ala Ile Ile Val Asp Ala Cys Thr Ser Arg Gln Asn Leu Ile Glu
225                 230                 235                 240

gag act aaa gag ctt tgt aat agg ctt aaa ttt cca gtt ttt gtt aca      768
Glu Thr Lys Glu Leu Cys Asn Arg Leu Lys Phe Pro Val Phe Val Thr
                245                 250                 255

cct atg ggt aag ggt aca gta aac gaa aca gac ccg caa ttt ggg ggc      816
Pro Met Gly Lys Gly Thr Val Asn Glu Thr Asp Pro Gln Phe Gly Gly
            260                 265                 270

gta ttc acg ggc tcg ata tca gcc cca gaa gta aga gaa gta gtt gat      864
Val Phe Thr Gly Ser Ile Ser Ala Pro Glu Val Arg Glu Val Val Asp
        275                 280                 285

ttt gcc gat ttt atc atc gtc att ggt tgc atg ctc tcc gaa ttc agc      912
Phe Ala Asp Phe Ile Ile Val Ile Gly Cys Met Leu Ser Glu Phe Ser
    290                 295                 300

acg tca act ttc cac ttc caa tat aaa act aag aat tgt gcg cta cta      960
Thr Ser Thr Phe His Phe Gln Tyr Lys Thr Lys Asn Cys Ala Leu Leu
305                 310                 315                 320

tat tct aca tct gtg aaa ttg aaa aat gcc aca tat cct gac ttg agc     1008
Tyr Ser Thr Ser Val Lys Leu Lys Asn Ala Thr Tyr Pro Asp Leu Ser
                325                 330                 335

att aaa tta cta cta cag aaa ata tta gca aat ctt gat gaa tct aaa     1056
Ile Lys Leu Leu Leu Gln Lys Ile Leu Ala Asn Leu Asp Glu Ser Lys
            340                 345                 350

ctg tct tac caa cca agc gaa caa ccc agt atg atg gtt cca aga cct     1104
Leu Ser Tyr Gln Pro Ser Glu Gln Pro Ser Met Met Val Pro Arg Pro
        355                 360                 365

tac cca gca gga aat gtc ctc ttg aga caa gaa tgg gtc tgg aat gaa     1152
Tyr Pro Ala Gly Asn Val Leu Leu Arg Gln Glu Trp Val Trp Asn Glu
    370                 375                 380

ata tcc cat tgg ttc caa cca ggt gac ata atc ata aca gaa act ggt     1200
Ile Ser His Trp Phe Gln Pro Gly Asp Ile Ile Ile Thr Glu Thr Gly
385                 390                 395                 400

gct tct gca ttt gga gtt aac cag acc aga ttt ccg gta aat aca cta     1248
Ala Ser Ala Phe Gly Val Asn Gln Thr Arg Phe Pro Val Asn Thr Leu
                405                 410                 415

ggt att tcg caa gct ctt tgg gga tct gtc gga tat aca atg ggg gcg     1296
Gly Ile Ser Gln Ala Leu Trp Gly Ser Val Gly Tyr Thr Met Gly Ala
            420                 425                 430

tgt ctt ggg gca gaa ttt gct gtt caa gag ata aac aag gat aaa ttc     1344
Cys Leu Gly Ala Glu Phe Ala Val Gln Glu Ile Asn Lys Asp Lys Phe
        435                 440                 445

ccc gca act aaa cat aga gtt att ctg ttt atg ggt gac ggt gct ttc     1392
Pro Ala Thr Lys His Arg Val Ile Leu Phe Met Gly Asp Gly Ala Phe
    450                 455                 460

caa ttg aca gtt caa gaa tta tcc aca att gtt aag tgg gga ttg aca     1440
Gln Leu Thr Val Gln Glu Leu Ser Thr Ile Val Lys Trp Gly Leu Thr
465                 470                 475                 480

cct tat att ttt gtg atg aat aac caa ggt tac tct gtg gac agg ttt     1488
Pro Tyr Ile Phe Val Met Asn Asn Gln Gly Tyr Ser Val Asp Arg Phe
                485                 490                 495

ttg cat cac agg tca gat gct agt tat tac gat atc caa cct tgg aac     1536
Leu His His Arg Ser Asp Ala Ser Tyr Tyr Asp Ile Gln Pro Trp Asn
            500                 505                 510

tac ttg gga tta ttg cga gta ttt ggt tgc acg aac tac gaa acg aaa     1584
Tyr Leu Gly Leu Leu Arg Val Phe Gly Cys Thr Asn Tyr Glu Thr Lys
        515                 520                 525

aaa att att act gtt gga gaa ttc aga tcc atg atc agt gac cca aac     1632
Lys Ile Ile Thr Val Gly Glu Phe Arg Ser Met Ile Ser Asp Pro Asn
    530                 535                 540
```

```
ttt gcg acc aat gac aaa att cgg atg ata gag att atg cta cca cca      1680
Phe Ala Thr Asn Asp Lys Ile Arg Met Ile Glu Ile Met Leu Pro Pro
545                 550                 555                 560

agg gat gtt cca cag gct ctg ctt gac agg tgg gtg gta gaa aaa gaa      1728
Arg Asp Val Pro Gln Ala Leu Leu Asp Arg Trp Val Val Glu Lys Glu
                565                 570                 575

cag agc aaa caa gtg caa gag gag aac gaa aat tct agc gca gta aat      1776
Gln Ser Lys Gln Val Gln Glu Glu Asn Glu Asn Ser Ser Ala Val Asn
            580                 585                 590

acg cca act cca gaa ttc caa cca ctt cta aaa aaa aat caa gtt gga      1824
Thr Pro Thr Pro Glu Phe Gln Pro Leu Leu Lys Lys Asn Gln Val Gly
        595                 600                 605

tac tga                                                              1830
Tyr


<210> SEQ ID NO 38
<211> LENGTH: 609
<212> TYPE: PRT
<213> ORGANISM: Saccharomyces cerevisiae

<400> SEQUENCE: 38

Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
    50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
    130                 135                 140

Cys Tyr Thr Thr Leu Ile Ile Asp Ser Glu Leu Cys Ala Asp Glu Val
145                 150                 155                 160

Asp Lys Cys Ile Lys Lys Ala Trp Ile Glu Gln Arg Pro Val Tyr Met
                165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
        195                 200                 205

Lys Glu Val Ile Ser Arg Ile Leu Ser Phe Ile Tyr Lys Ser Gln Asn
    210                 215                 220

Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
                245                 250                 255

Pro Met Gly Lys Gly Thr Val Asn Glu Thr Asp Pro Gln Phe Gly Gly
            260                 265                 270
```

-continued

```
Val Phe Thr Gly Ser Ile Ser Ala Pro Glu Val Arg Glu Val Val Asp
        275                 280                 285

Phe Ala Asp Phe Ile Ile Val Ile Gly Cys Met Leu Ser Glu Phe Ser
    290                 295                 300

Thr Ser Thr Phe His Phe Gln Tyr Lys Thr Lys Asn Cys Ala Leu Leu
305                 310                 315                 320

Tyr Ser Thr Ser Val Lys Leu Lys Asn Ala Thr Tyr Pro Asp Leu Ser
                325                 330                 335

Ile Lys Leu Leu Leu Gln Lys Ile Leu Ala Asn Leu Asp Glu Ser Lys
            340                 345                 350

Leu Ser Tyr Gln Pro Ser Glu Gln Pro Ser Met Met Val Pro Arg Pro
        355                 360                 365

Tyr Pro Ala Gly Asn Val Leu Leu Arg Gln Glu Trp Val Trp Asn Glu
    370                 375                 380

Ile Ser His Trp Phe Gln Pro Gly Asp Ile Ile Ile Thr Glu Thr Gly
385                 390                 395                 400

Ala Ser Ala Phe Gly Val Asn Gln Thr Arg Phe Pro Val Asn Thr Leu
                405                 410                 415

Gly Ile Ser Gln Ala Leu Trp Gly Ser Val Gly Tyr Thr Met Gly Ala
            420                 425                 430

Cys Leu Gly Ala Glu Phe Ala Val Gln Glu Ile Asn Lys Asp Lys Phe
        435                 440                 445

Pro Ala Thr Lys His Arg Val Ile Leu Phe Met Gly Asp Gly Ala Phe
    450                 455                 460

Gln Leu Thr Val Gln Glu Leu Ser Thr Ile Val Lys Trp Gly Leu Thr
465                 470                 475                 480

Pro Tyr Ile Phe Val Met Asn Asn Gln Gly Tyr Ser Val Asp Arg Phe
                485                 490                 495

Leu His His Arg Ser Asp Ala Ser Tyr Tyr Asp Ile Gln Pro Trp Asn
            500                 505                 510

Tyr Leu Gly Leu Leu Arg Val Phe Gly Cys Thr Asn Tyr Glu Thr Lys
        515                 520                 525

Lys Ile Ile Thr Val Gly Glu Phe Arg Ser Met Ile Ser Asp Pro Asn
    530                 535                 540

Phe Ala Thr Asn Asp Lys Ile Arg Met Ile Glu Ile Met Leu Pro Pro
545                 550                 555                 560

Arg Asp Val Pro Gln Ala Leu Leu Asp Arg Trp Val Val Glu Lys Glu
                565                 570                 575

Gln Ser Lys Gln Val Gln Glu Glu Asn Glu Asn Ser Ser Ala Val Asn
            580                 585                 590

Thr Pro Thr Pro Glu Phe Gln Pro Leu Leu Lys Lys Asn Gln Val Gly
        595                 600                 605

Tyr


<210> SEQ ID NO 39
<211> LENGTH: 1665
<212> TYPE: DNA
<213> ORGANISM: Clostridium acetobutylicum
<220> FEATURE:
<221> NAME/KEY: CDS
<222> LOCATION: (1)..(1665)

<400> SEQUENCE: 39

ttg aag agt gaa tac aca att gga aga tat ttg tta gac cgt tta tca       48
Leu Lys Ser Glu Tyr Thr Ile Gly Arg Tyr Leu Leu Asp Arg Leu Ser
1               5                   10                  15
```

-continued

```
gag ttg ggt att cgg cat atc ttt ggt gta cct gga gat tac aat cta       96
Glu Leu Gly Ile Arg His Ile Phe Gly Val Pro Gly Asp Tyr Asn Leu
            20                  25                  30

tcc ttt tta gac tat ata atg gag tac aaa ggg ata gat tgg gtt gga      144
Ser Phe Leu Asp Tyr Ile Met Glu Tyr Lys Gly Ile Asp Trp Val Gly
        35                  40                  45

aat tgc aat gaa ttg aat gct ggg tat gct gct gat gga tat gca aga      192
Asn Cys Asn Glu Leu Asn Ala Gly Tyr Ala Ala Asp Gly Tyr Ala Arg
    50                  55                  60

ata aat gga att gga gcc ata ctt aca aca ttt ggt gtt gga gaa tta      240
Ile Asn Gly Ile Gly Ala Ile Leu Thr Thr Phe Gly Val Gly Glu Leu
65                  70                  75                  80

agt gcc att aac gca att gct ggg gca tac gct gag caa gtt cca gtt      288
Ser Ala Ile Asn Ala Ile Ala Gly Ala Tyr Ala Glu Gln Val Pro Val
                85                  90                  95

gtt aaa att aca ggt atc ccc aca gca aaa gtt agg gac aat gga tta      336
Val Lys Ile Thr Gly Ile Pro Thr Ala Lys Val Arg Asp Asn Gly Leu
            100                 105                 110

tat gta cac cac aca tta ggt gac gga agg ttt gat cac ttt ttt gaa      384
Tyr Val His His Thr Leu Gly Asp Gly Arg Phe Asp His Phe Phe Glu
        115                 120                 125

atg ttt aga gaa gta aca gtt gct gag gca tta cta agc gaa gaa aat      432
Met Phe Arg Glu Val Thr Val Ala Glu Ala Leu Leu Ser Glu Glu Asn
    130                 135                 140

gca gca caa gaa att gat cgt gtt ctt att tca tgc tgg aga caa aaa      480
Ala Ala Gln Glu Ile Asp Arg Val Leu Ile Ser Cys Trp Arg Gln Lys
145                 150                 155                 160

cgt cct gtt ctt ata aat tta ccg att gat gta tat gat aaa cca att      528
Arg Pro Val Leu Ile Asn Leu Pro Ile Asp Val Tyr Asp Lys Pro Ile
                165                 170                 175

aac aaa cca tta aag cca tta ctc gat tat act att tca agt aac aaa      576
Asn Lys Pro Leu Lys Pro Leu Leu Asp Tyr Thr Ile Ser Ser Asn Lys
            180                 185                 190

gag gct gca tgt gaa ttt gtt aca gaa ata gta cct ata ata aat agg      624
Glu Ala Ala Cys Glu Phe Val Thr Glu Ile Val Pro Ile Ile Asn Arg
        195                 200                 205

gca aaa aag cct gtt att ctt gca gat tat gga gta tat cgt tac caa      672
Ala Lys Lys Pro Val Ile Leu Ala Asp Tyr Gly Val Tyr Arg Tyr Gln
    210                 215                 220

gtt caa cat gtg ctt aaa aac ttg gcc gaa aaa acc gga ttt cct gtg      720
Val Gln His Val Leu Lys Asn Leu Ala Glu Lys Thr Gly Phe Pro Val
225                 230                 235                 240

gct aca cta agt atg gga aaa ggt gtt ttc aat gaa gca cac cct caa      768
Ala Thr Leu Ser Met Gly Lys Gly Val Phe Asn Glu Ala His Pro Gln
                245                 250                 255

ttt att ggt gtt tat aat ggt gat gta agt tct cct tat tta agg cag      816
Phe Ile Gly Val Tyr Asn Gly Asp Val Ser Ser Pro Tyr Leu Arg Gln
            260                 265                 270

cga gtt gat gaa gca gac tgc att att agc gtt ggt gta aaa ttg acg      864
Arg Val Asp Glu Ala Asp Cys Ile Ile Ser Val Gly Val Lys Leu Thr
        275                 280                 285

gat tca acc aca ggg gga ttt tct cat gga ttt tct aaa agg aat gta      912
Asp Ser Thr Thr Gly Gly Phe Ser His Gly Phe Ser Lys Arg Asn Val
    290                 295                 300

att cac att gat cct ttt tca ata aag gca aaa ggt aaa aaa tat gca      960
Ile His Ile Asp Pro Phe Ser Ile Lys Ala Lys Gly Lys Lys Tyr Ala
305                 310                 315                 320

cct att acg atg aaa gat gct tta aca gaa tta aca agt aaa att gag     1008
Pro Ile Thr Met Lys Asp Ala Leu Thr Glu Leu Thr Ser Lys Ile Glu
```

```
                325                 330                 335

cat aga aac ttt gag gat tta gat ata aag cct tac aaa tca gat aat      1056
His Arg Asn Phe Glu Asp Leu Asp Ile Lys Pro Tyr Lys Ser Asp Asn
            340                 345                 350

caa aag tat ttt gca aaa gag aag cca att aca caa aaa cgt ttt ttt      1104
Gln Lys Tyr Phe Ala Lys Glu Lys Pro Ile Thr Gln Lys Arg Phe Phe
        355                 360                 365

gag cgt att gct cac ttt ata aaa gaa aaa gat gta tta tta gca gaa      1152
Glu Arg Ile Ala His Phe Ile Lys Glu Lys Asp Val Leu Leu Ala Glu
    370                 375                 380

cag ggt aca tgc ttt ttt ggt gcg tca acc ata caa cta ccc aaa gat      1200
Gln Gly Thr Cys Phe Phe Gly Ala Ser Thr Ile Gln Leu Pro Lys Asp
385                 390                 395                 400

gca act ttt att ggt caa cct tta tgg gga tct att gga tac aca ctt      1248
Ala Thr Phe Ile Gly Gln Pro Leu Trp Gly Ser Ile Gly Tyr Thr Leu
                405                 410                 415

cct gct tta tta ggt tca caa tta gct gat caa aaa agg cgt aat att      1296
Pro Ala Leu Leu Gly Ser Gln Leu Ala Asp Gln Lys Arg Arg Asn Ile
            420                 425                 430

ctt tta att ggg gat ggt gca ttt caa atg aca gca caa gaa att tca      1344
Leu Leu Ile Gly Asp Gly Ala Phe Gln Met Thr Ala Gln Glu Ile Ser
        435                 440                 445

aca atg ctt cgt tta caa atc aaa cct att att ttt tta att aat aac      1392
Thr Met Leu Arg Leu Gln Ile Lys Pro Ile Ile Phe Leu Ile Asn Asn
    450                 455                 460

gat ggt tat aca att gaa cgt gct att cat ggt aga gaa caa gta tat      1440
Asp Gly Tyr Thr Ile Glu Arg Ala Ile His Gly Arg Glu Gln Val Tyr
465                 470                 475                 480

aac aat att caa atg tgg cga tat cat aat gtt cca aag gtt tta ggt      1488
Asn Asn Ile Gln Met Trp Arg Tyr His Asn Val Pro Lys Val Leu Gly
                485                 490                 495

cct aaa gaa tgc agc tta acc ttt aaa gta caa agt gaa act gaa ctt      1536
Pro Lys Glu Cys Ser Leu Thr Phe Lys Val Gln Ser Glu Thr Glu Leu
            500                 505                 510

gaa aag gct ctt tta gtg gca gat aag gat tgt gaa cat ttg att ttt      1584
Glu Lys Ala Leu Leu Val Ala Asp Lys Asp Cys Glu His Leu Ile Phe
        515                 520                 525

ata gaa gtt gtt atg gat cgt tat gat aaa ccc gag cct tta gaa cgt      1632
Ile Glu Val Val Met Asp Arg Tyr Asp Lys Pro Glu Pro Leu Glu Arg
    530                 535                 540

ctt tcg aaa cgt ttt gca aat caa aat aat tag                          1665
Leu Ser Lys Arg Phe Ala Asn Gln Asn Asn
545                 550


<210> SEQ ID NO 40
<211> LENGTH: 554
<212> TYPE: PRT
<213> ORGANISM: Clostridium acetobutylicum

<400> SEQUENCE: 40

Leu Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
```

-continued

```
65                  70                  75                  80

Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
        115                 120                 125

Met Phe Arg Glu Val Thr Val Ala Glu Ala Leu Leu Ser Glu Glu Asn
    130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
        195                 200                 205

Ala Lys Lys Pro Val Ile Leu Ala Asp Tyr Gly Val Tyr Arg Tyr Gln
    210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
        275                 280                 285

Asp Ser Thr Thr Gly Gly Phe Ser His Gly Phe Ser Lys Arg Asn Val
    290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
        355                 360                 365

Glu Arg Ile Ala His Phe Ile Lys Glu Lys Asp Val Leu Leu Ala Glu
    370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
        435                 440                 445

Thr Met Leu Arg Leu Gln Ile Lys Pro Ile Ile Phe Leu Ile Asn Asn
    450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495
```

```
Pro Lys Glu Cys Ser Leu Thr Phe Lys Val Gln Ser Glu Thr Glu Leu
            500                 505                 510

Glu Lys Ala Leu Leu Val Ala Asp Lys Asp Cys Glu His Leu Ile Phe
        515                 520                 525

Ile Glu Val Val Met Asp Arg Tyr Asp Lys Pro Glu Pro Leu Glu Arg
    530                 535                 540

Leu Ser Lys Arg Phe Ala Asn Gln Asn Asn
545                 550


<210> SEQ ID NO 41
<211> LENGTH: 1056
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 41

atg cct tcg caa gtc att cct gaa aaa caa aag gct att gtc ttt tat       48
Met Pro Ser Gln Val Ile Pro Glu Lys Gln Lys Ala Ile Val Phe Tyr
1               5                   10                  15

gag aca gat gga aaa ttg gaa tat aaa gac gtc aca gtt ccg gaa cct       96
Glu Thr Asp Gly Lys Leu Glu Tyr Lys Asp Val Thr Val Pro Glu Pro
            20                  25                  30

aag cct aac gaa att tta gtc cac gtt aaa tat tct ggt gtt tgt cat      144
Lys Pro Asn Glu Ile Leu Val His Val Lys Tyr Ser Gly Val Cys His
        35                  40                  45

agt gac ttg cac gcg tgg cac ggt gat tgg cca ttt caa ttg aaa ttt      192
Ser Asp Leu His Ala Trp His Gly Asp Trp Pro Phe Gln Leu Lys Phe
    50                  55                  60

cca tta atc ggt ggt cac gaa ggt gct ggt gtt gtt gtt aag ttg gga      240
Pro Leu Ile Gly Gly His Glu Gly Ala Gly Val Val Val Lys Leu Gly
65                  70                  75                  80

tct aac gtt aag ggc tgg aaa gtc ggt gat ttt gca ggt ata aaa tgg      288
Ser Asn Val Lys Gly Trp Lys Val Gly Asp Phe Ala Gly Ile Lys Trp
                85                  90                  95

ttg aat ggg act tgc atg tcc tgt gaa tat tgt gaa gta ggt aat gaa      336
Leu Asn Gly Thr Cys Met Ser Cys Glu Tyr Cys Glu Val Gly Asn Glu
            100                 105                 110

tct caa tgt cct tat ttg gat ggt act ggc ttc aca cat gat ggt act      384
Ser Gln Cys Pro Tyr Leu Asp Gly Thr Gly Phe Thr His Asp Gly Thr
        115                 120                 125

ttt caa gaa tac gca act gcc gat gcc gtt caa gct gcc cat att cca      432
Phe Gln Glu Tyr Ala Thr Ala Asp Ala Val Gln Ala Ala His Ile Pro
    130                 135                 140

cca aac gtc aat ctt gct gaa gtt gcc cca atc ttg tgt gca ggt atc      480
Pro Asn Val Asn Leu Ala Glu Val Ala Pro Ile Leu Cys Ala Gly Ile
145                 150                 155                 160

act gtt tat aag gcg ttg aaa aga gcc aat gtg ata cca ggc caa tgg      528
Thr Val Tyr Lys Ala Leu Lys Arg Ala Asn Val Ile Pro Gly Gln Trp
                165                 170                 175

gtc act ata tcc ggt gca tgc ggt ggc ttg ggt tct ctg gca atc caa      576
Val Thr Ile Ser Gly Ala Cys Gly Gly Leu Gly Ser Leu Ala Ile Gln
            180                 185                 190

tac gcc ctt gct atg ggt tac agg gtc att ggt atc gat ggt ggt aat      624
Tyr Ala Leu Ala Met Gly Tyr Arg Val Ile Gly Ile Asp Gly Gly Asn
        195                 200                 205

gcc aag cga aag tta ttt gaa caa tta ggc gga gaa ata ttc atc gat      672
Ala Lys Arg Lys Leu Phe Glu Gln Leu Gly Gly Glu Ile Phe Ile Asp
    210                 215                 220
```

```
ttc acg gaa gaa aaa gac att gtt ggt gct ata ata aag gcc act aat      720
Phe Thr Glu Glu Lys Asp Ile Val Gly Ala Ile Ile Lys Ala Thr Asn
225                 230                 235                 240

ggc ggt tct cat gga gtt att aat gtg tct gtt tct gaa gca gct atc      768
Gly Gly Ser His Gly Val Ile Asn Val Ser Val Ser Glu Ala Ala Ile
                245                 250                 255

gag gct tct acg agg tat tgt agg ccc aat ggt act gtc gtc ctg gtt      816
Glu Ala Ser Thr Arg Tyr Cys Arg Pro Asn Gly Thr Val Val Leu Val
            260                 265                 270

ggt atg cca gct cat gct tac tgc aat tcc gat gtt ttc aat caa gtt      864
Gly Met Pro Ala His Ala Tyr Cys Asn Ser Asp Val Phe Asn Gln Val
        275                 280                 285

gta aaa tca atc tcc atc gtt gga tct tgt gtt gga aat aga gct gat      912
Val Lys Ser Ile Ser Ile Val Gly Ser Cys Val Gly Asn Arg Ala Asp
    290                 295                 300

aca agg gag gct tta gat ttc ttc gcc aga ggt ttg atc aaa tct ccg      960
Thr Arg Glu Ala Leu Asp Phe Phe Ala Arg Gly Leu Ile Lys Ser Pro
305                 310                 315                 320

atc cac tta gct ggc cta tcg gat gtt cct gaa att ttt gca aag atg     1008
Ile His Leu Ala Gly Leu Ser Asp Val Pro Glu Ile Phe Ala Lys Met
                325                 330                 335

gag aag ggt gaa att gtt ggt aga tat gtt gtt gag act tct aaa tga     1056
Glu Lys Gly Glu Ile Val Gly Arg Tyr Val Val Glu Thr Ser Lys
            340                 345                 350


<210> SEQ ID NO 42
<211> LENGTH: 351
<212> TYPE: PRT
<213> ORGANISM: Saccharomyces cerevisiae

<400> SEQUENCE: 42

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205
```

```
Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350


<210> SEQ ID NO 43
<211> LENGTH: 1725
<212> TYPE: DNA
<213> ORGANISM: Escherichia coli
<220> FEATURE:
<221> NAME/KEY: CDS
<222> LOCATION: (1)..(1725)

<400> SEQUENCE: 43

atg gag atg ttg tct gga gcc gag atg gtc gtc cga tcg ctt atc gat       48
Met Glu Met Leu Ser Gly Ala Glu Met Val Val Arg Ser Leu Ile Asp
1               5                   10                  15

cag ggc gtt aaa caa gta ttc ggt tat ccc gga ggc gca gtc ctt gat       96
Gln Gly Val Lys Gln Val Phe Gly Tyr Pro Gly Gly Ala Val Leu Asp
            20                  25                  30

att tat gat gca ttg cat acc gtg ggt ggt att gat cat gta tta gtt      144
Ile Tyr Asp Ala Leu His Thr Val Gly Gly Ile Asp His Val Leu Val
        35                  40                  45

cgt cat gag cag gcg gcg gtg cat atg gcc gat ggc ctg gcg cgc gcg      192
Arg His Glu Gln Ala Ala Val His Met Ala Asp Gly Leu Ala Arg Ala
    50                  55                  60

acc ggg gaa gtc ggc gtc gtg ctg gta acg tcg ggt cca ggg gcg acc      240
Thr Gly Glu Val Gly Val Val Leu Val Thr Ser Gly Pro Gly Ala Thr
65                  70                  75                  80

aat gcg att act ggc atc gcc acc gct tat atg gat tcc att cca tta      288
Asn Ala Ile Thr Gly Ile Ala Thr Ala Tyr Met Asp Ser Ile Pro Leu
                85                  90                  95

gtt gtc ctt tcc ggg cag gta gcg acc tcg ttg ata ggt tac gat gcc      336
Val Val Leu Ser Gly Gln Val Ala Thr Ser Leu Ile Gly Tyr Asp Ala
            100                 105                 110

ttt cag gag tgc gac atg gtg ggg att tcg cga ccg gtg gtt aaa cac      384
Phe Gln Glu Cys Asp Met Val Gly Ile Ser Arg Pro Val Val Lys His
        115                 120                 125

agt ttt ctg gtt aag caa acg gaa gac att ccg cag gtg ctg aaa aag      432
Ser Phe Leu Val Lys Gln Thr Glu Asp Ile Pro Gln Val Leu Lys Lys
    130                 135                 140

gct ttc tgg ctg gcg gca agt ggt cgc cca gga cca gta gtc gtt gat      480
Ala Phe Trp Leu Ala Ala Ser Gly Arg Pro Gly Pro Val Val Val Asp
145                 150                 155                 160
```

-continued tta ccg aaa gat att ctt aat ccg gcg aac aaa tta ccc tat gtc tgg 528
Leu Pro Lys Asp Ile Leu Asn Pro Ala Asn Lys Leu Pro Tyr Val Trp
165 170 175 ccg gag tcg gtc agt atg cgt tct tac aat ccc act act acc gga cat 576
Pro Glu Ser Val Ser Met Arg Ser Tyr Asn Pro Thr Thr Thr Gly His
180 185 190 aaa ggg caa att aag cgt gct ctg caa acg ctg gta gcg gca aaa aaa 624
Lys Gly Gln Ile Lys Arg Ala Leu Gln Thr Leu Val Ala Ala Lys Lys
195 200 205 ccg gtt gtc tac gta ggc ggt ggg gca atc acg gcg ggc tgc cat cag 672
Pro Val Val Tyr Val Gly Gly Gly Ala Ile Thr Ala Gly Cys His Gln
210 215 220 cag ttg aaa gaa acg gtg gag gcg ttg aat ctg ccc gtt gtt tgc tca 720
Gln Leu Lys Glu Thr Val Glu Ala Leu Asn Leu Pro Val Val Cys Ser
225 230 235 240 ttg atg ggg ctg ggg gcg ttt ccg gca acg cat cgt cag gca ctg ggc 768
Leu Met Gly Leu Gly Ala Phe Pro Ala Thr His Arg Gln Ala Leu Gly
245 250 255 atg ctg gga atg cac ggt acc tac gaa gcc aat atg acg atg cat aac 816
Met Leu Gly Met His Gly Thr Tyr Glu Ala Asn Met Thr Met His Asn
260 265 270 gcg gat gtg att ttc gcc gtc ggg gta cga ttt gat gac cga acg acg 864
Ala Asp Val Ile Phe Ala Val Gly Val Arg Phe Asp Asp Arg Thr Thr
275 280 285 aac aat ctg gca aag tac tgc cca aat gcc act gtt ctg cat atc gat 912
Asn Asn Leu Ala Lys Tyr Cys Pro Asn Ala Thr Val Leu His Ile Asp
290 295 300 att gat cct act tcc att tct aaa acc gtg act gcg gat atc ccg att 960
Ile Asp Pro Thr Ser Ile Ser Lys Thr Val Thr Ala Asp Ile Pro Ile
305 310 315 320 gtg ggg gat gct cgc cag gtc ctc gaa caa atg ctt gaa ctc ttg tcg 1008
Val Gly Asp Ala Arg Gln Val Leu Glu Gln Met Leu Glu Leu Leu Ser
325 330 335 caa gaa tcc gcc cat caa cca ctg gat gag atc cgc gac tgg tgg cag 1056
Gln Glu Ser Ala His Gln Pro Leu Asp Glu Ile Arg Asp Trp Trp Gln
340 345 350 caa att gaa cag tgg cgc gct cgt cag tgc ctg aaa tat gac act cac 1104
Gln Ile Glu Gln Trp Arg Ala Arg Gln Cys Leu Lys Tyr Asp Thr His
355 360 365 agt gaa aag att aaa ccg cag gcg gtg atc gag act ctt tgg cgg ttg 1152
Ser Glu Lys Ile Lys Pro Gln Ala Val Ile Glu Thr Leu Trp Arg Leu
370 375 380 acg aag gga gac gct tac gtg acg tcc gat gtc ggg cag cac cag atg 1200
Thr Lys Gly Asp Ala Tyr Val Thr Ser Asp Val Gly Gln His Gln Met
385 390 395 400 ttt gct gca ctt tat tat cca ttc gac aaa ccg cgt cgc tgg atc aat 1248
Phe Ala Ala Leu Tyr Tyr Pro Phe Asp Lys Pro Arg Arg Trp Ile Asn
405 410 415 tcc ggt ggc ctc ggc acg atg ggt ttt ggt tta cct gcg gca ctg ggc 1296
Ser Gly Gly Leu Gly Thr Met Gly Phe Gly Leu Pro Ala Ala Leu Gly
420 425 430 gtc aaa atg gcg ttg cca gaa gaa acc gtg gtt tgc gtc act ggc gac 1344
Val Lys Met Ala Leu Pro Glu Glu Thr Val Val Cys Val Thr Gly Asp
435 440 445 ggc agt att cag atg aac atc cag gaa ctg tct acc gcg ttg caa tac 1392
Gly Ser Ile Gln Met Asn Ile Gln Glu Leu Ser Thr Ala Leu Gln Tyr
450 455 460 gag ttg ccc gta ctg gtg gtg aat ctc aat aac cgc tat ctg ggg atg 1440
Glu Leu Pro Val Leu Val Val Asn Leu Asn Asn Arg Tyr Leu Gly Met
465 470 475 480

```
gtg aag cag tgg cag gac atg atc tat tcc ggc cgt cat tca caa tct     1488
Val Lys Gln Trp Gln Asp Met Ile Tyr Ser Gly Arg His Ser Gln Ser
                485                 490                 495

tat atg caa tcg cta ccc gat ttc gtc cgt ctg gcg gaa gcc tat ggg     1536
Tyr Met Gln Ser Leu Pro Asp Phe Val Arg Leu Ala Glu Ala Tyr Gly
            500                 505                 510

cat gtc ggg atc cag att tct cat ccg cat gag ctg gaa agc aaa ctt     1584
His Val Gly Ile Gln Ile Ser His Pro His Glu Leu Glu Ser Lys Leu
        515                 520                 525

agc gag gcg ctg gaa cag gtg cgc aat aat cgc ctg gtg ttt gtt gat     1632
Ser Glu Ala Leu Glu Gln Val Arg Asn Asn Arg Leu Val Phe Val Asp
    530                 535                 540

gtt acc gtc gat ggc agc gag cac gtc tac ccg atg cag att cgc ggg     1680
Val Thr Val Asp Gly Ser Glu His Val Tyr Pro Met Gln Ile Arg Gly
545                 550                 555                 560

ggc gga atg gat gaa atg tgg tta agc aaa acg gag aga acc tga         1725
Gly Gly Met Asp Glu Met Trp Leu Ser Lys Thr Glu Arg Thr
                565                 570


<210> SEQ ID NO 44
<211> LENGTH: 574
<212> TYPE: PRT
<213> ORGANISM: Escherichia coli

<400> SEQUENCE: 44

Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110

Phe Gln Glu Cys Asp Met Val Gly Ile Ser Arg Pro Val Val Lys His
        115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Ala Ala Lys Lys
        195                 200                 205

Pro Val Val Tyr Val Gly Gly Gly Ala Ile Thr Ala Gly Cys His Gln
    210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
```

```
                245                 250                 255

Met Leu Gly Met His Gly Thr Tyr Glu Ala Asn Met Thr Met His Asn
            260                 265                 270

Ala Asp Val Ile Phe Ala Val Gly Val Arg Phe Asp Asp Arg Thr Thr
        275                 280                 285

Asn Asn Leu Ala Lys Tyr Cys Pro Asn Ala Thr Val Leu His Ile Asp
    290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
            340                 345                 350

Gln Ile Glu Gln Trp Arg Ala Arg Gln Cys Leu Lys Tyr Asp Thr His
        355                 360                 365

Ser Glu Lys Ile Lys Pro Gln Ala Val Ile Glu Thr Leu Trp Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Met Ala Leu Pro Glu Glu Thr Val Val Cys Val Thr Gly Asp
        435                 440                 445

Gly Ser Ile Gln Met Asn Ile Gln Glu Leu Ser Thr Ala Leu Gln Tyr
    450                 455                 460

Glu Leu Pro Val Leu Val Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495

Tyr Met Gln Ser Leu Pro Asp Phe Val Arg Leu Ala Glu Ala Tyr Gly
            500                 505                 510

His Val Gly Ile Gln Ile Ser His Pro His Glu Leu Glu Ser Lys Leu
        515                 520                 525

Ser Glu Ala Leu Glu Gln Val Arg Asn Asn Arg Leu Val Phe Val Asp
    530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
                565                 570


<210> SEQ ID NO 45
<211> LENGTH: 492
<212> TYPE: DNA
<213> ORGANISM: Escherichia coli
<220> FEATURE:
<221> NAME/KEY: CDS
<222> LOCATION: (1)..(492)

<400> SEQUENCE: 45

atg cgc cgg ata tta tca gtc tta ctc gaa aat gaa tca ggc gcg tta       48
Met Arg Arg Ile Leu Ser Val Leu Leu Glu Asn Glu Ser Gly Ala Leu
1               5                   10                  15

tcc cgc gtg att ggc ctt ttt tcc cag cgt ggc tac aac att gaa agc       96
Ser Arg Val Ile Gly Leu Phe Ser Gln Arg Gly Tyr Asn Ile Glu Ser
```

```
            20                  25                  30

ctg acc gtt gcg cca acc gac gat ccg aca tta tcg cgt atg acc atc      144
Leu Thr Val Ala Pro Thr Asp Asp Pro Thr Leu Ser Arg Met Thr Ile
        35                  40                  45

cag acc gtg ggc gat gaa aaa gta ctt gag cag atc gaa aag caa tta      192
Gln Thr Val Gly Asp Glu Lys Val Leu Glu Gln Ile Glu Lys Gln Leu
    50                  55                  60

cac aaa ctg gtc gat gtc ttg cgc gtg agt gag ttg ggg cag ggc gcg      240
His Lys Leu Val Asp Val Leu Arg Val Ser Glu Leu Gly Gln Gly Ala
65                  70                  75                  80

cat gtt gag cgg gaa atc atg ctg gtg aaa att cag gcc agc ggt tac      288
His Val Glu Arg Glu Ile Met Leu Val Lys Ile Gln Ala Ser Gly Tyr
            85                  90                  95

ggg cgt gac gaa gtg aaa cgt aat acg gaa ata ttc cgt ggg caa att      336
Gly Arg Asp Glu Val Lys Arg Asn Thr Glu Ile Phe Arg Gly Gln Ile
            100                 105                 110

atc gat gtc aca ccc tcg ctt tat acc gtt caa tta gca ggc acc agc      384
Ile Asp Val Thr Pro Ser Leu Tyr Thr Val Gln Leu Ala Gly Thr Ser
        115                 120                 125

ggt aag ctt gat gca ttt tta gca tcg att cgc gat gtg gcg aaa att      432
Gly Lys Leu Asp Ala Phe Leu Ala Ser Ile Arg Asp Val Ala Lys Ile
    130                 135                 140

gtg gag gtt gct cgc tct ggt gtg gtc gga ctt tcg cgc ggc gat aaa      480
Val Glu Val Ala Arg Ser Gly Val Val Gly Leu Ser Arg Gly Asp Lys
145                 150                 155                 160

ata atg cgt tga                                                      492
Ile Met Arg


<210> SEQ ID NO 46
<211> LENGTH: 163
<212> TYPE: PRT
<213> ORGANISM: Escherichia coli

<400> SEQUENCE: 46

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
            85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg


<210> SEQ ID NO 47
```

```
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 47

atg gct aac tac ttc aat aca ctg aat ctg cgc cag cag ctg gca cag       48
Met Ala Asn Tyr Phe Asn Thr Leu Asn Leu Arg Gln Gln Leu Ala Gln
1               5                   10                  15

ctg ggc aaa tgt cgc ttt atg ggc cgc gat gaa ttc gcc gat ggc gcg       96
Leu Gly Lys Cys Arg Phe Met Gly Arg Asp Glu Phe Ala Asp Gly Ala
            20                  25                  30

agc tac ctt cag ggt aaa aaa gta gtc atc gtc ggc tgt ggc gca cag      144
Ser Tyr Leu Gln Gly Lys Lys Val Val Ile Val Gly Cys Gly Ala Gln
        35                  40                  45

ggt ctg aac cag ggc ctg aac atg cgt gat tct ggt ctc gat atc tcc      192
Gly Leu Asn Gln Gly Leu Asn Met Arg Asp Ser Gly Leu Asp Ile Ser
    50                  55                  60

tac gct ctg cgt aaa gaa gcg att gcc gag aag cgc gcg tcc tgg cgt      240
Tyr Ala Leu Arg Lys Glu Ala Ile Ala Glu Lys Arg Ala Ser Trp Arg
65                  70                  75                  80

aaa gcg acc gaa aat ggt ttt aaa gtg ggt act tac gaa gaa ctg atc      288
Lys Ala Thr Glu Asn Gly Phe Lys Val Gly Thr Tyr Glu Glu Leu Ile
                85                  90                  95

cca cag gcg gat ctg gtg att aac ctg acg ccg gac aag cag cac tct      336
Pro Gln Ala Asp Leu Val Ile Asn Leu Thr Pro Asp Lys Gln His Ser
            100                 105                 110

gat gta gtg cgc acc gta cag cca ctg atg aaa gac ggc gcg gcg ctg      384
Asp Val Val Arg Thr Val Gln Pro Leu Met Lys Asp Gly Ala Ala Leu
        115                 120                 125

ggc tac tcg cac ggt ttc aac atc gtc gaa gtg ggc gag cag atc cgt      432
Gly Tyr Ser His Gly Phe Asn Ile Val Glu Val Gly Glu Gln Ile Arg
    130                 135                 140

aaa gat atc acc gta gtg atg gtt gcg ccg aaa tgc cca ggc acc gaa      480
Lys Asp Ile Thr Val Val Met Val Ala Pro Lys Cys Pro Gly Thr Glu
145                 150                 155                 160

gtg cgt gaa gag tac aaa cgt ggg ttc ggc gta ccg acg ctg att gcc      528
Val Arg Glu Glu Tyr Lys Arg Gly Phe Gly Val Pro Thr Leu Ile Ala
                165                 170                 175

gtt cac ccg gaa aac gat ccg aaa ggc gaa ggc atg gcg att gcc aaa      576
Val His Pro Glu Asn Asp Pro Lys Gly Glu Gly Met Ala Ile Ala Lys
            180                 185                 190

gcc tgg gcg gct gca acc ggt ggt cac cgt gcg ggt gtg ctg gaa tcg      624
Ala Trp Ala Ala Ala Thr Gly Gly His Arg Ala Gly Val Leu Glu Ser
        195                 200                 205

tcc ttc gtt gcg gaa gtg aaa tct gac ctg atg ggc gag caa acc atc      672
Ser Phe Val Ala Glu Val Lys Ser Asp Leu Met Gly Glu Gln Thr Ile
    210                 215                 220

ctg tgc ggt atg ttg cag gct ggc tct ctg ctg tgc ttc gac aag ctg      720
Leu Cys Gly Met Leu Gln Ala Gly Ser Leu Leu Cys Phe Asp Lys Leu
225                 230                 235                 240

gtg gaa gaa ggt acc gat cca gca tac gca gaa aaa ctg att cag ttc      768
Val Glu Glu Gly Thr Asp Pro Ala Tyr Ala Glu Lys Leu Ile Gln Phe
                245                 250                 255

ggt tgg gaa acc atc acc gaa gca ctg aaa cag ggc ggc atc acc ctg      816
Gly Trp Glu Thr Ile Thr Glu Ala Leu Lys Gln Gly Gly Ile Thr Leu
            260                 265                 270

atg atg gac cgt ctc tct aac ccg gcg aaa ctg cgt gct tat gcg ctt      864
Met Met Asp Arg Leu Ser Asn Pro Ala Lys Leu Arg Ala Tyr Ala Leu
```

-continued 275 280 285 tct gaa cag ctg aaa gag atc atg gca ccc ctg ttc cag aaa cat atg 912
Ser Glu Gln Leu Lys Glu Ile Met Ala Pro Leu Phe Gln Lys His Met
290 295 300 gac gac atc atc tcc ggc gaa ttc tct tcc ggt atg atg gcg gac tgg 960
Asp Asp Ile Ile Ser Gly Glu Phe Ser Ser Gly Met Met Ala Asp Trp
305 310 315 320 gcc aac gat gat aag aaa ctg ctg acc tgg cgt gaa gag acc ggc aaa 1008
Ala Asn Asp Asp Lys Lys Leu Leu Thr Trp Arg Glu Glu Thr Gly Lys
325 330 335 acc gcg ttt gaa acc gcg ccg cag tat gaa ggc aaa atc ggc gag cag 1056
Thr Ala Phe Glu Thr Ala Pro Gln Tyr Glu Gly Lys Ile Gly Glu Gln
340 345 350 gag tac ttc gat aaa ggc gta ctg atg att gcg atg gtg aaa gcg ggc 1104
Glu Tyr Phe Asp Lys Gly Val Leu Met Ile Ala Met Val Lys Ala Gly
355 360 365 gtt gaa ctg gcg ttc gaa acc atg gtc gat tcc ggc atc att gaa gag 1152
Val Glu Leu Ala Phe Glu Thr Met Val Asp Ser Gly Ile Ile Glu Glu
370 375 380 tct gca tat tat gaa tca ctg cac gag ctg ccg ctg att gcc aac acc 1200
Ser Ala Tyr Tyr Glu Ser Leu His Glu Leu Pro Leu Ile Ala Asn Thr
385 390 395 400 atc gcc cgt aag cgt ctg tac gaa atg aac gtg gtt atc tct gat acc 1248
Ile Ala Arg Lys Arg Leu Tyr Glu Met Asn Val Val Ile Ser Asp Thr
405 410 415 gct gag tac ggt aac tat ctg ttc tct tac gct tgt gtg ccg ttg ctg 1296
Ala Glu Tyr Gly Asn Tyr Leu Phe Ser Tyr Ala Cys Val Pro Leu Leu
420 425 430 aaa ccg ttt atg gca gag ctg caa ccg ggc gac ctg ggt aaa gct att 1344
Lys Pro Phe Met Ala Glu Leu Gln Pro Gly Asp Leu Gly Lys Ala Ile
435 440 445 ccg gaa ggc gcg gta gat aac ggg caa ctg cgt gat gtg aac gaa gcg 1392
Pro Glu Gly Ala Val Asp Asn Gly Gln Leu Arg Asp Val Asn Glu Ala
450 455 460 att cgc agc cat gcg att gag cag gta ggt aag aaa ctg cgc ggc tat 1440
Ile Arg Ser His Ala Ile Glu Gln Val Gly Lys Lys Leu Arg Gly Tyr
465 470 475 480 atg aca gat atg aaa cgt att gct gtt gcg ggt taa 1476
Met Thr Asp Met Lys Arg Ile Ala Val Ala Gly
485 490

<210> SEQ ID NO 48
<211> LENGTH: 491
<212> TYPE: PRT
<213> ORGANISM: Escherichia coli

<400> SEQUENCE: 48

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

Tyr Ala Leu Arg Lys Glu Ala Ile Ala Glu Lys Arg Ala Ser Trp Arg
65 70 75 80

Lys Ala Thr Glu Asn Gly Phe Lys Val Gly Thr Tyr Glu Glu Leu Ile
85 90 95

```
Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 49
<211> LENGTH: 1851

```
<212> TYPE: DNA
<213> ORGANISM: Escherichia coli
<220> FEATURE:
<221> NAME/KEY: CDS
<222> LOCATION: (1)..(1851)

<400> SEQUENCE: 49

atg cct aag tac cgt tcc gcc acc acc act cat ggt cgt aat atg gcg       48
Met Pro Lys Tyr Arg Ser Ala Thr Thr Thr His Gly Arg Asn Met Ala
1               5                   10                  15

ggt gct cgt gcg ctg tgg cgc gcc acc gga atg acc gac gcc gat ttc       96
Gly Ala Arg Ala Leu Trp Arg Ala Thr Gly Met Thr Asp Ala Asp Phe
            20                  25                  30

ggt aag ccg att atc gcg gtt gtg aac tcg ttc acc caa ttt gta ccg      144
Gly Lys Pro Ile Ile Ala Val Val Asn Ser Phe Thr Gln Phe Val Pro
        35                  40                  45

ggt cac gtc cat ctg cgc gat ctc ggt aaa ctg gtc gcc gaa caa att      192
Gly His Val His Leu Arg Asp Leu Gly Lys Leu Val Ala Glu Gln Ile
    50                  55                  60

gaa gcg gct ggc ggc gtt gcc aaa gag ttc aac acc att gcg gtg gat      240
Glu Ala Ala Gly Gly Val Ala Lys Glu Phe Asn Thr Ile Ala Val Asp
65                  70                  75                  80

gat ggg att gcc atg ggc cac ggg ggg atg ctt tat tca ctg cca tct      288
Asp Gly Ile Ala Met Gly His Gly Gly Met Leu Tyr Ser Leu Pro Ser
                85                  90                  95

cgc gaa ctg atc gct gat tcc gtt gag tat atg gtc aac gcc cac tgc      336
Arg Glu Leu Ile Ala Asp Ser Val Glu Tyr Met Val Asn Ala His Cys
            100                 105                 110

gcc gac gcc atg gtc tgc atc tct aac tgc gac aaa atc acc ccg ggg      384
Ala Asp Ala Met Val Cys Ile Ser Asn Cys Asp Lys Ile Thr Pro Gly
        115                 120                 125

atg ctg atg gct tcc ctg cgc ctg aat att ccg gtg atc ttt gtt tcc      432
Met Leu Met Ala Ser Leu Arg Leu Asn Ile Pro Val Ile Phe Val Ser
    130                 135                 140

ggc ggc ccg atg gag gcc ggg aaa acc aaa ctt tcc gat cag atc atc      480
Gly Gly Pro Met Glu Ala Gly Lys Thr Lys Leu Ser Asp Gln Ile Ile
145                 150                 155                 160

aag ctc gat ctg gtt gat gcg atg atc cag ggc gca gac ccg aaa gta      528
Lys Leu Asp Leu Val Asp Ala Met Ile Gln Gly Ala Asp Pro Lys Val
                165                 170                 175

tct gac tcc cag agc gat cag gtt gaa cgt tcc gcg tgt ccg acc tgc      576
Ser Asp Ser Gln Ser Asp Gln Val Glu Arg Ser Ala Cys Pro Thr Cys
            180                 185                 190

ggt tcc tgc tcc ggg atg ttt acc gct aac tca atg aac tgc ctg acc      624
Gly Ser Cys Ser Gly Met Phe Thr Ala Asn Ser Met Asn Cys Leu Thr
        195                 200                 205

gaa gcg ctg ggc ctg tcg cag ccg ggc aac ggc tcg ctg ctg gca acc      672
Glu Ala Leu Gly Leu Ser Gln Pro Gly Asn Gly Ser Leu Leu Ala Thr
    210                 215                 220

cac gcc gac cgt aag cag ctg ttc ctt aat gct ggt aaa cgc att gtt      720
His Ala Asp Arg Lys Gln Leu Phe Leu Asn Ala Gly Lys Arg Ile Val
225                 230                 235                 240

gaa ttg acc aaa cgt tat tac gag caa aac gac gaa agt gca ctg ccg      768
Glu Leu Thr Lys Arg Tyr Tyr Glu Gln Asn Asp Glu Ser Ala Leu Pro
                245                 250                 255

cgt aat atc gcc agt aag gcg gcg ttt gaa aac gcc atg acg ctg gat      816
Arg Asn Ile Ala Ser Lys Ala Ala Phe Glu Asn Ala Met Thr Leu Asp
            260                 265                 270

atc gcg atg ggt gga tcg act aac acc gta ctt cac ctg ctg gcg gcg      864
Ile Ala Met Gly Gly Ser Thr Asn Thr Val Leu His Leu Leu Ala Ala
        275                 280                 285
```

```
gcg cag gaa gcg gaa atc gac ttc acc atg agt gat atc gat aag ctt      912
Ala Gln Glu Ala Glu Ile Asp Phe Thr Met Ser Asp Ile Asp Lys Leu
    290                 295                 300

tcc cgc aag gtt cca cag ctg tgt aaa gtt gcg ccg agc acc cag aaa      960
Ser Arg Lys Val Pro Gln Leu Cys Lys Val Ala Pro Ser Thr Gln Lys
305                 310                 315                 320

tac cat atg gaa gat gtt cac cgt gct ggt ggt gtt atc ggt att ctc     1008
Tyr His Met Glu Asp Val His Arg Ala Gly Gly Val Ile Gly Ile Leu
                325                 330                 335

ggc gaa ctg gat cgc gcg ggg tta ctg aac cgt gat gtg aaa aac gta     1056
Gly Glu Leu Asp Arg Ala Gly Leu Leu Asn Arg Asp Val Lys Asn Val
            340                 345                 350

ctt ggc ctg acg ttg ccg caa acg ctg gaa caa tac gac gtt atg ctg     1104
Leu Gly Leu Thr Leu Pro Gln Thr Leu Glu Gln Tyr Asp Val Met Leu
        355                 360                 365

acc cag gat gac gcg gta aaa aat atg ttc cgc gca ggt cct gca ggc     1152
Thr Gln Asp Asp Ala Val Lys Asn Met Phe Arg Ala Gly Pro Ala Gly
    370                 375                 380

att cgt acc aca cag gca ttc tcg caa gat tgc cgt tgg gat acg ctg     1200
Ile Arg Thr Thr Gln Ala Phe Ser Gln Asp Cys Arg Trp Asp Thr Leu
385                 390                 395                 400

gac gac gat cgc gcc aat ggc tgt atc cgc tcg ctg gaa cac gcc tac     1248
Asp Asp Asp Arg Ala Asn Gly Cys Ile Arg Ser Leu Glu His Ala Tyr
                405                 410                 415

agc aaa gac ggc ggc ctg gcg gtg ctc tac ggt aac ttt gcg gaa aac     1296
Ser Lys Asp Gly Gly Leu Ala Val Leu Tyr Gly Asn Phe Ala Glu Asn
            420                 425                 430

ggc tgc atc gtg aaa acg gca ggc gtc gat gac agc atc ctc aaa ttc     1344
Gly Cys Ile Val Lys Thr Ala Gly Val Asp Asp Ser Ile Leu Lys Phe
        435                 440                 445

acc ggc ccg gcg aaa gtg tac gaa agc cag gac gat gcg gta gaa gcg     1392
Thr Gly Pro Ala Lys Val Tyr Glu Ser Gln Asp Asp Ala Val Glu Ala
    450                 455                 460

att ctc ggc ggt aaa gtt gtc gcc gga gat gtg gta gta att cgc tat     1440
Ile Leu Gly Gly Lys Val Val Ala Gly Asp Val Val Val Ile Arg Tyr
465                 470                 475                 480

gaa ggc ccg aaa ggc ggt ccg ggg atg cag gaa atg ctc tac cca acc     1488
Glu Gly Pro Lys Gly Gly Pro Gly Met Gln Glu Met Leu Tyr Pro Thr
                485                 490                 495

agc ttc ctg aaa tca atg ggt ctc ggc aaa gcc tgt gcg ctg atc acc     1536
Ser Phe Leu Lys Ser Met Gly Leu Gly Lys Ala Cys Ala Leu Ile Thr
            500                 505                 510

gac ggt cgt ttc tct ggt ggc acc tct ggt ctt tcc atc ggc cac gtc     1584
Asp Gly Arg Phe Ser Gly Gly Thr Ser Gly Leu Ser Ile Gly His Val
        515                 520                 525

tca ccg gaa gcg gca agc ggc ggc agc att ggc ctg att gaa gat ggt     1632
Ser Pro Glu Ala Ala Ser Gly Gly Ser Ile Gly Leu Ile Glu Asp Gly
    530                 535                 540

gac ctg atc gct atc gac atc ccg aac cgt ggc att cag tta cag gta     1680
Asp Leu Ile Ala Ile Asp Ile Pro Asn Arg Gly Ile Gln Leu Gln Val
545                 550                 555                 560

agc gat gcc gaa ctg gcg gcg cgt cgt gaa gcg cag gac gct cga ggt     1728
Ser Asp Ala Glu Leu Ala Ala Arg Arg Glu Ala Gln Asp Ala Arg Gly
                565                 570                 575

gac aaa gcc tgg acg ccg aaa aat cgt gaa cgt cag gtc tcc ttt gcc     1776
Asp Lys Ala Trp Thr Pro Lys Asn Arg Glu Arg Gln Val Ser Phe Ala
            580                 585                 590

ctg cgt gct tat gcc agc ctg gca acc agc gcc gac aaa ggc gcg gtg     1824
Leu Arg Ala Tyr Ala Ser Leu Ala Thr Ser Ala Asp Lys Gly Ala Val
```

```
        595                 600                 605

cgc gat aaa tcg aaa ctg ggg ggt taa                            1851
Arg Asp Lys Ser Lys Leu Gly Gly
    610                 615


<210> SEQ ID NO 50
<211> LENGTH: 616
<212> TYPE: PRT
<213> ORGANISM: Escherichia coli

<400> SEQUENCE: 50

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350
```

```
Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615


<210> SEQ ID NO 51
<211> LENGTH: 1545
<212> TYPE: DNA
<213> ORGANISM: Escherichia coli
<220> FEATURE:
<221> NAME/KEY: CDS
<222> LOCATION: (1)..(1545)

<400> SEQUENCE: 51

atg gct gac tcg caa ccc ctg tcc ggt gct ccg gaa ggt gcc gaa tat       48
Met Ala Asp Ser Gln Pro Leu Ser Gly Ala Pro Glu Gly Ala Glu Tyr
1               5                   10                  15

tta aga gca gtg ctg cgc gcg ccg gtt tac gag gcg gcg cag gtt acg       96
Leu Arg Ala Val Leu Arg Ala Pro Val Tyr Glu Ala Ala Gln Val Thr
            20                  25                  30

ccg cta caa aaa atg gaa aaa ctg tcg tcg cgt ctt gat aac gtc att      144
Pro Leu Gln Lys Met Glu Lys Leu Ser Ser Arg Leu Asp Asn Val Ile
        35                  40                  45

ctg gtg aag cgc gaa gat cgc cag cca gtg cac agc ttt aag ctg cgc      192
Leu Val Lys Arg Glu Asp Arg Gln Pro Val His Ser Phe Lys Leu Arg
    50                  55                  60
```

-continued

```
ggc gca tac gcc atg atg gcg ggc ctg acg gaa gaa cag aaa gcg cac      240
Gly Ala Tyr Ala Met Met Ala Gly Leu Thr Glu Glu Gln Lys Ala His
65                  70                  75                  80

ggc gtg atc act gct tct gcg ggt aac cac gcg cag ggc gtc gcg ttt      288
Gly Val Ile Thr Ala Ser Ala Gly Asn His Ala Gln Gly Val Ala Phe
                85                  90                  95

tct tct gcg cgg tta ggc gtg aag gcc ctg atc gtt atg cca acc gcc      336
Ser Ser Ala Arg Leu Gly Val Lys Ala Leu Ile Val Met Pro Thr Ala
            100                 105                 110

acc gcc gac atc aaa gtc gac gcg gtg cgc ggc ttc ggc ggc gaa gtg      384
Thr Ala Asp Ile Lys Val Asp Ala Val Arg Gly Phe Gly Gly Glu Val
        115                 120                 125

ctg ctc cac ggc gcg aac ttt gat gaa gcg aaa gcc aaa gcg atc gaa      432
Leu Leu His Gly Ala Asn Phe Asp Glu Ala Lys Ala Lys Ala Ile Glu
    130                 135                 140

ctg tca cag cag cag ggg ttc acc tgg gtg ccg ccg ttc gac cat ccg      480
Leu Ser Gln Gln Gln Gly Phe Thr Trp Val Pro Pro Phe Asp His Pro
145                 150                 155                 160

atg gtg att gcc ggg caa ggc acg ctg gcg ctg gaa ctg ctc cag cag      528
Met Val Ile Ala Gly Gln Gly Thr Leu Ala Leu Glu Leu Leu Gln Gln
                165                 170                 175

gac gcc cat ctc gac cgc gta ttt gtg cca gtc ggc ggc ggc ggt ctg      576
Asp Ala His Leu Asp Arg Val Phe Val Pro Val Gly Gly Gly Gly Leu
            180                 185                 190

gct gct ggc gtg gcg gtg ctg atc aaa caa ctg atg ccg caa atc aaa      624
Ala Ala Gly Val Ala Val Leu Ile Lys Gln Leu Met Pro Gln Ile Lys
        195                 200                 205

gtg atc gcc gta gaa gcg gaa gac tcc gcc tgc ctg aaa gca gcg ctg      672
Val Ile Ala Val Glu Ala Glu Asp Ser Ala Cys Leu Lys Ala Ala Leu
    210                 215                 220

gat gcg ggt cat ccg gtt gat ctg ccg cgc gta ggg cta ttt gct gaa      720
Asp Ala Gly His Pro Val Asp Leu Pro Arg Val Gly Leu Phe Ala Glu
225                 230                 235                 240

ggc gta gcg gta aaa cgc atc ggt gac gaa acc ttc cgt tta tgc cag      768
Gly Val Ala Val Lys Arg Ile Gly Asp Glu Thr Phe Arg Leu Cys Gln
                245                 250                 255

gag tat ctc gac gac atc atc acc gtc gat agc gat gcg atc tgt gcg      816
Glu Tyr Leu Asp Asp Ile Ile Thr Val Asp Ser Asp Ala Ile Cys Ala
            260                 265                 270

gcg atg aag gat tta ttc gaa gat gtg cgc gcg gtg gcg gaa ccc tct      864
Ala Met Lys Asp Leu Phe Glu Asp Val Arg Ala Val Ala Glu Pro Ser
        275                 280                 285

ggc gcg ctg gcg ctg gcg gga atg aaa aaa tat atc gcc ctg cac aac      912
Gly Ala Leu Ala Leu Ala Gly Met Lys Lys Tyr Ile Ala Leu His Asn
    290                 295                 300

att cgc ggc gaa cgg ctg gcg cat att ctt tcc ggt gcc aac gtg aac      960
Ile Arg Gly Glu Arg Leu Ala His Ile Leu Ser Gly Ala Asn Val Asn
305                 310                 315                 320

ttc cac ggc ctg cgc tac gtc tca gaa cgc tgc gaa ctg ggc gaa cag     1008
Phe His Gly Leu Arg Tyr Val Ser Glu Arg Cys Glu Leu Gly Glu Gln
                325                 330                 335

cgt gaa gcg ttg ttg gcg gtg acc att ccg gaa gaa aaa ggc agc ttc     1056
Arg Glu Ala Leu Leu Ala Val Thr Ile Pro Glu Glu Lys Gly Ser Phe
            340                 345                 350

ctc aaa ttc tgc caa ctg ctt ggc ggg cgt tcg gtc acc gag ttc aac     1104
Leu Lys Phe Cys Gln Leu Leu Gly Gly Arg Ser Val Thr Glu Phe Asn
        355                 360                 365

tac cgt ttt gcc gat gcc aaa aac gcc tgc atc ttt gtc ggt gtg cgc     1152
Tyr Arg Phe Ala Asp Ala Lys Asn Ala Cys Ile Phe Val Gly Val Arg
    370                 375                 380
```

```
ctg agc cgc ggc ctc gaa gag cgc aaa gaa att ttg cag atg ctc aac      1200
Leu Ser Arg Gly Leu Glu Glu Arg Lys Glu Ile Leu Gln Met Leu Asn
385                 390                 395                 400

gac ggc ggc tac agc gtg gtt gat ctc tcc gac gac gaa atg gcg aag      1248
Asp Gly Gly Tyr Ser Val Val Asp Leu Ser Asp Asp Glu Met Ala Lys
                405                 410                 415

cta cac gtg cgc tat atg gtc ggc gga cgt cca tcg cat ccg ttg cag      1296
Leu His Val Arg Tyr Met Val Gly Gly Arg Pro Ser His Pro Leu Gln
            420                 425                 430

gaa cgc ctc tac agc ttc gaa ttc ccg gaa tca ccg ggc gcg ctg ctg      1344
Glu Arg Leu Tyr Ser Phe Glu Phe Pro Glu Ser Pro Gly Ala Leu Leu
        435                 440                 445

cgc ttc ctc aac acg ctg ggt acg tac tgg aac att tct ttg ttc cac      1392
Arg Phe Leu Asn Thr Leu Gly Thr Tyr Trp Asn Ile Ser Leu Phe His
    450                 455                 460

tat cgc agc cat ggc acc gac tac ggg cgc gta ctg gcg gcg ttc gaa      1440
Tyr Arg Ser His Gly Thr Asp Tyr Gly Arg Val Leu Ala Ala Phe Glu
465                 470                 475                 480

ctt ggc gac cat gaa ccg gat ttc gaa acc cgg ctg aat gag ctg ggc      1488
Leu Gly Asp His Glu Pro Asp Phe Glu Thr Arg Leu Asn Glu Leu Gly
                485                 490                 495

tac gat tgc cac gac gaa acc aat aac ccg gcg ttc agg ttc ttt ttg      1536
Tyr Asp Cys His Asp Glu Thr Asn Asn Pro Ala Phe Arg Phe Phe Leu
            500                 505                 510

gcg ggt tag                                                          1545
Ala Gly


<210> SEQ ID NO 52
<211> LENGTH: 514
<212> TYPE: PRT
<213> ORGANISM: Escherichia coli

<400> SEQUENCE: 52

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190
```

```
Ala Ala Gly Val Ala Val Leu Ile Lys Gln Leu Met Pro Gln Ile Lys
      195                 200                 205

Val Ile Ala Val Glu Ala Glu Asp Ser Ala Cys Leu Lys Ala Ala Leu
    210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
        275                 280                 285

Gly Ala Leu Ala Leu Ala Gly Met Lys Lys Tyr Ile Ala Leu His Asn
    290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
            340                 345                 350

Leu Lys Phe Cys Gln Leu Leu Gly Gly Arg Ser Val Thr Glu Phe Asn
        355                 360                 365

Tyr Arg Phe Ala Asp Ala Lys Asn Ala Cys Ile Phe Val Gly Val Arg
    370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Asp Glu Met Ala Lys
                405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
        435                 440                 445

Arg Phe Leu Asn Thr Leu Gly Thr Tyr Trp Asn Ile Ser Leu Phe His
    450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
            500                 505                 510

Ala Gly


<210> SEQ ID NO 53
<211> LENGTH: 1572
<212> TYPE: DNA
<213> ORGANISM: Escherichia coli
<220> FEATURE:
<221> NAME/KEY: CDS
<222> LOCATION: (1)..(1572)

<400> SEQUENCE: 53

atg agc cag caa gtc att att ttc gat acc aca ttg cgc gac ggt gaa       48
Met Ser Gln Gln Val Ile Ile Phe Asp Thr Thr Leu Arg Asp Gly Glu
1               5                   10                  15

cag gcg tta cag gca agc ttg agt gtg aaa gaa aaa ctg caa att gcg       96
```

-continued

```
Gln Ala Leu Gln Ala Ser Leu Ser Val Lys Glu Lys Leu Gln Ile Ala
            20                  25                  30

ctg gcc ctt gag cgt atg ggt gtt gac gtg atg gaa gtc ggt ttc ccc      144
Leu Ala Leu Glu Arg Met Gly Val Asp Val Met Glu Val Gly Phe Pro
        35                  40                  45

gtc tct tcg ccg ggc gat ttt gaa tcg gtg caa acc atc gcc cgc cag      192
Val Ser Ser Pro Gly Asp Phe Glu Ser Val Gln Thr Ile Ala Arg Gln
    50                  55                  60

gtt aaa aac agc cgc gta tgt gcg tta gct cgc tgc gtg gaa aaa gat      240
Val Lys Asn Ser Arg Val Cys Ala Leu Ala Arg Cys Val Glu Lys Asp
65                  70                  75                  80

atc gac gtg gcg gcc gaa tcc ctg aaa gtc gcc gaa gcc ttc cgt att      288
Ile Asp Val Ala Ala Glu Ser Leu Lys Val Ala Glu Ala Phe Arg Ile
                85                  90                  95

cat acc ttt att gcc act tcg cca atg cac atc gcc acc aag ctg cgc      336
His Thr Phe Ile Ala Thr Ser Pro Met His Ile Ala Thr Lys Leu Arg
            100                 105                 110

agc acg ctg gac gag gtg atc gaa cgc gct atc tat atg gtg aaa cgc      384
Ser Thr Leu Asp Glu Val Ile Glu Arg Ala Ile Tyr Met Val Lys Arg
        115                 120                 125

gcc cgt aat tac acc gat gat gtt gaa ttt tct tgc gaa gat gcc ggg      432
Ala Arg Asn Tyr Thr Asp Asp Val Glu Phe Ser Cys Glu Asp Ala Gly
    130                 135                 140

cgt aca ccc att gcc gat ctg gcg cga gtg gtc gaa gcg gcg att aat      480
Arg Thr Pro Ile Ala Asp Leu Ala Arg Val Val Glu Ala Ala Ile Asn
145                 150                 155                 160

gcc ggt gcc acc acc atc aac att ccg gac acc gtg ggc tac acc atg      528
Ala Gly Ala Thr Thr Ile Asn Ile Pro Asp Thr Val Gly Tyr Thr Met
                165                 170                 175

ccg ttt gag ttc gcc gga atc atc agc ggc ctg tat gaa cgc gtg cct      576
Pro Phe Glu Phe Ala Gly Ile Ile Ser Gly Leu Tyr Glu Arg Val Pro
            180                 185                 190

aac atc gac aaa gcc att atc tcc gta cat acc cac gac gat ttg ggc      624
Asn Ile Asp Lys Ala Ile Ile Ser Val His Thr His Asp Asp Leu Gly
        195                 200                 205

ctg gcg gtc gga aac tca ctg gcg gcg gta cat gcc ggt gca cgc cag      672
Leu Ala Val Gly Asn Ser Leu Ala Ala Val His Ala Gly Ala Arg Gln
    210                 215                 220

gtg gaa ggc gca atg aac ggg atc ggc gag cgt gcc gga aac tgt tcc      720
Val Glu Gly Ala Met Asn Gly Ile Gly Glu Arg Ala Gly Asn Cys Ser
225                 230                 235                 240

ctg gaa gaa gtc atc atg gcg atc aaa gtt cgt aag gat att ctc aac      768
Leu Glu Glu Val Ile Met Ala Ile Lys Val Arg Lys Asp Ile Leu Asn
                245                 250                 255

gtc cac acc gcc att aat cac cag gag ata tgg cgc acc agc cag tta      816
Val His Thr Ala Ile Asn His Gln Glu Ile Trp Arg Thr Ser Gln Leu
            260                 265                 270

gtt agc cag att tgt aat atg ccg atc ccg gca aac aaa gcc att gtt      864
Val Ser Gln Ile Cys Asn Met Pro Ile Pro Ala Asn Lys Ala Ile Val
        275                 280                 285

ggc agc ggc gca ttc gca cac tcc tcc ggt ata cac cag gat ggc gtg      912
Gly Ser Gly Ala Phe Ala His Ser Ser Gly Ile His Gln Asp Gly Val
    290                 295                 300

ctg aaa aac cgc gaa aac tac gaa atc atg aca cca gaa tct att ggt      960
Leu Lys Asn Arg Glu Asn Tyr Glu Ile Met Thr Pro Glu Ser Ile Gly
305                 310                 315                 320

ctg aac caa atc cag ctg aat ctg acc tct cgt tcg ggg cgt gcg gcg     1008
Leu Asn Gln Ile Gln Leu Asn Leu Thr Ser Arg Ser Gly Arg Ala Ala
                325                 330                 335
```

-continued

```
gtg aaa cat cgc atg gat gag atg ggg tat aaa gaa agt gaa tat aat      1056
Val Lys His Arg Met Asp Glu Met Gly Tyr Lys Glu Ser Glu Tyr Asn
            340                 345                 350

tta gac aat ttg tac gat gct ttc ctg aag ctg gcg gac aaa aaa ggt      1104
Leu Asp Asn Leu Tyr Asp Ala Phe Leu Lys Leu Ala Asp Lys Lys Gly
        355                 360                 365

cag gtg ttt gat tac gat ctg gag gcg ctg gcc ttc atc ggt aag cag      1152
Gln Val Phe Asp Tyr Asp Leu Glu Ala Leu Ala Phe Ile Gly Lys Gln
    370                 375                 380

caa gaa gag ccg gag cat ttc cgt ctg gat tac ttc agc gtg cag tct      1200
Gln Glu Glu Pro Glu His Phe Arg Leu Asp Tyr Phe Ser Val Gln Ser
385                 390                 395                 400

ggc tct aac gat atc gcc acc gcc gcc gtc aaa ctg gcc tgt ggc gaa      1248
Gly Ser Asn Asp Ile Ala Thr Ala Ala Val Lys Leu Ala Cys Gly Glu
            405                 410                 415

gaa gtc aaa gca gaa gcc gcc aac ggt aac ggt ccg gtc gat gcc gtc      1296
Glu Val Lys Ala Glu Ala Ala Asn Gly Asn Gly Pro Val Asp Ala Val
            420                 425                 430

tat cag gca att aac cgc atc act gaa tat aac gtc gaa ctg gtg aaa      1344
Tyr Gln Ala Ile Asn Arg Ile Thr Glu Tyr Asn Val Glu Leu Val Lys
        435                 440                 445

tac agc ctg acc gcc aaa ggc cac ggt aaa gat gcg ctg ggt cag gtg      1392
Tyr Ser Leu Thr Ala Lys Gly His Gly Lys Asp Ala Leu Gly Gln Val
    450                 455                 460

gat atc gtc gct aac tac aac ggt cgc cgc ttc cac ggc gtc ggc ctg      1440
Asp Ile Val Ala Asn Tyr Asn Gly Arg Arg Phe His Gly Val Gly Leu
465                 470                 475                 480

gct acc gat att gtc gag tca tct gcc aaa gcc atg gtg cac gtt ctg      1488
Ala Thr Asp Ile Val Glu Ser Ser Ala Lys Ala Met Val His Val Leu
            485                 490                 495

aac aat atc tgg cgt gcc gca gaa gtc gaa aaa gag ttg caa cgc aaa      1536
Asn Asn Ile Trp Arg Ala Ala Glu Val Glu Lys Glu Leu Gln Arg Lys
            500                 505                 510

gct caa cac aac gaa aac aac aag gaa acc gtg tga                      1572
Ala Gln His Asn Glu Asn Asn Lys Glu Thr Val
        515                 520
```

<210> SEQ ID NO 54
<211> LENGTH: 523
<212> TYPE: PRT
<213> ORGANISM: Escherichia coli

<400> SEQUENCE: 54

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
            85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125
```

```
Ala Arg Asn Tyr Thr Asp Asp Val Glu Phe Ser Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
        435                 440                 445

Tyr Ser Leu Thr Ala Lys Gly His Gly Lys Asp Ala Leu Gly Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520
```

<210> SEQ ID NO 55
<211> LENGTH: 1095

-continued

<212> TYPE: DNA
<213> ORGANISM: Escherichia coli
<220> FEATURE:
<221> NAME/KEY: CDS
<222> LOCATION: (1)..(1095)

<400> SEQUENCE: 55

```
gtg atg tcg aag aat tac cat att gcc gta ttg ccg ggg gac ggt att       48
Val Met Ser Lys Asn Tyr His Ile Ala Val Leu Pro Gly Asp Gly Ile
1               5                   10                  15

ggt ccg gaa gtg atg acc cag gcg ctg aaa gtg ctg gat gcc gtg cgc       96
Gly Pro Glu Val Met Thr Gln Ala Leu Lys Val Leu Asp Ala Val Arg
            20                  25                  30

aac cgc ttt gcg atg cgc atc acc acc agc cat tac gat gta ggc ggc      144
Asn Arg Phe Ala Met Arg Ile Thr Thr Ser His Tyr Asp Val Gly Gly
        35                  40                  45

gca gcc att gat aac cac ggg caa cca ctg ccg cct gcg acg gtt gaa      192
Ala Ala Ile Asp Asn His Gly Gln Pro Leu Pro Pro Ala Thr Val Glu
    50                  55                  60

ggt tgt gag caa gcc gat gcc gtg ctg ttt ggc tcg gta ggc ggc ccg      240
Gly Cys Glu Gln Ala Asp Ala Val Leu Phe Gly Ser Val Gly Gly Pro
65                  70                  75                  80

aag tgg gaa cat tta cca cca gac cag caa cca gaa cgc ggc gcg ctg      288
Lys Trp Glu His Leu Pro Pro Asp Gln Gln Pro Glu Arg Gly Ala Leu
                85                  90                  95

ctg cct ctg cgt aag cac ttc aaa tta ttc agc aac ctg cgc ccg gca      336
Leu Pro Leu Arg Lys His Phe Lys Leu Phe Ser Asn Leu Arg Pro Ala
            100                 105                 110

aaa ctg tat cag ggg ctg gaa gca ttc tgt ccg ctg cgt gca gac att      384
Lys Leu Tyr Gln Gly Leu Glu Ala Phe Cys Pro Leu Arg Ala Asp Ile
        115                 120                 125

gcc gca aac ggc ttc gac atc ctg tgt gtg cgc gaa ctg acc ggc ggc      432
Ala Ala Asn Gly Phe Asp Ile Leu Cys Val Arg Glu Leu Thr Gly Gly
    130                 135                 140

atc tat ttc ggt cag cca aaa ggc cgc gaa ggt agc gga caa tat gaa      480
Ile Tyr Phe Gly Gln Pro Lys Gly Arg Glu Gly Ser Gly Gln Tyr Glu
145                 150                 155                 160

aaa gcc ttt gat acc gag gtg tat cac cgt ttt gag atc gaa cgt atc      528
Lys Ala Phe Asp Thr Glu Val Tyr His Arg Phe Glu Ile Glu Arg Ile
                165                 170                 175

gcc cgc atc gcg ttt gaa tct gct cgc aag cgt cgc cac aaa gtg acg      576
Ala Arg Ile Ala Phe Glu Ser Ala Arg Lys Arg Arg His Lys Val Thr
            180                 185                 190

tcg atc gat aaa gcc aac gtg ctg caa tcc tct att tta tgg cgg gag      624
Ser Ile Asp Lys Ala Asn Val Leu Gln Ser Ser Ile Leu Trp Arg Glu
        195                 200                 205

atc gtt aac gag atc gcc acg gaa tac ccg gat gtc gaa ctg gcg cat      672
Ile Val Asn Glu Ile Ala Thr Glu Tyr Pro Asp Val Glu Leu Ala His
    210                 215                 220

atg tac atc gac aac gcc acc atg cag ctg att aaa gat cca tca cag      720
Met Tyr Ile Asp Asn Ala Thr Met Gln Leu Ile Lys Asp Pro Ser Gln
225                 230                 235                 240

ttt gac gtt ctg ctg tgc tcc aac ctg ttt ggc gac att ctg tct gac      768
Phe Asp Val Leu Leu Cys Ser Asn Leu Phe Gly Asp Ile Leu Ser Asp
                245                 250                 255

gag tgc gca atg atc act ggc tcg atg ggg atg ttg cct tcc gcc agc      816
Glu Cys Ala Met Ile Thr Gly Ser Met Gly Met Leu Pro Ser Ala Ser
            260                 265                 270

ctg aac gag caa ggt ttt gga ctg tat gaa ccg gcg ggc ggc tcg gca      864
Leu Asn Glu Gln Gly Phe Gly Leu Tyr Glu Pro Ala Gly Gly Ser Ala
        275                 280                 285
```

```
cca gat atc gca ggc aaa aac atc gcc aac ccg att gca caa atc ctt      912
Pro Asp Ile Ala Gly Lys Asn Ile Ala Asn Pro Ile Ala Gln Ile Leu
    290                 295                 300

tcg ctg gca ctg ctg ctg cgt tac agc ctg gat gcc gat gat gcg gct      960
Ser Leu Ala Leu Leu Leu Arg Tyr Ser Leu Asp Ala Asp Asp Ala Ala
305                 310                 315                 320

tgc gcc att gaa cgc gcc att aac cgc gca tta gaa gaa ggc att cgc     1008
Cys Ala Ile Glu Arg Ala Ile Asn Arg Ala Leu Glu Glu Gly Ile Arg
                325                 330                 335

acc ggg gat tta gcc cgt ggc gct gcc gcc gtt agt acc gat gaa atg     1056
Thr Gly Asp Leu Ala Arg Gly Ala Ala Ala Val Ser Thr Asp Glu Met
            340                 345                 350

ggc gat atc att gcc cgc tat gta gca gaa ggg gtg taa                 1095
Gly Asp Ile Ile Ala Arg Tyr Val Ala Glu Gly Val
        355                 360


<210> SEQ ID NO 56
<211> LENGTH: 364
<212> TYPE: PRT
<213> ORGANISM: Escherichia coli

<400> SEQUENCE: 56

Val Met Ser Lys Asn Tyr His Ile Ala Val Leu Pro Gly Asp Gly Ile
1               5                   10                  15

Gly Pro Glu Val Met Thr Gln Ala Leu Lys Val Leu Asp Ala Val Arg
            20                  25                  30

Asn Arg Phe Ala Met Arg Ile Thr Thr Ser His Tyr Asp Val Gly Gly
        35                  40                  45

Ala Ala Ile Asp Asn His Gly Gln Pro Leu Pro Pro Ala Thr Val Glu
    50                  55                  60

Gly Cys Glu Gln Ala Asp Ala Val Leu Phe Gly Ser Val Gly Gly Pro
65                  70                  75                  80

Lys Trp Glu His Leu Pro Pro Asp Gln Gln Pro Glu Arg Gly Ala Leu
                85                  90                  95

Leu Pro Leu Arg Lys His Phe Lys Leu Phe Ser Asn Leu Arg Pro Ala
            100                 105                 110

Lys Leu Tyr Gln Gly Leu Glu Ala Phe Cys Pro Leu Arg Ala Asp Ile
        115                 120                 125

Ala Ala Asn Gly Phe Asp Ile Leu Cys Val Arg Glu Leu Thr Gly Gly
    130                 135                 140

Ile Tyr Phe Gly Gln Pro Lys Gly Arg Glu Gly Ser Gly Gln Tyr Glu
145                 150                 155                 160

Lys Ala Phe Asp Thr Glu Val Tyr His Arg Phe Glu Ile Glu Arg Ile
                165                 170                 175

Ala Arg Ile Ala Phe Glu Ser Ala Arg Lys Arg Arg His Lys Val Thr
            180                 185                 190

Ser Ile Asp Lys Ala Asn Val Leu Gln Ser Ser Ile Leu Trp Arg Glu
        195                 200                 205

Ile Val Asn Glu Ile Ala Thr Glu Tyr Pro Asp Val Glu Leu Ala His
    210                 215                 220

Met Tyr Ile Asp Asn Ala Thr Met Gln Leu Ile Lys Asp Pro Ser Gln
225                 230                 235                 240

Phe Asp Val Leu Leu Cys Ser Asn Leu Phe Gly Asp Ile Leu Ser Asp
                245                 250                 255

Glu Cys Ala Met Ile Thr Gly Ser Met Gly Met Leu Pro Ser Ala Ser
            260                 265                 270
```

```
Leu Asn Glu Gln Gly Phe Gly Leu Tyr Glu Pro Ala Gly Gly Ser Ala
        275                 280                 285

Pro Asp Ile Ala Gly Lys Asn Ile Ala Asn Pro Ile Ala Gln Ile Leu
    290                 295                 300

Ser Leu Ala Leu Leu Leu Arg Tyr Ser Leu Asp Ala Asp Asp Ala Ala
305                 310                 315                 320

Cys Ala Ile Glu Arg Ala Ile Asn Arg Ala Leu Glu Glu Gly Ile Arg
                325                 330                 335

Thr Gly Asp Leu Ala Arg Gly Ala Ala Ala Val Ser Thr Asp Glu Met
            340                 345                 350

Gly Asp Ile Ile Ala Arg Tyr Val Ala Glu Gly Val
        355                 360


<210> SEQ ID NO 57
<211> LENGTH: 1401
<212> TYPE: DNA
<213> ORGANISM: Escherichia coli
<220> FEATURE:
<221> NAME/KEY: CDS
<222> LOCATION: (1)..(1401)

<400> SEQUENCE: 57

atg gct aag acg tta tac gaa aaa ttg ttc gac gct cac gtt gtg tac       48
Met Ala Lys Thr Leu Tyr Glu Lys Leu Phe Asp Ala His Val Val Tyr
1               5                   10                  15

gaa gcc gaa aac gaa acc cca ctg tta tat atc gac cgc cac ctg gtg       96
Glu Ala Glu Asn Glu Thr Pro Leu Leu Tyr Ile Asp Arg His Leu Val
            20                  25                  30

cat gaa gtg acc tca ccg cag gcg ttc gat ggt ctg cgc gcc cac ggt      144
His Glu Val Thr Ser Pro Gln Ala Phe Asp Gly Leu Arg Ala His Gly
        35                  40                  45

cgc ccg gta cgt cag ccg ggc aaa acc ttc gct acc atg gat cac aac      192
Arg Pro Val Arg Gln Pro Gly Lys Thr Phe Ala Thr Met Asp His Asn
    50                  55                  60

gtc tct acc cag acc aaa gac att aat gcc tgc ggt gaa atg gcg cgt      240
Val Ser Thr Gln Thr Lys Asp Ile Asn Ala Cys Gly Glu Met Ala Arg
65                  70                  75                  80

atc cag atg cag gaa ctg atc aaa aac tgc aaa gaa ttt ggc gtc gaa      288
Ile Gln Met Gln Glu Leu Ile Lys Asn Cys Lys Glu Phe Gly Val Glu
                85                  90                  95

ctg tat gac ctg aat cac ccg tat cag ggg atc gtc cac gta atg ggg      336
Leu Tyr Asp Leu Asn His Pro Tyr Gln Gly Ile Val His Val Met Gly
            100                 105                 110

ccg gaa cag ggc gtc acc ttg ccg ggg atg acc att gtc tgc ggc gac      384
Pro Glu Gln Gly Val Thr Leu Pro Gly Met Thr Ile Val Cys Gly Asp
        115                 120                 125

tcg cat acc gcc acc cac ggc gcg ttt ggc gca ctg gcc ttt ggt atc      432
Ser His Thr Ala Thr His Gly Ala Phe Gly Ala Leu Ala Phe Gly Ile
    130                 135                 140

ggc act tcc gaa gtt gaa cac gta ctg gca acg caa acc ctg aaa cag      480
Gly Thr Ser Glu Val Glu His Val Leu Ala Thr Gln Thr Leu Lys Gln
145                 150                 155                 160

ggc cgc gca aaa acc atg aaa att gaa gtc cag ggc aaa gcc gcg ccg      528
Gly Arg Ala Lys Thr Met Lys Ile Glu Val Gln Gly Lys Ala Ala Pro
                165                 170                 175

ggc att acc gca aaa gat atc gtg ctg gca att atc ggt aaa acc ggt      576
Gly Ile Thr Ala Lys Asp Ile Val Leu Ala Ile Ile Gly Lys Thr Gly
            180                 185                 190

agc gca ggc ggc acc ggg cat gtg gtg gag ttt tgc ggc gaa gca atc      624
```

```
Ser Ala Gly Gly Thr Gly His Val Val Glu Phe Cys Gly Glu Ala Ile
        195                 200                 205

cgt gat tta agc atg gaa ggt cgt atg acc ctg tgc aat atg gca atc      672
Arg Asp Leu Ser Met Glu Gly Arg Met Thr Leu Cys Asn Met Ala Ile
    210                 215                 220

gaa atg ggc gca aaa gcc ggt ctg gtt gca ccg gac gaa acc acc ttt      720
Glu Met Gly Ala Lys Ala Gly Leu Val Ala Pro Asp Glu Thr Thr Phe
225                 230                 235                 240

aac tat gtc aaa ggc cgt ctg cat gcg ccg aaa ggc aaa gat ttc gac      768
Asn Tyr Val Lys Gly Arg Leu His Ala Pro Lys Gly Lys Asp Phe Asp
                245                 250                 255

gac gcc gtt gcc tac tgg aaa acc ctg caa acc gac gaa ggc gca act      816
Asp Ala Val Ala Tyr Trp Lys Thr Leu Gln Thr Asp Glu Gly Ala Thr
            260                 265                 270

ttc gat acc gtt gtc act ctg caa gca gaa gaa att tca ccg cag gtc      864
Phe Asp Thr Val Val Thr Leu Gln Ala Glu Glu Ile Ser Pro Gln Val
        275                 280                 285

acc tgg ggc acc aat ccc ggc cag gtg att tcc gtg aac gac aat att      912
Thr Trp Gly Thr Asn Pro Gly Gln Val Ile Ser Val Asn Asp Asn Ile
    290                 295                 300

ccc gat ccg gct tcg ttt gcc gat ccg gtt gaa cgc gcg tcg gca gaa      960
Pro Asp Pro Ala Ser Phe Ala Asp Pro Val Glu Arg Ala Ser Ala Glu
305                 310                 315                 320

aaa gcg ctg gcc tat atg ggg ctg aaa ccg ggt att ccg ctg acc gaa     1008
Lys Ala Leu Ala Tyr Met Gly Leu Lys Pro Gly Ile Pro Leu Thr Glu
                325                 330                 335

gtg gct atc gac aaa gtg ttt atc ggt tcc tgt acc aac tcg cgc att     1056
Val Ala Ile Asp Lys Val Phe Ile Gly Ser Cys Thr Asn Ser Arg Ile
            340                 345                 350

gaa gat tta cgc gcg gca gcg gag atc gcc aaa ggg cga aaa gtc gcg     1104
Glu Asp Leu Arg Ala Ala Ala Glu Ile Ala Lys Gly Arg Lys Val Ala
        355                 360                 365

cca ggc gtg cag gca ctg gtg gtt ccc ggc tct ggc ccg gta aaa gcc     1152
Pro Gly Val Gln Ala Leu Val Val Pro Gly Ser Gly Pro Val Lys Ala
    370                 375                 380

cag gcg gaa gcg gaa ggt ctg gat aaa atc ttt att gaa gcc ggt ttt     1200
Gln Ala Glu Ala Glu Gly Leu Asp Lys Ile Phe Ile Glu Ala Gly Phe
385                 390                 395                 400

gaa tgg cgc ttg cct ggc tgc tca atg tgt ctg gcg atg aac aac gac     1248
Glu Trp Arg Leu Pro Gly Cys Ser Met Cys Leu Ala Met Asn Asn Asp
                405                 410                 415

cgt ctg aat ccg ggc gaa cgt tgt gcc tcc acc agc aac cgt aac ttt     1296
Arg Leu Asn Pro Gly Glu Arg Cys Ala Ser Thr Ser Asn Arg Asn Phe
            420                 425                 430

gaa ggc cgc cag ggg cgc ggc ggg cgc acg cat ctg gtc agc ccg gca     1344
Glu Gly Arg Gln Gly Arg Gly Gly Arg Thr His Leu Val Ser Pro Ala
        435                 440                 445

atg gct gcc gct gct gct gtg acc gga cat ttc gcc gac att cgc aac     1392
Met Ala Ala Ala Ala Ala Val Thr Gly His Phe Ala Asp Ile Arg Asn
    450                 455                 460

att aaa taa                                                         1401
Ile Lys
465


<210> SEQ ID NO 58
<211> LENGTH: 466
<212> TYPE: PRT
<213> ORGANISM: Escherichia coli

<400> SEQUENCE: 58
```

-continued

```
Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
```

```
        420                 425                 430

Glu Gly Arg Gln Gly Arg Gly Gly Arg Thr His Leu Val Ser Pro Ala
        435                 440                 445

Met Ala Ala Ala Ala Ala Val Thr Gly His Phe Ala Asp Ile Arg Asn
    450                 455                 460

Ile Lys
465


<210> SEQ ID NO 59
<211> LENGTH: 606
<212> TYPE: DNA
<213> ORGANISM: Escherichia coli
<220> FEATURE:
<221> NAME/KEY: CDS
<222> LOCATION: (1)..(606)

<400> SEQUENCE: 59

atg gca gag aaa ttt atc aaa cac aca ggc ctg gtg gtt ccg ctg gat       48
Met Ala Glu Lys Phe Ile Lys His Thr Gly Leu Val Val Pro Leu Asp
1               5                   10                  15

gcc gcc aat gtc gat acc gat gca atc atc ccg aaa cag ttt ttg cag       96
Ala Ala Asn Val Asp Thr Asp Ala Ile Ile Pro Lys Gln Phe Leu Gln
            20                  25                  30

aaa gtg acc cgt acg ggt ttt ggc gcg cat ctg ttt aac gac tgg cgt      144
Lys Val Thr Arg Thr Gly Phe Gly Ala His Leu Phe Asn Asp Trp Arg
        35                  40                  45

ttt ctg gat gaa aaa ggc caa cag cca aac ccg gac ttc gtg ctg aac      192
Phe Leu Asp Glu Lys Gly Gln Gln Pro Asn Pro Asp Phe Val Leu Asn
    50                  55                  60

ttc ccg cag tat cag ggc gct tcc att ttg ctg gca cga gaa aac ttc      240
Phe Pro Gln Tyr Gln Gly Ala Ser Ile Leu Leu Ala Arg Glu Asn Phe
65                  70                  75                  80

ggc tgt ggc tct tcg cgt gag cac gcg ccc tgg gca ttg acc gac tac      288
Gly Cys Gly Ser Ser Arg Glu His Ala Pro Trp Ala Leu Thr Asp Tyr
                85                  90                  95

ggt ttt aaa gtg gtg att gcg ccg agt ttt gct gac atc ttc tac ggc      336
Gly Phe Lys Val Val Ile Ala Pro Ser Phe Ala Asp Ile Phe Tyr Gly
            100                 105                 110

aat agc ttt aac aac cag ctg ctg ccg gtg aaa tta agc gat gca gaa      384
Asn Ser Phe Asn Asn Gln Leu Leu Pro Val Lys Leu Ser Asp Ala Glu
        115                 120                 125

gtg gac gaa ctg ttt gcg ctg gtg aaa gct aat ccg ggg atc cat ttc      432
Val Asp Glu Leu Phe Ala Leu Val Lys Ala Asn Pro Gly Ile His Phe
    130                 135                 140

gac gtg gat ctg gaa gcg caa gag gtg aaa gcg gga gag aaa acc tat      480
Asp Val Asp Leu Glu Ala Gln Glu Val Lys Ala Gly Glu Lys Thr Tyr
145                 150                 155                 160

cgc ttt acc atc gat gcc ttc cgc cgc cac tgc atg atg aac ggt ctg      528
Arg Phe Thr Ile Asp Ala Phe Arg Arg His Cys Met Met Asn Gly Leu
                165                 170                 175

gac agt att ggg ctt acc ttg cag cac gac gac gcc att gcc gct tat      576
Asp Ser Ile Gly Leu Thr Leu Gln His Asp Asp Ala Ile Ala Ala Tyr
            180                 185                 190

gaa gca aaa caa cct gcg ttt atg aat taa                              606
Glu Ala Lys Gln Pro Ala Phe Met Asn
        195                 200


<210> SEQ ID NO 60
<211> LENGTH: 201
<212> TYPE: PRT
<213> ORGANISM: Escherichia coli
```

<400> SEQUENCE: 60

```
Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200
```

<210> SEQ ID NO 61
<211> LENGTH: 1476
<212> TYPE: DNA
<213> ORGANISM: Methanocaldococcus jannaschii
<220> FEATURE:
<221> NAME/KEY: CDS
<222> LOCATION: (1)..(1476)

<400> SEQUENCE: 61

```
atg atg gta agg ata ttt gat aca aca ctt aga gat gga gag caa aca      48
Met Met Val Arg Ile Phe Asp Thr Thr Leu Arg Asp Gly Glu Gln Thr
1               5                   10                  15

cca gga gtt tct tta aca cca aat gat aag tta gag ata gca aaa aaa      96
Pro Gly Val Ser Leu Thr Pro Asn Asp Lys Leu Glu Ile Ala Lys Lys
            20                  25                  30

ttg gat gag ctt gga gtt gat gtt ata gag gca ggt tca gct ata act     144
Leu Asp Glu Leu Gly Val Asp Val Ile Glu Ala Gly Ser Ala Ile Thr
        35                  40                  45

tca aaa gga gag aga gaa gga ata aaa tta ata aca aaa gaa ggt tta     192
Ser Lys Gly Glu Arg Glu Gly Ile Lys Leu Ile Thr Lys Glu Gly Leu
    50                  55                  60

aat gca gaa atc tgc tca ttt gtt aga gct tta cct gta gat att gat     240
Asn Ala Glu Ile Cys Ser Phe Val Arg Ala Leu Pro Val Asp Ile Asp
65                  70                  75                  80

gct gcc tta gaa tgt gat gta gat agt gtc cat tta gta gtg cca aca     288
Ala Ala Leu Glu Cys Asp Val Asp Ser Val His Leu Val Val Pro Thr
                85                  90                  95

tct cca ata cac atg aaa tat aag ctt aga aaa aca gaa gat gag gtt     336
Ser Pro Ile His Met Lys Tyr Lys Leu Arg Lys Thr Glu Asp Glu Val
```

-continued

```
            100                 105                 110

tta gag aca gct tta aag gct gta gag tat gct aaa gaa cat gga ttg      384
Leu Glu Thr Ala Leu Lys Ala Val Glu Tyr Ala Lys Glu His Gly Leu
        115                 120                 125

att gtt gag tta tct gca gag gat gca aca aga agt gat gta aat ttc      432
Ile Val Glu Leu Ser Ala Glu Asp Ala Thr Arg Ser Asp Val Asn Phe
    130                 135                 140

tta ata aaa cta ttt aat gaa ggg gaa aag gtt gga gca gac aga gtt      480
Leu Ile Lys Leu Phe Asn Glu Gly Glu Lys Val Gly Ala Asp Arg Val
145                 150                 155                 160

tgt gtt tgt gac aca gta gga gtt tta act cca caa aag agt cag gaa      528
Cys Val Cys Asp Thr Val Gly Val Leu Thr Pro Gln Lys Ser Gln Glu
                165                 170                 175

tta ttt aaa aaa ata act gaa aat gtt aat tta ccg gtc tca gtt cat      576
Leu Phe Lys Lys Ile Thr Glu Asn Val Asn Leu Pro Val Ser Val His
            180                 185                 190

tgc cac aac gac ttt gga atg gct act gct aat act tgc tca gca gtt      624
Cys His Asn Asp Phe Gly Met Ala Thr Ala Asn Thr Cys Ser Ala Val
        195                 200                 205

tta ggt gga gct gtt cag tgc cac gta aca gtt aat ggt att gga gag      672
Leu Gly Gly Ala Val Gln Cys His Val Thr Val Asn Gly Ile Gly Glu
    210                 215                 220

aga gca gga aat gcc tca ttg gaa gag gtt gtt gct gct tta aaa ata      720
Arg Ala Gly Asn Ala Ser Leu Glu Glu Val Val Ala Ala Leu Lys Ile
225                 230                 235                 240

ctc tat ggc tat gat act aag ata aag atg gaa aag tta tat gag gtt      768
Leu Tyr Gly Tyr Asp Thr Lys Ile Lys Met Glu Lys Leu Tyr Glu Val
                245                 250                 255

tca aga att gtc tca aga ttg atg aaa ctt cct gtt cca cca aat aaa      816
Ser Arg Ile Val Ser Arg Leu Met Lys Leu Pro Val Pro Pro Asn Lys
            260                 265                 270

gca att gtt ggg gac aat gca ttt gct cat gaa gca gga ata cat gtt      864
Ala Ile Val Gly Asp Asn Ala Phe Ala His Glu Ala Gly Ile His Val
        275                 280                 285

gat gga tta ata aaa aat act gaa acc tat gag cca ata aaa cca gaa      912
Asp Gly Leu Ile Lys Asn Thr Glu Thr Tyr Glu Pro Ile Lys Pro Glu
    290                 295                 300

atg gtt ggg aat aga aga aga att att ttg ggt aag cat tct ggt aga      960
Met Val Gly Asn Arg Arg Arg Ile Ile Leu Gly Lys His Ser Gly Arg
305                 310                 315                 320

aaa gct tta aaa tac aaa ctt gat ttg atg ggc ata aac gtt agt gat     1008
Lys Ala Leu Lys Tyr Lys Leu Asp Leu Met Gly Ile Asn Val Ser Asp
                325                 330                 335

gag caa tta aat aaa ata tat gaa aga gtt aaa gaa ttt ggg gat ttg     1056
Glu Gln Leu Asn Lys Ile Tyr Glu Arg Val Lys Glu Phe Gly Asp Leu
            340                 345                 350

ggt aaa tac att tca gac gct gat ttg ttg gct ata gtt aga gaa gtt     1104
Gly Lys Tyr Ile Ser Asp Ala Asp Leu Leu Ala Ile Val Arg Glu Val
        355                 360                 365

act gga aaa ttg gta gaa gag aaa atc aaa tta gat gaa tta act gtt     1152
Thr Gly Lys Leu Val Glu Glu Lys Ile Lys Leu Asp Glu Leu Thr Val
    370                 375                 380

gta tct gga aat aaa ata aca cca att gca tct gtt aaa ctc cat tat     1200
Val Ser Gly Asn Lys Ile Thr Pro Ile Ala Ser Val Lys Leu His Tyr
385                 390                 395                 400

aaa gga gaa gat ata act tta ata gaa act gct tat ggt gtt gga ccg     1248
Lys Gly Glu Asp Ile Thr Leu Ile Glu Thr Ala Tyr Gly Val Gly Pro
                405                 410                 415

gta gat gca gca ata aat gct gtg aga aag gca ata agt gga gtt gca     1296
```

```
Val Asp Ala Ala Ile Asn Ala Val Arg Lys Ala Ile Ser Gly Val Ala
            420                 425                 430

gat att aag ttg gta gag tat aga gtt gaa gca att ggt gga gga act      1344
Asp Ile Lys Leu Val Glu Tyr Arg Val Glu Ala Ile Gly Gly Gly Thr
        435                 440                 445

gat gcg tta ata gag gtt gtt gtt aaa tta aga aaa gga act gaa att      1392
Asp Ala Leu Ile Glu Val Val Val Lys Leu Arg Lys Gly Thr Glu Ile
    450                 455                 460

gtt gaa gtt aga aaa tca gac gct gat ata ata agg gct tct gta gat      1440
Val Glu Val Arg Lys Ser Asp Ala Asp Ile Ile Arg Ala Ser Val Asp
465                 470                 475                 480

gct gta atg gaa gga atc aat atg tta ttg aat taa                      1476
Ala Val Met Glu Gly Ile Asn Met Leu Leu Asn
                485                 490


<210> SEQ ID NO 62
<211> LENGTH: 491
<212> TYPE: PRT
<213> ORGANISM: Methanocaldococcus jannaschii

<400> SEQUENCE: 62

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Ile Thr
        35                  40                  45

Ser Lys Gly Glu Arg Glu Gly Ile Lys Leu Ile Thr Lys Glu Gly Leu
    50                  55                  60

Asn Ala Glu Ile Cys Ser Phe Val Arg Ala Leu Pro Val Asp Ile Asp
65                  70                  75                  80

Ala Ala Leu Glu Cys Asp Val Asp Ser Val His Leu Val Val Pro Thr
                85                  90                  95

Ser Pro Ile His Met Lys Tyr Lys Leu Arg Lys Thr Glu Asp Glu Val
            100                 105                 110

Leu Glu Thr Ala Leu Lys Ala Val Glu Tyr Ala Lys Glu His Gly Leu
        115                 120                 125

Ile Val Glu Leu Ser Ala Glu Asp Ala Thr Arg Ser Asp Val Asn Phe
    130                 135                 140

Leu Ile Lys Leu Phe Asn Glu Gly Glu Lys Val Gly Ala Asp Arg Val
145                 150                 155                 160

Cys Val Cys Asp Thr Val Gly Val Leu Thr Pro Gln Lys Ser Gln Glu
                165                 170                 175

Leu Phe Lys Lys Ile Thr Glu Asn Val Asn Leu Pro Val Ser Val His
            180                 185                 190

Cys His Asn Asp Phe Gly Met Ala Thr Ala Asn Thr Cys Ser Ala Val
        195                 200                 205

Leu Gly Gly Ala Val Gln Cys His Val Thr Val Asn Gly Ile Gly Glu
    210                 215                 220

Arg Ala Gly Asn Ala Ser Leu Glu Glu Val Val Ala Ala Leu Lys Ile
225                 230                 235                 240

Leu Tyr Gly Tyr Asp Thr Lys Ile Lys Met Glu Lys Leu Tyr Glu Val
                245                 250                 255

Ser Arg Ile Val Ser Arg Leu Met Lys Leu Pro Val Pro Pro Asn Lys
            260                 265                 270

Ala Ile Val Gly Asp Asn Ala Phe Ala His Glu Ala Gly Ile His Val
```

-continued

```
        275                 280                 285

Asp Gly Leu Ile Lys Asn Thr Glu Thr Tyr Glu Pro Ile Lys Pro Glu
    290                 295                 300

Met Val Gly Asn Arg Arg Arg Ile Ile Leu Gly Lys His Ser Gly Arg
305                 310                 315                 320

Lys Ala Leu Lys Tyr Lys Leu Asp Leu Met Gly Ile Asn Val Ser Asp
                325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
        355                 360                 365

Thr Gly Lys Leu Val Glu Glu Lys Ile Lys Leu Asp Glu Leu Thr Val
    370                 375                 380

Val Ser Gly Asn Lys Ile Thr Pro Ile Ala Ser Val Lys Leu His Tyr
385                 390                 395                 400

Lys Gly Glu Asp Ile Thr Leu Ile Glu Thr Ala Tyr Gly Val Gly Pro
                405                 410                 415

Val Asp Ala Ala Ile Asn Ala Val Arg Lys Ala Ile Ser Gly Val Ala
            420                 425                 430

Asp Ile Lys Leu Val Glu Tyr Arg Val Glu Ala Ile Gly Gly Gly Thr
        435                 440                 445

Asp Ala Leu Ile Glu Val Val Val Lys Leu Arg Lys Gly Thr Glu Ile
    450                 455                 460

Val Glu Val Arg Lys Ser Asp Ala Asp Ile Ile Arg Ala Ser Val Asp
465                 470                 475                 480

Ala Val Met Glu Gly Ile Asn Met Leu Leu Asn
                485                 490


<210> SEQ ID NO 63
<211> LENGTH: 264
<212> TYPE: DNA
<213> ORGANISM: Escherichia coli
<220> FEATURE:
<221> NAME/KEY: CDS
<222> LOCATION: (1)..(264)

<400> SEQUENCE: 63

atg atg caa cat cag gtc aat gta tcg gct cgc ttc aat cca gaa acc       48
Met Met Gln His Gln Val Asn Val Ser Ala Arg Phe Asn Pro Glu Thr
1               5                   10                  15

tta gaa cgt gtt tta cgc gtg gtg cgt cat cgt ggt ttc cac gtc tgc       96
Leu Glu Arg Val Leu Arg Val Val Arg His Arg Gly Phe His Val Cys
            20                  25                  30

tca atg aat atg gcc gcc gcc agc gat gca caa aat ata aat atc gaa      144
Ser Met Asn Met Ala Ala Ala Ser Asp Ala Gln Asn Ile Asn Ile Glu
        35                  40                  45

ttg acc gtt gcc agc cca cgg tcg gtc gac tta ctg ttt agt cag tta      192
Leu Thr Val Ala Ser Pro Arg Ser Val Asp Leu Leu Phe Ser Gln Leu
    50                  55                  60

aat aaa ctg gtg gac gtc gca cac gtt gcc atc tgc cag agc aca acc      240
Asn Lys Leu Val Asp Val Ala His Val Ala Ile Cys Gln Ser Thr Thr
65                  70                  75                  80

aca tca caa caa atc cgc gcc tga                                      264
Thr Ser Gln Gln Ile Arg Ala
                85


<210> SEQ ID NO 64
<211> LENGTH: 87
```

<212> TYPE: PRT
<213> ORGANISM: Escherichia coli

<400> SEQUENCE: 64

```
Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
            20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85
```

<210> SEQ ID NO 65
<211> LENGTH: 582
<212> TYPE: DNA
<213> ORGANISM: Escherichia coli
<220> FEATURE:
<221> NAME/KEY: CDS
<222> LOCATION: (1)..(582)

<400> SEQUENCE: 65

```
ttg ttg tta aaa caa ctg tcg gat cgt aaa cct gcg gat tgc gtc gtg       48
Leu Leu Leu Lys Gln Leu Ser Asp Arg Lys Pro Ala Asp Cys Val Val
1               5                   10                  15

acc aca gat gtg ggg cag cac cag atg tgg gct gcg cag cac atc gcc       96
Thr Thr Asp Val Gly Gln His Gln Met Trp Ala Ala Gln His Ile Ala
            20                  25                  30

cac act cgc ccg gaa aat ttc atc acc tcc agc ggt tta ggt acc atg      144
His Thr Arg Pro Glu Asn Phe Ile Thr Ser Ser Gly Leu Gly Thr Met
        35                  40                  45

ggt ttt ggt tta ccg gcg gcg gtt ggc gca caa gtc gcg cga ccg aac      192
Gly Phe Gly Leu Pro Ala Ala Val Gly Ala Gln Val Ala Arg Pro Asn
    50                  55                  60

gat acc gtt gtc tgt atc tcc ggt gac ggc tct ttc atg atg aat gtg      240
Asp Thr Val Val Cys Ile Ser Gly Asp Gly Ser Phe Met Met Asn Val
65                  70                  75                  80

caa gag ctg ggc acc gta aaa cgc aag cag tta ccg ttg aaa atc gtc      288
Gln Glu Leu Gly Thr Val Lys Arg Lys Gln Leu Pro Leu Lys Ile Val
                85                  90                  95

tta ctc gat aac caa cgg tta ggg atg gtt cga caa tgg cag caa ctg      336
Leu Leu Asp Asn Gln Arg Leu Gly Met Val Arg Gln Trp Gln Gln Leu
            100                 105                 110

ttt ttt cag gaa cga tac agc gaa acc acc ctt act gat aac ccc gat      384
Phe Phe Gln Glu Arg Tyr Ser Glu Thr Thr Leu Thr Asp Asn Pro Asp
        115                 120                 125

ttc ctc atg tta gcc agc gcc ttc ggc atc cat ggc caa cac atc acc      432
Phe Leu Met Leu Ala Ser Ala Phe Gly Ile His Gly Gln His Ile Thr
    130                 135                 140

cgg aaa gac cag gtt gaa gcg gca ctc gac acc atg ctg aac agt gat      480
Arg Lys Asp Gln Val Glu Ala Ala Leu Asp Thr Met Leu Asn Ser Asp
145                 150                 155                 160

ggg cca tac ctg ctt cat gtc tca atc gac gaa ctt gag aac gtc tgg      528
Gly Pro Tyr Leu Leu His Val Ser Ile Asp Glu Leu Glu Asn Val Trp
                165                 170                 175

ccg ctg gtg ccg cct ggc gcc agt aat tca gaa atg ttg gag aaa tta      576
```

```
Pro Leu Val Pro Pro Gly Ala Ser Asn Ser Glu Met Leu Glu Lys Leu
            180                 185                 190

tca tga                                                           582
Ser


<210> SEQ ID NO 66
<211> LENGTH: 193
<212> TYPE: PRT
<213> ORGANISM: Escherichia coli

<400> SEQUENCE: 66

Leu Leu Leu Lys Gln Leu Ser Asp Arg Lys Pro Ala Asp Cys Val Val
1               5                   10                  15

Thr Thr Asp Val Gly Gln His Gln Met Trp Ala Ala Gln His Ile Ala
            20                  25                  30

His Thr Arg Pro Glu Asn Phe Ile Thr Ser Ser Gly Leu Gly Thr Met
        35                  40                  45

Gly Phe Gly Leu Pro Ala Ala Val Gly Ala Gln Val Ala Arg Pro Asn
    50                  55                  60

Asp Thr Val Val Cys Ile Ser Gly Asp Gly Ser Phe Met Met Asn Val
65                  70                  75                  80

Gln Glu Leu Gly Thr Val Lys Arg Lys Gln Leu Pro Leu Lys Ile Val
                85                  90                  95

Leu Leu Asp Asn Gln Arg Leu Gly Met Val Arg Gln Trp Gln Gln Leu
            100                 105                 110

Phe Phe Gln Glu Arg Tyr Ser Glu Thr Thr Leu Thr Asp Asn Pro Asp
        115                 120                 125

Phe Leu Met Leu Ala Ser Ala Phe Gly Ile His Gly Gln His Ile Thr
    130                 135                 140

Arg Lys Asp Gln Val Glu Ala Ala Leu Asp Thr Met Leu Asn Ser Asp
145                 150                 155                 160

Gly Pro Tyr Leu Leu His Val Ser Ile Asp Glu Leu Glu Asn Val Trp
                165                 170                 175

Pro Leu Val Pro Pro Gly Ala Ser Asn Ser Glu Met Leu Glu Lys Leu
            180                 185                 190

Ser


<210> SEQ ID NO 67
<211> LENGTH: 291
<212> TYPE: DNA
<213> ORGANISM: Escherichia coli
<220> FEATURE:
<221> NAME/KEY: CDS
<222> LOCATION: (1)..(291)

<400> SEQUENCE: 67

atg caa aac aca act cat gac aac gta att ctg gag ctc acc gtt cgc       48
Met Gln Asn Thr Thr His Asp Asn Val Ile Leu Glu Leu Thr Val Arg
1               5                   10                  15

aac cat ccg ggc gta atg acc cac gtt tgt ggc ctt ttt gcc cgc cgc       96
Asn His Pro Gly Val Met Thr His Val Cys Gly Leu Phe Ala Arg Arg
            20                  25                  30

gct ttt aac gtt gaa ggc att ctt tgt ctg ccg att cag gac agc gac      144
Ala Phe Asn Val Glu Gly Ile Leu Cys Leu Pro Ile Gln Asp Ser Asp
        35                  40                  45

aaa agc cat atc tgg cta ctg gtc aat gac gac cag cgt ctg gag cag      192
Lys Ser His Ile Trp Leu Leu Val Asn Asp Asp Gln Arg Leu Glu Gln
    50                  55                  60
```

```
atg ata agc caa atc gat aag ctg gaa gat gtc gtg aaa gtg cag cgt      240
Met Ile Ser Gln Ile Asp Lys Leu Glu Asp Val Val Lys Val Gln Arg
65                  70                  75                  80

aat cag tcc gat ccg acg atg ttt aac aag atc gcg gtg ttt ttt cag      288
Asn Gln Ser Asp Pro Thr Met Phe Asn Lys Ile Ala Val Phe Phe Gln
                85                  90                  95

taa                                                                  291


<210> SEQ ID NO 68
<211> LENGTH: 96
<212> TYPE: PRT
<213> ORGANISM: Escherichia coli

<400> SEQUENCE: 68

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95


<210> SEQ ID NO 69
<211> LENGTH: 1689
<212> TYPE: DNA
<213> ORGANISM: Clostridium acetobutylicum
<220> FEATURE:
<221> NAME/KEY: CDS
<222> LOCATION: (1)..(1689)

<400> SEQUENCE: 69

atg gca agt tcg ggc aca aca tcg acg cgt aag cgc ttt acc ggc gca       48
Met Ala Ser Ser Gly Thr Thr Ser Thr Arg Lys Arg Phe Thr Gly Ala
1               5                   10                  15

gaa ttt atc gtt cat ttc ctg gaa cag cag ggc att aag att gtg aca       96
Glu Phe Ile Val His Phe Leu Glu Gln Gln Gly Ile Lys Ile Val Thr
            20                  25                  30

ggc att ccg ggc ggt tct atc ctg cct gtt tac gat gcc tta agc caa      144
Gly Ile Pro Gly Gly Ser Ile Leu Pro Val Tyr Asp Ala Leu Ser Gln
        35                  40                  45

agc acg caa atc cgc cat att ctg gcc cgt cat gaa cag ggc gcg ggc      192
Ser Thr Gln Ile Arg His Ile Leu Ala Arg His Glu Gln Gly Ala Gly
    50                  55                  60

ttt atc gct cag gga atg gcg cgc acc gac ggt aaa ccg gcg gtc tgt      240
Phe Ile Ala Gln Gly Met Ala Arg Thr Asp Gly Lys Pro Ala Val Cys
65                  70                  75                  80

atg gcc tgt agc gga ccg ggt gcg act aac ctg gtg acc gcc att gcc      288
Met Ala Cys Ser Gly Pro Gly Ala Thr Asn Leu Val Thr Ala Ile Ala
                85                  90                  95

gat gcg cgg ctg gac tcc atc ccg ctg att tgc atc act ggt cag gtt      336
Asp Ala Arg Leu Asp Ser Ile Pro Leu Ile Cys Ile Thr Gly Gln Val
            100                 105                 110

ccc gcc tcg atg atc ggc acc gac gcc ttc cag gaa gtg gac acc tac      384
Pro Ala Ser Met Ile Gly Thr Asp Ala Phe Gln Glu Val Asp Thr Tyr
        115                 120                 125
```

-continued

```
ggc atc tct atc ccc atc acc aaa cac aac tat ctg gtc aga cat atc      432
Gly Ile Ser Ile Pro Ile Thr Lys His Asn Tyr Leu Val Arg His Ile
    130                 135                 140

gaa gaa ctc ccg cag gtc atg agc gat gcc ttc cgc att gcg caa tca      480
Glu Glu Leu Pro Gln Val Met Ser Asp Ala Phe Arg Ile Ala Gln Ser
145                 150                 155                 160

ggc cgc cca ggc ccg gtg tgg ata gac att cct aag gat gtg caa acg      528
Gly Arg Pro Gly Pro Val Trp Ile Asp Ile Pro Lys Asp Val Gln Thr
                165                 170                 175

gca gtt ttt gag att gaa aca cag ccc gct atg gca gaa aaa gcc gcc      576
Ala Val Phe Glu Ile Glu Thr Gln Pro Ala Met Ala Glu Lys Ala Ala
            180                 185                 190

gcc ccc gcc ttt agc gaa gaa agc att cgt gac gca gcg gcg atg att      624
Ala Pro Ala Phe Ser Glu Glu Ser Ile Arg Asp Ala Ala Ala Met Ile
        195                 200                 205

aac gct gcc aaa cgc ccg gtg ctt tat ctg ggc ggc ggt gtg atc aat      672
Asn Ala Ala Lys Arg Pro Val Leu Tyr Leu Gly Gly Gly Val Ile Asn
    210                 215                 220

gcg ccc gca cgg gtg cgt gaa ctg gcg gag aaa gcg caa ctg cct acc      720
Ala Pro Ala Arg Val Arg Glu Leu Ala Glu Lys Ala Gln Leu Pro Thr
225                 230                 235                 240

acc atg act tta atg gcg ctg ggc atg ttg cca aaa gcg cat ccg ttg      768
Thr Met Thr Leu Met Ala Leu Gly Met Leu Pro Lys Ala His Pro Leu
                245                 250                 255

tcg ctg ggt atg ctg ggg atg cac ggc gtg cgc agc acc aac tat att      816
Ser Leu Gly Met Leu Gly Met His Gly Val Arg Ser Thr Asn Tyr Ile
            260                 265                 270

ttg cag gag gcg gat ttg ttg ata gtg ctc ggt gcg cgt ttt gat gac      864
Leu Gln Glu Ala Asp Leu Leu Ile Val Leu Gly Ala Arg Phe Asp Asp
        275                 280                 285

cgg gcg att ggc aaa acc gag cag ttc tgt ccg aat gcc aaa atc att      912
Arg Ala Ile Gly Lys Thr Glu Gln Phe Cys Pro Asn Ala Lys Ile Ile
    290                 295                 300

cat gtc gat atc gac cgt gca gag ctg ggt aaa atc aag cag ccg cac      960
His Val Asp Ile Asp Arg Ala Glu Leu Gly Lys Ile Lys Gln Pro His
305                 310                 315                 320

gtg gcg att cag gcg gat gtt gat gac gtg ctg gcg cag ttg atc ccg     1008
Val Ala Ile Gln Ala Asp Val Asp Asp Val Leu Ala Gln Leu Ile Pro
                325                 330                 335

ctg gtg gaa gcg caa ccg cgt gca gag tgg cac cag ttg gta gcg gat     1056
Leu Val Glu Ala Gln Pro Arg Ala Glu Trp His Gln Leu Val Ala Asp
            340                 345                 350

ttg cag cgt gag ttt ccg tgt cca atc ccg aaa gcg tgc gat ccg tta     1104
Leu Gln Arg Glu Phe Pro Cys Pro Ile Pro Lys Ala Cys Asp Pro Leu
        355                 360                 365

agc cat tac ggc ctg atc aac gcc gtt gcc gcc tgt gtc gat gac aat     1152
Ser His Tyr Gly Leu Ile Asn Ala Val Ala Ala Cys Val Asp Asp Asn
    370                 375                 380

gca att atc acc acc gac gtt ggt cag cat cag atg tgg acc gcg caa     1200
Ala Ile Ile Thr Thr Asp Val Gly Gln His Gln Met Trp Thr Ala Gln
385                 390                 395                 400

gct tat ccg ctc aat cgc cca cgc cag tgg ctg acc tcc ggt ggg ctg     1248
Ala Tyr Pro Leu Asn Arg Pro Arg Gln Trp Leu Thr Ser Gly Gly Leu
                405                 410                 415

ggc acg atg ggt ttt ggc ctg cct gcg gcg att ggc gct gcg ctg gcg     1296
Gly Thr Met Gly Phe Gly Leu Pro Ala Ala Ile Gly Ala Ala Leu Ala
            420                 425                 430

aac ccg gat cgc aaa gtg ttg tgt ttc tcc ggc gac ggc agc ctg atg     1344
Asn Pro Asp Arg Lys Val Leu Cys Phe Ser Gly Asp Gly Ser Leu Met
        435                 440                 445
```

```
atg aat att cag gag atg gcg acc gcc agt gaa aat cag ctg gat gtc      1392
Met Asn Ile Gln Glu Met Ala Thr Ala Ser Glu Asn Gln Leu Asp Val
    450                 455                 460

aaa atc att ctg atg aac aac gaa gcg ctg ggg ctg gtg cat cag caa      1440
Lys Ile Ile Leu Met Asn Asn Glu Ala Leu Gly Leu Val His Gln Gln
465                 470                 475                 480

cag agt ctg ttc tac gag caa ggc gtt ttt gcc gcc acc tat ccg ggc      1488
Gln Ser Leu Phe Tyr Glu Gln Gly Val Phe Ala Ala Thr Tyr Pro Gly
                485                 490                 495

aaa atc aac ttt atg cag att gcc gcc gga ttc ggc ctc gaa acc tgt      1536
Lys Ile Asn Phe Met Gln Ile Ala Ala Gly Phe Gly Leu Glu Thr Cys
            500                 505                 510

gat ttg aat aac gaa gcc gat ccg cag gct tca ttg cag gaa atc atc      1584
Asp Leu Asn Asn Glu Ala Asp Pro Gln Ala Ser Leu Gln Glu Ile Ile
        515                 520                 525

aat cgc cct ggc ccg gcg ctg atc cat gtg cgc att gat gcc gaa gaa      1632
Asn Arg Pro Gly Pro Ala Leu Ile His Val Arg Ile Asp Ala Glu Glu
    530                 535                 540

aaa gtt tac ccg atg gtg ccg cca ggt gcg gcg aat act gaa atg gtg      1680
Lys Val Tyr Pro Met Val Pro Pro Gly Ala Ala Asn Thr Glu Met Val
545                 550                 555                 560

ggg gaa taa                                                          1689
Gly Glu


<210> SEQ ID NO 70
<211> LENGTH: 562
<212> TYPE: PRT
<213> ORGANISM: Clostridium acetobutylicum

<400> SEQUENCE: 70

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
            20                  25                  30

Gly Ile Pro Gly Gly Ser Ile Leu Pro Val Tyr Asp Ala Leu Ser Gln
        35                  40                  45

Ser Thr Gln Ile Arg His Ile Leu Ala Arg His Glu Gln Gly Ala Gly
    50                  55                  60

Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
        195                 200                 205
```

```
Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
    290                 295                 300

His Val Asp Ile Asp Arg Ala Glu Leu Gly Lys Ile Lys Gln Pro His
305                 310                 315                 320

Val Ala Ile Gln Ala Asp Val Asp Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
    450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
            500                 505                 510

Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
    530                 535                 540

Lys Val Tyr Pro Met Val Pro Pro Gly Ala Ala Asn Thr Glu Met Val
545                 550                 555                 560

Gly Glu
```

<210> SEQ ID NO 71
<211> LENGTH: 2577
<212> TYPE: DNA
<213> ORGANISM: Clostridium acetobutylicum
<220> FEATURE:
<221> NAME/KEY: CDS
<222> LOCATION: (1)..(2577)

<400> SEQUENCE: 71

```
atg aaa gtt aca aat caa aaa gaa cta aaa caa aag cta aat gaa ttg        48
Met Lys Val Thr Asn Gln Lys Glu Leu Lys Gln Lys Leu Asn Glu Leu
1               5                   10                  15

aga gaa gcg caa aag aag ttt gca acc tat act caa gag caa gtt gat        96
Arg Glu Ala Gln Lys Lys Phe Ala Thr Tyr Thr Gln Glu Gln Val Asp
            20                  25                  30

aaa att ttt aaa caa tgt gcc ata gcc gca gct aaa gaa aga ata aac       144
Lys Ile Phe Lys Gln Cys Ala Ile Ala Ala Ala Lys Glu Arg Ile Asn
        35                  40                  45

tta gct aaa tta gca gta gaa gaa aca gga ata ggt ctt gta gaa gat       192
Leu Ala Lys Leu Ala Val Glu Glu Thr Gly Ile Gly Leu Val Glu Asp
    50                  55                  60

aaa att ata aaa aat cat ttt gca gca gaa tat ata tac aat aaa tat       240
Lys Ile Ile Lys Asn His Phe Ala Ala Glu Tyr Ile Tyr Asn Lys Tyr
65                  70                  75                  80

aaa aat gaa aaa act tgt ggc ata ata gac cat gac gat tct tta ggc       288
Lys Asn Glu Lys Thr Cys Gly Ile Ile Asp His Asp Asp Ser Leu Gly
                85                  90                  95

ata aca aag gtt gct gaa cca att gga att gtt gca gcc ata gtt cct       336
Ile Thr Lys Val Ala Glu Pro Ile Gly Ile Val Ala Ala Ile Val Pro
            100                 105                 110

act act aat cca act tcc aca gca att ttc aaa tca tta att tct tta       384
Thr Thr Asn Pro Thr Ser Thr Ala Ile Phe Lys Ser Leu Ile Ser Leu
        115                 120                 125

aaa aca aga aac gca ata ttc ttt tca cca cat cca cgt gca aaa aaa       432
Lys Thr Arg Asn Ala Ile Phe Phe Ser Pro His Pro Arg Ala Lys Lys
    130                 135                 140

tct aca att gct gca gca aaa tta att tta gat gca gct gtt aaa gca       480
Ser Thr Ile Ala Ala Ala Lys Leu Ile Leu Asp Ala Ala Val Lys Ala
145                 150                 155                 160

gga gca cct aaa aat ata ata ggc tgg ata gat gag cca tca ata gaa       528
Gly Ala Pro Lys Asn Ile Ile Gly Trp Ile Asp Glu Pro Ser Ile Glu
                165                 170                 175

ctt tct caa gat ttg atg agt gaa gct gat ata ata tta gca aca gga       576
Leu Ser Gln Asp Leu Met Ser Glu Ala Asp Ile Ile Leu Ala Thr Gly
            180                 185                 190

ggt cct tca atg gtt aaa gcg gcc tat tca tct gga aaa cct gca att       624
Gly Pro Ser Met Val Lys Ala Ala Tyr Ser Ser Gly Lys Pro Ala Ile
        195                 200                 205

ggt gtt gga gca gga aat aca cca gca ata ata gat gag agt gca gat       672
Gly Val Gly Ala Gly Asn Thr Pro Ala Ile Ile Asp Glu Ser Ala Asp
    210                 215                 220

ata gat atg gca gta agc tcc ata att tta tca aag act tat gac aat       720
Ile Asp Met Ala Val Ser Ser Ile Ile Leu Ser Lys Thr Tyr Asp Asn
225                 230                 235                 240

gga gta ata tgc gct tct gaa caa tca ata tta gtt atg aat tca ata       768
Gly Val Ile Cys Ala Ser Glu Gln Ser Ile Leu Val Met Asn Ser Ile
                245                 250                 255

tac gaa aaa gtt aaa gag gaa ttt gta aaa cga gga tca tat ata ctc       816
Tyr Glu Lys Val Lys Glu Glu Phe Val Lys Arg Gly Ser Tyr Ile Leu
            260                 265                 270

aat caa aat gaa ata gct aaa ata aaa gaa act atg ttt aaa aat gga       864
Asn Gln Asn Glu Ile Ala Lys Ile Lys Glu Thr Met Phe Lys Asn Gly
        275                 280                 285

gct att aat gct gac ata gtt gga aaa tct gct tat ata att gct aaa       912
Ala Ile Asn Ala Asp Ile Val Gly Lys Ser Ala Tyr Ile Ile Ala Lys
    290                 295                 300

atg gca gga att gaa gtt cct caa act aca aag ata ctt ata ggc gaa       960
Met Ala Gly Ile Glu Val Pro Gln Thr Thr Lys Ile Leu Ile Gly Glu
305                 310                 315                 320
```

```
gta caa tct gtt gaa aaa agc gag ctg ttc tca cat gaa aaa cta tca      1008
Val Gln Ser Val Glu Lys Ser Glu Leu Phe Ser His Glu Lys Leu Ser
                325                 330                 335

cca gta ctt gca atg tat aaa gtt aag gat ttt gat gaa gct cta aaa      1056
Pro Val Leu Ala Met Tyr Lys Val Lys Asp Phe Asp Glu Ala Leu Lys
            340                 345                 350

aag gca caa agg cta ata gaa tta ggt gga agt gga cac acg tca tct      1104
Lys Ala Gln Arg Leu Ile Glu Leu Gly Gly Ser Gly His Thr Ser Ser
        355                 360                 365

tta tat ata gat tca caa aac aat aag gat aaa gtt aaa gaa ttt gga      1152
Leu Tyr Ile Asp Ser Gln Asn Asn Lys Asp Lys Val Lys Glu Phe Gly
    370                 375                 380

tta gca atg aaa act tca agg aca ttt att aac atg cct tct tca cag      1200
Leu Ala Met Lys Thr Ser Arg Thr Phe Ile Asn Met Pro Ser Ser Gln
385                 390                 395                 400

gga gca agc gga gat tta tac aat ttt gcg ata gca cca tca ttt act      1248
Gly Ala Ser Gly Asp Leu Tyr Asn Phe Ala Ile Ala Pro Ser Phe Thr
                405                 410                 415

ctt gga tgc ggc act tgg gga gga aac tct gta tcg caa aat gta gag      1296
Leu Gly Cys Gly Thr Trp Gly Gly Asn Ser Val Ser Gln Asn Val Glu
            420                 425                 430

cct aaa cat tta tta aat att aaa agt gtt gct gaa aga agg gaa aat      1344
Pro Lys His Leu Leu Asn Ile Lys Ser Val Ala Glu Arg Arg Glu Asn
        435                 440                 445

atg ctt tgg ttt aaa gtg cca caa aaa ata tat ttt aaa tat gga tgt      1392
Met Leu Trp Phe Lys Val Pro Gln Lys Ile Tyr Phe Lys Tyr Gly Cys
    450                 455                 460

ctt aga ttt gca tta aaa gaa tta aaa gat atg aat aag aaa aga gcc      1440
Leu Arg Phe Ala Leu Lys Glu Leu Lys Asp Met Asn Lys Lys Arg Ala
465                 470                 475                 480

ttt ata gta aca gat aaa gat ctt ttt aaa ctt gga tat gtt aat aaa      1488
Phe Ile Val Thr Asp Lys Asp Leu Phe Lys Leu Gly Tyr Val Asn Lys
                485                 490                 495

ata aca aag gta cta gat gag ata gat att aaa tac agt ata ttt aca      1536
Ile Thr Lys Val Leu Asp Glu Ile Asp Ile Lys Tyr Ser Ile Phe Thr
            500                 505                 510

gat att aaa tct gat cca act att gat tca gta aaa aaa ggt gct aaa      1584
Asp Ile Lys Ser Asp Pro Thr Ile Asp Ser Val Lys Lys Gly Ala Lys
        515                 520                 525

gaa atg ctt aac ttt gaa cct gat act ata atc tct att ggt ggt gga      1632
Glu Met Leu Asn Phe Glu Pro Asp Thr Ile Ile Ser Ile Gly Gly Gly
    530                 535                 540

tcg cca atg gat gca gca aag gtt atg cac ttg tta tat gaa tat cca      1680
Ser Pro Met Asp Ala Ala Lys Val Met His Leu Leu Tyr Glu Tyr Pro
545                 550                 555                 560

gaa gca gaa att gaa aat cta gct ata aac ttt atg gat ata aga aag      1728
Glu Ala Glu Ile Glu Asn Leu Ala Ile Asn Phe Met Asp Ile Arg Lys
                565                 570                 575

aga ata tgc aat ttc cct aaa tta ggt aca aag gcg att tca gta gct      1776
Arg Ile Cys Asn Phe Pro Lys Leu Gly Thr Lys Ala Ile Ser Val Ala
            580                 585                 590

att cct aca act gct ggt acc ggt tca gag gca aca cct ttt gca gtt      1824
Ile Pro Thr Thr Ala Gly Thr Gly Ser Glu Ala Thr Pro Phe Ala Val
        595                 600                 605

ata act aat gat gaa aca gga atg aaa tac cct tta act tct tat gaa      1872
Ile Thr Asn Asp Glu Thr Gly Met Lys Tyr Pro Leu Thr Ser Tyr Glu
    610                 615                 620

ttg acc cca aac atg gca ata ata gat act gaa tta atg tta aat atg      1920
Leu Thr Pro Asn Met Ala Ile Ile Asp Thr Glu Leu Met Leu Asn Met
```

-continued

```
625                 630                 635                 640

cct aga aaa tta aca gca gca act gga ata gat gca tta gtt cat gct      1968
Pro Arg Lys Leu Thr Ala Ala Thr Gly Ile Asp Ala Leu Val His Ala
                645                 650                 655

ata gaa gca tat gtt tcg gtt atg gct acg gat tat act gat gaa tta      2016
Ile Glu Ala Tyr Val Ser Val Met Ala Thr Asp Tyr Thr Asp Glu Leu
            660                 665                 670

gcc tta aga gca ata aaa atg ata ttt aaa tat ttg cct aga gcc tat      2064
Ala Leu Arg Ala Ile Lys Met Ile Phe Lys Tyr Leu Pro Arg Ala Tyr
        675                 680                 685

aaa aat ggg act aac gac att gaa gca aga gaa aaa atg gca cat gcc      2112
Lys Asn Gly Thr Asn Asp Ile Glu Ala Arg Glu Lys Met Ala His Ala
    690                 695                 700

tct aat att gcg ggg atg gca ttt gca aat gct ttc tta ggt gta tgc      2160
Ser Asn Ile Ala Gly Met Ala Phe Ala Asn Ala Phe Leu Gly Val Cys
705                 710                 715                 720

cat tca atg gct cat aaa ctt ggg gca atg cat cac gtt cca cat gga      2208
His Ser Met Ala His Lys Leu Gly Ala Met His His Val Pro His Gly
                725                 730                 735

att gct tgt gct gta tta ata gaa gaa gtt att aaa tat aac gct aca      2256
Ile Ala Cys Ala Val Leu Ile Glu Glu Val Ile Lys Tyr Asn Ala Thr
            740                 745                 750

gac tgt cca aca aag caa aca gca ttc cct caa tat aaa tct cct aat      2304
Asp Cys Pro Thr Lys Gln Thr Ala Phe Pro Gln Tyr Lys Ser Pro Asn
        755                 760                 765

gct aag aga aaa tat gct gaa att gca gag tat ttg aat tta aag ggt      2352
Ala Lys Arg Lys Tyr Ala Glu Ile Ala Glu Tyr Leu Asn Leu Lys Gly
    770                 775                 780

act agc gat acc gaa aag gta aca gcc tta ata gaa gct att tca aag      2400
Thr Ser Asp Thr Glu Lys Val Thr Ala Leu Ile Glu Ala Ile Ser Lys
785                 790                 795                 800

tta aag ata gat ttg agt att cca caa aat ata agt gcc gct gga ata      2448
Leu Lys Ile Asp Leu Ser Ile Pro Gln Asn Ile Ser Ala Ala Gly Ile
                805                 810                 815

aat aaa aaa gat ttt tat aat acg cta gat aaa atg tca gag ctt gct      2496
Asn Lys Lys Asp Phe Tyr Asn Thr Leu Asp Lys Met Ser Glu Leu Ala
            820                 825                 830

ttt gat gac caa tgt aca aca gct aat cct agg tat cca ctt ata agt      2544
Phe Asp Asp Gln Cys Thr Thr Ala Asn Pro Arg Tyr Pro Leu Ile Ser
        835                 840                 845

gaa ctt aag gat atc tat ata aaa tca ttt taa                          2577
Glu Leu Lys Asp Ile Tyr Ile Lys Ser Phe
    850                 855


<210> SEQ ID NO 72
<211> LENGTH: 858
<212> TYPE: PRT
<213> ORGANISM: Clostridium acetobutylicum

<400> SEQUENCE: 72

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
```

-continued

```
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495
```

```
Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855
```

```
<210> SEQ ID NO 73
<211> LENGTH: 1551
<212> TYPE: DNA
<213> ORGANISM: Leptospira interrogans
<220> FEATURE:
<221> NAME/KEY: CDS
<222> LOCATION: (1)..(1551)
```

```
<400> SEQUENCE: 73

atg aca aaa gta gaa act cga ttg gaa att tta gac gta act ttg aga       48
Met Thr Lys Val Glu Thr Arg Leu Glu Ile Leu Asp Val Thr Leu Arg
1               5                   10                  15

gac ggg gag cag acc aga ggg gtc agt ttt tcc act tcc gaa aaa cta       96
Asp Gly Glu Gln Thr Arg Gly Val Ser Phe Ser Thr Ser Glu Lys Leu
            20                  25                  30

aat atc gca aaa ttt cta tta caa aaa cta aat gta gat cgg gta gag      144
Asn Ile Ala Lys Phe Leu Leu Gln Lys Leu Asn Val Asp Arg Val Glu
        35                  40                  45

att gcg tct gca aga gtt tct aaa ggg gaa ttg gaa acg gtc caa aaa      192
Ile Ala Ser Ala Arg Val Ser Lys Gly Glu Leu Glu Thr Val Gln Lys
    50                  55                  60

atc atg gaa tgg gct gca aca gaa cag ctt acg gaa aga atc gaa atc      240
Ile Met Glu Trp Ala Ala Thr Glu Gln Leu Thr Glu Arg Ile Glu Ile
65                  70                  75                  80

tta ggt ttt gta gac ggg aat aaa acc gta gat tgg atc aaa gat agt      288
Leu Gly Phe Val Asp Gly Asn Lys Thr Val Asp Trp Ile Lys Asp Ser
                85                  90                  95

ggg gct aag gtt tta aat ctt ttg act aag gga tcg ctt cat cat tta      336
Gly Ala Lys Val Leu Asn Leu Leu Thr Lys Gly Ser Leu His His Leu
            100                 105                 110

gaa aaa caa tta ggc aaa act ccg aaa gaa ttc ttt aca gac gtt tct      384
Glu Lys Gln Leu Gly Lys Thr Pro Lys Glu Phe Phe Thr Asp Val Ser
        115                 120                 125

ttt gta ata gaa tac gcg atc aaa agc gga ctt aaa ata aac gta tat      432
Phe Val Ile Glu Tyr Ala Ile Lys Ser Gly Leu Lys Ile Asn Val Tyr
    130                 135                 140

tta gaa gat tgg tcc aac ggt ttc aga aac agt cca gat tac gtc aaa      480
Leu Glu Asp Trp Ser Asn Gly Phe Arg Asn Ser Pro Asp Tyr Val Lys
145                 150                 155                 160

tcg ctc gta gaa cat cta agt aaa gaa cat ata gaa aga att ttt ctt      528
Ser Leu Val Glu His Leu Ser Lys Glu His Ile Glu Arg Ile Phe Leu
                165                 170                 175

cca gac acg tta ggc gtt ctt tcg cca gaa gag acg ttt caa gga gtg      576
Pro Asp Thr Leu Gly Val Leu Ser Pro Glu Glu Thr Phe Gln Gly Val
            180                 185                 190

gat tca ctc att caa aaa tac ccg gat att cat ttt gaa ttt cac gga      624
Asp Ser Leu Ile Gln Lys Tyr Pro Asp Ile His Phe Glu Phe His Gly
        195                 200                 205

cat aac gac tac gat ctt tcc gtg gca aat agt ctt caa gcg att cgt      672
His Asn Asp Tyr Asp Leu Ser Val Ala Asn Ser Leu Gln Ala Ile Arg
    210                 215                 220

gcc gga gtc aaa ggt ctt cac gct tct ata aat ggt ctc gga gaa aga      720
Ala Gly Val Lys Gly Leu His Ala Ser Ile Asn Gly Leu Gly Glu Arg
225                 230                 235                 240

gcc gga aat act ccg ttg gaa gca ctc gta acc acg att cat gat aag      768
Ala Gly Asn Thr Pro Leu Glu Ala Leu Val Thr Thr Ile His Asp Lys
                245                 250                 255

tct aac tct aaa acg aac ata aac gaa att gca att acg gaa gca agc      816
Ser Asn Ser Lys Thr Asn Ile Asn Glu Ile Ala Ile Thr Glu Ala Ser
            260                 265                 270

cgt ctt gta gaa gta ttc agc gga aaa aga att tct gca aat aga ccg      864
Arg Leu Val Glu Val Phe Ser Gly Lys Arg Ile Ser Ala Asn Arg Pro
        275                 280                 285

atc gta gga gaa gac gtg ttt act cag acc gcg gga gta cac gca gac      912
Ile Val Gly Glu Asp Val Phe Thr Gln Thr Ala Gly Val His Ala Asp
    290                 295                 300

gga gac aaa aaa gga aat tta tac gca aat cct att tta ccg gaa aga      960
```

```
Gly Asp Lys Lys Gly Asn Leu Tyr Ala Asn Pro Ile Leu Pro Glu Arg
305                 310                 315                 320

ttt ggt agg aaa aga agt tac gcg tta ggc aaa ctt gca ggt aag gcg      1008
Phe Gly Arg Lys Arg Ser Tyr Ala Leu Gly Lys Leu Ala Gly Lys Ala
                325                 330                 335

agt atc tcc gaa aat gta aaa caa ctc gga atg gtt tta agt gaa gtg      1056
Ser Ile Ser Glu Asn Val Lys Gln Leu Gly Met Val Leu Ser Glu Val
            340                 345                 350

gtt tta caa aag gtt tta gaa agg gtg atc gaa tta gga gat cag aat      1104
Val Leu Gln Lys Val Leu Glu Arg Val Ile Glu Leu Gly Asp Gln Asn
        355                 360                 365

aaa cta gtg aca cct gaa gat ctt cca ttt atc att gcg gac gtt tct      1152
Lys Leu Val Thr Pro Glu Asp Leu Pro Phe Ile Ile Ala Asp Val Ser
    370                 375                 380

gga aga acc gga gaa aag gta ctt aca atc aaa tct tgt aat att cat      1200
Gly Arg Thr Gly Glu Lys Val Leu Thr Ile Lys Ser Cys Asn Ile His
385                 390                 395                 400

tcc gga att gga att cgt cct cac gca caa att gaa ttg gaa tat cag      1248
Ser Gly Ile Gly Ile Arg Pro His Ala Gln Ile Glu Leu Glu Tyr Gln
                405                 410                 415

gga aag att cat aag gaa att tct gaa gga gac gga ggg tat gat gcg      1296
Gly Lys Ile His Lys Glu Ile Ser Glu Gly Asp Gly Gly Tyr Asp Ala
            420                 425                 430

ttt atg aat gca ctt act aaa att acg aat cgc ctc ggt att agt att      1344
Phe Met Asn Ala Leu Thr Lys Ile Thr Asn Arg Leu Gly Ile Ser Ile
        435                 440                 445

cct aaa ttg ata gat tac gaa gta agg att cct cct ggt gga aaa aca      1392
Pro Lys Leu Ile Asp Tyr Glu Val Arg Ile Pro Pro Gly Gly Lys Thr
    450                 455                 460

gat gca ctt gta gaa act agg atc acc tgg aac aag tcc tta gat tta      1440
Asp Ala Leu Val Glu Thr Arg Ile Thr Trp Asn Lys Ser Leu Asp Leu
465                 470                 475                 480

gaa gag gac cag act ttc aaa acg atg gga gtt cat ccg gat caa acg      1488
Glu Glu Asp Gln Thr Phe Lys Thr Met Gly Val His Pro Asp Gln Thr
                485                 490                 495

gtt gca gcg gtt cat gca act gaa aag atg ctc aat caa att cta caa      1536
Val Ala Ala Val His Ala Thr Glu Lys Met Leu Asn Gln Ile Leu Gln
            500                 505                 510

cca tgg caa atc taa                                                  1551
Pro Trp Gln Ile
        515


<210> SEQ ID NO 74
<211> LENGTH: 516
<212> TYPE: PRT
<213> ORGANISM: Leptospira interrogans

<400> SEQUENCE: 74

Met Thr Lys Val Glu Thr Arg Leu Glu Ile Leu Asp Val Thr Leu Arg
1               5                   10                  15

Asp Gly Glu Gln Thr Arg Gly Val Ser Phe Ser Thr Ser Glu Lys Leu
            20                  25                  30

Asn Ile Ala Lys Phe Leu Leu Gln Lys Leu Asn Val Asp Arg Val Glu
        35                  40                  45

Ile Ala Ser Ala Arg Val Ser Lys Gly Glu Leu Glu Thr Val Gln Lys
    50                  55                  60

Ile Met Glu Trp Ala Ala Thr Glu Gln Leu Thr Glu Arg Ile Glu Ile
65                  70                  75                  80

Leu Gly Phe Val Asp Gly Asn Lys Thr Val Asp Trp Ile Lys Asp Ser
```

-continued

```
                85                  90                  95

Gly Ala Lys Val Leu Asn Leu Leu Thr Lys Gly Ser Leu His His Leu
            100                 105                 110

Glu Lys Gln Leu Gly Lys Thr Pro Lys Glu Phe Phe Thr Asp Val Ser
        115                 120                 125

Phe Val Ile Glu Tyr Ala Ile Lys Ser Gly Leu Lys Ile Asn Val Tyr
    130                 135                 140

Leu Glu Asp Trp Ser Asn Gly Phe Arg Asn Ser Pro Asp Tyr Val Lys
145                 150                 155                 160

Ser Leu Val Glu His Leu Ser Lys Glu His Ile Glu Arg Ile Phe Leu
                165                 170                 175

Pro Asp Thr Leu Gly Val Leu Ser Pro Glu Glu Thr Phe Gln Gly Val
            180                 185                 190

Asp Ser Leu Ile Gln Lys Tyr Pro Asp Ile His Phe Glu Phe His Gly
        195                 200                 205

His Asn Asp Tyr Asp Leu Ser Val Ala Asn Ser Leu Gln Ala Ile Arg
    210                 215                 220

Ala Gly Val Lys Gly Leu His Ala Ser Ile Asn Gly Leu Gly Glu Arg
225                 230                 235                 240

Ala Gly Asn Thr Pro Leu Glu Ala Leu Val Thr Thr Ile His Asp Lys
                245                 250                 255

Ser Asn Ser Lys Thr Asn Ile Asn Glu Ile Ala Ile Thr Glu Ala Ser
            260                 265                 270

Arg Leu Val Glu Val Phe Ser Gly Lys Arg Ile Ser Ala Asn Arg Pro
        275                 280                 285

Ile Val Gly Glu Asp Val Phe Thr Gln Thr Ala Gly Val His Ala Asp
    290                 295                 300

Gly Asp Lys Lys Gly Asn Leu Tyr Ala Asn Pro Ile Leu Pro Glu Arg
305                 310                 315                 320

Phe Gly Arg Lys Arg Ser Tyr Ala Leu Gly Lys Leu Ala Gly Lys Ala
                325                 330                 335

Ser Ile Ser Glu Asn Val Lys Gln Leu Gly Met Val Leu Ser Glu Val
            340                 345                 350

Val Leu Gln Lys Val Leu Glu Arg Val Ile Glu Leu Gly Asp Gln Asn
        355                 360                 365

Lys Leu Val Thr Pro Glu Asp Leu Pro Phe Ile Ile Ala Asp Val Ser
    370                 375                 380

Gly Arg Thr Gly Glu Lys Val Leu Thr Ile Lys Ser Cys Asn Ile His
385                 390                 395                 400

Ser Gly Ile Gly Ile Arg Pro His Ala Gln Ile Glu Leu Glu Tyr Gln
                405                 410                 415

Gly Lys Ile His Lys Glu Ile Ser Glu Gly Asp Gly Gly Tyr Asp Ala
            420                 425                 430

Phe Met Asn Ala Leu Thr Lys Ile Thr Asn Arg Leu Gly Ile Ser Ile
        435                 440                 445

Pro Lys Leu Ile Asp Tyr Glu Val Arg Ile Pro Pro Gly Gly Lys Thr
    450                 455                 460

Asp Ala Leu Val Glu Thr Arg Ile Thr Trp Asn Lys Ser Leu Asp Leu
465                 470                 475                 480

Glu Glu Asp Gln Thr Phe Lys Thr Met Gly Val His Pro Asp Gln Thr
                485                 490                 495

Val Ala Ala Val His Ala Thr Glu Lys Met Leu Asn Gln Ile Leu Gln
            500                 505                 510
```

```
Pro Trp Gln Ile
        515


<210> SEQ ID NO 75
<211> LENGTH: 1398
<212> TYPE: DNA
<213> ORGANISM: Leptospira interrogans
<220> FEATURE:
<221> NAME/KEY: CDS
<222> LOCATION: (1)..(1398)

<400> SEQUENCE: 75

atg aag aca atg ttc gaa aaa att tgg gaa gat cat cta gtc gga gaa       48
Met Lys Thr Met Phe Glu Lys Ile Trp Glu Asp His Leu Val Gly Glu
1               5                   10                  15

cta gat gct gga tcc tat cta atc tat ata gat cgc cat ctc att cat       96
Leu Asp Ala Gly Ser Tyr Leu Ile Tyr Ile Asp Arg His Leu Ile His
            20                  25                  30

gaa gtt aca agt cct cag gcg ttt gaa gga ctt aaa ctt gca ggc aga      144
Glu Val Thr Ser Pro Gln Ala Phe Glu Gly Leu Lys Leu Ala Gly Arg
        35                  40                  45

aag gtt cgt cgt cct gaa gct act ttt gcc aca atg gat cat aac gtt      192
Lys Val Arg Arg Pro Glu Ala Thr Phe Ala Thr Met Asp His Asn Val
    50                  55                  60

tct act aga aca cgt gat tta agt ctg gcc gat cct gtt tcc gca att      240
Ser Thr Arg Thr Arg Asp Leu Ser Leu Ala Asp Pro Val Ser Ala Ile
65                  70                  75                  80

caa atg cag act tta aaa aag aac tgc gac gaa aac gga atc cgc gtt      288
Gln Met Gln Thr Leu Lys Lys Asn Cys Asp Glu Asn Gly Ile Arg Val
                85                  90                  95

tat gat ttt caa aac cct gac caa gga atc att cac gta atc gct cct      336
Tyr Asp Phe Gln Asn Pro Asp Gln Gly Ile Ile His Val Ile Ala Pro
            100                 105                 110

gaa atg gga ctg act cat cct gga atg aca atc gta tgc gga gat tct      384
Glu Met Gly Leu Thr His Pro Gly Met Thr Ile Val Cys Gly Asp Ser
        115                 120                 125

cat act tct aca cac ggt gcg ttt ggt gcg ctt gct ttc ggg atc gga      432
His Thr Ser Thr His Gly Ala Phe Gly Ala Leu Ala Phe Gly Ile Gly
    130                 135                 140

acc agc gaa gta gag cac gtt ctt gcg act caa acc tta gtt caa aaa      480
Thr Ser Glu Val Glu His Val Leu Ala Thr Gln Thr Leu Val Gln Lys
145                 150                 155                 160

aga gca aaa aca atg gag att aga gtc gat gga aaa ctt tcc gat aag      528
Arg Ala Lys Thr Met Glu Ile Arg Val Asp Gly Lys Leu Ser Asp Lys
                165                 170                 175

gtc aca gca aaa gac atc att ctt gcg atc att gga aaa att gga acc      576
Val Thr Ala Lys Asp Ile Ile Leu Ala Ile Ile Gly Lys Ile Gly Thr
            180                 185                 190

gca ggt gcg aca ggt tat gtg atc gaa tat aga ggt tct gca att caa      624
Ala Gly Ala Thr Gly Tyr Val Ile Glu Tyr Arg Gly Ser Ala Ile Gln
        195                 200                 205

gcc ctc agt atg gaa gct aga atg act att tgt aat atg tct atc gaa      672
Ala Leu Ser Met Glu Ala Arg Met Thr Ile Cys Asn Met Ser Ile Glu
    210                 215                 220

gcg gga gct aga gca ggt tta atc gca cca gat gaa act act ttt aat      720
Ala Gly Ala Arg Ala Gly Leu Ile Ala Pro Asp Glu Thr Thr Phe Asn
225                 230                 235                 240

tat att caa gga aag gac ttt tct cca aaa gga gtc gaa tgg gat ctt      768
Tyr Ile Gln Gly Lys Asp Phe Ser Pro Lys Gly Val Glu Trp Asp Leu
                245                 250                 255
```

```
gcg gtc aaa aaa tgg aaa cac tat gta acg gac gaa ggt gct aaa ttt      816
Ala Val Lys Lys Trp Lys His Tyr Val Thr Asp Glu Gly Ala Lys Phe
            260                 265                 270

gat aga acc gta att ctt cat gca gat gaa atc gct cct atg gta act      864
Asp Arg Thr Val Ile Leu His Ala Asp Glu Ile Ala Pro Met Val Thr
        275                 280                 285

tgg gga act tct ccc agt cag gtt gtt tcg ata aaa gga gtc gtt cca      912
Trp Gly Thr Ser Pro Ser Gln Val Val Ser Ile Lys Gly Val Val Pro
    290                 295                 300

gat cca aaa gat gca aat gat ccg gtg gaa aaa att gga att gag tct      960
Asp Pro Lys Asp Ala Asn Asp Pro Val Glu Lys Ile Gly Ile Glu Ser
305                 310                 315                 320

gcg ctt aaa tat atg gat ctc aaa tcg ggc cag aag ata gaa gac att     1008
Ala Leu Lys Tyr Met Asp Leu Lys Ser Gly Gln Lys Ile Glu Asp Ile
                325                 330                 335

tca att aat aaa gtg ttt atc ggt tcc tgt act aat tct aga atc gaa     1056
Ser Ile Asn Lys Val Phe Ile Gly Ser Cys Thr Asn Ser Arg Ile Glu
            340                 345                 350

gat tta aga gcg gcc gct gct acc gta aaa gga aaa aaa gtt tcc tct     1104
Asp Leu Arg Ala Ala Ala Ala Thr Val Lys Gly Lys Lys Val Ser Ser
        355                 360                 365

aag gtt cag gcg att gtg gtt ccc ggt tca ggc aga gtc aaa cgt cag     1152
Lys Val Gln Ala Ile Val Val Pro Gly Ser Gly Arg Val Lys Arg Gln
    370                 375                 380

gcg gaa caa gaa ggt ctg gat aaa att ttt acc gcg gcc ggt ttt gaa     1200
Ala Glu Gln Glu Gly Leu Asp Lys Ile Phe Thr Ala Ala Gly Phe Glu
385                 390                 395                 400

tgg aga aat cca ggc tgt tct atg tgt ctt gcg atg aac gac gac gta     1248
Trp Arg Asn Pro Gly Cys Ser Met Cys Leu Ala Met Asn Asp Asp Val
                405                 410                 415

tta gaa ccg gga gat cgt tgt gct tct act tct aac cga aac ttt gaa     1296
Leu Glu Pro Gly Asp Arg Cys Ala Ser Thr Ser Asn Arg Asn Phe Glu
            420                 425                 430

ggt cgt caa gga aaa ggt gga aga acc cat cta gta gga ccg gaa atg     1344
Gly Arg Gln Gly Lys Gly Gly Arg Thr His Leu Val Gly Pro Glu Met
        435                 440                 445

gcc gcc gcc gcg gct atc gaa ggc cat ttt gtg gat att cga aac tgg     1392
Ala Ala Ala Ala Ala Ile Glu Gly His Phe Val Asp Ile Arg Asn Trp
    450                 455                 460

aaa taa                                                             1398
Lys
465
```

<210> SEQ ID NO 76
<211> LENGTH: 465
<212> TYPE: PRT
<213> ORGANISM: Leptospira interrogans

<400> SEQUENCE: 76

```
Met Lys Thr Met Phe Glu Lys Ile Trp Glu Asp His Leu Val Gly Glu
1               5                   10                  15

Leu Asp Ala Gly Ser Tyr Leu Ile Tyr Ile Asp Arg His Leu Ile His
            20                  25                  30

Glu Val Thr Ser Pro Gln Ala Phe Glu Gly Leu Lys Leu Ala Gly Arg
        35                  40                  45

Lys Val Arg Arg Pro Glu Ala Thr Phe Ala Thr Met Asp His Asn Val
    50                  55                  60

Ser Thr Arg Thr Arg Asp Leu Ser Leu Ala Asp Pro Val Ser Ala Ile
65                  70                  75                  80
```

```
Gln Met Gln Thr Leu Lys Lys Asn Cys Asp Glu Asn Gly Ile Arg Val
                85                  90                  95

Tyr Asp Phe Gln Asn Pro Asp Gln Gly Ile Ile His Val Ile Ala Pro
            100                 105                 110

Glu Met Gly Leu Thr His Pro Gly Met Thr Ile Val Cys Gly Asp Ser
        115                 120                 125

His Thr Ser Thr His Gly Ala Phe Gly Ala Leu Ala Phe Gly Ile Gly
    130                 135                 140

Thr Ser Glu Val Glu His Val Leu Ala Thr Gln Thr Leu Val Gln Lys
145                 150                 155                 160

Arg Ala Lys Thr Met Glu Ile Arg Val Asp Gly Lys Leu Ser Asp Lys
                165                 170                 175

Val Thr Ala Lys Asp Ile Ile Leu Ala Ile Ile Gly Lys Ile Gly Thr
            180                 185                 190

Ala Gly Ala Thr Gly Tyr Val Ile Glu Tyr Arg Gly Ser Ala Ile Gln
        195                 200                 205

Ala Leu Ser Met Glu Ala Arg Met Thr Ile Cys Asn Met Ser Ile Glu
    210                 215                 220

Ala Gly Ala Arg Ala Gly Leu Ile Ala Pro Asp Glu Thr Thr Phe Asn
225                 230                 235                 240

Tyr Ile Gln Gly Lys Asp Phe Ser Pro Lys Gly Val Glu Trp Asp Leu
                245                 250                 255

Ala Val Lys Lys Trp Lys His Tyr Val Thr Asp Glu Gly Ala Lys Phe
            260                 265                 270

Asp Arg Thr Val Ile Leu His Ala Asp Glu Ile Ala Pro Met Val Thr
        275                 280                 285

Trp Gly Thr Ser Pro Ser Gln Val Val Ser Ile Lys Gly Val Val Pro
    290                 295                 300

Asp Pro Lys Asp Ala Asn Asp Pro Val Glu Lys Ile Gly Ile Glu Ser
305                 310                 315                 320

Ala Leu Lys Tyr Met Asp Leu Lys Ser Gly Gln Lys Ile Glu Asp Ile
                325                 330                 335

Ser Ile Asn Lys Val Phe Ile Gly Ser Cys Thr Asn Ser Arg Ile Glu
            340                 345                 350

Asp Leu Arg Ala Ala Ala Ala Thr Val Lys Gly Lys Lys Val Ser Ser
        355                 360                 365

Lys Val Gln Ala Ile Val Val Pro Gly Ser Gly Arg Val Lys Arg Gln
    370                 375                 380

Ala Glu Gln Glu Gly Leu Asp Lys Ile Phe Thr Ala Ala Gly Phe Glu
385                 390                 395                 400

Trp Arg Asn Pro Gly Cys Ser Met Cys Leu Ala Met Asn Asp Asp Val
                405                 410                 415

Leu Glu Pro Gly Asp Arg Cys Ala Ser Thr Ser Asn Arg Asn Phe Glu
            420                 425                 430

Gly Arg Gln Gly Lys Gly Gly Arg Thr His Leu Val Gly Pro Glu Met
        435                 440                 445

Ala Ala Ala Ala Ala Ile Glu Gly His Phe Val Asp Ile Arg Asn Trp
    450                 455                 460

Lys
465
```

<210> SEQ ID NO 77
<211> LENGTH: 621
<212> TYPE: DNA

```
<213> ORGANISM: Leptospira interrogans
<220> FEATURE:
<221> NAME/KEY: CDS
<222> LOCATION: (1)..(621)

<400> SEQUENCE: 77

atg aaa ccc ttt act ata tta aat gga att gcc gcc tta ctg gac aga       48
Met Lys Pro Phe Thr Ile Leu Asn Gly Ile Ala Ala Leu Leu Asp Arg
1               5                   10                  15

ccc aac gtg gat acg gat cag atc att cca aaa caa ttt tta cgg aag       96
Pro Asn Val Asp Thr Asp Gln Ile Ile Pro Lys Gln Phe Leu Arg Lys
            20                  25                  30

ata gaa cga acc ggt ttc gga gtt cat ctg ttt cac gat tgg aga tac      144
Ile Glu Arg Thr Gly Phe Gly Val His Leu Phe His Asp Trp Arg Tyr
        35                  40                  45

tta gac gac gcg ggt acc aaa ctc aat cct gat ttt tcc ctc aat caa      192
Leu Asp Asp Ala Gly Thr Lys Leu Asn Pro Asp Phe Ser Leu Asn Gln
    50                  55                  60

gaa cga tat aag gga gct tct atc ctt atc acc aga gat aac ttt ggt      240
Glu Arg Tyr Lys Gly Ala Ser Ile Leu Ile Thr Arg Asp Asn Phe Gly
65                  70                  75                  80

tgt gga tct tcc aga gaa cac gct cct tgg gct tta gaa gac tac ggg      288
Cys Gly Ser Ser Arg Glu His Ala Pro Trp Ala Leu Glu Asp Tyr Gly
                85                  90                  95

ttt agg gca atc att gct cct tct tac gcg gat att ttt ttc aac aac      336
Phe Arg Ala Ile Ile Ala Pro Ser Tyr Ala Asp Ile Phe Phe Asn Asn
            100                 105                 110

tgc ttt aaa aac gga atg ctt cca gtc att tta aaa tcg gaa gaa gta      384
Cys Phe Lys Asn Gly Met Leu Pro Val Ile Leu Lys Ser Glu Glu Val
        115                 120                 125

gaa gag ctg ttc cat ttg gtt tcg act aac gta gga gcg aaa gtc ata      432
Glu Glu Leu Phe His Leu Val Ser Thr Asn Val Gly Ala Lys Val Ile
    130                 135                 140

gtg gat ctg gac aaa caa act gta acc gga ccg act gga aaa ata tat      480
Val Asp Leu Asp Lys Gln Thr Val Thr Gly Pro Thr Gly Lys Ile Tyr
145                 150                 155                 160

tat ttt gaa gtg gat tct ttt cgt aaa tac tgt ctt tat aac gga ctt      528
Tyr Phe Glu Val Asp Ser Phe Arg Lys Tyr Cys Leu Tyr Asn Gly Leu
                165                 170                 175

gat gac ata ggt cta act cta aaa caa gaa agt aaa att gga gag ttt      576
Asp Asp Ile Gly Leu Thr Leu Lys Gln Glu Ser Lys Ile Gly Glu Phe
            180                 185                 190

gaa aaa aag cag aaa gaa gtt gaa cct tgg tta tac gcc ata taa          621
Glu Lys Lys Gln Lys Glu Val Glu Pro Trp Leu Tyr Ala Ile
        195                 200                 205


<210> SEQ ID NO 78
<211> LENGTH: 206
<212> TYPE: PRT
<213> ORGANISM: Leptospira interrogans

<400> SEQUENCE: 78

Met Lys Pro Phe Thr Ile Leu Asn Gly Ile Ala Ala Leu Leu Asp Arg
1               5                   10                  15

Pro Asn Val Asp Thr Asp Gln Ile Ile Pro Lys Gln Phe Leu Arg Lys
            20                  25                  30

Ile Glu Arg Thr Gly Phe Gly Val His Leu Phe His Asp Trp Arg Tyr
        35                  40                  45

Leu Asp Asp Ala Gly Thr Lys Leu Asn Pro Asp Phe Ser Leu Asn Gln
    50                  55                  60
```

-continued

```
Glu Arg Tyr Lys Gly Ala Ser Ile Leu Ile Thr Arg Asp Asn Phe Gly
65                  70                  75                  80

Cys Gly Ser Ser Arg Glu His Ala Pro Trp Ala Leu Glu Asp Tyr Gly
                85                  90                  95

Phe Arg Ala Ile Ile Ala Pro Ser Tyr Ala Asp Ile Phe Phe Asn Asn
            100                 105                 110

Cys Phe Lys Asn Gly Met Leu Pro Val Ile Leu Lys Ser Glu Glu Val
        115                 120                 125

Glu Glu Leu Phe His Leu Val Ser Thr Asn Val Gly Ala Lys Val Ile
    130                 135                 140

Val Asp Leu Asp Lys Gln Thr Val Thr Gly Pro Thr Gly Lys Ile Tyr
145                 150                 155                 160

Tyr Phe Glu Val Asp Ser Phe Arg Lys Tyr Cys Leu Tyr Asn Gly Leu
                165                 170                 175

Asp Asp Ile Gly Leu Thr Leu Lys Gln Glu Ser Lys Ile Gly Glu Phe
            180                 185                 190

Glu Lys Lys Gln Lys Glu Val Glu Pro Trp Leu Tyr Ala Ile
        195                 200                 205


<210> SEQ ID NO 79
<211> LENGTH: 1077
<212> TYPE: DNA
<213> ORGANISM: Leptospira interrogans
<220> FEATURE:
<221> NAME/KEY: CDS
<222> LOCATION: (1)..(1077)

<400> SEQUENCE: 79

atg aag aat gta gca gta ctt tca gga gac gga atc gga ccg gaa gtc       48
Met Lys Asn Val Ala Val Leu Ser Gly Asp Gly Ile Gly Pro Glu Val
1               5                   10                  15

atg gag ata gcc atc tcc gtt ttg aaa aag gct ctc ggt gca aaa gtt       96
Met Glu Ile Ala Ile Ser Val Leu Lys Lys Ala Leu Gly Ala Lys Val
            20                  25                  30

tcc gag ttt caa ttt aaa gaa gga ttt gta ggt gga atc gca atc gat      144
Ser Glu Phe Gln Phe Lys Glu Gly Phe Val Gly Gly Ile Ala Ile Asp
        35                  40                  45

aaa act gga cac cca ctt cca ccg gaa act ctt aaa cta tgt gaa gaa      192
Lys Thr Gly His Pro Leu Pro Pro Glu Thr Leu Lys Leu Cys Glu Glu
    50                  55                  60

tct tcc gca att ctt ttc gga agt gtg gga ggt cct aaa tgg gaa aca      240
Ser Ser Ala Ile Leu Phe Gly Ser Val Gly Gly Pro Lys Trp Glu Thr
65                  70                  75                  80

ctc cct ccg gaa aaa caa ccg gaa cga ggg gca ctt cta cct ttg aga      288
Leu Pro Pro Glu Lys Gln Pro Glu Arg Gly Ala Leu Leu Pro Leu Arg
                85                  90                  95

aaa cat ttt gat cta ttt gca aac tta aga cct gcg atc att tat cca      336
Lys His Phe Asp Leu Phe Ala Asn Leu Arg Pro Ala Ile Ile Tyr Pro
            100                 105                 110

gag ttg aaa aat gct tct cca gtt cgt tct gat att att gga aac gga      384
Glu Leu Lys Asn Ala Ser Pro Val Arg Ser Asp Ile Ile Gly Asn Gly
        115                 120                 125

tta gat att ctc ata tta aga gag tta acc gga gga att tat ttt gga      432
Leu Asp Ile Leu Ile Leu Arg Glu Leu Thr Gly Gly Ile Tyr Phe Gly
    130                 135                 140

caa cca aaa gga aga gaa gga tca ggt cag gaa gaa ttt gca tac gac      480
Gln Pro Lys Gly Arg Glu Gly Ser Gly Gln Glu Glu Phe Ala Tyr Asp
145                 150                 155                 160

acg atg aag tat tcc aga aga gaa atc gaa agg att gct aaa gtc gca      528
```

-continued

```
Thr Met Lys Tyr Ser Arg Arg Glu Ile Glu Arg Ile Ala Lys Val Ala
                165                 170                 175

ttc cag gcg gcc aga aaa aga aat aat aaa gtg act agt atc gat aaa      576
Phe Gln Ala Ala Arg Lys Arg Asn Asn Lys Val Thr Ser Ile Asp Lys
            180                 185                 190

gca aac gtc ttg act act tcc gtt ttt tgg aag gaa gta gta atc gaa      624
Ala Asn Val Leu Thr Thr Ser Val Phe Trp Lys Glu Val Val Ile Glu
        195                 200                 205

ttg cat aag aaa gaa ttt tca gac gtc caa ttg aat cat ctt tat gtg      672
Leu His Lys Lys Glu Phe Ser Asp Val Gln Leu Asn His Leu Tyr Val
    210                 215                 220

gac aat gcg gcg atg cag tta atc gta aat ccg aaa caa ttc gac gtg      720
Asp Asn Ala Ala Met Gln Leu Ile Val Asn Pro Lys Gln Phe Asp Val
225                 230                 235                 240

gtt ctt tgt gag aat atg ttt ggt gat att ctt tcg gac gag gct tcc      768
Val Leu Cys Glu Asn Met Phe Gly Asp Ile Leu Ser Asp Glu Ala Ser
                245                 250                 255

atc att acg ggt tca atc gga atg ctt cct tct gcc tct ctt tcc gaa      816
Ile Ile Thr Gly Ser Ile Gly Met Leu Pro Ser Ala Ser Leu Ser Glu
            260                 265                 270

tct gga ttt gga ttg tat gaa cct tct ggt ggt tct gcg ccg gac ata      864
Ser Gly Phe Gly Leu Tyr Glu Pro Ser Gly Gly Ser Ala Pro Asp Ile
        275                 280                 285

gcc gga aaa gga gtg gca aat ccg att gct caa gta ttg agt gcg gcg      912
Ala Gly Lys Gly Val Ala Asn Pro Ile Ala Gln Val Leu Ser Ala Ala
    290                 295                 300

ttg atg tta cgt tat tct ttt tct atg gaa gaa gaa gca aac aag ata      960
Leu Met Leu Arg Tyr Ser Phe Ser Met Glu Glu Glu Ala Asn Lys Ile
305                 310                 315                 320

gaa acc gcc gtg cgt aaa acg att gcc tcc gga aaa aga acc aga gac     1008
Glu Thr Ala Val Arg Lys Thr Ile Ala Ser Gly Lys Arg Thr Arg Asp
                325                 330                 335

ata gcg gaa gta gga tct acg atc gta gga act aaa gaa atc ggt caa     1056
Ile Ala Glu Val Gly Ser Thr Ile Val Gly Thr Lys Glu Ile Gly Gln
            340                 345                 350

ttg atc gaa tcc ttt ctc taa                                         1077
Leu Ile Glu Ser Phe Leu
        355


<210> SEQ ID NO 80
<211> LENGTH: 358
<212> TYPE: PRT
<213> ORGANISM: Leptospira interrogans

<400> SEQUENCE: 80

Met Lys Asn Val Ala Val Leu Ser Gly Asp Gly Ile Gly Pro Glu Val
1               5                   10                  15

Met Glu Ile Ala Ile Ser Val Leu Lys Lys Ala Leu Gly Ala Lys Val
            20                  25                  30

Ser Glu Phe Gln Phe Lys Glu Gly Phe Val Gly Gly Ile Ala Ile Asp
        35                  40                  45

Lys Thr Gly His Pro Leu Pro Pro Glu Thr Leu Lys Leu Cys Glu Glu
    50                  55                  60

Ser Ser Ala Ile Leu Phe Gly Ser Val Gly Gly Pro Lys Trp Glu Thr
65                  70                  75                  80

Leu Pro Pro Glu Lys Gln Pro Glu Arg Gly Ala Leu Leu Pro Leu Arg
                85                  90                  95

Lys His Phe Asp Leu Phe Ala Asn Leu Arg Pro Ala Ile Ile Tyr Pro
            100                 105                 110
```

```
Glu Leu Lys Asn Ala Ser Pro Val Arg Ser Asp Ile Ile Gly Asn Gly
        115                 120                 125

Leu Asp Ile Leu Ile Leu Arg Glu Leu Thr Gly Gly Ile Tyr Phe Gly
    130                 135                 140

Gln Pro Lys Gly Arg Glu Gly Ser Gly Gln Glu Glu Phe Ala Tyr Asp
145                 150                 155                 160

Thr Met Lys Tyr Ser Arg Arg Glu Ile Glu Arg Ile Ala Lys Val Ala
                165                 170                 175

Phe Gln Ala Ala Arg Lys Arg Asn Asn Lys Val Thr Ser Ile Asp Lys
            180                 185                 190

Ala Asn Val Leu Thr Thr Ser Val Phe Trp Lys Glu Val Val Ile Glu
        195                 200                 205

Leu His Lys Lys Glu Phe Ser Asp Val Gln Leu Asn His Leu Tyr Val
    210                 215                 220

Asp Asn Ala Ala Met Gln Leu Ile Val Asn Pro Lys Gln Phe Asp Val
225                 230                 235                 240

Val Leu Cys Glu Asn Met Phe Gly Asp Ile Leu Ser Asp Glu Ala Ser
                245                 250                 255

Ile Ile Thr Gly Ser Ile Gly Met Leu Pro Ser Ala Ser Leu Ser Glu
            260                 265                 270

Ser Gly Phe Gly Leu Tyr Glu Pro Ser Gly Gly Ser Ala Pro Asp Ile
        275                 280                 285

Ala Gly Lys Gly Val Ala Asn Pro Ile Ala Gln Val Leu Ser Ala Ala
    290                 295                 300

Leu Met Leu Arg Tyr Ser Phe Ser Met Glu Glu Glu Ala Asn Lys Ile
305                 310                 315                 320

Glu Thr Ala Val Arg Lys Thr Ile Ala Ser Gly Lys Arg Thr Arg Asp
                325                 330                 335

Ile Ala Glu Val Gly Ser Thr Ile Val Gly Thr Lys Glu Ile Gly Gln
            340                 345                 350

Leu Ile Glu Ser Phe Leu
        355


<210> SEQ ID NO 81
<211> LENGTH: 1161
<212> TYPE: DNA
<213> ORGANISM: Escherichia coli
<220> FEATURE:
<221> NAME/KEY: CDS
<222> LOCATION: (1)..(1161)

<400> SEQUENCE: 81

atg aca tcg gaa aac ccg tta ctg gcg ctg cga gag aaa atc agc gcg       48
Met Thr Ser Glu Asn Pro Leu Leu Ala Leu Arg Glu Lys Ile Ser Ala
1               5                   10                  15

ctg gat gaa aaa tta tta gcg tta ctg gca gaa cgg cgc gaa ctg gcc       96
Leu Asp Glu Lys Leu Leu Ala Leu Leu Ala Glu Arg Arg Glu Leu Ala
            20                  25                  30

gtc gag gtg gga aaa gcc aaa ctg ctc tcg cat cgc ccg gta cgt gat      144
Val Glu Val Gly Lys Ala Lys Leu Leu Ser His Arg Pro Val Arg Asp
        35                  40                  45

att gat cgt gaa cgc gat ttg ctg gaa aga tta att acg ctc ggt aaa      192
Ile Asp Arg Glu Arg Asp Leu Leu Glu Arg Leu Ile Thr Leu Gly Lys
    50                  55                  60

gcg cac cat ctg gac gcc cat tac att act cgc ctg ttc cag ctc atc      240
Ala His His Leu Asp Ala His Tyr Ile Thr Arg Leu Phe Gln Leu Ile
65                  70                  75                  80
```

```
att gaa gat tcc gta tta act cag cag gct ttg ctc caa caa cat ctc      288
Ile Glu Asp Ser Val Leu Thr Gln Gln Ala Leu Leu Gln Gln His Leu
                85                  90                  95

aat aaa att aat ccg cac tca gca cgc atc gct ttt ctc ggc ccc aaa      336
Asn Lys Ile Asn Pro His Ser Ala Arg Ile Ala Phe Leu Gly Pro Lys
            100                 105                 110

ggt tct tat tcc cat ctt gcg gcg cgc cag tat gct gcc cgt cac ttt      384
Gly Ser Tyr Ser His Leu Ala Ala Arg Gln Tyr Ala Ala Arg His Phe
        115                 120                 125

gag caa ttc att gaa agt ggc tgc gcc aaa ttt gcc gat att ttt aat      432
Glu Gln Phe Ile Glu Ser Gly Cys Ala Lys Phe Ala Asp Ile Phe Asn
    130                 135                 140

cag gtg gaa acc ggc cag gcc gac tat gcc gtc gta ccg att gaa aat      480
Gln Val Glu Thr Gly Gln Ala Asp Tyr Ala Val Val Pro Ile Glu Asn
145                 150                 155                 160

acc agc tcc ggt gcc ata aac gac gtt tac gat ctg ctg caa cat acc      528
Thr Ser Ser Gly Ala Ile Asn Asp Val Tyr Asp Leu Leu Gln His Thr
                165                 170                 175

agc ttg tcg att gtt ggc gag atg acg tta act atc gac cat tgt ttg      576
Ser Leu Ser Ile Val Gly Glu Met Thr Leu Thr Ile Asp His Cys Leu
            180                 185                 190

ttg gtc tcc ggc act act gat tta tcc acc atc aat acg gtc tac agc      624
Leu Val Ser Gly Thr Thr Asp Leu Ser Thr Ile Asn Thr Val Tyr Ser
        195                 200                 205

cat ccg cag cca ttc cag caa tgc agc aaa ttc ctt aat cgt tat ccg      672
His Pro Gln Pro Phe Gln Gln Cys Ser Lys Phe Leu Asn Arg Tyr Pro
    210                 215                 220

cac tgg aag att gaa tat acc gaa agt acg tct gcg gca atg gaa aag      720
His Trp Lys Ile Glu Tyr Thr Glu Ser Thr Ser Ala Ala Met Glu Lys
225                 230                 235                 240

gtt gca cag gca aaa tca ccg cat gtt gct gcg ttg gga agc gaa gct      768
Val Ala Gln Ala Lys Ser Pro His Val Ala Ala Leu Gly Ser Glu Ala
                245                 250                 255

ggc ggc act ttg tac ggt ttg cag gta ctg gag cgt att gaa gca aat      816
Gly Gly Thr Leu Tyr Gly Leu Gln Val Leu Glu Arg Ile Glu Ala Asn
            260                 265                 270

cag cga caa aac ttc acc cga ttt gtg gtg ttg gcg cgt aaa gcc att      864
Gln Arg Gln Asn Phe Thr Arg Phe Val Val Leu Ala Arg Lys Ala Ile
        275                 280                 285

aac gtg tct gat cag gtt ccg gcg aaa acc acg ttg tta atg gcg acc      912
Asn Val Ser Asp Gln Val Pro Ala Lys Thr Thr Leu Leu Met Ala Thr
    290                 295                 300

ggg caa caa gcc ggt gcg ctg gtt gaa gcg ttg ctg gta ctg cgc aac      960
Gly Gln Gln Ala Gly Ala Leu Val Glu Ala Leu Leu Val Leu Arg Asn
305                 310                 315                 320

cac aat ctg att atg acc cgt ctg gaa tca cgc ccg att cac ggt aat     1008
His Asn Leu Ile Met Thr Arg Leu Glu Ser Arg Pro Ile His Gly Asn
                325                 330                 335

cca tgg gaa gag atg ttc tat ctg gat att cag gcc aat ctt gaa tca     1056
Pro Trp Glu Glu Met Phe Tyr Leu Asp Ile Gln Ala Asn Leu Glu Ser
            340                 345                 350

gcg gaa atg caa aaa gca ttg aaa gag tta ggg gaa atc acc cgt tca     1104
Ala Glu Met Gln Lys Ala Leu Lys Glu Leu Gly Glu Ile Thr Arg Ser
        355                 360                 365

atg aag gta ttg ggc tgt tac cca agt gag aac gta gtg cct gtt gat     1152
Met Lys Val Leu Gly Cys Tyr Pro Ser Glu Asn Val Val Pro Val Asp
    370                 375                 380

cca acc tga                                                         1161
Pro Thr
```

385

<210> SEQ ID NO 82
<211> LENGTH: 386
<212> TYPE: PRT
<213> ORGANISM: Escherichia coli

<400> SEQUENCE: 82

Met Thr Ser Glu Asn Pro Leu Leu Ala Leu Arg Glu Lys Ile Ser Ala
1 5 10 15

Leu Asp Glu Lys Leu Leu Ala Leu Leu Ala Glu Arg Arg Glu Leu Ala
20 25 30

Val Glu Val Gly Lys Ala Lys Leu Leu Ser His Arg Pro Val Arg Asp
35 40 45

Ile Asp Arg Glu Arg Asp Leu Leu Glu Arg Leu Ile Thr Leu Gly Lys
50 55 60

Ala His His Leu Asp Ala His Tyr Ile Thr Arg Leu Phe Gln Leu Ile
65 70 75 80

Ile Glu Asp Ser Val Leu Thr Gln Gln Ala Leu Leu Gln Gln His Leu
85 90 95

Asn Lys Ile Asn Pro His Ser Ala Arg Ile Ala Phe Leu Gly Pro Lys
100 105 110

Gly Ser Tyr Ser His Leu Ala Ala Arg Gln Tyr Ala Ala Arg His Phe
115 120 125

Glu Gln Phe Ile Glu Ser Gly Cys Ala Lys Phe Ala Asp Ile Phe Asn
130 135 140

Gln Val Glu Thr Gly Gln Ala Asp Tyr Ala Val Val Pro Ile Glu Asn
145 150 155 160

Thr Ser Ser Gly Ala Ile Asn Asp Val Tyr Asp Leu Leu Gln His Thr
165 170 175

Ser Leu Ser Ile Val Gly Glu Met Thr Leu Thr Ile Asp His Cys Leu
180 185 190

Leu Val Ser Gly Thr Thr Asp Leu Ser Thr Ile Asn Thr Val Tyr Ser
195 200 205

His Pro Gln Pro Phe Gln Gln Cys Ser Lys Phe Leu Asn Arg Tyr Pro
210 215 220

His Trp Lys Ile Glu Tyr Thr Glu Ser Thr Ser Ala Ala Met Glu Lys
225 230 235 240

Val Ala Gln Ala Lys Ser Pro His Val Ala Ala Leu Gly Ser Glu Ala
245 250 255

Gly Gly Thr Leu Tyr Gly Leu Gln Val Leu Glu Arg Ile Glu Ala Asn
260 265 270

Gln Arg Gln Asn Phe Thr Arg Phe Val Val Leu Ala Arg Lys Ala Ile
275 280 285

Asn Val Ser Asp Gln Val Pro Ala Lys Thr Thr Leu Leu Met Ala Thr
290 295 300

Gly Gln Gln Ala Gly Ala Leu Val Glu Ala Leu Leu Val Leu Arg Asn
305 310 315 320

His Asn Leu Ile Met Thr Arg Leu Glu Ser Arg Pro Ile His Gly Asn
325 330 335

Pro Trp Glu Glu Met Phe Tyr Leu Asp Ile Gln Ala Asn Leu Glu Ser
340 345 350

Ala Glu Met Gln Lys Ala Leu Lys Glu Leu Gly Glu Ile Thr Arg Ser
355 360 365

-continued

```
Met Lys Val Leu Gly Cys Tyr Pro Ser Glu Asn Val Val Pro Val Asp
    370                 375                 380

Pro Thr
385


<210> SEQ ID NO 83
<211> LENGTH: 1122
<212> TYPE: DNA
<213> ORGANISM: Escherichia coli
<220> FEATURE:
<221> NAME/KEY: CDS
<222> LOCATION: (1)..(1122)

<400> SEQUENCE: 83

atg gtt gct gaa ttg acc gca tta cgc gat caa att gat gaa gtc gat       48
Met Val Ala Glu Leu Thr Ala Leu Arg Asp Gln Ile Asp Glu Val Asp
1               5                   10                  15

aaa gcg ctg ctg aat tta tta gcg aag cgt ctg gaa ctg gtt gct gaa       96
Lys Ala Leu Leu Asn Leu Leu Ala Lys Arg Leu Glu Leu Val Ala Glu
            20                  25                  30

gtg ggc gag gtg aaa agc cgc ttt gga ctg cct att tat gtt ccg gag      144
Val Gly Glu Val Lys Ser Arg Phe Gly Leu Pro Ile Tyr Val Pro Glu
        35                  40                  45

cgc gag gca tct atg ttg gcc tcg cgt cgt gca gag gcg gaa gct ctg      192
Arg Glu Ala Ser Met Leu Ala Ser Arg Arg Ala Glu Ala Glu Ala Leu
    50                  55                  60

ggt gta ccg cca gat ctg att gag gat gtt ttg cgt cgg gtg atg cgt      240
Gly Val Pro Pro Asp Leu Ile Glu Asp Val Leu Arg Arg Val Met Arg
65                  70                  75                  80

gaa tct tac tcc agt gaa aac gac aaa gga ttt aaa aca ctt tgt ccg      288
Glu Ser Tyr Ser Ser Glu Asn Asp Lys Gly Phe Lys Thr Leu Cys Pro
                85                  90                  95

tca ctg cgt ccg gtg gtt atc gtc ggc ggt ggc ggt cag atg gga cgc      336
Ser Leu Arg Pro Val Val Ile Val Gly Gly Gly Gly Gln Met Gly Arg
            100                 105                 110

ctg ttc gag aag atg ctg acc ctc tcg ggt tat cag gtg cgg att ctg      384
Leu Phe Glu Lys Met Leu Thr Leu Ser Gly Tyr Gln Val Arg Ile Leu
        115                 120                 125

gag caa cat gac tgg gat cga gcg gct gat att gtt gcc gat gcc gga      432
Glu Gln His Asp Trp Asp Arg Ala Ala Asp Ile Val Ala Asp Ala Gly
    130                 135                 140

atg gtg att gtt agt gtg cca atc cac gtt act gag caa gtt att ggc      480
Met Val Ile Val Ser Val Pro Ile His Val Thr Glu Gln Val Ile Gly
145                 150                 155                 160

aaa tta ccg cct tta ccg aaa gat tgt att ctg gtc gat ctg gca tca      528
Lys Leu Pro Pro Leu Pro Lys Asp Cys Ile Leu Val Asp Leu Ala Ser
                165                 170                 175

gtg aaa aat ggg cca tta cag gcc atg ctg gtg gcg cat gat ggt ccg      576
Val Lys Asn Gly Pro Leu Gln Ala Met Leu Val Ala His Asp Gly Pro
            180                 185                 190

gtg ctg ggg cta cac ccg atg ttc ggt ccg gac agc ggt agc ctg gca      624
Val Leu Gly Leu His Pro Met Phe Gly Pro Asp Ser Gly Ser Leu Ala
        195                 200                 205

aag caa gtt gtg gtc tgg tgt gat gga cgt aaa ccg gaa gca tac caa      672
Lys Gln Val Val Val Trp Cys Asp Gly Arg Lys Pro Glu Ala Tyr Gln
    210                 215                 220

tgg ttt ctg gag caa att cag gtc tgg ggc gct cgg ctg cat cgt att      720
Trp Phe Leu Glu Gln Ile Gln Val Trp Gly Ala Arg Leu His Arg Ile
225                 230                 235                 240

agc gcc gtc gag cac gat cag aat atg gcg ttt att cag gca ctg cgc      768
Ser Ala Val Glu His Asp Gln Asn Met Ala Phe Ile Gln Ala Leu Arg
```

```
                245                 250                 255

cac ttt gct act ttt gct tac ggg ctg cac ctg gca gaa gaa aat gtt      816
His Phe Ala Thr Phe Ala Tyr Gly Leu His Leu Ala Glu Glu Asn Val
            260                 265                 270

cag ctt gag caa ctt ctg gcg ctc tct tcg ccg att tac cgc ctt gag      864
Gln Leu Glu Gln Leu Leu Ala Leu Ser Ser Pro Ile Tyr Arg Leu Glu
        275                 280                 285

ctg gcg atg gtc ggg cga ctg ttt gct cag gat ccg cag ctt tat gcc      912
Leu Ala Met Val Gly Arg Leu Phe Ala Gln Asp Pro Gln Leu Tyr Ala
    290                 295                 300

gac atc att atg tcg tca gag cgt aat ctg gcg tta atc aaa cgt tac      960
Asp Ile Ile Met Ser Ser Glu Arg Asn Leu Ala Leu Ile Lys Arg Tyr
305                 310                 315                 320

tat aag cgt ttc ggc gag gcg att gag ttg ctg gag cag ggc gat aag     1008
Tyr Lys Arg Phe Gly Glu Ala Ile Glu Leu Leu Glu Gln Gly Asp Lys
                325                 330                 335

cag gcg ttt att gac agt ttc cgc aag gtg gag cac tgg ttc ggc gat     1056
Gln Ala Phe Ile Asp Ser Phe Arg Lys Val Glu His Trp Phe Gly Asp
            340                 345                 350

tac gca cag cgt ttt cag agt gaa agc cgc gtg tta ttg cgt cag gcg     1104
Tyr Ala Gln Arg Phe Gln Ser Glu Ser Arg Val Leu Leu Arg Gln Ala
        355                 360                 365

aat gac aat cgc cag taa                                             1122
Asn Asp Asn Arg Gln
    370


<210> SEQ ID NO 84
<211> LENGTH: 373
<212> TYPE: PRT
<213> ORGANISM: Escherichia coli

<400> SEQUENCE: 84

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
```

```
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
    370


<210> SEQ ID NO 85
<211> LENGTH: 1716
<212> TYPE: DNA
<213> ORGANISM: Bacillus subtilis
<220> FEATURE:
<221> NAME/KEY: CDS
<222> LOCATION: (1)..(1716)

<400> SEQUENCE: 85

atg ttg aca aaa gca aca aaa gaa caa aaa tcc ctt gtg aaa aac aga       48
Met Leu Thr Lys Ala Thr Lys Glu Gln Lys Ser Leu Val Lys Asn Arg
1               5                   10                  15

ggg gcg gag ctt gtt gtt gat tgc tta gtg gag caa ggt gtc aca cat       96
Gly Ala Glu Leu Val Val Asp Cys Leu Val Glu Gln Gly Val Thr His
            20                  25                  30

gta ttt ggc att cca ggt gca aaa att gat gcg gta ttt gac gct tta      144
Val Phe Gly Ile Pro Gly Ala Lys Ile Asp Ala Val Phe Asp Ala Leu
        35                  40                  45

caa gat aaa gga cct gaa att atc gtt gcc cgg cac gaa caa aac gca      192
Gln Asp Lys Gly Pro Glu Ile Ile Val Ala Arg His Glu Gln Asn Ala
    50                  55                  60

gca ttc atg gcc caa gca gtc ggc cgt tta act gga aaa ccg gga gtc      240
Ala Phe Met Ala Gln Ala Val Gly Arg Leu Thr Gly Lys Pro Gly Val
65                  70                  75                  80

gtg tta gtc aca tca gga ccg ggt gcc tct aac ttg gca aca ggc ctg      288
Val Leu Val Thr Ser Gly Pro Gly Ala Ser Asn Leu Ala Thr Gly Leu
                85                  90                  95

ctg aca gcg aac act gaa gga gac cct gtc gtt gcg ctt gct gga aac      336
Leu Thr Ala Asn Thr Glu Gly Asp Pro Val Val Ala Leu Ala Gly Asn
            100                 105                 110

gtg atc cgt gca gat cgt tta aaa cgg aca cat caa tct ttg gat aat      384
Val Ile Arg Ala Asp Arg Leu Lys Arg Thr His Gln Ser Leu Asp Asn
        115                 120                 125

gcg gcg cta ttc cag ccg att aca aaa tac agt gta gaa gtt caa gat      432
```

-continued

```
Ala Ala Leu Phe Gln Pro Ile Thr Lys Tyr Ser Val Glu Val Gln Asp
    130                 135                 140

gta aaa aat ata ccg gaa gct gtt aca aat gca ttt agg ata gcg tca      480
Val Lys Asn Ile Pro Glu Ala Val Thr Asn Ala Phe Arg Ile Ala Ser
145                 150                 155                 160

gca ggg cag gct ggg gcc gct ttt gtg agc ttt ccg caa gat gtt gtg      528
Ala Gly Gln Ala Gly Ala Ala Phe Val Ser Phe Pro Gln Asp Val Val
                165                 170                 175

aat gaa gtc aca aat acg aaa aac gtg cgt gct gtt gca gcg cca aaa      576
Asn Glu Val Thr Asn Thr Lys Asn Val Arg Ala Val Ala Ala Pro Lys
            180                 185                 190

ctc ggt cct gca gca gat gat gca atc agt gcg gcc ata gca aaa atc      624
Leu Gly Pro Ala Ala Asp Asp Ala Ile Ser Ala Ala Ile Ala Lys Ile
        195                 200                 205

caa aca gca aaa ctt cct gtc gtt ttg gtc ggc atg aaa ggc gga aga      672
Gln Thr Ala Lys Leu Pro Val Val Leu Val Gly Met Lys Gly Gly Arg
    210                 215                 220

ccg gaa gca att aaa gcg gtt cgc aag ctt ttg aaa aag gtt cag ctt      720
Pro Glu Ala Ile Lys Ala Val Arg Lys Leu Leu Lys Lys Val Gln Leu
225                 230                 235                 240

cca ttt gtt gaa aca tat caa gct gcc ggt acc ctt tct aga gat tta      768
Pro Phe Val Glu Thr Tyr Gln Ala Ala Gly Thr Leu Ser Arg Asp Leu
                245                 250                 255

gag gat caa tat ttt ggc cgt atc ggt ttg ttc cgc aac cag cct ggc      816
Glu Asp Gln Tyr Phe Gly Arg Ile Gly Leu Phe Arg Asn Gln Pro Gly
            260                 265                 270

gat tta ctg cta gag cag gca gat gtt gtt ctg acg atc ggc tat gac      864
Asp Leu Leu Leu Glu Gln Ala Asp Val Val Leu Thr Ile Gly Tyr Asp
        275                 280                 285

ccg att gaa tat gat ccg aaa ttc tgg aat atc aat gga gac cgg aca      912
Pro Ile Glu Tyr Asp Pro Lys Phe Trp Asn Ile Asn Gly Asp Arg Thr
    290                 295                 300

att atc cat tta gac gag att atc gct gac att gat cat gct tac cag      960
Ile Ile His Leu Asp Glu Ile Ile Ala Asp Ile Asp His Ala Tyr Gln
305                 310                 315                 320

cct gat ctt gaa ttg atc ggt gac att ccg tcc acg atc aat cat atc     1008
Pro Asp Leu Glu Leu Ile Gly Asp Ile Pro Ser Thr Ile Asn His Ile
                325                 330                 335

gaa cac gat gct gtg aaa gtg gaa ttt gca gag cgt gag cag aaa atc     1056
Glu His Asp Ala Val Lys Val Glu Phe Ala Glu Arg Glu Gln Lys Ile
            340                 345                 350

ctt tct gat tta aaa caa tat atg cat gaa ggt gag cag gtg cct gca     1104
Leu Ser Asp Leu Lys Gln Tyr Met His Glu Gly Glu Gln Val Pro Ala
        355                 360                 365

gat tgg aaa tca gac aga gcg cac cct ctt gaa atc gtt aaa gag ttg     1152
Asp Trp Lys Ser Asp Arg Ala His Pro Leu Glu Ile Val Lys Glu Leu
    370                 375                 380

cgt aat gca gtc gat gat cat gtt aca gta act tgc gat atc ggt tcg     1200
Arg Asn Ala Val Asp Asp His Val Thr Val Thr Cys Asp Ile Gly Ser
385                 390                 395                 400

cac gcc att tgg atg tca cgt tat ttc cgc agc tac gag ccg tta aca     1248
His Ala Ile Trp Met Ser Arg Tyr Phe Arg Ser Tyr Glu Pro Leu Thr
                405                 410                 415

tta atg atc agt aac ggt atg caa aca ctc ggc gtt gcg ctt cct tgg     1296
Leu Met Ile Ser Asn Gly Met Gln Thr Leu Gly Val Ala Leu Pro Trp
            420                 425                 430

gca atc ggc gct tca ttg gtg aaa ccg gga gaa aaa gtg gtt tct gtc     1344
Ala Ile Gly Ala Ser Leu Val Lys Pro Gly Glu Lys Val Val Ser Val
        435                 440                 445
```

```
tct ggt gac ggc ggt ttc tta ttc tca gca atg gaa tta gag aca gca      1392
Ser Gly Asp Gly Gly Phe Leu Phe Ser Ala Met Glu Leu Glu Thr Ala
    450                 455                 460

gtt cga cta aaa gca cca att gta cac att gta tgg aac gac agc aca      1440
Val Arg Leu Lys Ala Pro Ile Val His Ile Val Trp Asn Asp Ser Thr
465                 470                 475                 480

tat gac atg gtt gca ttc cag caa ttg aaa aaa tat aac cgt aca tct      1488
Tyr Asp Met Val Ala Phe Gln Gln Leu Lys Lys Tyr Asn Arg Thr Ser
                485                 490                 495

gcg gtc gat ttc gga aat atc gat atc gtg aaa tat gcg gaa agc ttc      1536
Ala Val Asp Phe Gly Asn Ile Asp Ile Val Lys Tyr Ala Glu Ser Phe
            500                 505                 510

gga gca act ggc ttg cgc gta gaa tca cca gac cag ctg gca gat gtt      1584
Gly Ala Thr Gly Leu Arg Val Glu Ser Pro Asp Gln Leu Ala Asp Val
        515                 520                 525

ctg cgt caa ggc atg aac gct gaa ggt cct gtc atc atc gat gtc ccg      1632
Leu Arg Gln Gly Met Asn Ala Glu Gly Pro Val Ile Ile Asp Val Pro
    530                 535                 540

gtt gac tac agt gat aac att aat tta gca agt gac aag ctt ccg aaa      1680
Val Asp Tyr Ser Asp Asn Ile Asn Leu Ala Ser Asp Lys Leu Pro Lys
545                 550                 555                 560

gaa ttc ggg gaa ctc atg aaa acg aaa gct ctc tag                      1716
Glu Phe Gly Glu Leu Met Lys Thr Lys Ala Leu
                565                 570


<210> SEQ ID NO 86
<211> LENGTH: 571
<212> TYPE: PRT
<213> ORGANISM: Bacillus subtilis

<400> SEQUENCE: 86

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205
```

```
Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 87
<211> LENGTH: 427
<212> TYPE: DNA
<213> ORGANISM: Escherichia coli

<400> SEQUENCE: 87

```
cgatcatacc cggatggaag cgcctgcagt tcgggtggcg aaaacaatga acaccccgca      60
```

tggcgacgca atcaccgtgt tcgatctgcg cttctgcgtg ccgaacaaag aagtgatgcc 120
agaaagaggg atccataccc tggagcacct gtttgctggt tttatgcgta accatcttaa 180
cggtaatggt gtagagatta tcgatatctc gccaatgggc tgccgcaccg gtttttatat 240
gagtctgatt ggtacgccag atgagcagcg tgttgctgat gcctggaaag cggcaatgga 300
agacgtgctg aaagtgcagg atcagaatca gatcccggaa ctgaacgtct accagtgtgg 360
cacttaccag atgcactcgt tgcaggaagc gcaggatatt gcgcgtagca ttctggaacg 420
tgacgta 427

<210> SEQ ID NO 88
<211> LENGTH: 142
<212> TYPE: PRT
<213> ORGANISM: Escherichia coli

<400> SEQUENCE: 88

Asp His Thr Arg Met Glu Ala Pro Ala Val Arg Val Ala Lys Thr Met
1 5 10 15

Asn Thr Pro His Gly Asp Ala Ile Thr Val Phe Asp Leu Arg Phe Cys
20 25 30

Val Pro Asn Lys Glu Val Met Pro Glu Arg Gly Ile His Thr Leu Glu
35 40 45

His Leu Phe Ala Gly Phe Met Arg Asn His Leu Asn Gly Asn Gly Val
50 55 60

Glu Ile Ile Asp Ile Ser Pro Met Gly Cys Arg Thr Gly Phe Tyr Met
65 70 75 80

Ser Leu Ile Gly Thr Pro Asp Glu Gln Arg Val Ala Asp Ala Trp Lys
85 90 95

Ala Ala Met Glu Asp Val Leu Lys Val Gln Asp Gln Asn Gln Ile Pro
100 105 110

Glu Leu Asn Val Tyr Gln Cys Gly Thr Tyr Gln Met His Ser Leu Gln
115 120 125

Glu Ala Gln Asp Ile Ala Arg Ser Ile Leu Glu Arg Asp Val
130 135 140

<210> SEQ ID NO 89
<211> LENGTH: 1536
<212> TYPE: DNA
<213> ORGANISM: Escherichia coli

<400> SEQUENCE: 89
tcagcatgcc gcctcctgac gctgactatc gccgaaggca acgcgcataa tagtctcgac 60
attaatatcg cgcccggtca gtgcagagtg ggtaatttcg ccctgatgca tcacatacac 120
acgatctgcc atcagttcga tctcttccag atcagaggag ataagcagca cagccacatt 180
ctgtgcggcg atgctgcgca acagttggta gatatcatta cgcgccgaga catccacgcc 240
gcgcgtcggc tcatcgacaa tcaatacttg cggcgaggct tccaggcatt tggcaatcag 300
gattttttgc tggttaccac cggataatgt ccgtgcagct tgttccggtt ggttatattt 360
aatattcagc gcccgacgat aaagttccag ggtggcatta tctttcgcgg ttttcgccca 420
gaatccacga aggttatgag taagggcgca gacgttccag gccagcgaag catcgagatt 480
cagtccggat gactggcgat cttccggcag ataaaccaga ccgcgcagta aacgttctcc 540
agtggataat ctattgatct ctttatcatt cagcataatg cgtccgccac gcaaagtacg 600
tagaccatag agcgtctcgg ccagttctgt gcgtccggca cccaccagcc cagccagacc 660

```
cagaatttct ccggcattta gcgtcaggct gacattcctg aaaccttcgc cagtcagatt    720

ttccagtgtc agcaccgacg ttcctgcggc atgttgtggg cggttgccag gtaactccag    780

ccataatttt tggctggcag agagcgattt ttcccgtacc gctggggtga tggcctgaat    840

aatgtcgtcg gtagacagtt cgctggtttt gccgcttaag gcgatggttc cgtcgcgcat    900

cacgctaatc cgatcggcaa tctggcgaat ttccggcagc ttatgcgaga taaaaacaat    960

acccacgcca gtagcaagca gctcttgcaa gcgagtaaac aagcgttcgg tttccgcagg   1020

ggtaagcgag gcggtaggtt catcgaggat cagaatccgc gagtcgcgca tcagcccgcg   1080

gaggatttcc accatttggc gatcggcgac atccagcgat cctgccagac tatgcagatc   1140

aaactggcag cccagcgccg ccagcaagtt cttcattttc tgcatggaga gctgtttttt   1200

tgccagccca aacaggatgt tttcttttat cgacaggctt gggaaaagca gcggttcctg   1260

gggaacgaga taaataccca gctgatgagc atgaactggc gttaatctgg cgtagttgtt   1320

gcccccaatc tccagcgtac cgctatcagc agaggtaata ccggcaataa tcttcattaa   1380

cgtcgattta ccggcaccat tgccgccgag cagggcgtgg acctccccct gatgcaacgt   1440

aaaatcgatg cctttcagga cattgacccc tgaatactgt ttataaaccg agcgggcgca   1500

aagtagcggt aacgcgcggg tatcactcgt ttgcat                             1536


<210> SEQ ID NO 90
<211> LENGTH: 511
<212> TYPE: PRT
<213> ORGANISM: Escherichia coli

<400> SEQUENCE: 90

Met Gln Thr Ser Asp Thr Arg Ala Leu Pro Leu Leu Cys Ala Arg Ser
1               5                   10                  15

Val Tyr Lys Gln Tyr Ser Gly Val Asn Val Leu Lys Gly Ile Asp Phe
            20                  25                  30

Thr Leu His Gln Gly Glu Val His Ala Leu Leu Gly Gly Asn Gly Ala
        35                  40                  45

Gly Lys Ser Thr Leu Met Lys Ile Ile Ala Gly Ile Thr Ser Ala Asp
    50                  55                  60

Ser Gly Thr Leu Glu Ile Gly Gly Asn Asn Tyr Ala Arg Leu Thr Pro
65                  70                  75                  80

Val His Ala His Gln Leu Gly Ile Tyr Leu Val Pro Gln Glu Pro Leu
                85                  90                  95

Leu Phe Pro Ser Leu Ser Ile Lys Glu Asn Ile Leu Phe Gly Leu Ala
            100                 105                 110

Lys Lys Gln Leu Ser Met Gln Lys Met Lys Asn Leu Leu Ala Ala Leu
        115                 120                 125

Gly Cys Gln Phe Asp Leu His Ser Leu Ala Gly Ser Leu Asp Val Ala
    130                 135                 140

Asp Arg Gln Met Val Glu Ile Leu Arg Gly Leu Met Arg Asp Ser Arg
145                 150                 155                 160

Ile Leu Ile Leu Asp Glu Pro Thr Ala Ser Leu Thr Pro Ala Glu Thr
                165                 170                 175

Glu Arg Leu Phe Thr Arg Leu Gln Glu Leu Leu Ala Thr Gly Val Gly
            180                 185                 190

Ile Val Phe Ile Ser His Lys Leu Pro Glu Ile Arg Gln Ile Ala Asp
        195                 200                 205

Arg Ile Ser Val Met Arg Asp Gly Thr Ile Ala Leu Ser Gly Lys Thr
    210                 215                 220
```

-continued

```
Ser Glu Leu Ser Thr Asp Asp Ile Ile Gln Ala Ile Thr Pro Ala Val
225                 230                 235                 240

Arg Glu Lys Ser Leu Ser Ala Ser Gln Lys Leu Trp Leu Glu Leu Pro
                245                 250                 255

Gly Asn Arg Pro Gln His Ala Ala Gly Thr Ser Val Leu Thr Leu Glu
            260                 265                 270

Asn Leu Thr Gly Glu Gly Phe Arg Asn Val Ser Leu Thr Leu Asn Ala
        275                 280                 285

Gly Glu Ile Leu Gly Leu Ala Gly Leu Val Gly Ala Gly Arg Thr Glu
    290                 295                 300

Leu Ala Glu Thr Leu Tyr Gly Leu Arg Thr Leu Arg Gly Gly Arg Ile
305                 310                 315                 320

Met Leu Asn Asp Lys Glu Ile Asn Arg Leu Ser Thr Gly Glu Arg Leu
                325                 330                 335

Leu Arg Gly Leu Val Tyr Leu Pro Glu Asp Arg Gln Ser Ser Gly Leu
            340                 345                 350

Asn Leu Asp Ala Ser Leu Ala Trp Asn Val Cys Ala Leu Thr His Asn
        355                 360                 365

Leu Arg Gly Phe Trp Ala Lys Thr Ala Lys Asp Asn Ala Thr Leu Glu
    370                 375                 380

Leu Tyr Arg Arg Ala Leu Asn Ile Lys Tyr Asn Gln Pro Glu Gln Ala
385                 390                 395                 400

Ala Arg Thr Leu Ser Gly Gly Asn Gln Gln Lys Ile Leu Ile Ala Lys
                405                 410                 415

Cys Leu Glu Ala Ser Pro Gln Val Leu Ile Val Asp Glu Pro Thr Arg
            420                 425                 430

Gly Val Asp Val Ser Ala Arg Asn Asp Ile Tyr Gln Leu Leu Arg Ser
        435                 440                 445

Ile Ala Ala Gln Asn Val Ala Val Leu Leu Ile Ser Ser Asp Leu Glu
    450                 455                 460

Glu Ile Glu Leu Met Ala Asp Arg Val Tyr Val Met His Gln Gly Glu
465                 470                 475                 480

Ile Thr His Ser Ala Leu Thr Gly Arg Asp Ile Asn Val Glu Thr Ile
                485                 490                 495

Met Arg Val Ala Phe Gly Asp Ser Gln Arg Gln Glu Ala Ala Cys
            500                 505                 510
```

<210> SEQ ID NO 91
<211> LENGTH: 1344
<212> TYPE: DNA
<213> ORGANISM: Escherichia coli

<400> SEQUENCE: 91

```
atggatcaga catattctct ggagtcattc ctcaaccatg tccaaaagcg cgacccgaat      60

caaaccgagt tcgcgcaagc cgttcgtgaa gtaatgacca cactctggcc ttttcttgaa     120

caaaatccaa aatatcgcca gatgtcatta ctggagcgtc tggttgaacc ggagcgcgtg     180

atccagtttc gcgtggtatg ggttgatgat cgcaaccaga tacaggtcaa ccgtgcatgg     240

cgtgtgcagt tcagctctgc catcggcccg tacaaaggcg gtatgcgctt ccatccgtca     300

gttaaccttt ccattctcaa attcctcggc tttgaacaaa ccttcaaaaa tgccctgact     360

actctgccga tgggcggtgg taaaggcggc agcgatttcg atccgaaagg aaaaagcgaa     420

ggtgaagtga tgcgtttttg ccaggcgctg atgactgaac tgtatcgcca cctgggcgcg     480
```

```
gataccgacg ttccggcagg tgatatcggg gttggtggtc gtgaagtcgg ctttatggcg    540

gggatgatga aaaagctctc caacaatacc gcctgcgtct tcaccggtaa gggcctttca    600

tttggcggca gtcttattcg cccggaagct accggctacg gtctggttta tttcacagaa    660

gcaatgctaa aacgccacgg tatgggtttt gaagggatgc gcgtttccgt ttctggctcc    720

ggcaacgtcg cccagtacgc tatcgaaaaa gcgatggaat ttggtgctcg tgtgatcact    780

gcgtcagact ccagcggcac tgtagttgat gaaagcggat tcacgaaaga gaaactggca    840

cgtcttatcg aaatcaaagc cagccgcgat ggtcgagtgg cagattacgc caaagaattt    900

ggtctggtct atctcgaagg ccaacagccg tggtctctac cggttgatat cgccctgcct    960

tgcgccaccc agaatgaact ggatgttgac gccgcgcatc agcttatcgc taatggcgtt   1020

aaagccgtcg ccgaaggggc aaatatgccg accaccatcg aagcgactga actgttccag   1080

caggcaggcg tactatttgc accgggtaaa gcggctaatg ctggtggcgt cgctacatcg   1140

ggcctggaaa tggcacaaaa cgctgcgcgc ctgggctgga aagccgagaa agttgacgca   1200

cgtttgcatc acatcatgct ggatatccac catgcctgtg ttgagcatgg tggtgaaggt   1260

gagcaaacca actacgtgca gggcgcgaac attgccggtt ttgtgaaggt tgccgatgcg   1320

atgctggcgc agggtgtgat ttaa                                          1344
```

```
<210> SEQ ID NO 92
<211> LENGTH: 448
<212> TYPE: PRT
<213> ORGANISM: Escherichia coli

<400> SEQUENCE: 92

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Arg Asn Lys Lys Leu Ser Asn Asn Thr Ala
            180                 185                 190

Cys Val Phe Thr Gly Lys Gly Leu Ser Phe Gly Gly Ser Leu Ile Arg
        195                 200                 205

Pro Glu Ala Thr Gly Tyr Gly Leu Val Tyr Phe Thr Glu Ala Met Leu
    210                 215                 220
```

```
Lys Arg His Gly Met Gly Phe Glu Gly Met Arg Val Ser Val Ser Gly
225                 230                 235                 240

Ser Gly Asn Val Ala Gln Tyr Ala Ile Glu Lys Ala Met Glu Phe Gly
                245                 250                 255

Ala Arg Val Ile Thr Ala Ser Asp Ser Ser Gly Thr Val Val Asp Glu
            260                 265                 270

Ser Gly Phe Thr Lys Glu Lys Leu Ala Arg Leu Ile Glu Ile Lys Ala
        275                 280                 285

Ser Arg Asp Gly Arg Val Ala Asp Tyr Ala Lys Glu Phe Gly Leu Val
    290                 295                 300

Tyr Leu Glu Gly Gln Gln Pro Trp Ser Leu Pro Val Asp Ile Ala Leu
305                 310                 315                 320

Pro Cys Ala Thr Gln Asn Glu Leu Asp Val Asp Ala Ala His Gln Leu
                325                 330                 335

Ile Ala Asn Gly Val Lys Ala Val Ala Glu Gly Ala Asn Met Pro Thr
            340                 345                 350

Thr Ile Glu Ala Thr Glu Leu Phe Gln Gln Ala Gly Val Leu Phe Ala
        355                 360                 365

Pro Gly Lys Ala Ala Asn Ala Gly Gly Val Ala Thr Ser Gly Leu Glu
    370                 375                 380

Met Ala Gln Asn Ala Ala Arg Leu Gly Trp Lys Ala Glu Lys Val Asp
385                 390                 395                 400

Ala Arg Leu His His Ile Met Leu Asp Ile His His Ala Cys Val Glu
                405                 410                 415

His Gly Gly Glu Gly Glu Gln Thr Asn Tyr Val Gln Gly Ala Asn Ile
            420                 425                 430

Ala Gly Phe Val Lys Val Ala Asp Ala Met Leu Ala Gln Gly Val Ile
        435                 440                 445
```

<210> SEQ ID NO 93
<211> LENGTH: 1410
<212> TYPE: DNA
<213> ORGANISM: Escherichia coli

<400> SEQUENCE: 93

```
atgtccgctg aacacgtact gacgatgctg aacgagcacg aagtgaagtt tgttgatttg      60

cgcttcaccg atactaaagg taaagaacag cacgtcacta tccctgctca tcaggtgaat     120

gctgaattct tcgaagaagg caaaatgttt gacggctcct cgattggcgg ctggaaaggc     180

attaacgagt ccgacatggt gctgatgcca gacgcatcca ccgcagtgat tgacccgttc     240

ttcgccgact ccaccctgat tatccgttcg gacatccttg aacctggcac cctgcaaggc     300

tatgaccgtg acccgcgctc catgtcgaag cgcgccgaag attacctgcg ttccactggc     360

attgccgaca ccgtactgtt cgggccagaa cctgaattct tcctgttcga tgacatccgt     420

ttcggatcat ctatctccgg ttcccacgtt gctatcgacg atatcgaagg cgcatggaac     480

tcctccaccc aatacgaagg tggtaacaaa ggtcaccgtc cggcagtgaa aggcggttac     540

ttcccggttc caccggtaga ctcggctcag gatattcgtt ctgaaatgtc tctggtgatg     600

gaacagatgg gtctggtggt tgaagcccat caccacgaag tagcgactgc tggtcagaac     660

gaagtggcta cccgcttcaa taccatgacc aaaaaagctg acgaaattca gatctacaaa     720

tatgttgtgc acaacgtagc gcaccgcttc ggtaaaaccg cgacctttat gccaaaaccg     780

atgttcggtg ataacggctc cggtatgcac tgccacatgt ctctgtctaa aaacggcgtt     840
```

```
aacctgttcg caggcgacaa atacgcaggt ctgtctgagc aggcgctgta ctacattggc    900

ggcgtaatca aacacgctaa agcgattaac gccctggcaa acccgaccac caactcttat    960

aagcgtctgg tcccgggcta tgaagcaccg gtaatgctgg cttactctgc gcgtaaccgt   1020

tctgcgtcta tccgtattcc ggtggtttct tctccgaaag cacgtcgtat cgaagtacgt   1080

ttcccggatc cggcagctaa cccgtacctg tgctttgctg ccctgctgat ggccggtctt   1140

gatggtatca agaacaagat ccatccgggc gaagccatgg acaaaaacct gtatgacctg   1200

ccgccagaag aagcgaaaga gatcccacag gttgcaggct ctctggaaga agcactgaac   1260

gaactggatc tggaccgcga gttcctgaaa gccggtggcg tgttcactga cgaagcaatt   1320

gatgcgtaca tcgctctgcg tcgcgaagaa gatgaccgcg tgcgtatgac tccgcatccg   1380

gtagagtttg agctgtacta cagcgtctaa                                    1410


<210> SEQ ID NO 94
<211> LENGTH: 469
<212> TYPE: PRT
<213> ORGANISM: Escherichia coli

<400> SEQUENCE: 94

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Ile Asp Pro Phe
65                  70                  75                  80

Phe Ala Asp Ser Thr Leu Ile Ile Arg Ser Asp Ile Leu Glu Pro Gly
                85                  90                  95

Thr Leu Gln Gly Tyr Asp Arg Asp Pro Arg Ser Met Ser Lys Arg Ala
            100                 105                 110

Glu Asp Tyr Leu Arg Ser Thr Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Ser Gly Ser His Val Ala Ile Asp Asp Ile Glu Gly Ala Trp Asn
145                 150                 155                 160

Ser Ser Thr Gln Tyr Glu Gly Gly Asn Lys Gly His Arg Pro Ala Val
                165                 170                 175

Lys Gly Gly Tyr Phe Pro Val Pro Pro Val Asp Ser Ala Gln Asp Ile
            180                 185                 190

Arg Ser Glu Met Ser Leu Val Met Glu Gln Met Gly Leu Val Val Glu
        195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270
```

```
Met Ser Leu Ser Lys Asn Gly Val Asn Leu Phe Ala Gly Asp Lys Tyr
        275                 280                 285

Ala Gly Leu Ser Glu Gln Ala Leu Tyr Tyr Ile Gly Gly Val Ile Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ser Ser Pro
            340                 345                 350

Lys Ala Arg Arg Ile Glu Val Arg Phe Pro Asp Pro Ala Ala Asn Pro
        355                 360                 365

Tyr Leu Cys Phe Ala Ala Leu Leu Met Ala Gly Leu Asp Gly Ile Lys
    370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415

Glu Ala Leu Asn Glu Leu Asp Leu Asp Arg Glu Phe Leu Lys Ala Gly
            420                 425                 430

Gly Val Phe Thr Asp Glu Ala Ile Asp Ala Tyr Ile Ala Leu Arg Arg
        435                 440                 445

Glu Glu Asp Asp Arg Val Arg Met Thr Pro His Pro Val Glu Phe Glu
    450                 455                 460

Leu Tyr Tyr Ser Val
465
```

<210> SEQ ID NO 95
<211> LENGTH: 60
<212> TYPE: DNA
<213> ORGANISM: Artificial Sequence
<220> FEATURE:
<223> OTHER INFORMATION: Synthetic

<400> SEQUENCE: 95
acgcgtcgac aagaaggaga tataccatga cattctccct ttttggtgac aaatttaccc 60

<210> SEQ ID NO 96
<211> LENGTH: 44
<212> TYPE: DNA
<213> ORGANISM: Artificial Sequence
<220> FEATURE:
<223> OTHER INFORMATION: Synthetic

<400> SEQUENCE: 96
ccgggctgca gttagtgact ttcagcccag gctctttcta tctc 44

<210> SEQ ID NO 97
<211> LENGTH: 60
<212> TYPE: DNA
<213> ORGANISM: Artificial Sequence
<220> FEATURE:
<223> OTHER INFORMATION: Synthetic

<400> SEQUENCE: 97
gacatgcatg caagaaggag atataccatg aacaacttta atctgcacac cccaacccgc 60

<210> SEQ ID NO 98
<211> LENGTH: 44
<212> TYPE: DNA

<213> ORGANISM: Artificial Sequence
<220> FEATURE:
<223> OTHER INFORMATION: Synthetic

<400> SEQUENCE: 98
ctcctgcatg cttagcgggc ggcttcgtat atacggcggc tgac 44

<210> SEQ ID NO 99
<211> LENGTH: 44
<212> TYPE: DNA
<213> ORGANISM: Artificial Sequence
<220> FEATURE:
<223> OTHER INFORMATION: Synthetic

<400> SEQUENCE: 99
gcatggtcga cttagctgtg tgcgccatgt aaatggcccg gacg 44

<210> SEQ ID NO 100
<211> LENGTH: 43
<212> TYPE: DNA
<213> ORGANISM: Artificial Sequence
<220> FEATURE:
<223> OTHER INFORMATION: Synthetic

<400> SEQUENCE: 100
gcatggtacc atgaccacga agaaagctga ttacatttgg ttc 43

<210> SEQ ID NO 101
<211> LENGTH: 39
<212> TYPE: DNA
<213> ORGANISM: Artificial Sequence
<220> FEATURE:
<223> OTHER INFORMATION: Synthetic

<400> SEQUENCE: 101
gccaatgcat ttattgatta acttgatcta accagcccc 39

<210> SEQ ID NO 102
<211> LENGTH: 60
<212> TYPE: DNA
<213> ORGANISM: Artificial Sequence
<220> FEATURE:
<223> OTHER INFORMATION: Synthetic

<400> SEQUENCE: 102
cgggctgcag aagaaggaga tataccatgc atattacata cgatctgccg gttgctattg 60

<210> SEQ ID NO 103
<211> LENGTH: 60
<212> TYPE: DNA
<213> ORGANISM: Artificial Sequence
<220> FEATURE:
<223> OTHER INFORMATION: Synthetic

<400> SEQUENCE: 103
ccggaggatc cgaagcggcc gcacctctag attaagcgtc aacgaaaccg gtgatttgag 60

<210> SEQ ID NO 104
<211> LENGTH: 59
<212> TYPE: DNA
<213> ORGANISM: Artificial Sequence
<220> FEATURE:
<223> OTHER INFORMATION: Synthetic

<400> SEQUENCE: 104
ctagtctaga aagaaggaga tataccatga ttagtgcatt cgatattttc aaaattggg 59

<210> SEQ ID NO 105
<211> LENGTH: 41
<212> TYPE: DNA
<213> ORGANISM: Artificial Sequence
<220> FEATURE:
<223> OTHER INFORMATION: Synthetic

<400> SEQUENCE: 105
gctgacggcc gtcagccgca gaccacttta atggccagtc c 41

<210> SEQ ID NO 106
<211> LENGTH: 60
<212> TYPE: DNA
<213> ORGANISM: Artificial Sequence
<220> FEATURE:
<223> OTHER INFORMATION: Synthetic

<400> SEQUENCE: 106
gctgacggcc gaagaaggag atataccatg attagcgtat tcgatatttt caaaatcggc 60

<210> SEQ ID NO 107
<211> LENGTH: 42
<212> TYPE: DNA
<213> ORGANISM: Artificial Sequence
<220> FEATURE:
<223> OTHER INFORMATION: Synthetic

<400> SEQUENCE: 107
ccggaggatc cttaatcgca ggcaacgatc ttcattgcca gg 42

<210> SEQ ID NO 108
<211> LENGTH: 41
<212> TYPE: DNA
<213> ORGANISM: Artificial Sequence
<220> FEATURE:
<223> OTHER INFORMATION: Synthetic

<400> SEQUENCE: 108
ccacctcgag caagtgctgc cagagggaac ccggctggtg g 41

<210> SEQ ID NO 109
<211> LENGTH: 58
<212> TYPE: DNA
<213> ORGANISM: Artificial Sequence
<220> FEATURE:
<223> OTHER INFORMATION: Synthetic

<400> SEQUENCE: 109
gcatggtacc tttctcctct ttaatcccgg cggcgtgttt gccgttgttc cgtgtcag 58

<210> SEQ ID NO 110
<211> LENGTH: 60
<212> TYPE: DNA
<213> ORGANISM: Artificial Sequence
<220> FEATURE:
<223> OTHER INFORMATION: Synthetic

<400> SEQUENCE: 110
gtcgatgcat aagaaggaga tataccatgg ctgactcgca acccctgtcc ggtgctccgg 60

<210> SEQ ID NO 111
<211> LENGTH: 49
<212> TYPE: DNA
<213> ORGANISM: Artificial Sequence
<220> FEATURE:

<223> OTHER INFORMATION: Synthetic

<400> SEQUENCE: 111
ccgggctgca gctaacccgc caaaaagaac ctgaacgccg ggttattgg 49

<210> SEQ ID NO 112
<211> LENGTH: 60
<212> TYPE: DNA
<213> ORGANISM: Artificial Sequence
<220> FEATURE:
<223> OTHER INFORMATION: Synthetic

<400> SEQUENCE: 112
ctagtctaga aagaaggaga tataccatga cccgtccgat acaggccagc ctcgatctgc 60

<210> SEQ ID NO 113
<211> LENGTH: 59
<212> TYPE: DNA
<213> ORGANISM: Artificial Sequence
<220> FEATURE:
<223> OTHER INFORMATION: Synthetic

<400> SEQUENCE: 113
ctcgcctagg ccagtcgacc acggatcctt acaccgtcac aaccgggacg cgtagcgcc 59

<210> SEQ ID NO 114
<211> LENGTH: 58
<212> TYPE: DNA
<213> ORGANISM: Artificial Sequence
<220> FEATURE:
<223> OTHER INFORMATION: Synthetic

<400> SEQUENCE: 114
gcatgggatc caagaaggag atataccatg cgagttgtca tactgggaag tggtgtgg 58

<210> SEQ ID NO 115
<211> LENGTH: 39
<212> TYPE: DNA
<213> ORGANISM: Artificial Sequence
<220> FEATURE:
<223> OTHER INFORMATION: Synthetic

<400> SEQUENCE: 115
gcatgtcgac ggcatcaaat aaaacgaaag gctcagtcg 39

<210> SEQ ID NO 116
<211> LENGTH: 49
<212> TYPE: DNA
<213> ORGANISM: Artificial Sequence
<220> FEATURE:
<223> OTHER INFORMATION: Synthetic

<400> SEQUENCE: 116
gagcactagt catgaccaaa atcccttaac gtgagttttc gttccactg 49

<210> SEQ ID NO 117
<211> LENGTH: 40
<212> TYPE: DNA
<213> ORGANISM: Artificial Sequence
<220> FEATURE:
<223> OTHER INFORMATION: Synthetic

<400> SEQUENCE: 117
gagcactagt aattgtgagc ggataacaat tgacattgtg 40

<210> SEQ ID NO 118
<211> LENGTH: 42
<212> TYPE: DNA
<213> ORGANISM: Artificial Sequence
<220> FEATURE:
<223> OTHER INFORMATION: Synthetic

<400> SEQUENCE: 118
gcatggagct ctctagggcg gcggatttgt cctactcagg ag 42

<210> SEQ ID NO 119
<211> LENGTH: 44
<212> TYPE: DNA
<213> ORGANISM: Artificial Sequence
<220> FEATURE:
<223> OTHER INFORMATION: Synthetic

<400> SEQUENCE: 119
gaaaggtacc atggctgact cgcaacccct gtccggtgct ccgg 44

<210> SEQ ID NO 120
<211> LENGTH: 44
<212> TYPE: DNA
<213> ORGANISM: Artificial Sequence
<220> FEATURE:
<223> OTHER INFORMATION: Synthetic

<400> SEQUENCE: 120
cttcttctgc aggctaaccc gccaaaaaga acctgaacgc cggg 44

<210> SEQ ID NO 121
<211> LENGTH: 60
<212> TYPE: DNA
<213> ORGANISM: Artificial Sequence
<220> FEATURE:
<223> OTHER INFORMATION: Synthetic

<400> SEQUENCE: 121
ccgggctgca gaagaaggag atataccatg attagcgtat tcgatatttt caaaatcggc 60

<210> SEQ ID NO 122
<211> LENGTH: 60
<212> TYPE: DNA
<213> ORGANISM: Artificial Sequence
<220> FEATURE:
<223> OTHER INFORMATION: Synthetic

<400> SEQUENCE: 122
acgcacgcgt aagaaggaga tataccatga cattctccct ttttggtgac aaatttaccc 60

<210> SEQ ID NO 123
<211> LENGTH: 44
<212> TYPE: DNA
<213> ORGANISM: Artificial Sequence
<220> FEATURE:
<223> OTHER INFORMATION: Synthetic

<400> SEQUENCE: 123
ccgggacgcg tttagtgact ttcagcccag gctctttcta tctc 44

<210> SEQ ID NO 124
<211> LENGTH: 42
<212> TYPE: DNA
<213> ORGANISM: Artificial Sequence
<220> FEATURE:
<223> OTHER INFORMATION: Synthetic

<400> SEQUENCE: 124
cgcatggtac catgaaaatc ttcgattaca tggaaaaata tg 42

<210> SEQ ID NO 125
<211> LENGTH: 41
<212> TYPE: DNA
<213> ORGANISM: Artificial Sequence
<220> FEATURE:
<223> OTHER INFORMATION: Synthetic

<400> SEQUENCE: 125
gcatggtcga cttatttgtt gttaaaattg atcaggttgc g 41

<210> SEQ ID NO 126
<211> LENGTH: 45
<212> TYPE: DNA
<213> ORGANISM: Artificial Sequence
<220> FEATURE:
<223> OTHER INFORMATION: Synthetic

<400> SEQUENCE: 126
gcatggtcga caggagatat accatgtata cagtaggaga ttacc 45

<210> SEQ ID NO 127
<211> LENGTH: 44
<212> TYPE: DNA
<213> ORGANISM: Artificial Sequence
<220> FEATURE:
<223> OTHER INFORMATION: Synthetic

<400> SEQUENCE: 127
ccggaggatc cttagcgggc ggcttcgtat atacggcggc tgac 44

<210> SEQ ID NO 128
<211> LENGTH: 1368
<212> TYPE: DNA
<213> ORGANISM: Escherichia coli

<400> SEQUENCE: 128
atgattagcg tattcgatat tttcaaaatc ggcattggcc cttccagttc tcataccgtt 60
ggaccaatga aagcgggtaa acaatttacc gacgatctga ttgcccgtaa cctgcttaaa 120
gacgtgaccc gcgtggtggt tgacgtgtac ggctcgctct ctctgaccgg taaaggccac 180
cacactgata tcgccattat tatgggcctg gcgggtaacc tgccggatac cgtggatatc 240
gattccatcc ccagttttat tcaggatgtg aatactcatg gtcgcctgat gctggcaaac 300
ggtcagcatg aagtggagtt cccggttgat cagtgcatga acttccacgc cgacaacctt 360
tctctgcatg aaaacggtat gcgcattacc gcgctggcgg gcgataaagt cgtttacagc 420
cagacttact actctattgg cggtggcttt atcgttgatg aagagcattt tggccagcag 480
gatagcgcac cggttgaagt tccttatccg tacagttcag cagccgatct gcaaaaacat 540
tgtcaggaaa ccgggctgtc actctctggc ctgatgatga aaaacgagct ggcgctgcac 600
agcaaagaag agctggaaca gcacctggcg aacgtctggg aagtcatgcg cggcggtatt 660
gagcgcggta tttccaccga aggcgtgttg cctggcaaac tgcgcgttcc acgccgtgct 720
gcggcactac gccggatgct ggtcagccag gataaaacca ccactgaccc gatggcggtt 780
gttgactgga tcaacatgtt tgcactggca gtgaacgaag agaacgctgc tggcggtcgc 840
gtggtgactg cgccgactaa cggtgcgtgc gggattatcc cggcagttct ggcgtactac 900
gacaagttta tccgcgaagt gaacgctaac tcactggctc gttacctgct ggtagccagc 960
gccattggtt ctctttataa gatgaacgcg tcgatttctg gtgctgaagt gggttgccag 1020
ggtgaagttg gcgtggcgtg ctcaatggcg gcggctggtc tggcagaact attaggcgca 1080
agcccggcgc aggtgtgcat cgcggcggaa atcgccatgg agcacaacct cggtctgacg 1140
tgtgacccgg tcgccggaca ggtacaggtg ccatgcatcg agcgtaacgc cattgcggca 1200
gtaaaagcgg tgaacgccgc acgtatggcg ctgcgccgta ccagcgagcc gcgcgtctgc 1260
ctcgataaag ttatcgaaac catgtacgaa acaggtaaag atatgaacgc caagtaccgc 1320
gaaacctctc gcggcggcct ggcaatgaag atcgttgcct gcgattaa 1368

<210> SEQ ID NO 129
<211> LENGTH: 455
<212> TYPE: PRT
<213> ORGANISM: Escherichia coli

<400> SEQUENCE: 129

Met Ile Ser Val Phe Asp Ile Phe Lys Ile Gly Ile Gly Pro Ser Ser
1 5 10 15

Ser His Thr Val Gly Pro Met Lys Ala Gly Lys Gln Phe Thr Asp Asp
20 25 30

Leu Ile Ala Arg Asn Leu Leu Lys Asp Val Thr Arg Val Val Val Asp
35 40 45

Val Tyr Gly Ser Leu Ser Leu Thr Gly Lys Gly His His Thr Asp Ile
50 55 60

Ala Ile Ile Met Gly Leu Ala Gly Asn Leu Pro Asp Thr Val Asp Ile
65 70 75 80

Asp Ser Ile Pro Ser Phe Ile Gln Asp Val Asn Thr His Gly Arg Leu
85 90 95

Met Leu Ala Asn Gly Gln His Glu Val Glu Phe Pro Val Asp Gln Cys
100 105 110

Met Asn Phe His Ala Asp Asn Leu Ser Leu His Glu Asn Gly Met Arg
115 120 125

Ile Thr Ala Leu Ala Gly Asp Lys Val Val Tyr Ser Gln Thr Tyr Tyr
130 135 140

Ser Ile Gly Gly Gly Phe Ile Val Asp Glu Glu His Phe Gly Gln Gln
145 150 155 160

Asp Ser Ala Pro Val Glu Val Pro Tyr Pro Tyr Ser Ser Ala Ala Asp
165 170 175

Leu Gln Lys His Cys Gln Glu Thr Gly Leu Ser Leu Ser Gly Leu Met
180 185 190

Met Lys Asn Glu Leu Ala Leu His Ser Lys Glu Glu Leu Glu Gln His
195 200 205

Leu Ala Asn Val Trp Glu Val Met Arg Gly Gly Ile Glu Arg Gly Ile
210 215 220

Ser Thr Glu Gly Val Leu Pro Gly Lys Leu Arg Val Pro Arg Arg Ala
225 230 235 240

Ala Ala Leu Arg Arg Met Leu Val Ser Gln Asp Lys Thr Thr Thr Asp
245 250 255

Pro Met Ala Val Val Asp Trp Ile Asn Met Phe Ala Leu Ala Val Asn
260 265 270

Glu Glu Asn Ala Ala Gly Gly Arg Val Val Thr Ala Pro Thr Asn Gly
275 280 285

Ala Cys Gly Ile Ile Pro Ala Val Leu Ala Tyr Tyr Asp Lys Phe Ile
290 295 300

```
Arg Glu Val Asn Ala Asn Ser Leu Ala Arg Tyr Leu Leu Val Ala Ser
305                 310                 315                 320

Ala Ile Gly Ser Leu Tyr Lys Met Asn Ala Ser Ile Ser Gly Ala Glu
                325                 330                 335

Val Gly Cys Gln Gly Glu Val Gly Val Ala Cys Ser Met Ala Ala Ala
            340                 345                 350

Gly Leu Ala Glu Leu Leu Gly Ala Ser Pro Ala Gln Val Cys Ile Ala
        355                 360                 365

Ala Glu Ile Ala Met Glu His Asn Leu Gly Leu Thr Cys Asp Pro Val
    370                 375                 380

Ala Gly Gln Val Gln Val Pro Cys Ile Glu Arg Asn Ala Ile Ala Ala
385                 390                 395                 400

Val Lys Ala Val Asn Ala Ala Arg Met Ala Leu Arg Arg Thr Ser Glu
                405                 410                 415

Pro Arg Val Cys Leu Asp Lys Val Ile Glu Thr Met Tyr Glu Thr Gly
            420                 425                 430

Lys Asp Met Asn Ala Lys Tyr Arg Glu Thr Ser Arg Gly Gly Leu Ala
        435                 440                 445

Met Lys Ile Val Ala Cys Asp
    450                 455
```

<210> SEQ ID NO 130
<211> LENGTH: 1101
<212> TYPE: DNA
<213> ORGANISM: Thermoactinomyces intermedius

<400> SEQUENCE: 130

```
atgaaaatct tcgattacat ggaaaaatat gattatgaac aactcgtcat gtgccaagat     60

aaagagtccg gcctcaaagc catcatttgt atccatgtta ccaccctggg gccggctctg    120

ggtggtatgc gcatgtggac ttacgcttcg gaagaagaag ccatcgagga tgcgctgcgc    180

ctgggaagag ggatgactta caaaaatgca gctgccggct taaacctcgg cggcggaaaa    240

acggtgatca tcggcgatcc gagaaaagac aaaaacgaag ccatgttccg tgctttggga    300

cgctttatcc aaggattgaa cggacggtac atcacggcgg aagacgtggg aaccactgtg    360

gaagacatgg atatcattca tgaggaaacc cgttacgtga caggcgtatc gcccgctttc    420

ggttccagcg gcaacccttc accggtgacg gcttacggcg tataccgtgg aatgaaagcg    480

gctgcaaaag aagctttcgg cgatgactca ctcgaaggca aagtggtggc tgttcaagga    540

gtgggacatg ttgcttacga attatgtaag cacttgcata atgaaggggc caaattgatt    600

gtgaccgaca tcaacaaaga aaatgcagac cgtgccgtgc aagaatttgg tgccgaattt    660

gttcatccgg acaaaatcta tgatgtggaa tgcgacattt ttgctccttg tgcgctcggg    720

gcgatcatta atgacgaaac cattgaacgc ttgaaatgca aagtggtggc cggttcggca    780

aacaatcagc tgaaagaaga gcgccatgga aaaatgcttg aagaaaaagg aatcgtctat    840

gcgccggatt atgtgatcaa tgccggaggc gtgatcaatg tcgccgatga attgctgggt    900

tataaccgtg agcgtgcgat gaaaaaagtg gaaggcattt acgacaaaat cctgaaagtg    960

tttgagatcg caaaacggga cggcattccg agctatctcg cagcagaccg catggcggaa   1020

gaacggattg aaatgatgcg caaaacaaga agcacatttt tgcaagatca acgcaacctg   1080

atcaatttta acaacaaata a                                             1101
```

<210> SEQ ID NO 131

<211> LENGTH: 366
<212> TYPE: PRT
<213> ORGANISM: Thermoactinomyces intermedius

<400> SEQUENCE: 131

```
Met Lys Ile Phe Asp Tyr Met Glu Lys Tyr Asp Tyr Glu Gln Leu Val
1               5                   10                  15

Met Cys Gln Asp Lys Glu Ser Gly Leu Lys Ala Ile Ile Cys Ile His
            20                  25                  30

Val Thr Thr Leu Gly Pro Ala Leu Gly Gly Met Arg Met Trp Thr Tyr
        35                  40                  45

Ala Ser Glu Glu Glu Ala Ile Glu Asp Ala Leu Arg Leu Gly Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Glu Asp Met Asp Ile Ile His Glu
        115                 120                 125

Glu Thr Arg Tyr Val Thr Gly Val Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Asp Asp Ser Leu Glu Gly Lys Val Val
                165                 170                 175

Ala Val Gln Gly Val Gly His Val Ala Tyr Glu Leu Cys Lys His Leu
            180                 185                 190

His Asn Glu Gly Ala Lys Leu Ile Val Thr Asp Ile Asn Lys Glu Asn
        195                 200                 205

Ala Asp Arg Ala Val Gln Glu Phe Gly Ala Glu Phe Val His Pro Asp
    210                 215                 220

Lys Ile Tyr Asp Val Glu Cys Asp Ile Phe Ala Pro Cys Ala Leu Gly
225                 230                 235                 240

Ala Ile Ile Asn Asp Glu Thr Ile Glu Arg Leu Lys Cys Lys Val Val
                245                 250                 255

Ala Gly Ser Ala Asn Asn Gln Leu Lys Glu Glu Arg His Gly Lys Met
            260                 265                 270

Leu Glu Glu Lys Gly Ile Val Tyr Ala Pro Asp Tyr Val Ile Asn Ala
        275                 280                 285

Gly Gly Val Ile Asn Val Ala Asp Glu Leu Leu Gly Tyr Asn Arg Glu
    290                 295                 300

Arg Ala Met Lys Lys Val Glu Gly Ile Tyr Asp Lys Ile Leu Lys Val
305                 310                 315                 320

Phe Glu Ile Ala Lys Arg Asp Gly Ile Pro Ser Tyr Leu Ala Ala Asp
                325                 330                 335

Arg Met Ala Glu Glu Arg Ile Glu Met Met Arg Lys Thr Arg Ser Thr
            340                 345                 350

Phe Leu Gln Asp Gln Arg Asn Leu Ile Asn Phe Asn Asn Lys
        355                 360                 365
```

<210> SEQ ID NO 132
<211> LENGTH: 1254
<212> TYPE: DNA

<213> ORGANISM: Escherichia coli

<400> SEQUENCE: 132
atgacattct cccttttttgg tgacaaattt acccgccact ccggcattac gctgttgatg 60
gaagatctga acgacggttt acgcacgcct ggcgcgatta tgctcggcgg cggtaatccg 120
gcgcagatcc cggaaatgca ggactacttc cagacgctac tgaccgacat gctggaaagt 180
ggcaaagcga ctgatgcact gtgtaactac gacggtccac aggggaaaac ggagctactc 240
acactgcttg ccggaatgct gcgcgagaag ttgggttggg atatcgaacc acagaatatt 300
gcactaacaa acggcagcca gagcgcgttt ttctacttat ttaacctgtt tgccggacgc 360
cgtgccgatg gtcgggtcaa aaaagtgctg ttcccgcttg caccggaata cattggctat 420
gctgacgccg gactggaaga agatctgttt gtctctgcgc gtccgaatat tgaactgctg 480
ccggaaggcc agtttaaata ccacgtcgat tttgagcatc tgcatattgg cgaagaaacc 540
gggatgattt gcgtctcccg gccgacgaat ccaacaggca atgtgattac tgacgaagag 600
ttgctgaagc ttgacgcgct ggcgaatcaa cacggcattc cgctggtgat tgataacgct 660
tatggcgtcc cgttcccggg tatcatcttc agtgaagcgc gcccgctatg gaatccgaat 720
atcgtgctgt gcatgagtct ttccaagctg ggtctacctg gctcccgctg cggcattatc 780
atcgccaatg aaaaaatcat caccgccatc accaatatga acggcattat cagcctggca 840
cctggcggta ttggtccggc gatgatgtgt gaaatgatta agcgtaacga tctgctgcgc 900
ctgtctgaaa cagtcatcaa accgttttac taccagcgtg ttcaggaaac tatcgccatc 960
attcgccgct atttaccgga aaatcgctgc ctgattcata aaccggaagg agccattttc 1020
ctctggctat ggtttaagga tttgcccatt acgaccaagc agctctatca gcgcctgaaa 1080
gcacgcggcg tgctgatggt gccggggcac aacttcttcc cagggctgga taaaccgtgg 1140
ccgcatacgc atcaatgtat gcgcatgaac tacgtaccag agccggagaa aattgaggcg 1200
ggggtgaaga ttctggcgga agagatagaa agagcctggg ctgaaagtca ctaa 1254

<210> SEQ ID NO 133
<211> LENGTH: 417
<212> TYPE: PRT
<213> ORGANISM: Escherichia coli

<400> SEQUENCE: 133

Met Thr Phe Ser Leu Phe Gly Asp Lys Phe Thr Arg His Ser Gly Ile
1 5 10 15

Thr Leu Leu Met Glu Asp Leu Asn Asp Gly Leu Arg Thr Pro Gly Ala
20 25 30

Ile Met Leu Gly Gly Gly Asn Pro Ala Gln Ile Pro Glu Met Gln Asp
35 40 45

Tyr Phe Gln Thr Leu Leu Thr Asp Met Leu Glu Ser Gly Lys Ala Thr
50 55 60

Asp Ala Leu Cys Asn Tyr Asp Gly Pro Gln Gly Lys Thr Glu Leu Leu
65 70 75 80

Thr Leu Leu Ala Gly Met Leu Arg Glu Lys Leu Gly Trp Asp Ile Glu
85 90 95

Pro Gln Asn Ile Ala Leu Thr Asn Gly Ser Gln Ser Ala Phe Phe Tyr
100 105 110

Leu Phe Asn Leu Phe Ala Gly Arg Arg Ala Asp Gly Arg Val Lys Lys
115 120 125

Val Leu Phe Pro Leu Ala Pro Glu Tyr Ile Gly Tyr Ala Asp Ala Gly

-continued

```
    130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Glu Leu Leu Lys Leu Asp Ala Leu Ala
        195                 200                 205

Asn Gln His Gly Ile Pro Leu Val Ile Asp Asn Ala Tyr Gly Val Pro
    210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
            260                 265                 270

Met Asn Gly Ile Ile Ser Leu Ala Pro Gly Gly Ile Gly Pro Ala Met
        275                 280                 285

Met Cys Glu Met Ile Lys Arg Asn Asp Leu Leu Arg Leu Ser Glu Thr
    290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
            340                 345                 350

Lys Gln Leu Tyr Gln Arg Leu Lys Ala Arg Gly Val Leu Met Val Pro
        355                 360                 365

Gly His Asn Phe Phe Pro Gly Leu Asp Lys Pro Trp Pro His Thr His
    370                 375                 380

Gln Cys Met Arg Met Asn Tyr Val Pro Glu Pro Glu Lys Ile Glu Ala
385                 390                 395                 400

Gly Val Lys Ile Leu Ala Glu Glu Ile Glu Arg Ala Trp Ala Glu Ser
                405                 410                 415

His
```